United States Patent
Fredens et al.

(10) Patent No.: US 12,385,035 B2
(45) Date of Patent: *Aug. 12, 2025

(54) SYNTHETIC GENOME

(71) Applicants: United Kingdom Research and Innovation, Swindon (GB); Scarab Genomics, LLC, Madison, WI (US)

(72) Inventors: Julius Fredens, Swindon (GB); Kaihang Wang, Swindon (GB); Daniel De La Torre, Swindon (GB); Louise F. H. Funke, Swindon (GB); Wesley E. Robertson, Swindon (GB); Jason W. Chin, Swindon (GB)

(73) Assignees: United Kingdom Research and Innovation, Swindon (GB); Scarab Genomics, LLC, Madison, WI (US)

( * ) Notice: Subject to any disclaimer, the term of this patent is extended or adjusted under 35 U.S.C. 154(b) by 600 days.

This patent is subject to a terminal disclaimer.

(21) Appl. No.: 17/610,974

(22) PCT Filed: May 14, 2020

(86) PCT No.: PCT/EP2020/063445
§ 371 (c)(1),
(2) Date: Nov. 12, 2021

(87) PCT Pub. No.: WO2020/229592
PCT Pub. Date: Nov. 19, 2020

(65) Prior Publication Data
US 2022/0282241 A1   Sep. 8, 2022

(30) Foreign Application Priority Data
May 14, 2019   (GB) .................... 1906775

(51) Int. Cl.
C12N 15/10  (2006.01)
C12N 1/20   (2006.01)
C12N 15/90  (2006.01)

(52) U.S. Cl.
CPC ......... *C12N 15/1031* (2013.01); *C12N 1/205* (2021.05); *C12N 15/902* (2013.01)

(58) Field of Classification Search
CPC ... C12N 15/1031; C12N 1/205; C12N 15/902
See application file for complete search history.

(56) References Cited

U.S. PATENT DOCUMENTS

| | | |
|---|---|---|
| 9,868,956 B2 | 1/2018 | Nguyen et al. |
| 11,408,007 B2 * | 8/2022 | Isaacs .................... C12N 1/205 |
| 11,667,933 B2 | 6/2023 | Fredens et al. |
| 11,732,001 B2 | 8/2023 | Chin et al. |
| 2015/0148525 A1 | 5/2015 | Chin et al. |
| 2022/0010296 A1 | 1/2022 | Chin et al. |
| 2023/0340013 A1 | 10/2023 | Chin et al. |
| 2023/0392138 A1 | 12/2023 | Fredens et al. |

FOREIGN PATENT DOCUMENTS

| | | |
|---|---|---|
| EP | 2192185 A1 | 6/2010 |
| WO | WO-2016/066995 A1 | 5/2016 |
| WO | WO-2016/073079 A2 | 5/2016 |
| WO | WO-2018020248 A1 | 2/2018 |
| WO | WO-2020/229592 A1 | 11/2020 |
| WO | WO-2022248061 A1 | 12/2022 |

OTHER PUBLICATIONS

Nakabachi A et al. Science. Oct. 13, 2006;314(5797):267 (Year: 2006).*
Beare et al., "Coxiella burnetti: Recent Advances and New Perspectives in Research of the Q Fever Bacterium," text book published by Springer, 2012, Chapter 13 (Year: 2012).*
McClure EE et al. Nat Rev Microbiol. Sep. 2017;15(9):544-558 (Year: 2017).*
Serres MH et al. Genome Biol. 2001;2(9) (Year: 2001).*
Martínez-Carranza E et al. Front Microbiol. May 29, 2018;9:1059 (Year: 2018).*
U.S. Appl. No. 18/288,340, United Kingdom Research and Innovation.
U.S. Appl. No. 18/504,827, United Kingdom Research and Innovation.
U.S. Appl. No. 18/493,307, United Kingdom Research and Innovation.
Ostrov et al., "Design, synthesis, and testing toward a 57-codon genome," Science. 353(6301):819-22 (Aug. 2016).
Sample, "World's first living organism with fully redesigned DNA created," The Guardian. <https://www.theguardian.com/science/2019/may/15/cambridge-scientists-create-worlds-first-living-organism-with-fully-redesigned-dna>, (May 15, 2019) (4 pages).
"P0AG40—RIBF_E. coli", UniProtKB Database. <https://rest.uniprot.org/uniprotkb/P0AG40.txt>, Accessed Nov. 13, 2023 (3 pages).
Isaacs et al., "Precise manipulation of chromosomes in vivo enables genome-wide codon replacement," Science. 333(6040):348-53 (Jul. 2011).
Lajoie et al., "Probing the limits of genetic recoding in essential genes," Science. 342(6156):361-3 (Oct. 2013).

(Continued)

*Primary Examiner* — Kimberly Chong
*Assistant Examiner* — Douglas Charles Ryan
(74) *Attorney, Agent, or Firm* — Clark & Elbing LLP

(57) ABSTRACT

The current invention provides a synthetic prokaryotic genome comprising 5 or fewer occurrences of one or more sense codons; and/or a synthetic prokaryotic genome derived from a parent genome, wherein the synthetic prokaryotic genome comprises less than 10%, 5%, 2%, 1%, 0.5%, 0.1% of the occurrences of one or more sense codons, relative to the parent genome; and/or a synthetic prokaryotic genome comprising 100 or more, 200 or more, or 1000 or more genes with no occurrences of one or more sense codons.

11 Claims, 49 Drawing Sheets
Specification includes a Sequence Listing.

(56) References Cited

OTHER PUBLICATIONS

Lajoie et al., "Genomically recoded organisms expand biological functions," Science. 342(6156):357-60 (Oct. 2013).
Napolitano et al. "Emergent rules for codon choice elucidated by editing rare arginine codons in *Escherichia coli.*" *Proceedings of the National Academy of Sciences* 113.38 (2016): E5588-E5597.
International Search Report for International Application No. PCT/EP2020/063445, mailed Jul. 31, 2020 (5 pages).
International Preliminary Report on Patentability for International Application No. PCT/EP2020/063445, issued Nov. 16, 2021 (6 pages).
Wang et al. "Defining synonymous codon compression schemes by genome recoding." available in PMC May 3, 2017, published in final edited form as: *Nature* 539.7627 (2016): 59-64 (38 pages).
Cambray et al. "Evaluation of 244,000 synthetic sequences reveals design principles to optimize translation in *Escherichia coli.*" *Nature biotechnology* 36.10 (2018): 1005-1015.
Mukai et al. "Highly reproductive *Escherichia coli* cells with no specific assignment to the UAG codon." *Scientific reports* 5.1 (2015): 9699 (9 pages).
Gibson et al. "Creation of a bacterial cell controlled by a chemically synthesized genome." *Science* 329.5987 (2010): 52-56.
Zhang et al. "Engineering the ribosomal DNA in a megabase synthetic chromosome." *Science* 355.6329 (2017): eaaf3981 (8 pages).
Richardson et al. "Design of a synthetic yeast genome." *Science* 355.6329 (2017): 1040-1044.
Lau et al. "Large-scale recoding of a bacterial genome by iterative recombineering of synthetic DNA." *Nucleic acids research* 45.11 (2017): 6971-6980.
Ma et al. "Precise manipulation of bacterial chromosomes by conjugative assembly genome engineering." available in PMC Aug. 23, 2017, published in final edited form as: *Nature Protocols* 9.10 (2014): 2285-2300 (32 pages).
Pósfai et al. "Emergent properties of reduced-genome *Escherichia coli.*" *science* 312.5776 (2006): 1044-1046.
Gibson et al. "Complete chemical synthesis, assembly, and cloning of a Mycoplasma genitalium genome." *science* 319.5867 (2008): 1215-1220.
Shen et al. "Deep functional analysis of synll, a 770-kilobase synthetic yeast chromosome." *Science* 355.6329 (2017): eaaf4791 (10 pages).
Annaluru et al. "Total synthesis of a functional designer eukaryotic chromosome." available in PMC May 27, 2014, published in final edited form as: *Science* 344.6179 (2014): 55-58 (11 pages).
Xie et al. "Perfect designer chromosome V and behavior of a ring derivative." Science 355.6329 (2017): eaaf4704 (9 pages).
Mitchell et al. "Synthesis, debugging, and effects of synthetic chromosome consolidation: synVI and beyond." Science 355.6329 (2017): eaaf4831 (12 pages).
Dymond et al. "Synthetic chromosome arms function in yeast and generate phenotypic diversity by design." available in PMC Sep. 16, 2013, published in final edited form as: *Nature* 477.7365 (2011): 471-476 (14 pages).
Wu et al. "Bug mapping and fitness testing of chemically synthesized chromosome X." *Science* 355.6329 (2017): eaaf4706 (7 pages).
Elliott et al. "Proteome labelling and protein identification in specific tissues and at specific developmental stages in an animal." available in PMC Nov. 1, 2014, published in final edited form as: *Nature biotechnology* 32.5 (2014): 465-472 (32 pages).
Elliott et al. "Tagging and enriching proteins enables cell-specific proteomics." *Cell chemical biology* 23.7 (2016): 805-815.
Krogager et al. "Labeling and identifying cell-specific proteomes in the mouse brain." available in PMC Aug. 1, 2018, published in final edited form as: *Nature biotechnology* 36.2 (2018): 156-159 (18 pages).
Kouprina et al. "Exploring transformation-associated recombination cloning for selective isolation of genomic regions." *Bacterial Artificial Chromosomes: vol. 1 Library Construction, Physical Mapping, and Sequencing* (2004): 69-89.
Chin. "Expanding and reprogramming the genetic code." *Nature* 550.7674 (2017): 53-60.
Neumann. "Rewiring translation-genetic code expansion and its applications." *FEBS letters* 586.15 (2012): 2057-2064.
Liu et al. "Adding new chemistries to the genetic code." *Annual review of biochemistry* 79 (2010): 413-444 (35 pages).
Wals et al. "Unnatural amino acid incorporation in *E. coli:* current and future applications in the design of therapeutic proteins." *Frontiers in chemistry* 2 (2014): 15 (12 pages).
Badran et al. "Development of potent in vivo mutagenesis plasmids with broad mutational spectra." Nature communications 6(1) (2015) (10 pages).
Beyer et al. "Overcoming near-cognate suppression in a release factor 1-deficient host with an improved nitro-tyrosine tRNA synthetase," available in PMC Jul. 24, 2021, published in final edited form as: Journal of molecular biology 432(16) (Jul. 2021): 4690-4704 (28 pages).
Cervettini et al. "Rapid discovery and evolution of orthogonal aminoacyl-tRNA synthetase-tRNA pairs," available in PMC Feb. 1, 2021, published in final edited form as: Nature Biotechnology 38(8) (2020): 989-999 (33 pages).
De la Torre and Chin. "Reprogramming the genetic code." Nature Reviews Genetics 22.3 (Mar. 2021): 169-184 (16 pages).
Dunkelmann et al. "Engineered triply orthogonal pyrrolysyl-tRNA synthetase/tRNA pairs enable the genetic encoding of three distinct non-canonical amino acids," available in PMC Jan. 4, 2021, published in final edited form as: Nature chemistry 12(6) (Jun. 2020): 535-544 (28 pages).
Fan et al. "Rationally evolving tRNAPyl for efficient incorporation of noncanonical amino acids." Nucleic acids research 43(22) (2015) (10 pages).
Ferrer-Miralles and Villaverde. "Bacterial cell factories for recombinant protein production; expanding the catalogue." Microbial cell factories 12(113) (2013): 1-4 (4 pages).
Fischer et al. "New codons for efficient production of unnatural proteins in a semisynthetic organism," available in PMC Oct. 6, 2020, published in final edited form as: Nature chemical biology 16(5) (Oct. 2020): 570-576 (22 pages).
Forster et al. "Programming peptidomimetic syntheses by translating genetic codes designed de novo." Proceedings of the National Academy of Sciences 100(11) (2003): 6353-6357 (5 pages).
Fredens et al. "Total synthesis of *Escherichia coli* with a recoded genome." Nature 569.7757 (May 2019): 514-518 and extended data (18 pages).
Italia et al. "Mutually orthogonal nonsense-suppression systems and conjugation chemistries for precise protein labeling at up to three distinct sites," available in PMC Apr. 17, 2020, published in final edited form as: Journal of the American Chemical Society 141.15 (Apr. 2019): 6204-6212 (19 pages).
Katz et al. "Non-canonical roles of tRNAs and tRNA mimics in bacterial cell biology." Molecular microbiology 101.4 (2016): 545-558 (14 pages).
Korkmaz et al. "Comprehensive analysis of stop codon usage in bacteria and its correlation with release factor abundance." Journal of Biological Chemistry 289(44) (2014): 30334-30342 (9 pages).
Ma and Isaacs. "Genomic recoding broadly obstructs the propagation of horizontally transferred genetic elements." Cell systems 3(2) (2016): 199-207 (10 pages).
Martinez-Carranza E et al., Variability of Bacterial Essential Genes Among Closely Related Bacteria: The Case of *Escherichia coli.* Front Microbiol. May 29, 2018;9: 1059 (Year: 2018) (7 pages).
Meydan et al. "Retapamulin-assisted ribosome profiling reveals the alternative bacterial proteome." Molecular cell 74.3 (May 2019): 481-493 (20 pages).
Neumann et al. "Encoding multiple unnatural amino acids via evolution of a quadruplet-decoding ribosome." Nature 464.7287 (2010): 441-444 (4 pages).
Neumann et al. "Genetically encoding Nε-acetyllysine in recombinant proteins." Nature chemical biology 4(4) (2008): 232-234 (3 pages).

(56) References Cited

OTHER PUBLICATIONS

Passioura et al. "Reprogramming the genetic code in vitro." Trends in biochemical sciences 39(9) (2014): 400-408 (9 pages).
Robertson et al. "Sense codon reassignment enables viral resistance and encoded polymer synthesis." Science 372.6546 (Jun. 2021): 1057-1062 (6 pages).
Rode CK, Melkerson-Watson LJ, Johnson AT, Bloch CA Type-specific contributions to chromosome size differences in *Escherichia coli*. Infect Immun. Jan. 1999;67(1):230-6 (Year: 1999).
Schmied et al. "Controlling orthogonal ribosome subunit interactions enables evolution of new function," available in PMC Jun. 1, 2019, published in final edited form as: Nature 564.7736 (2018): 444-448 (42 pages).
Su et al. "Noncanonical roles of tRNAs: tRNA fragments and beyond." Annual review of genetics 54 (Aug. 2020): 47-69 (25 pages).
Wang et al. "Optimized orthogonal translation of unnatural amino acids enables spontaneous protein double-labelling and FRET," available in PMC May 14, 2015, published in final edited form as: Nature chemistry 6(5) (2014): 393-403 (22 pages).
Yanagisawa et al. "Multistep engineering of pyrrolysyl-tRNA synthetase to genetically encode Nε-(o-azidobenzyloxycarbonyl) lysine for site-specific protein modification." Chemistry & biology 15(11) (2008): 1187-1197 (11 pages).
Young and Schultz. "Playing with the molecules of life," available in PMC Jul. 26, 2018, published in final form as: ACS chemical biology 13(4) (2018): 854-870 (39 pages).
Zhang et al. "A semi-synthetic organism that stores and retrieves increased genetic information." Nature 551.7682 (2017): 644-647 (4 pages).

\* cited by examiner

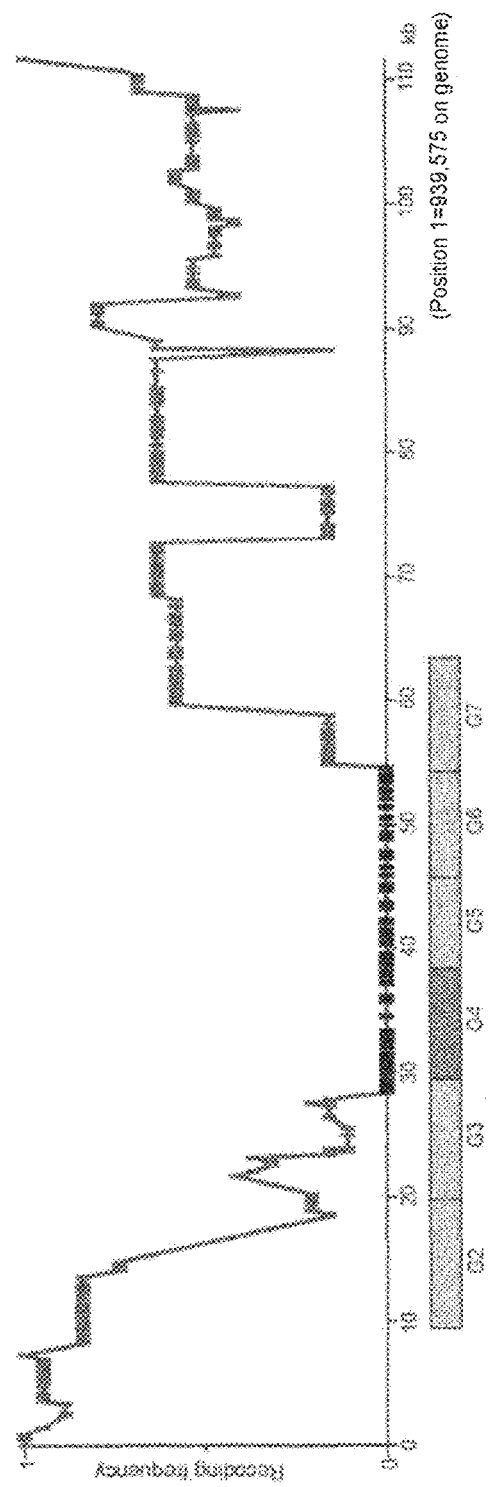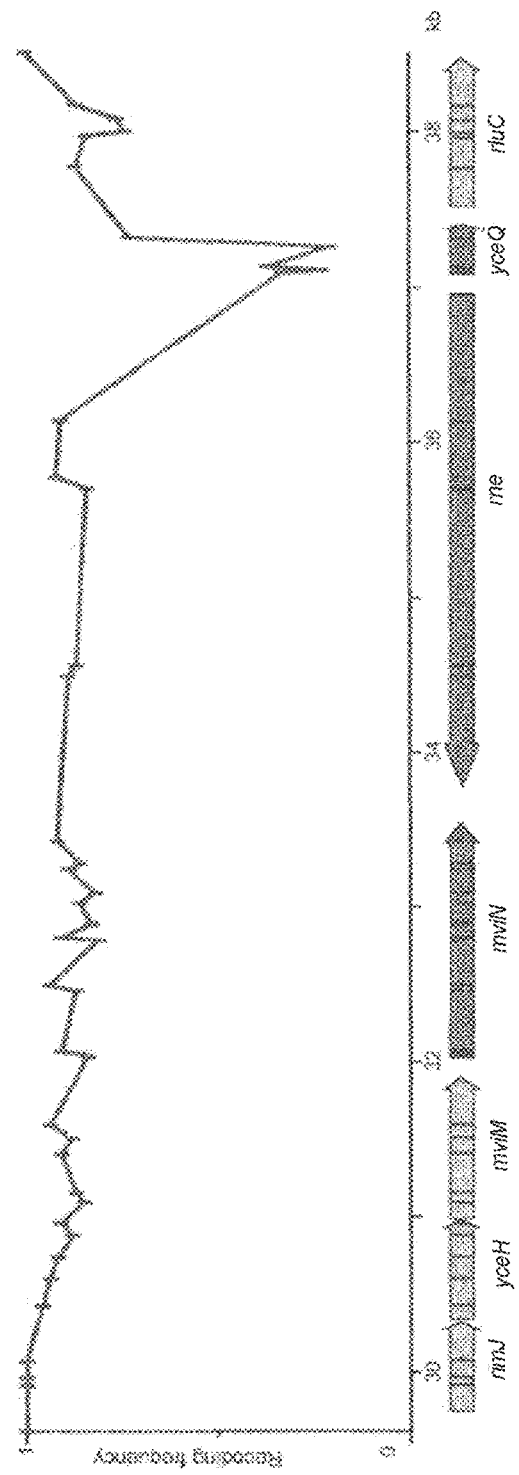
Fig. 6A
Fig. 6B

ACAAGGCTTGCAGTGGAATAATGAGGCCGTTTCCGT   SEQ ID NO: 361
TGTTCCGAACGTCACCTTATTACTCCGGCAAAGGCA   SEQ ID NO: 362

↓ Synonymous codon compression

ACAAGGCTTGCAGTGGAATAAACTGGCCGTTTCCGT   SEQ ID NO: 363
TGTTCCGAACGTCACCTTATTTGACCGGCAAAGGCA   SEQ ID NO: 364

SEQ ID NO: 365 junction 1: SEQ ID NO: 366 junction 2: SEQ ID NO: 367 junction 1: SEQ ID NO: 368 junction 2: SEQ ID NO: 369 junction 1: SEQ ID NO: 370 junction 2: SEQ ID NO: 371

Fig. 18

SEQ ID NO: 1 (see sequence listing)

Fig. 19

SEQ ID NO: 2 (see sequence listing)

A - BAC-sCr Fig. 20A

SEQ ID NO: 3 (see sequence listing)

B - BAC-rKs Fig. 20B

SEQ ID NO: 4 (see sequence listing)

C - BAC-rKpH Fig. 20C

SEQ ID NO: 5 (see sequence listing)

FIG. 20D – Table of BAC construction and protospacers

Oligos used for amplifying BAC backbones for yeast assembly

| BAC of fragment | BAC oligo F (5'->3') | BAC oligo R (5'->3') |
|---|---|---|
| 1 | AACCTATAAAAATAGGCGTATCA CGAGGC (SEQ ID NO:6) | AGTCCCGTACTCTACGCGCCAGAGGAAATTCACCTGGCGCGTATTTTGTTCGCGGCTTAGCTACGGCTGAGC ACGCCCctagggcctgtcgacagcgacacacttgcatc (SEQ ID NO: 7) |
| 2 | AACCTATAAAAATAGGCGTATCA CGAGGC (SEQ ID NO: 8) | TTTTGGCCCCGGCAGTGCTGCTCGCCATCTCACGTACTTTTGTACGCTCCGGTTGCTGCGCCTGCCGTGACCA AACTGCCTGcctaggcctgtcgacagcgacacacttgcatc (SEQ ID NO: 9) |
| 3 | AACCTATAAAAATAGGCGTATCA CGAGGC (SEQ ID NO: 10) | CGCCGTAGTGTATTGGGGTGAAGTCCCTTTCGCCCCTGCCTAATAAGGCACGTCAGGCATCGGCGCACGGCTG TATTCGcctaggcctgtcgacagcgacacacttgcatc (SEQ ID NO: 11) |
| 4 | AACCTATAAAAATAGGCGTATCA CGAGGC (SEQ ID NO: 12) | AGCGTTACGTTTTAACGGTACGGATCCATCCAGCGTAAACCGGCTTCCGTGGTGGTTTGGGGTTTATATTCACA CCCAACcctaggcctgtcgacagcgacacacttgcatc (SEQ ID NO: 13) |
| 5 | AACCTATAAAAATAGGCGTATCA CGAGGC (SEQ ID NO: 14) | GTAAAAAACATCATAATAATTGCGGCCGCAAAGCGACGGTTGTTTAAGACGGGCAGTTGCGCGCACCTG ACGCACACcctaggcctgtcgacagcgacacacttgcatc (SEQ ID NO: 15) |
| 6 | AACCTATAAAAATAGGCGTATCA CGAGGC (SEQ ID NO: 16) | GAATTCTGATTTAAAAGAAGAGAAAGAAAATCAGCCCGACAATGAGAACAATATCGGCAAGCAATGGGCAAAAATC CCTTGCcctaggcctgtcgacagcgacacacttgcatc (SEQ ID NO: 17) |
| 7 | AACCTATAAAAATAGGCGTATCA CGAGGC (SEQ ID NO: 18) | GTTTTTCAGGCCTTCTCAAGCATGGCTGCTTCTGCAGGCTCTGATACTCAGCGTTAAGCTCATCAGACAATTT TCAAGCcctaggcctgtcgacagcgacacacttgcatc (SEQ ID NO: 19) |
| 8 | AACCTATAAAAATAGGCGTATCA CGAGGC (SEQ ID NO: 20) | GAATCGCCCCCAATCATGCCTAATTATTACGACAACTGATTTCCCCGAACTACTTCATTTACCTGATTAATTGTT CCGCTTcctaggcctgtcgacagcgacacacttgcatc (SEQ ID NO: 21) |
| 9 | AACCTATAAAAATAGGCGTATCA CGAGGC (SEQ ID NO: 22) | CCGCAATAACGCGCTTCCGAAATAATCGTTCGCGTTCCTTCACCCCCCGGCAGCGCAAAAAATAACCGCCCGA TAGGcctaggcctgtcgacagcgacacacttgcatc (SEQ ID NO: 23) |
| 10 | AACCTATAAAAATAGGCGTATCA CGAGGC (SEQ ID NO: 24) | TATGAAAAATCTTATTCTCTTCCGACAGGCGGAATATGCCCAGAACGAGAATAGCTCCCACCGCCACCAGG AAGCTGcctaggcctgtcgacagcgacacacttgcatc (SEQ ID NO: 25) |
| 11 | AACCTATAAAAATAGGCGTATCA CGAGGC (SEQ ID NO: 26) | AACATTAATAATTAGTATGTTGTAACTAAAGTCGGATTTTTTTTAAAAATTACAGGCCATCAAGACCGCGAATC GGTTTAATGGCctaggcctgtcgacagcgacacacttgcatc (SEQ ID NO: 27) |
| 12 | AACCTATAAAAATAGGCGTATCA CGAGGC (SEQ ID NO: 28) | TCACCTGATGAATAATAAATAAGCAATAGCATAGAAAAATAATGACAACTCCCCGAGGGGACCATTTCCAAAGCA CTGCACcctaggcctgtcgacagcgacacacttgcatc (SEQ ID NO: 29) |
| 13 | AACCTATAAAAATAGGCGTATCA CGAGGC (SEQ ID NO: 30) | AGTGCCGTGCTTTAAGAGATAAAAACGTGACACTGTAACCTATTATTGCCGGATTGCGCGTAATCGTCACCAT CCCctagggcctgtcgacagcgacacacttgcatc (SEQ ID NO: 31) |
| 14 | AACCTATAAAAATAGGCGTATCA CGAGGC (SEQ ID NO: 32) | GTACATGGCATAAAGTTTATGTTTCCAGAATATTGCATGTCATAGTTGTTGTTTTGATCGCGATTTTCCTTAGT TAGCCGCAGcctaggcctgtcgacagcgacacacttgcatc (SEQ ID NO: 33) |
| 15 | AACCTATAAAAATAGGCGTATCA CGAGGC (SEQ ID NO: 34) | GCAAAATAATTTGCAAATCGCCGTCGGCCAACCTGGCGTGGTGCCATTGCCCTTTCATATCCAGTGTTTTCGGC CCGTGAGcctaggcctgtcgacagcgacacacttgcatc (SEQ ID NO: 35) |

FIG. 20E

| # | Col2 | Col3 |
|---|---|---|
| 16 | AACCTATAAAAAATAGGCGTATCA CGAGGC (SEQ ID NO: 36) | TTGACCTGTGAAGCAAGTATCAGAGCTGCCGTTTTGCTTCATACTTACACCCTTCAACAATAAAAATGAGAGG GAATGCcctagggcctgtcgacagcgacacacttgcatc (SEQ ID NO: 37) |
| 17 | AACCTATAAAAAATAGGCGTATCA CGAGGC (SEQ ID NO: 38) | TTATTCTATTTCTTGGTTGAATATATTCTGTAGTTCACGATTAAAAATTGCTATTACAGTTTCAGGcctaggc ctgtcgacagcgacacacttgcatc (SEQ ID NO: 39) |
| 18 | AACCTATAAAAAATAGGCGTATCA CGAGGC (SEQ ID NO: 40) | GCGCGTTAATGATGATGGAAGTCAATGTGAAGATTGATGCATCCCGTCGGGGCATACTCACTGGTCGCTGGCAA AGCCAGcctaggcctgtcgacagcgacacacttgcatc (SEQ ID NO: 41) |
| 19 | AACCTATAAAAAATAGGCGTATCA CGAGGC (SEQ ID NO: 42) | TGATGATAACCAGAAAGGAAACGCGCGAACTTGCTCAAAGACAGCTCGATATCATCGACACGCGGTAGCGTGAC cctagggcctgtcgacagcgacacacttgcatc (SEQ ID NO: 43) |
| 20 | AACCTATAAAAAATAGGCGTATCA CGAGGC (SEQ ID NO: 44) | CCTGTTTCACACAACGGTTTACAAAATAACCGTAGATTGTTACCGCCACATCGCGTGTTATCGCGATAGCA ATCGACcctagggcctgtcgacagcgacacacttgcatc (SEQ ID NO: 45) |
| 21 | AACCTATAAAAAATAGGCGTATCA CGAGGC (SEQ ID NO: 46) | ATTTATTAAAAATTCACGCAGGGAATAATTTATAAAAATATATCATTACAACATATATTAATTTTATATTTAT TTCGCAGCcctaggcctgtcgacagcgacacacttgcatc (SEQ ID NO: 47) |
| 22 | AACCTATAAAAAATAGGCGTATCA CGAGGC (SEQ ID NO: 48) | TGTGCTGGCATTTTCATCAGCCCCCTTTTTGCCATATCTTCATGCAGTTGGCTGGCATTTTCAACATTGTTGCAGC TGGCAGcctaggcctgtcgacagcgacacacttgcatc (SEQ ID NO: 49) |
| 23 | AACCTATAAAAAATAGGCGTATCA CGAGGC (SEQ ID NO: 50) | TCGCCGCGATAGATACAACCTGCGGTGCAGGTTTCTTTTACCATCACCGCACTTAACAGCGGCACAACGGGTTT AACCTGcctaggcctgtcgacagcgacacacttgcatc (SEQ ID NO: 51) |
| 24 | AACCTATAAAAAATAGGCGTATCA CGAGGC (SEQ ID NO: 52) | AGAGGTGCTGGTTATAGTGGTTAACTGCACTATAACGCAGCAAATTTAACCAAATGATTGTAATGCTAGCCATT ATCTTCcctaggcctgtcgacagcgacacacttgcatc (SEQ ID NO: 53) |
| 25 | AACCTATAAAAAATAGGCGTATCA CGAGGC (SEQ ID NO: 54) | GTCTCAACGACGAGATCCTTCGCTAAGGTGGGTTACTGCTGTAAACGTGCTCGATGGCATCCATTAACATT CCGGTGcctaggcctgtcgacagcgacacacttgcatc (SEQ ID NO: 55) |
| 26 | AACCTATAAAAAATAGGCGTATCA CGAGGC (SEQ ID NO: 56) | CTGCTCATTTTTTTATTCTGCTTAATCACATTGCTAATCAACATTGCTGGCGTCGCTTCAATATGGCGCTCTTCAGCCGT TAATCCcctaggcctgtcgacagcgacacacttgcatc (SEQ ID NO: 57) |
| 27 | AACCTATAAAAAATAGGCGTATCA CGAGGC (SEQ ID NO: 58) | CAGACCGCCATGCACATAATGAGAGGTCAGGTGTTATGCTGACGGTGACGAAACCTAACAGGAAGC CGTGCCAGcctaggcctgtcgacagcgacacacttgcatc (SEQ ID NO: 59) |
| 28 | AACCTATAAAAAATAGGCGTATCA CGAGGC (SEQ ID NO: 60) | GTCCGGCATGGCAATTAATGAGAGTCAGGTTATGCTGACGGTGACGGCTGACGAAACCTAACAGGAAGC ACATCACcctaggcctgtcgacagcgacacacttgcatc (SEQ ID NO: 61) |
| 29 | AACCTATAAAAAATAGGCGTATCA CGAGGC (SEQ ID NO: 62) | GAAGATTATTCTTCTTCGTCGCCAGCAATCAGCATATCAACGTGAACGGTGTTGATCAGCTGACGTGC GGAAGACcctaggcctgtcgacagcgacacacttgcatc (SEQ ID NO: 63) |
| 30 | AACCTATAAAAAATAGGCGTATCA CGAGGC (SEQ ID NO: 64) | GAGAGGGTGGATTGGATTACTTACGACTTGGACAGTTCCAGCACTTCATCCACGCTGGTGGTGTGCCAG ACGCTCcctaggcctgtcgacagcgacacacttgcatc (SEQ ID NO: 65) |
| 31 | AACCTATAAAAAATAGGCGTATCA CGAGGC (SEQ ID NO: 66) | TGACAGTTCAGAATCGGCTTCGTAAGCGCGGTTACTTACCAATACAGAAGCTGGAGAAAATCCGCCCAGCAGG TCGTCcctagggcctgtcgacagcgacacacttgcatc (SEQ ID NO: 67) |
| 32 | AACCTATAAAAAATAGGCGTATCA CGAGGC (SEQ ID NO: 68) | GAGGAAAATCATAGGTTGCCGGTGTAGTGCCAGCGTAAATAACGCAGCAAACGAAGCTGACGCTTAATGCGGCT CGGCTGcctaggcctgtcgacagcgacacacttgcatc (SEQ ID NO: 69) |
| 33 | AACCTATAAAAAATAGGCGTATCA CGAGGC (SEQ ID NO: 70) | TGAAAAATTTTTGTCATTCCTTACACTGATCATCAACACCAACTACCTCCCCCTTTTGCCTGCCT CCCTTTGcctaggcctgtcgacagcgacacacttgcatc (SEQ ID NO: 71) |
| 34 | AACCTATAAAAAATAGGCGTATCA CGAGGC (SEQ ID NO: 72) | CTTATTGCTGAAAATTATACCAATATTGCTCTCACCCGCCCTCACGCAGGTCTGCCCTAAGGCCTTTTATCAGC TCGATATCGcctagggcctgtcgacagcgacacacttgcatc (SEQ ID NO: 73) |

FIG. 20F

| | | |
|---|---|---|
| 35 | AACCTATAAAAATAGGCCGTATCA CGAGGC (SEQ ID NO: 74) | GTTTTGTAGATTTTTTAAGCGCTTATGATCAGTATCATTTGCGGTATGTTGCGCAACCCTTTAACAACAGAGC TTTTCGCTGcctagggcctgtcgacagcgacacacttgcatc (SEQ ID NO: 75) |
| 36 | AACCTATAAAAATAGGCCGTATCA CGAGGC (SEQ ID NO: 76) | GAATTACGCGTCGAACGGGTCGCGCAGAATCATGTTTCAGTACGATCCGGACCGGTAGAGATGATATCGATCG GCACACcctagggcctgtcgacagcgacacacttgcatc (SEQ ID NO: 77) |
| 37a | AACCTATAAAAATAGGCCGTATCA CGAGGC (SEQ ID NO: 78) | GGCAAGAATTAATGCTCGCGGGTCTGGTGGAACTGTCCGATAACGTTCCTGTGCCAGGCGCAGGTTGAC CATGCTGcctagggcctgtcgacagcgacacacttgcatc (SEQ ID NO: 79) |
| 37b | AACCTATAAAAATAGGCCGTATCA CGAGGC (SEQ ID NO: 80) | TTACACGGACTAATTTTCCCGACTGTTATTGCGCAGGCGCGTAAATTTGCTCcctagggcctgtcgacagc gacacacttgcatc (SEQ ID NO: 81) |
| 9 (stretch 4) | AACCTATAAAAATAGGCCGTATCA CGAGGC (SEQ ID NO: 82) | GTGAGCCAGGCGAGGAACCTGGGTAAATATTTCCTGCTcctagggcctgtcgacagcgacacacttgcatc (SEQ ID NO: 83) |

Homology Regions and Selection Cassettes in BACs for REXER

| BAC of frag-ment | HR1 (5' end of synthetic DNA fragments)(5'→3') | 3' end of synthetic DNA fragments (5'→3') | Double selection cassette | HR2 (flanking 3' of double selection cassette )(5'→3') | Negative selection cassette in BAC backbone |
|---|---|---|---|---|---|
| 1 | GGCGTGCTCAGCCGTAAGCCGCGCAGCAACCGGAGCG GCCAGGTGAATTTC (SEQ ID NO: 84) | TTGTTGCAGGCAGTTTGGTCACGGCCAGC GCCAGCAACCGGAGCGTACAAAAGTACG TGAGGATGGCGAGCACTGCCCGGGG (SEQ ID NO: 85) | SacB-Cm$^R$ | TGGCAAATAAATAGCCTA ATAATCCAGACGATTACCC GTAATATGTTTAATCAGGG CTATAC (SEQ ID NO: 86) | rpsL |
| 2 | CAGGCAGTTTGGTCACGGCCAGCGCCAGCAACCGGAGCG TACAAAAGTACGTGAGGATGGCGAGCACTGCCCGGGG (SEQ ID NO:87) | TGATGAGCCGGAGAAGTCGAATACAGCCG TGCGCCGATGCCTGACGTGCCTTATTAGG CAGGGGCGAAAGGACTTCACC (SEQ ID NO: 88) | rpsL-Kan$^R$ | CACCTACGGCCGTTACAGG TATACTCGCTAAAAATTAT TCAGCGGGTTTGGAAACAA AGATG (SEQ ID NO: 89) | pheST251A-A294G-Hyg$^R$ |
| 3 | CGAATACAGCCGTGCGCCGATGCCTGACGTGCCTTATTAG GCAGGGGCGAAAGGACTTCACC (SEQ ID NO: 90) | ATAAACCCCAAAACCACCACGGAAGCCGGT TTACGCTGGATGGATCCGTACCCGTTAAAA CGTAACGCTATTCAGACAATGCTTTTTTA GG (SEQ ID NO: 91) | SacB-Cm$^R$ | AGTTGGCAGGGGATCCGTGT TGTCTGAATTCAGGAAAAG CGAAATTTAAAAGAG (SEQ ID NO: 92) | rpsL |
| 4 | GTTGGGTGTGAATATAAACCCCAAAACCACCACGGAAGCCG GTTTACGCTGGATGGATCCGTACCGTTAAACGTAACGCT ATTCAGACAATGCTTTTTTAGG (SEQ ID NO: 93) | GAACGTGTGCGTCAGGTGCCGCGCAACT GCCCGTCTTAAACAACCGTCGCTTTGCGC | rpsL-Kan$^R$ | TACAGATTGCTATTGTGTG CGGCCGTCGAATGACCGTT AATATTCTCTGGTTTTTAA | SacB |

FIG. 20G

| # | | | | |
|---|---|---|---|---|
| 5 | GTGTGCGTCAGGTGCGCGCGCAACTGCCCGTCTTAAACAA CCGTTCGGCTTTGCGCCGCCGCGCCAATTATTGATGTTTTTTT ACTCGGGCGCTTGATTCA (SEQ ID NO: 96) | CGCCGCGCAATTATTGATGTTTTTTACT CGGGCGCTTGATTCA (SEQ ID NO: 94) | | |
| | | CTTGCCGATATTGTTCTCATTGTCGGCT GATTTCTTCCTTCTTTAAATCAGAATTC TCTTTAAAAAATTATGGGCCGCT (SEQ ID NO: 97) | SacB-Cm$^R$ | GGCGCG (SEQ ID NO: 95) |
| 6 | GCAAGGGATTTTTTGCCCATTGCTTGCCGATATTGTTCTC ATTGTCGGCTGATTTCTTCCTTCTTTAAATCAGAATTC TCTTTAAAAAATTATGGGCCGCT (SEQ ID NO: 99) | TTAACGCTGAGTATCCAGAGCCTGCAGAA GCACGCCATGCTTGAGAAGGCCTGAAAAC TAAGGGGAGAAAGCGTCCC (SEQ ID NO: 100) | | CCATAAATTTTACGCTCC CTTAACTTGCCCTCATTCC CAAACCTCAATCG (SEQ ID NO: 98) |
| | | | rpsL-Kan$^R$ | TGTTTAAGTTTTTGTAAAA ATGAATTTGTTATCTCCTC CACTGACTACGCTTTAAGC CAGAGTC (SEQ ID NO: 101) |
| 7 | GCTTGAAAATTGTCTGATGAGCTTAACGCTGAGTATCCAG AGCCTGCAGAATGCTTGAGAAGGCCTGAAAAC TAAGGGGAGAAAGCGTCCCC (SEQ ID NO: 102) | AAGCGGAACAATTAATCAGGTAAATGAAG TAGTTCGGGAAATCAGTGTCGTAATAA TTAGCATGATTGGGGGCGATTCTGCAG CCC (SEQ ID NO: 103) | SacB-Cm$^R$ | CTGCTGGGTTGCTCTTACGGG TTGACGTCTGCTTTACGGG CGGTTAAGGTGCCTCTTGT GC (SEQ ID NO: 104) | pheS$^{T251A}$ A294G-Hyg$^R$ |
| 8 | AAGCGGAACAATTAATCAGTAAATGAAGTAGTTCGGGA AATCAGTGTCGTAATAATTAGCATGATTGGGGGCGATTC TCTGCAGCCC (SEQ ID NO: 105) | GTTATTGCGGGTTTAATGTTTTTAGGCGG ATAAGCATTTGTGCGCAGATG (SEQ ID NO: 106) | rpsL-Kan$^R$ | GCGACGCGCTTGCGCGTCTTA TCATGCCTACAATCAGTGC GGGTTTGGTAGGCTGGATA AGG (SEQ ID NO: 107) | pheS$^{T251A}$ A294G-Hyg$^R$ |
| 9 | CCTATCGGCGGCGGTTATTTTTTGCGCTGCCGCGGGGTGA AGGACGCGAACGATTATTTCGGAAGCGCGTTATTGCGGGT TTAATGTTTTTAGGCGGGATAAGGCATTTGTGCGCAGATG (SEQ ID NO: 108) | CAGCTTCCTGGTGGCGGTGGGCATATTCCGCCTCCTG CGAAGAGAATAAGATTTTCATAAGGCGGA TAGCGGATACAGATG (SEQ ID NO: 109) | SacB-Cm$^R$ | TCCGCTTTCACATCAGAAC GTATACTCGACACCTGCTT TACGGGTGAAAAAAATCAA (SEQ ID NO: 110) | |
| 10 | ACCATTAAACCGATTCGCGGTTCGCGGTCTTGATGGCCTGTGT AATTTTTAAAAAAAATCCGACTTTAGTTA CAACATACTAATTATTAATGTT (SEQ ID NO: 112) | TAAACCGATTCGCGTCTTGATGGCCTGT AATTTTTAAAAAAAATCCGACTTTAGTTA CAACATACTAATTATTAATGTT (SEQ ID NO: 112) | rpsL-Kan$^R$ | TGCTCCGGCAACGACGGCG CAGAAAAAGCCTGCCAGGG GAGAAATCGCAACTG (SEQ ID NO: 113) | rpsL |
| 11 | GTGCAGTGCTTTGAGTTGTCATTTATATTGCTTAGTTGAACGA AAATTCCTAATTTGAAATAT (SEQ ID NO: 114) | GTGCAGTGCTTTGGAAATGGTCCCCTCGG GCTTATTATATTGCTTCTATGCTATTT AAATTCCTAATTTGAAATAT (SEQ ID NO: 115) | SacB-Cm$^R$ | TTAAGCTAGTGTTTAACGA CGTTAAGAGATGGCAATGTGC AGATCATGTTATCAGGGTG (SEQ ID NO: 116) | |
| 12 | AGGTTACAGTGTCACGTTTTTTATCTCT TAAAGCACGCACTGCTTTTGCGGCTGGCC TCTTTGCCGCAAAATAGTCGC (SEQ ID NO: 117) | AGGTTACAGTGTCACGTTTTTTATCTCT TAAAGCACGCACTGCTTTTGCGGCTGGCC TCTTTGCCGCAAAATAGTCGC (SEQ ID NO: 118) | rpsL-Kan$^R$ | TTCATTGCCCATTTCTGCT CATGCATCATCTACACATC TATCCGGATCTGCCACTA TG (SEQ ID NO: 119) | pheS$^{T251A}$ A294G-Hyg$^R$ |
| 13 | GGATGGTGACGATTACGCGCAATCCGGCAATAATAGGTTA CAGTGTCACGTTTTTTATCTCTTAAAGCACGCACTGCTT (SEQ ID NO: 117) | TGACATGCAATATTCCTGGAAACATAAAC TTTATGCCATGTACCCAGGGAAATCATC | SacB-Cm$^R$ | GAGAACAATACGTACGGTA ACGAAATTATCTTTCAGCA | rpsL |

FIG. 20H

| | | | | |
|---|---|---|---|---|
| | TTGCGGGCTGGCCCTCTTTGCCGCAAAATAGTCGC (SEQ ID NO: 120) | TTCAGTATATAGTAATTATGTAAA (SEQ ID NO: 121) | AGGAGCTGTGAAAATGTCTC (SEQ ID NO: 122) | |
| 14 | CTGCGCTAACTGAAGGAAATCGCGATCAAAAACAAACTATGACATGCAATATTCCTGACGCGATTTGAAACATTTATGCCATGTACCCAGGGAAAATCATCTTCAGTATATAGTAATTATGTAAA (SEQ ID NO: 123) | AAGGCAATGCCACCACGCCACAGGTTGCCGAGGCGATTTGCAAATATTTTGCGTTAAGTGTCAAACCAGTTTATTTGCGTTA (SEQ ID NO: 124) | CACTGACGCGGTTTTTTATTCGTTCTTTGCAGTAAATAACCTGCTCATTTCACCTTTTATTG (SEQ ID NO: 125) | SacB |
| 15 | CTCACGGGCCGAAAACACCTGATATGAAAGGCAATGCCACCACGCCACAGGTTGCCGACGCGATTTGCAAAATTATTTTGCGTTAAGTGTCAAACCAGTTTATTTGAA (SEQ ID NO: 126) | TATGAAGCAAAAACGGCAGCTCTGATACTTGCTTCACAGTGCAATCATTTTTAACAATCAAGTGCAATTATATCTCTCG (SEQ ID NO: 127 | GAATGATTTCACGTTTACTATGAACCACCTTTTTATTTCCACCCGTGAGGGATTATG (SEQ ID NO: 128) | rpsL |
| 16 | GCATTCCCTCCTCATTTTATTGTTGAAGGGTGTAAGTATGAAGCAAAAACGGCAGCTCTGATACTTGCTTCACAGTGCAACAATTTTTAACAATCAAGTGCAATTATATCTCTCG (SEQ ID NO: 129) | AATAGCAATTTTTAATCGTGAACTACAGAATATATTCAACCAAGAAATAGAATAATAATACTCTAAATAATTCAAATAATTCAAATTGGT (SEQ ID NO: 130) | CGGCGCAACGTCCCAATGGCCTGGATTATAAAATCTCATTATCTTAATTGCAACGGGGTCC (SEQ ID NO: 131) | pheS<sup>T251A</sup>_A294G_Hyg<sup>R</sup> |
| 17 | CCTGAAACTGTAATAGCAATTTTTAATCGTGAACTACAGAATATATTCAACCAAGAAATAGAATAATACTCTAAATAATTTCAAATTGGT (SEQ ID NO: 132) | ATGCCCCGACGGGATGCATCAATCTTCACATTGACCTTCCATCATTCAACGCGCTCTGAAAATTGAGAGCGACCAAATAAA (SEQ ID NO: 133) | AATTAATAAGCCATTTTTATAGCCGCTAAGATATTAAAGGATGTGTCAAAGATGCATAC (SEQ ID NO: 134) | rpsL |
| 18 | CTGGCTTTGCGCGACCAGTGACGCGGAGTATGCCCCGACGGGATGCAATCAATCTTCACATTGACCTTCCATCATTACGCGCTCTGAAAATTGAGAGCGACCAAATAAA (SEQ ID NO: 135) | AGCTGTCTTTGAGCAAGTTCGCGCGTTTCCTTTCTGGTTATCATCAGCTGTAATCTTAATTTCACTGCCGGAGATTGCAT (SEQ ID NO: 136) | GCGTTATCCGCCACAATGACCTGATGATGTCATCATACGTAAGGTCACTATGAAAACAG (SEQ ID NO: 137) | SacB |
| 19 | GTCACGCTACCGCGTGTCGATGATATCGAGCTGTCTTTGAGCAAGTTCGCGCGTTCCTTTCTGGTTATCATCAGCTGTAATCTTAATTTCACTGCCGGAGATTGCAT (SEQ ID NO: 138) | CGGCGATGTGGCGGTAACAATCTACCGGTTATTTGTAAACCGTTTGTGAAACAGGGTGGCTTATGCCGCCCCTTATT (SEQ ID NO: 139) | TGCATGTCATTATTTCCCTTCTGTATATAGATATGCTAAATCCTTACTTCCGCATATTCTC (SEQ ID NO: 140) | rpsL |
| 20 | GTCGATTGCTATCGCGATAAACACGCGATGTGGCGGTAACAATCTACCGGTTATTTGTAAACCGTTTGTGTGAAACAGGAATCTTACCGGTTATTTGTAAACCGTTTGTGAACAGGGTGGCTTATGCCGCCCCTTATT (SEQ ID NO: 141) | ATGATATATTTTTATAAATTAATTAATTCCCTGCGTGAATTTTGAATAAATAATCTATCCCTTATACGCAATACATTTACTTT (SEQ ID NO: 142) | TTGATGATCTTAAATGTCTTATTTTCGTAATGTGTATAACAAGGAATAGTGATG (SEQ ID NO: 143) | SacB |
| 21 | GCTGCGAAATAAATAAAATTAATAATATATGTTGTAATGATATATTTTTAATAAATTATTCCCTGCGTGAATTTTAATAAATTTAATCTATCCCTTATACGCAATACATTTACTTT (SEQ ID NO: 144) | CAATGTTGAAAATGCCAGCCAACTGCATGAAGTATGCAAAAAAGGGGCTGATGAAAATGCCAGCACAATACGATTAATTAAGCCAGCACAATACGATTAATTAAAACC (SEQ ID NO: 145) | ATAAATTAAACATAAGATTTTACTCATTGTGTTTTATTTCTCACATTGATGACGGTCGCATG (SEQ ID NO: 146) | rpsL |

FIG. 20I

| | | | | |
|---|---|---|---|---|
| 22 | CTGCCAGCTGCAACAATGTTGAAAATGCCAGCCAACTGCA TGAAGTATGGCAAAAGGGGCTGATGAAAATGCCAGCACA ATACGATTAAATTAATTAAAACC (SEQ ID NO: 147) | GTGCGGTGATGGTAAAAGAAACCTGCACC GCAGTTGTATCTATCGCGGCGAATGATA AGAGTGTGTCGGCGGTCAATTTC (SEQ ID NO: 148) | rpsL-Kan^R | pheS^T251A-A294G-Hyg^R |
| 23 | CAGGTTAAACCCGTTGTGCCGCTGTTAAGTGCGGTGATGG TAAAAGAAACCTGCACCGCAGTTGTATCTATCGCGGCGA ATGATAAGAGTGTGTCGGCGGTCAATTTC (SEQ ID NO: 150) | AACGATAATAGTGAAGATAAATGGCTAAGC ATTACAATCATTTGGTTAAATTTGCTGGT TATAGTGCAGTTAACCACTATAA (SEQ ID NO: 151) | | CCTCTTATGTTTTCTTAAA TCAGCATCTAAAACAGTT AAGAGCATACTATAAATC (SEQ ID NO: 152) | rpsL |
| 24 | GAAGATAATGGCTAAGCATTACAATCATTTGGTTAAATTT GCTGGTTATAGTGCAGTTAACCACTATAA (SEQ ID NO: 153) | GATGCCATCGAAGCACGTTTACAGCAGCA GTAACCCACCTTAGCGAGAAGGATCTCGT TGAGACTCGAGTGACAGCGC (SEQ ID NO: 154) | rpsL-Kan^R | TTCCACGCATACTGGGCGC TGTTGCTTTTTTGAACCAG GAAACAGAACCTCTGACAA TG (SEQ ID NO: 155) | pheS^T251A-A294G-Hyg^R |
| 25 | CACCGGAATGTTAATGGATGCCATCGAAGCACGTTTACAG CAGCAGTAACCCACCTTAGCGAGAAGGATCTCGTTGAGAC TCTGAGTGACAGCGC (SEQ ID NO: 156) | TTAACGCTGAAGAGCGCCATATTGAAGC GACGCCAGCCAATGTTGATTAAGCAG AATAATAAAAAATGAGCAGGCATTTTCCC TCTT (SEQ ID NO: 157) | SacB-Cm^R | TGAGGAGAGGGAAAATAGT TTCTGCCTTTATATTTTTA TAATTACAACGATAAAAGG CTG (SEQ ID NO: 158) | rpsL |
| 26 | GGATTAACGCTGAAGAGCGCCATATTGAAGCGACGCCAG CCAATGTTGATTAAGCAGAATAATAAAAAATGAGCAG GCATTTTCCCTCTT (SEQ ID NO: 159) | GACCAAACATAAAGATAAACTGAAACAAC ACTAATTGTCCGGGCAATTAGCATGTGCA TGGCGGTCTCGTGTTGCGGCACAACGGG (SEQ ID NO: 160) | | GTACGGTTAATGCTCCGAG CCTGTTCCACTGTTTGAGT GGGCAGTTTCTTAGGTGAA ATTATG (SEQ ID NO: 161) | pheS^T251A-A294G-Hyg^R |
| 27 | CTGGCACGCCAGTTGACCAAACATAAAGATAAACTGAAAC AACACTAATTGTCCGGGCAATTAGCATGTGCATGGCGGTC TGTTGTGCGGCACAACGGG (SEQ ID NO: 162) | TTAGGTTTCGTCAGCCGTCACCGTCAGCA TAACACCCGTCAGCCTCCTCATTAATTGCTCA TGCCGGACGGCACTATCGTCGTCCGGCCT TTT (SEQ ID NO: 163) | SacB-Cm^R | TTCCCCCGCTACGTGCATC TATTTCTATAAACCGCTC ATTTTGTCTATTTTTTGCA C (SEQ ID NO: 164) | rpsL |
| 28 | CTGATGTGTTCCTGTTAGGTTTCGTCAGCCGTCACCGTC AACTAACACCCGTCAGCCTCCTCATTAATTGCTCATGCCGGA CGGCACTATCGTCGTCCGGCCTTTT (SEQ ID NO: 165) | CACCGTTCACGTTGATATGCTCAGCCGTC CGTCGCGACGAAGAAGAATAATCTTCC CTCTACGACGTGTTCCTGAACGC (SEQ ID NO: 166) | rpsL-Kan^R | ATGCGGGGCGTTTTGCTTTT TGGCGCGCCTTGTTACCTG ATCAGCGTAAACACC (SEQ ID NO: 167) | pheS^T251A-A294G-Hyg^R |
| 29 | GTCTTCCGCACGTCAGCTGATCAACACCGTTCACGTTGAT ATGCTCAGCCGTCGTCGCGACGAAGAAGAATAATCTT CCCTCTACGACGTGTTCCTGAACGC (SEQ ID NO: 168) | CACCACCAGCAGGTGGATGAAGTGCTGGAAAC TGCTGGCAGGTCGTAAGTAATCCAATCCC ACCCTCTCCACATGGAGAAGGTGGGGTTA ATTG (SEQ ID NO: 169) | SacB-Cm^R | GCGCTACGCTTATCAGGCC TACAGGATGCATCACAATT TGTTGAATTTGCACGTTCT TGTAG (SEQ ID NO: 170) | rpsL |
| 30 | GAGCGTCTGCGCACACCAGCAGGTGGATGAAGTGCTGG AACTGCTGGCAGGTCGTAAGTAATCCAATCCCACCCTCTC CACATGGAGAAGGTGGGGTTAATTG (SEQ ID NO: 171) | CACCGGGAATTTACTAGTGACGACCTGC TGGGGCGGATTTTCTCCAGCTTCGTATT GGTAAGTAACCGCGCTTACGAAG (SEQ ID NO: 172) | rpsL-Kan^R | TCTGACTGTCAGATGCGGC TTCGCTTCATTGTTACCAC TCCTGTTATTCCTCAAC (SEQ ID NO: 173) | pheS^T251A-A294G-Hyg^R |

FIG. 20J

| # | | | | |
|---|---|---|---|---|
| 31 | GACGACCTGCTGGGGCGGATTTTCTCCAGCTTCTGTATTG GTAAGTAACCGCGCTTACGAAG (SEQ ID NO: 174) | AGCCGTCAGCTTCGTTTGCTGCGTTATTTA CGCTGGCACTACACCGGCAACCTATGATT TTCCTCTCTTTGTAAGCGACGGAGTGGT CACT (SEQ ID NO: 175) | SacB-CmR | CCTGTCTGCTTTTTATTA CACAAAGCATTCAAATTTT TAATGCTTTATTGCCATT TC (SEQ ID NO: 176) | rpsL |
| 32 | ATTTCGGAGCCGAGCCGCATTAAGCGTCAGCTTCGTTTGCTGCGTT ATTTGTAAGCGACGGAGTGGTCACT (SEQ ID NO: 177) | GAGGTAGTTGGTTGTTGATGATCAGTGTAA GGAGCATAAGGAATGACAAAAATTTTTCA TTTCTTGAATATAAAAAACAGATGC (SEQ ID NO: 178) | rpsL-KanR | TCTGGTATTAATACAAGGC TGTTTTACTTGAACTTATA ATAACTGCAACTGTTACAT C (SEQ ID NO: 179) | pheS^T251A_A294G_HygR |
| 33 | CAAAGGGAGGCAGGCAAAAGGGGAGGTAGTTGGTGTGA TGATCAGTGTAAGGACATAAGGAATGACAAAAATTTTTC ATTCTTGAATATAAAAAACAGATGC (SEQ ID NO: 180) | ATAAAAGGCCTTAGGGCAGACCTGCTGA GGCGGGTGAGAGCAATATTGGTATAATTT TTCAGCAATAAGACCAGAAAACGTGATTT AACG (SEQ ID NO: 181) | SacB-CmR | TTGTCGTACCTGGAGTCTT CCCTTTCGCCCCCCGTCTG GTCTACATTGG (SEQ ID NO: 182) | rpsL |
| 34 | CGATATCGAGCTGATAAAAAGGCCTTAGGGCAGACCTGCT GAGGCGGGTGAGAGCAATATTGGTATAATTTTTCAGCAAT AAGACCAGAAAACGTGATTTAACG (SEQ ID NO: 183) | CTGTTGTTAAAGGGTTGCGCAACATACCG CGCAAATGATACTGATCATAAGCGTTAAA AAAATCTACAACCAACGCAACACAATTC ATGC (SEQ ID NO: 184) | rpsL-KanR | AGTATGTCACGTTCTCGCG TTTCTGAACGGGAACGGC GCTCCATTGAGGAAGTCAT TCATATG (SEQ ID NO: 185) | pheS^T251A_A294G_HygR |
| 35 | CAGCGAAAAGCTCTGTTGTTAAAGGGTTGCGCAACATACC GCGCAAATGATACTGATCATAAGCGTTAAAAAAATCTACA AACCAACGCAACACAATTCATGC (SEQ ID NO: 186) | GATATCATCTCTACCGGTCCGGATCGTAC TGAAACCATGATCTCTGCGCGACCCGTTCG ACGCGTAATTCTGGCTACGCCTGGCAGATA TTTTG (SEQ ID NO: 187) | SacB-CmR | GGGCGAACAGTGTGATACA TTGCTGTGTCGGGTAAGCC ATTACGCTATCCGACAC (SEQ ID NO: 188) | rpsL |
| 36 | GTGTGCCGATCGATATCATCTCTACCGGTCCGGATCGTAC TGAAACCATGATCTCTGCGCGACCCGTTCGACGCGTAATTC TGGTACGCCTGGCAGATATTTTG (SEQ ID NO: 189) | CTGCGCCTGGCACAGGAACGTTATCCGGA CGTTCAGTTCTTGCCTCCAGGGCGCGGTAGCCGC AATTCTTGCCTCCAGGGCGCGGTAGCCGC TGCGC (SEQ ID NO: 190) | rpsL-KanR | AATTTCCCTTCCTTATTAG CCGCTTACGGAATGTTCTT AAAACATTCACTTTTGC (SEQ ID NO: 191) | pheS^T251A_A294G_HygR |
| 37a | CAGCATGGTCAACCTGCGCCTGGCACAGGAACGTTATCCG GACGTTCAGTTCTTGCCTCCACGGAGCTGGCAGATGATGTTGA CTCCAGGGCGCGGTAGCCGCTGCGC (SEQ ID NO: 192) | ATTCCTGCCGTTCCGCTCACGGAACTTAA CCGCGAGCAGAAGTGGCAGATGATGTTGA GTAAGAGTATGCGTCGTTAA (SEQ ID NO: 193) | SacB-CmR | GTCCTGCTTGCCAGATGCG ATGTTGTAGCATCTTATCC AGCAACCAGGTCGCATC (SEQ ID NO: 194) | rpsL |
| 37b | GAGCAAATTTACGCGCCTGCGCAATAACAGTCGGGAAA AATTAGTCGGTGTAAGAAAGACGCCGCGTATTCCTGCGT TCCGCTCACGGAACTTAACCGCGAGCAGAAGTGGCAGATG ATGTTGAGTAAGAGTATGCGTCGTTAA (SEQ ID NO: 195) | CGGCGTGCTCAGCCGTAGCTAAGCCGCGA CAAGTGGGAATAAGCGCCGA ACAAAAATACGCGCCAGTGAATTTC (SEQ ID NO: 196) | | TCAGTGGGAAATTGTGGGG CAAGTGGGAATAAGGGGT GAGGCTGGCATG (SEQ ID NO: 197) | pheS^T251A_A294G_HygR |
| 9 (stretch 4) | AGCAGGAAATATTTACCCAGGTTCCTCGCCTGGCTCACGC GGACCATTCCCCTCCCGGGAATAAAAGATGAGCACTTT CTATTCTGCATTGCCGTAAGACTTTTCCCATCACTTCGG GGACAATATTTTTTTATCAAAACGTCGCTTTG (SEQ ID NO: 198) | CGTAACGCGCTAATACAAGCATATAAA CCTGATAATGGGCGGTTGG (SEQ ID NO: 199) | SacB-CmR | AAGGCGTTTACGCCGCATC AGGCCGCCAGCGACCGATTG CCGGATGCGACGTAACC (SEQ ID NO: 200) | rpsL |

FIG. 20K

Table of plasmid backbones used to encode the protospacer sequences required for REXER

| REXER of fragment: | Plasmid backbone | Protospacer sequences targeting the BAC for cleavage | Protospacer sequences targeting the genome for cleavage | |
|---|---|---|---|---|
| | | Sequence 1 (5' -> 3') | Sequence 2 (5' -> 3') Only required in REXER4 | Sequence 3 (5' -> 3') |
| 1 | pKW3_MB1Amp_TracrK_Spacer | CGCGGCTTAGCTACGGCTGA GCACGCCCCT (SEQ ID NO: 201) | CCGTAATATGTTAATCAGG GCTATACCCT (SEQ ID NO: 202) | |
| 2 | pKW3_MB1Amp_TracrK_Spacer | GCGCGCTGGCCGTGACCAAA CTGCCTGCCT (SEQ ID NO: 203) | TATTCAGGGGGTTTGGAAAC AAAGATGCCT (SEQ ID NO: 204) | |
| 3 | pKW3_MB1Amp_TracrK_Spacer | TCAGGCATGGCGCACGGCT GTATTCGCCT (SEQ ID NO: 205) | ATTCAGGAAAAGCGAAATTT AAAAGAGCCT (SEQ ID NO: 206) | |
| 4 | pKW1_MB1Amp_Spacer | GGTTTGGGGTTTATATTCAC ACCCAACCCT (SEQ ID NO: 207) | TTAATATTCTCTGGTTTTTA AGGCGCGCCT (SEQ ID NO: 208) | |
| 5 | pKW1_MB1Amp_Spacer | GCAGTTGCGCGCGCACCTGA CGCACACCCT (SEQ ID NO: 209) | CTTGCCCTCATTCCCAAACC TCAATCGCCT (SEQ ID NO: 210) | |
| 6 | pKW1_MB1Amp_Spacer | GCAAGCAATGGGCAAAAAAT CCCTTGCCCT (SEQ ID NO: 211) | CCACTGACTACGCTTTAAGC CAGAGTCCCT (SEQ ID NO: 212) | |
| 7 | pKW1_MB1Amp_Spacer | GTTAAGCTCATCAGACACAATT TTCAAGCCCT (SEQ ID NO: 213) | TACGGGCGGTTAAGGTGCCT CTTGTGCCCT (SEQ ID NO: 214) | |
| 8 | pKW1_MB1Amp_Spacer | TCATTTACCTGATTAATTGT TCCGCTTCCT (SEQ ID NO: 215) | AGTGCGGGTTTGGTAGGCTG GATAAGGCCT (SEQ ID NO: 216) | |

FIG. 20L

| | | | | |
|---|---|---|---|---|
| 9 | pKW1_MB1Amp_Spacer | CGCAAAAAAATAACCGCCGC CGATAGGCCT (SEQ ID NO: 217) | ACCTGCTTTACGGGTGAAAA AAATCAACCT (SEQ ID NO: 218) | |
| 10 | pKW1_MB1Amp_Spacer | GCTCCCACCACCGCCACCAG GAAGCTGCCT (SEQ ID NO: 219) | AGCCTGCCAGGGGAGAAATC GCAACTGCCT (SEQ ID NO: 220) | |
| 11 | pKW1_MB1Amp_Spacer | ATCAAGACCGCGAATCGGTT TAATGGTCCT (SEQ ID NO: 221) | CAATGTGCAGATCATGTTAT CAGGGTGCCT (SEQ ID NO: 222) | |
| 12 | pKW1_MB1Amp_Spacer | GAGGGGACCATTTCCAAAGC ACTGCACCCT (SEQ ID NO: 223) | CACATCTATCCGGATCTGCG CACTATGCCT (SEQ ID NO: 224) | |
| 13 | pKW1_MB1Amp_Spacer | CCGGATTGCGCGTAATCGTC ACCATCCCCT (SEQ ID NO: 225) | TTCAGCAAGGAGAGCTGTGAAAA ATGTCTCCCT (SEQ ID NO: 226) | |
| 14 | pKW1_MB1Amp_Spacer | GATCGCGATTTTCCTTAGTT AGCGCAGCCT (SEQ ID NO: 227) | TAACCTGCGTCATTTCACCT TTTATTGCCT (SEQ ID NO: 228) | |
| 15 | pKW1_MB1Amp_Spacer | TCATATCAGGTGTTTTCGGC CCGTGAGCCT (SEQ ID NO: 229) | TTTTTATTTCCACCGTGAGG GATTATGCCT (SEQ ID NO: 230) | |
| 16 | pKW1_MB1Amp_Spacer | TTCAACAATAAAAATGAGAG GGAATGCCCT (SEQ ID NO: 231) | CTCATTATCTTAATTGCAAC GGGGTCCCCT (SEQ ID NO: 232) | |
| 17 | pKW1_MB1Amp_Spacer | ATTAAAAATTGCTATTACAG TTTCAGGCCT (SEQ ID NO: 233) | ATTAAAGGATGTGTCAAAGA TGCATACCCT (SEQ ID NO: 234) | |
| 18 | pKW1_MB1Amp_Spacer | ACTCACTGGTCGCTGGCGCA AAGCCAGCCT (SEQ ID NO: 235) | ATCATACGTAAGGTCACTAT GAAACAGCCT (SEQ ID NO: 236) | |
| 19 | pKW1_MB1Amp_Spacer | GATATCATCGACACGCGGTA GCGTGACCCT (SEQ ID NO: 237) | GCTAAATCCTTACTTCCGCA TATTCTCCCT (SEQ ID NO: 238) | |
| 20 | pKW5_MB1Amp_Cas9_Spacer | CGCGTGTTTATCGCGATAGC AATGACCCT (SEQ ID NO: 239) | TAAGTGTATAAACAAGGAAT AGTGATGCCT (SEQ ID NO: 240) | TCCCACATGGAGAAGGTGGGG TTAATTGact (SEQ ID NO: 241) | GAAGCGAAGCCGCATCTGAC AGTCAGAatg (SEQ ID NO: 242) |
| 21 | pKW1_MB1Amp_Spacer | ATATTAATTTTATATTTATT TCGCAGCCT (SEQ ID NO: 243) | ATTTCTCACATTGATGACGG TCGCATGCCT (SEQ ID NO: 244) | |

FIG. 20M

| | | | |
|---|---|---|---|
| 22 | pKW1_MB1Amp_Spa cer | CATTTTCAACATTGTTGCAG CTGGGCAGCCT (SEQ ID NO: 245) | GGATATCTGGGGCATGACAT GGAAGACCCT (SEQ ID NO: 246) |
| 23 | pKW1_MB1Amp_Spa cer | TAACAGCGGCACAACGGGGTT TAACCTGCCT (SEQ ID NO: 247) | AAAACAGTTAAGAGAGCATACT ATAAATCCCT (SEQ ID NO: 248) |
| 24 | pKW1_MB1Amp_Spa cer | TGATTGTAATGCTTAGCCAT TATCTTCCCT (SEQ ID NO: 249) | AACCAGAAACAGAAACCTCT GACAATGCCT (SEQ ID NO: 250) |
| 25 | pKW1_MB1Amp_Spa cer | TCGATGGCATCCATTAACAT TCCGGGTGCCT (SEQ ID NO: 251) | TTTTATAATTACAACGATAA AAGGCTGCCT (SEQ ID NO: 252) |
| 26 | pKW1_MB1Amp_Spa cer | AATATGGCGCTCTTCAGCCG TTAATCCCCT (SEQ ID NO: 253) | GTGGGCAGGTTCTTAGGTGA AATTATGCCT (SEQ ID NO: 254) |
| 27 | pKW1_MB1Amp_Spa cer | TTTATGTTGGTCAACTGGC GTGCCAGCCT (SEQ ID NO: 255) | CCCGCTCATTTTGTCTATTT TTTGCACCCT (SEQ ID NO: 256) |
| 28 | pKW1_MB1Amp_Spa cer | GACGAAACCTAACAGGAAGC ACATCACCCT (SEQ ID NO: 257) | CCTTGTTACCTGATCAGCGT AAACACCCCT (SEQ ID NO: 258) |
| 29 | pKW1_MB1Amp_Spa cer | GTGTTGATCAGCTGACGTGC GGAAGACCCT (SEQ ID NO: 259) | ATTTGTTGAATTTGCACGTT CTTGTAGCCT (SEQ ID NO: 260) |
| 30 | pKW1_MB1Amp_Spa cer | CACGCTGGTGGTGGTGTGCCA GACGCTCCCT (SEQ ID NO: 261) | TTGTTACCACTCCTGTTATT CCTCAACCCT (SEQ ID NO: 262) |
| 31 | pKW1_MB1Amp_Spa cer | GGAGAAAATCCGCCCCAGCA GGTCGTCCCT (SEQ ID NO: 263) | AATTTTTAATGCTTTATTTG CCATTTCCCT (SEQ ID NO: 264) |
| 32 | pKW1_MB1Amp_Spa cer | AAGCTGACGCTTAATGCGGC TCGGCTGCCT (SEQ ID NO: 265) | ACTTATAATAACTGCAACTG TTACATCCCT (SEQ ID NO: 266) |
| 33 | pKW1_MB1Amp_Spa cer | CCTCCCCCTTTTGCCTGCCT CCCTTTGCCT (SEQ ID NO: 267) | TTCGCCCCCCGTCCTGGTCTA CATTTGGCCT (SEQ ID NO: 268) |
| 34 | pKW1_MB1Amp_Spa cer | CTAAGGCCTTTTTATCAGCTC GATATCGCCT (SEQ ID NO: 269) | CGCTCCATTGAGGAAGTCAT TCATATGCCT (SEQ ID NO: 270) |

FIG. 20N

| | | | |
|---|---|---|---|
| 35 | pKW1_MB1Amp_Spacer | ACCCTTTAACAACAGAGCTT TTCGCTGCcct (SEQ ID NO: 271) | CGGGTAAGCCATTACGCTAT CCGACACCCT (SEQ ID NO: 272) |
| 36 | pKW1_MB1Amp_Spacer | CGGTAGAGATGATATCGATC GGCACACCCT (SEQ ID NO: 273) | GAATGTTCTTAAAACATTCA CTTTTGCCCT (SEQ ID NO: 274) |
| 37a | pKW3_MB1Amp_TracrK_Spacer | TGTGCCCAGGCGCAGGTTGAC CATGCTGcct (SEQ ID NO: 275) | CATCTTATCCAGCAACCAGG TCGCATCcct (SEQ ID NO: 276) |
| 37b | pKW1_MB1Amp_Spacer | ATTGCGCAGGCGCGCGTAAA TTTGCTCcct (SEQ ID NO: 277) | GTGGGAATAAGGGGTGAGGC TGGCATGcct (SEQ ID NO: 278) |
| 9 (stretch 4) | pKW1_MB1Amp_Spacer | GAGGAACCTGGGTAAATATT TCCTGCTcct (SEQ ID NO: 279) | GCACCGATTGCCGGATGCGA CGTAACCcct (SEQ ID NO: 280) |

Fig. 21A

A - pKW1_MB1amp_Spacers_REXER2

```
   1 ttcttgaaga cgaaagggcc tcgtgatacg cctattttta taggttaatg tcatgataat
  61 aatggtttct tagacgtcag gtggcacttt tcggggaaat gtgcgcggaa ccctatttg
 121 tttatttttc taaatacatt caaatatgta tccgctcatg agacaataac cctgataaat
 181 gcttcaataa tattgaaaaa ggaagagtat gagtattcaa catttccgtg tcgccttat
 241 tccttttttt gcggcatttt gccttcctgt ttttgctcac cagaaacgc tggtgaaagt
 301 aaaagatgct gaagatcagt tgggtgcacg agtgggttac atcgaactgg atctcaacag
 361 cggtaagatc cttgagagtt ttcgccccga agaacgtttt ccaatgatga gcacttttaa
 421 agttctgcta tgtggcgcgg tattatcccg tgttgacgcc gggcaagagc aactcggtcg
 481 ccgcatacac tattctcaga atgacttggt tgagtactca ccagtcacag aaaagcatct
 541 tacggatggc atgacagtaa gagaattatg cagtgctgcc ataaccatga gtgataacac
 601 tgcggccaac ttacttctga acgatcgg aggaccgaag gagctaaccg cttttttgca
 661 caacatgggg gatcatgtaa ctcgccttga tcgttgggaa ccggagctga tgaagccat
 721 accaaacgac gagcgtgaca ccacgatgcc tgcagcaatg caacaacgt tgcgcaaact
 781 attaactggc gaactactta ctctagcttc ccggcaacaa ttaatagact ggatggaggc
 841 ggataaagtt gcaggaccac ttctgcgctc ggcccttccg gctggctggt ttattgctga
 901 taaatctgga gccggtgagc gtgggtctcg cggtatcatt gcagcactgg ggccagatgg
 961 taagccctcc cgtatcgtag ttatctacac gacggggagt caggcaacta tggatgaacg
1021 aaatagacag atcgctgaga taggtgcctc actgattaag cattggtaac tgtcagacca
1081 agtttactca tatatacttt agattgattt aaaacttcat ttttaattta aaaggatcta
1141 ggtgaagatc cttttgata atctcatgac caaatcct taacgtgagt ttcgttcca
1201 ctgagcgtca gaccccgtag aaaagatcaa aggatcttct tgagatcctt ttttctgcg
1261 cgtaatctgc tgcttgcaaa caaaaaaacc accgctacca gcggtggttt gtttgccgga
1321 tcaagagcta ccaactcttt tccgaaggt aactggcttc agcagagcgc agataccaaa
1381 tactgtcctt ctagtgtagc cgtagttagg ccaccacttc aagaactctg tagcaccgcc
1441 tacatacctc gctctgctaa tcctgttacc agtggctgct gccagtggcg ataagtcgtg
1501 tcttaccggg ttggactcaa gacgatagtt accggataag gcgcagcggt cgggctgaac
1561 ggggggttcg tgcacacagc ccagcttgga gcgaacgacc tacaccgaac tgagatacct
1621 acagcgtgag ctatgagaaa gcgccacgct tcccgaaggg agaaaggcgg acaggtatcc
1681 ggtaagcggc agggtcggaa caggagagcg cacgagggag cttccagggg gaaacgcctg
1741 gtatctttat agtcctgtcg ggtttcgcca cctctgactt gagcgtcgat ttttgtgatg
1801 ctcgtcaggg ggcggagcc tatgaaaaa cgccagcaac gcggcctttt tacggttcct
1861 ggccttttgc tggccttttg ctcacatgtt ctttcctgcg ttatccctg attctgtgga
1921 taaccgtatt accgcctttg agtgagctga taccgctcgc cgcagccgaa cgctaggtc
1981 tagggcggcg gatttgtcct actcaggaga gcgttcaccg acaaacaaca gataaaacga
2041 aaggcccagt ctttcgactg agcctttcgt tttatttgat gcctctagca cgcgtaccat
2101 gggatcctat ttcttaataa ctaaaatat ggtataatac tcttaataaa tgcagtaata
2161 cagggctt tcaagactga agtctagctg agacaaatag tgcgattacg aatttttta
2221 gacaaaaata gtctacgagg ttagagct atgctgtttt gaatggtccc aaaacnnnnn
2281 nnnnnnnnnn nnnnnnnnnn nnnngtttt agagctatgc tgttgaat ggtcccaaaa
2341 cnnnnnnnnn nnnnnnnnnn nnnnnnnnnn ngttagag ctatgctgtt tgaatggtc
2401 ccaaaacttc agcacactga gacttgttga gttgaattcg gtcagtcgt cctgctgatg
2461 tgctcagtat ctctatcact gatagggatg tcaatctcta tcactgatag ggactcgag
```
(SEQ ID NO: 281)

Fig. 21B

B - pKW3 MB1amp Spacers REXER2

```
   1 ttcttgaaga cgaaagggcc tcgtgatacg cctatttttα taggttaatg tcatgataat
  61 aatggtttct tagacgtcag gtggcacttt tcggggaaat gtgcgcggaa ccctatttg
 121 tttatttttc taaatacatt caaatatgta tccgctcatg agacaataac cctgataaat
 181 gcttcaataa tattgaaaaa ggaagagtat gagtattcaa catttccgtg tcgcccttat
 241 tcccttttt gcggcatttt gccttcctgt ttttgctcac cagaaacgc tggtgaaagt
 301 aaaagatgct gaagatcagt tgggtgcacg agtgggttac atcgaactgg atctcaacag
 361 cggtaagatc cttgagagtt ttcgccccga agaacgtttt ccaatgatga gcacttttaa
 421 agttctgcta tgtggcgcgg tattatcccg tgttgacgcc gggcaagagc aactcggtcg
 481 ccgcatacac tattctcaga atgacttggt tgagtactca ccagtcacag aaaagcatct
 541 tacggatggc atgacagtaa gagaattatg cagtgctgcc ataaccatga gtgataacac
 601 tgcggccaac ttacttctga caacgatcgg aggaccgaag gagctaaccg cttttttgca
 661 caacatgggg gatcatgtaa ctcgccttga tcgttgggaa ccggagctga atgaagccat
 721 accaaacgac gagcgtgaca ccacgatgcc tgcagcaatg gcaacaacgt tgcgcaaact
 781 attaactggc gaactactta ctctagcttc ccggcaacaa ttaatagact ggatggaggc
 841 ggataaagtt gcaggaccac ttctgcgctc ggcccttccg gctggctggt ttattgctga
 901 taaatctgga gccggtgagc gtgggtctcg cggtatcatt gcagcactgg ggccagatgg
 961 taagccctcc cgtatcgtag ttatctacac gacgggagt caggcaacta tggatgaacg
1021 aaatagacag atcgctgaga taggtgcctc actgattaag cattggtaac tgtcagacca
1081 agtttactca tatatacttt agattgattt aaaacttcat ttttaattta aaaggatcta
1141 ggtgaagatc ctttttgata atctcatgac caaaatccct taacgtgagt ttcgttcca
1201 ctgagcgtca gaccccgtag aaaagatcaa aggatcttct tgagatcctt ttttctgcg
1261 cgtaatctgc tgcttgcaaa caaaaaaacc accgctacca gcggtggttt gtttgccgga
1321 tcaagagcta ccaactcttt tccgaaggt aactggcttc agcagagcgc agataccaaa
1381 tactgtcctt ctagtgtagc cgtagttagg ccaccactte aagaactctg tagcaccgcc
1441 tacataccctc gctctgctaa tcctgttacc agtggctgct gccagtggcg ataagtcgtg
1501 tcttaccggg ttggactcaa gacgatagtt accggataag cgcagcggt cgggctgaac
1561 gggggggttcg tgcacacagc ccagcttgga gcgaacgacc tacaccgaac tgagatacct
1621 acagcgtgag ctatgagaaa gcgccacgct tcccgaaggg agaaaggcgg acaggtatcc
1681 ggtaagcggc agggtcggaa cagggagagcg cacgagggag cttccagggg gaaacgcctg
1741 gtatctttat agtcctgtcg ggtttcgcca cctctgactt gagcgtcgat ttttgtgatg
1801 ctcgtcaggg gggcggagcc tatggaaaaa cgccagcaac gcggcctttt tacggttcct
1861 ggccttttgc tggccttttg ctcacatgtt ctttcctgcg ttatccctg attctgtgga
1921 taaccgtatt accgctttg agtgagctga taccgctcgc cgcagccgaa cgctaggtc
1981 tagggcggcg gatttgtcct actcaggaga gcgttcaccg acaaacaaca gataaaacga
2041 aaggcccagt ctttcgactg agcctttcgt tttatttgat gcctctagca cgcgtaccat
2101 ggaaaaagtt taaattaaat ccataatgat tgatgatttt caataatagt ttaatgacc
2161 tccgaaatta gtttaatatg ctttaattttt tcttttttcaa aatatctctt caaaaaatat
2221 tacccaatac ttaataataa atagattata acacaaaatt cttttaaaaa gtagtttatt
2281 ttgttatcat tctatagtat taagtattgt tttatggctg ataaatttct ttgaatttct
2341 ccttgattat ttgttataaa agttataaaa taatcttgtt ggaaccattc aaaacagcat
2401 agcaagttaa ataaggcta gtccgttatc aacttgaaaa agtggcaccg agtcggtgct
2461 ttttttgata cttctattct actctgactg caaaccaaaa aaacaagcgc ttcaaaacg
2521 cttgttttat cattttttagg gaaattaatc tcttaatcct ttaggatcc tatttcttaa
2581 taactaaaaa tatggtataa tactcttaat aaatgcagta atacagggcc ttttcaagac
2641 tgaagtctag ctgagacaaa tagtgcgatt acgaaatttt ttagacaaaa atagtctacg
2701 aggttttaga gctatgctgt tttgaatggt cccaaaacnn nnnnnnnnnn nnnnnnnnnn
2761 nnnnnnngt tttagagcta tgctgttttg aatggtccca aaacnnnnnn nnnnnnnnnn
2821 nnnnnnnnnn nnngttttta gagctatgct gttttgaatg gtcccaaaac ttcagcacac
2881 tgagacttgt tgagttgaat tcggtcagtg cgtcctgctg atgtgctcag tatctctatc
2941 actgataggg atgtcaatct ctatcactga tagggactcg ag (SEQ ID NO: 282)
```

Fig. 22A

A - GentamycinR-OriT cassette

```
   1 aattcctgcc gacatggaag ccatcacaaa cggcatgatg aacctgaatc gccagcggca
  61 tcagcacctt gtcgccttgc gtataatatt tgcccatgga cgcacaccgt ggaaacggat
 121 gaaggcacga acccagttga cataagcctg ttcggttcgt aaactgtaat gcaagtagcg
 181 tatgcgctca cgcaactggt ccagaacctt gaccgaacgc agcggtggta acggcgcagt
 241 ggcggttttc atggcttgtt atgactgttt ttttgtacag tctatgcctc gggcatccaa
 301 gcagcaagcg cgttacgccg tgggtcgatg tttgatgtta tggagcagca acgatgttac
 361 gcagcagcaa cgatgttacg cagcaggca gtcgcctaa aacaaagtta ggtggctcaa
 421 gtatgggcat cattcgcaca tgtaggctcg gccctgacca agtcaaatcc atgcgggctg
 481 ctcttgatct tttcggtcgt gagttcggag acgtagccac ctactcccaa catcagccgg
 541 actccgatta cctcgggaac ttgctccgta gtaagacatt catcgcgctt gctgccttcg
 601 accaagaagc ggttgttggc gctctcgcgg cttacgttct gcccaggttt gagcagccgc
 661 gtagtgagat ctatatctat gatctcgcag tctccggcga gcaccggagg cagggcattg
 721 ccaccgcgct catcaatctc ctcaagcatg aggccaacgc gcttggtgct tatgtgatct
 781 acgtgcaagc agattacggt gacgatcccg cagtggctct ctatacaaag ttgggcatac
 841 gggaagaagt gatgcacttt gatatcgacc caagtaccgc cacctaaggc gctcggtctt
 901 gccttgctcg tcggtgatgt acttcaccag ctccgcgaag tgctcttct tgatggagcg
 961 catgggggacg tgcttggcaa tcacgcgcac ccccggccg ttttagcggc taaaaaagtc
1021 atggctctgc cctcgggcgg accacgccca tcatgacctt gccaagctcg tcctgcttct
1081 cttcgatctt cgccagcagg gcgaggatcg tggcatcacc gaaccgcgcc gtgcgcgggt
1141 cgtcggtgag ccagagtttc agcaggccgc ccaggcggcc caggtcgcca ttgatgcggg
1201 ccagctcgcg gacgtgctca tagtccacga cgcccgtgat tttgtagccc tggccgacgg
1261 ccagcaggta ggccgacagg ctcatgccgg ccgccgccga ctttcctca atgctcttc
1321 gttcgtctgg aaggcagtac accttgatag gtgggctgcc cttcctggtt ggcttggttt
1381 catcagccat ccgcttgccc tcatctgtta gccggcggt agccggccag cctgcagag
1441 caggattccc gttgagcacc gccaggtgcg aataagggac agtgaagaag gaacacccgc
1501 tcgcggtgg gcctacttca cctatcctgc ccggctgacg ccgttggata caccaaggaa
1561 agtctacacg aaccctttgg caaaatcctg tatatcgtgc gaaaaggat ggatataccg
1621 aaaaatcgc tataatgacc ccgaagcagg gttatgcagc ggaaaagcgc t (SEQ ID
NO: 283)
```

FIG. 22B - Table of primers for conjugation

| Donor Fragment | Position of oriT | Cassette | Oligo F (5'→3') | Oligo R (5'→3') |
|---|---|---|---|---|
| Fragment 1-3 | 3kb 5' of L00 | Gm-oriT | AAGGCCATCAGTGGATGGAAGAGCAATTAGTCAGTATTTGCAAAC GCTAAaattcctgccgacatggaagccatcac (SEQ ID NO: 284) | CTTGCTTAAGCAATTGGCAGCCAGAGACATAAACACGGGGT AATAAGAATagcgcttttccgctgcataacc (SEQ ID NO: 285) |
| Fragment 4-13 | L03 | Gm-oriT | TGGATCCGTACCGTTAAAACGTAACGCTATTCAGACAATGCTTTT TTAGGaattcctgccgacatggaagccatcac (SEQ ID NO: 286) | TTTTAAATTTCGCTTTTCCTGAATTCAGACAACACGATCCC CTGCCAACTagcgcttttccgctgcataacc (SEQ ID NO: 287) |
| Fragment 10-13 | L09 | rpsL-Hyg-oriT | CCTCCTGCGAAGAGAATAAGATTTTCATAAGGCGGATAGCGATAC AGATGggcctggtgatgatggcgggatcgtt (SEQ ID NO: 288) | TTTTCACCCGTAAAGCAGGTGTCGAGTATACGTTCTGATGT GAAAGCGGAagcgcttttccgctgcataacc (SEQ ID NO: 289) |
| Fragment 14-18 | L13 | Gm-oriT | TTATGCCATGTACCCAGGGAAAATCATCTTCAGTATAGTAATTAT GTAAAaattcctgccgacatggaagccatcac (SEQ ID NO: 290) | TTCACAGCTCCTTGCTGAAAGATAATTTCGTTACCGTACGT ATTGTTCTCagcgcttttccgctgcataacc (SEQ ID NO: 291) |
| Fragment 19-23 | L18 | Gm-oriT | TTTTCTGGTTATCATCAGCTGTAATCTTAATTTCACTGCCGAGAT TGCATAaattcctgccgacatggaagccatcac (SEQ ID NO: 292) | AGTGACCTTACGTATGATGACATCATCAGGTCATTGTGGCG GGATAACGCagcgcttttccgctgcataacc (SEQ ID NO: 293) |
| Fragment 24-28 | L23 | Gm-oriT | TACAATCATTTGGTTAAATTGCTGGTTATAGTGCAGTTAACCAC TATAAaattcctgccgacatggaagccatcac (SEQ ID NO: 294) | TAGTATGCTCTTAACTGTTTTAAGATGCTGATTAAGAAAA CATAAGAGGagcgcttttccgctgcataacc (SEQ ID NO: 295) |

FIG. 22C

| Fragment | | | Oligo R (5'->3') |
|---|---|---|---|
| Fragment 29-32 | L28 | Gm-oriT | CTGCGCGACGAAGAGAATAATCTTCCCTCTACGACGTGTTCCTG AACGCaattcctgccgacatggaagccatcac (SEQ ID NO: 296) | GTTTACGCGTGATCAGTAGTAACAAGGCCGCCAAAAAGCAAAA CGCCCGCAtagcgcttttccgctgcataacc (SEQ ID NO: 297) |
| Fragment 33-36 | L32 | Gm-oriT | GCATAAGGAATGAGACAAAAATTTTTCATTCTTGAATATAAAAACA GATGCaattcctgccgacatggaagccatcac (SEQ ID NO: 298) | AGTTGCAGTTATTATAAGTTCAAGTAAACAGCCTTGTATT AATACCAGAagcgcttttccgctgcataacc (SEQ ID NO: 299) |
| Fragment 37a-13 | L36 | Gm-oriT | CAGACCCGCGAGCATTAATTCTTGCCTCCAGGGCGCGGTAGCCGC TGCGCaattcctgccgacatggaagccatcac (SEQ ID NO: 300) | AGTGAATGTTTTAAGAACATTCCGTAAGCGGCTAATAAGGA AGGGAAAATtagcgcttttccgctgcataacc (SEQ ID NO: 301) |

| Reci- pient Fragment | Position of selection cassette | | Oligo F (5'->3') | Oligo R (5'->3') |
|---|---|---|---|---|
| Fragment 37a-37b | L00 | rpsL-KanR | GGCGTGCTCAGCCGTAGCTAAGCCGCGAACAAAATACGCGCCAG GTGAAttcctaaggcctggtgatgatgcggagcggatcgttgtatat ttcttg (SEQ ID NO: 302) | CATGCCAGCCTCACCCCTTTATTCCCACTTTGCCCACAATT TCCCACTGAtcagaagaactcgtcaagaaggcgatagaagg cgatg (SEQ ID NO: 303) |
| Fragment 37a-3 | L03 | 3kb 3' of pheS-HygR | gcttcccctgttgcgccgaaaggtcaattttatcctttaaacatcagc agtaaAAGCTTGAGCTTGTTGACAATTAATCATCGG (SEQ ID NO: 304) | accttaaccggagaatgccgccgcaaggacgggcattgca gggccagaTTATTCCTTTGCCCTTCGGACGAGTGCTGG (SEQ ID NO: 305) |

FIG. 22D

| Fragment | | Sequence |
|---|---|---|
| Fragment 4-9 | 3kb 3' of L09 phe S- Hyg R | gacacccttctcccagtcggctgctatgactaactatgaccaggtt taccatTTATTCCTTTGCCCTTGCCCTCGGACGAGTGCTGG (SEQ ID NO: 306) gtttatgatgcaaatgttggcgttagcgcaaagagtaag gaattggtgAAGCTTGAGCACGTGTTGACAATTAATCATCG G (SEQ ID NO: 307) |
| Fragment 4-13 | 3kb 3' of L13 phe S- Hyg R | tcagcgtaaatgattgcgcacggtattaactatttacaccagg cataaAAGCTTGAGCACGTGTTGACAATTAATCATCGG (SEQ ID NO: 308) atatatttttagttcggcggggagggtgttcccgccgaaa tattattgcTTATTCCTTTGCCCTCGGACGAGTGCTGG (SEQ ID NO: 309) |
| Fragment 4-18 | 3kb 3' of L18 phe S- Hyg R | gaatccaccagcgttccatcaagatcaaacagaaaaccttgcac cgcacTTATTCCTTTGCCCTCGGACGAGTGCTGG (SEQ ID NO: 310) tttgagcgccaacgaaattaatcaaattatcaatgcctgag gaggcccgcAAGCTTGAGCACGTGTTGACAATTAATCATCG G (SEQ ID NO: 311) |
| Fragment 19-23 | 3kb 3' of L23 phe S- Hyg R | ataaggtgttttacctgggttgttacaaaaggattgcattgcgta aacgcTTATTCCTTTGCCCTCGGACGAGTGCTGG (SEQ ID NO: 312) ctccaatttatcttcgcgtaatacttcccattttgttgt aaataaaaaAAGCTTGAGCACGTGTTGACAATTAATCATCG G (SEQ ID NO: 313) |
| Fragment 4-28 | 3kb 3' of L28 phe S- Hyg R | tttgccagatcggttaagaaatccagcacctgctgcgggttttct gccatCTTATTCCTTTGCCCTCGGACGAGTGCTGG (SEQ ID NO: 314) cgcaactgctgggctttgaaaactacgccttaaatcccctt gccactaaaAAGCTTGAGCACGTGTTGACAATTAATCATCG G (SEQ ID NO: 315) |
| Fragment 4-32 | 3kb 3' of L32 phe S- Hyg R | agcggccatgccatgcccagccccagccgtgttaccgaggccagac ggatcTTATTCCTTTGCCCTCGGACGAGTGCTGG (SEQ ID NO: 316) ccggtagctggacgccgaaggcaaccagatgcacgccgt gataacgccAAGCTTGAGCACGTGTTGACAATTAATCATCG G (SEQ ID NO: 317) |
| Fragment 4-36 | 3kb 3' of L36 phe S- Hyg R | tcttatcaggcctacaagtctgtgccgaaccgtaggccgtatccg gcatgTTATTCCTTTGCCCTCGGACGAGTGCTGG (SEQ ID NO: 318) taaaggtgcgcggggtgagccggttgatatttccggcgctc tatttgtgaAAGCTTGAGCACGTGTTGACAATTAATCATCG G (SEQ ID NO: 319) |

FIG.22E - pJF146

SEQ ID NO: 320 (see sequence listing)

Fig. 23

| Target deletion | Selection cassette | Oligos for amplifying selection cassette for recombination (5' -> 3') | |
|---|---|---|---|
| prfA | rpsL$^{K43R}$-Kan$^R$ | Fwd | ctggagtaacagtacatcattttctttttttacagggtgcatttacgcctatgGGCCTGGTGATGATGGCGGGATCGTTG (SEQ ID NO: 321) |
| | | Rev | gctcgcctgaagttggcttattgcttcacgtaaccagtgttgatattccatcaGAAGAACTCGTCAAGAAGGCG (SEQ ID NO: 322) |
| serU | pheS*-Hyg$^R$ | Fwd | cgtcacttgaacaaaattgcacggacagggactgttaaaatgccaaatttcctggcatcatggcaaccatctgaaAAGCTTGAGCACGTGTTGACAATTAATCATCG (SEQ ID NO: 323) |
| | | Rev | ccttcaagaatattctacgattgttctgtttaggaaaagcaaggcgggaagtcgggagataagtcattgataaagttattcctttgccctcggacgagtgctgg (SEQ ID NO: 324) |
| serT | pheS*-Hyg$^R$ | Fwd | cttttggctgtttttcaggcaaacaaacaaattaggggtttacacgccgcatcgggatgtttatagtgcgcgtcattcAAGCTTGAGCACGTGTTGACAATTAATCATCG (SEQ ID NO: 325) |
| | | Rev | gcaaatataacgccctgagaatttcgacaggcaaaagaaaaaggggttagcatttagctaaccccttatcttatttattcctttgccctcggacgagtgctgg (SEQ ID NO: 326) |

SYNTHETIC GENOME

CROSS-REFERENCE TO RELATED APPLICATIONS

This application is a national phase filing under 35 U.S.C. § 371 of International PCT Application No. PCT/EP2020/063445, filed May 14, 2020, which claims the benefit of priority to United Kingdom Application No. 1906775.0 filed on May 14, 2019, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 21, 2024, is named 51689-008002_Sequence_Listing_11_21_24 ST25 and is 10,587,951 bytes in size.

FIELD OF THE INVENTION

The present invention relates to synthetic genomes and methods of their production.

BACKGROUND TO THE INVENTION

The design and synthesis of genomes provides a powerful approach for understanding and engineering biology. Genome synthesis has the potential to accelerate metabolic engineering. In particular, genome synthesis has the potential to elucidate synonymous codon function and to facilitate genetically encoded unnatural polymer synthesis (Wang, K., et al., 2016. Nature, 539(7627), 59-64).

The standard genetic code encodes the 20 canonical amino acids using 61 sense codons, and eighteen of the twenty amino acids are encoded by more than one synonymous codon. Nature chooses one sense codon, from up to six synonyms, to encode each amino acid at each position in a gene. Synonymous codon choice can influence mRNA folding, transcriptional and translational regulatory sequences, translation rate, co-translational folding, protein levels, and has emerging and yet to be understood roles (Wang, K., et al., 2016. Nature, 539(7627), 59-64; and Cambray, G., et al., 2018. Nature biotechnology, 36(10), 1005-1015).

Genome-wide replacement of a target codon with synonymous codons (synonymous codon compression) may provide a foundation for reassigning sense codons to non-canonical amino acids (or other monomers) to facilitate the in vivo biosynthesis of genetically encoded non-canonical biopolymers (Chin, J. W., 2017. Nature, 550(7674), 53-60).

Site-directed mutagenesis approaches have been used to replace up to 321 amber stop codons in the E. coli genome (Mukai, T., et al., 2015. Scientific reports, 5, p. 9699). However, sense codons are commonly orders of magnitude more abundant than stop codons, and genome synthesis, rather than mutagenesis, may be the preferred route to tackling sense codon removal in many cases.

Genome synthesis has enabled the creation of *Mycoplasma* with synthetic genomes (Gibson, D. G., et al., 2010. Science, 329(5987), 52-56) and the creation of nine strains of *S. cerevisiae* in which the DNA for one or two of the sixteen chromosomes is replaced by synthetic DNA (Zhang, W., et al., 2017. Science, 355(6329), eaaf3981; and Richardson, S. M., et al., 2017. Science, 355(6329), 1040-1044). These experiments have replaced up to 1 Mb of DNA (0.99 Mb, yeast; 1.08 Mb, *Mycoplasma*) in individual strains. Replicon excision for enhanced genome engineering through programmed recombination (REXER) has been reported for replacing >100 kb of the E. coli genome with synthetic DNA in a single step. Moreover, it has been shown that REXER can be iterated via genome stepwise interchange synthesis (GENESIS) to replace 220 kb of the E. coli genome with 230 kb of synthetic DNA (Wang, K., et al., 2016. Nature, 539(7627), 59-64; WO 2018/020248).

Genome synthesis has been used to alter synonymous codons in individual genes (Napolitano, M. G., et al., 2016. PNAS, 113(38), E5588-E5597), genomic regions and essential operons (Wang, K., et al., 2016. Nature, 539(7627), 59-64; and Lau, Y. H., et al. 2017. Nucleic acids research, 45(11), 6971-6980). For instance, Wang et al. used defined 'recoding schemes' to replace a 20 kb region of the E. coli genome rich in both essential genes and target codons.

However, these studies have mutated only a small fraction (up to 4.7%) of targeted sense codons in the genome of a single strain. Consequently, it is not known whether the application of these methods to genome-wide synonymous codon compression will be able to produce viable genomes. For instance, it is not known whether the defined recoding schemes tested in Wang et al. can be applied genome-wide to create an organism in which a reduced number of sense codons are used to encode the 20 canonical amino acids.

Thus, there is a demand for synthetic genomes, wherein one or more sense codon has been removed. There is also a demand for improved methods to produce synthetic genomes.

SUMMARY OF THE INVENTION

The inventors have surprisingly found that a viable synthetic prokaryotic genome may be produced, wherein one or more sense codon has been removed. In particular, they produced a viable synthetic genome in which the number of codons used to encode cellular protein is reduced from 64 to 61, by genome-wide recoding of two sense codons and one stop codon. They also produced an E. coli host cell comprising said synthetic genome.

They inventors have also surprisingly found that defined recoding and refactoring schemes can enable genome-wide synonymous codon compression for more than 99.9% of target codons. They found that alternative recoding and refactoring at non-tolerated positions enabled genome-wide synonymous codon compression.

The inventors have also surprisingly found that recombination-mediated genetic engineering (e.g. REXER and/or GENESIS) may be combined with directed conjugation to efficiently produce synthetic genomes. In particular, they found, for example, that at least about 4 Mb of DNA can be efficiently replaced by said method and that said method allows failures in the design of synthetic DNA (non-tolerated positions) to be identified at codon-level resolution.

Accordingly, in one aspect the present invention provides a synthetic prokaryotic genome comprising 5 or fewer occurrences of one or more sense codons. In some embodiments the synthetic prokaryotic genome comprises 4 or fewer, 3 or fewer, 2 or fewer, 1 or fewer, or no occurrences of one or more sense codons. In some embodiments the one or more sense codons consist of one sense codon or two sense codons, preferably two sense codons. In some embodiments the synthetic prokaryotic genome comprises no occurrences of two or more sense codons, preferably two sense codons, and no occurrences of one stop codon, preferably the amber stop codon (TAG).

The synthetic prokaryotic genome may be a synthetic bacterial genome, preferably a synthetic *Escherichia coli*, *Salmonella enterica*, or *Shigella dysenteriae* genome. In some embodiments the synthetic prokaryotic genome is 100 kb to 10 Mb, or 1 Mb to 10 Mb, or 2 Mb to 6 Mb in size. The synthetic prokaryotic genome may be viable. In some embodiments the synthetic prokaryotic genome comprises 100 or more, 200 or more, or 1000 or more genes, optionally wherein the genes have no occurrences of the one or more sense codons, preferably wherein the genes are essential genes.

In some embodiments the one or more sense codons are selected from TCG, TCA, TCT, TCC, AGT, AGC, GCG, GCA, GCT, GCC, CTG, CTA, CTT, CTC, TTG, and TTA, preferably the one or more sense codons are selected from TCG, TCA, AGT, AGC, GCG, GCA, CTG, CTA, TTG, and TTA, more preferably the one or more sense codons are selected from TCG, TCA, AGT, AGC, TTG, TTA, GCG and GCA, most preferably the one or more sense codons are TCG and/or TCA.

In some embodiments the synthetic prokaryotic genome comprises 10 or fewer, 5 or fewer, or no occurrences of the amber stop codon (TAG).

In a further aspect the present invention provides a synthetic prokaryotic genome comprising 100 or more, 200 or more, or 1000 or more genes, wherein the genes collectively comprise 5 or fewer occurrences of one or more sense codons, preferably wherein the genes are essential genes. In some embodiments the genes collectively comprise 4 or fewer, 3 or fewer, 2 or fewer, 1 or fewer, or no occurrences of one or more sense codons. In some embodiments the one or more sense codons consist of one sense codon or two sense codons, preferably two sense codons.

The synthetic prokaryotic genome may be a synthetic bacterial genome, preferably a synthetic *Escherichia coli*, *Salmonella enterica*, or *Shigella dysenteriae* genome. In some embodiments the synthetic prokaryotic genome is 100 kb to 10 Mb, or 1 Mb to 10 Mb, or 2 Mb to 6 Mb in size. The synthetic prokaryotic genome may be viable.

In some embodiments the one or more sense codons are selected from TCG, TCA, TCT, TCC, AGT, AGC, GCG, GCA, GCT, GCC, CTG, CTA, CTT, CTC, TTG, and TTA, preferably the one or more sense codons are selected from TCG, TCA, AGT, AGC, GCG, GCA, CTG, CTA, TTG, and TTA, more preferably the one or more sense codons are selected from TCG, TCA, AGT, AGC, TTG, TTA, GCG and GCA, most preferably the one or more sense codons are TCG and/or TCA.

In some embodiments the synthetic prokaryotic genome comprises 10 or fewer, 5 or fewer, or no occurrences of the amber stop codon (TAG).

In a further aspect the present invention provides a synthetic prokaryotic genome derived from a parent prokaryotic genome, wherein the synthetic prokaryotic genome comprises less than 10%, 5%, 2%, 1%, 0.5%, 0.1% of the occurrences of one or more sense codons, relative to the parent prokaryotic genome, or wherein the synthetic prokaryotic genome comprises no occurrences of one or more sense codons. In some embodiments the one or more sense codons consist of one sense codon or two sense codons, preferably two sense codons.

The synthetic prokaryotic genome may be a bacterial genome, preferably an *Escherichia coli, Salmonella enterica*, or *Shigella dysenteriae* genome. In some embodiments the synthetic prokaryotic genome is 100 kb to 10 Mb, or 1 Mb to 10 Mb, or 2 Mb to 6 Mb in size. The synthetic prokaryotic genome may be viable.

In some embodiments the one or more sense codons are selected from TCG, TCA, TCT, TCC, AGT, AGC, GCG, GCA, GCT, GCC, CTG, CTA, CTT, CTC, TTG, and TTA, preferably the one or more sense codons are selected from TCG, TCA, AGT, AGC, GCG, GCA, CTG, CTA, TTG, and TTA, more preferably the one or more sense codons are selected from TCG, TCA, AGT, AGC, TTG, TTA, GCG and GCA, most preferably the one or more sense codons are TCG and/or TCA, optionally wherein TCG and/or TCA are replaced with synonymous sense codons.

Preferably 90% or more, 95% or more, 98% or more, 99% or more, 99.5% or more, 99.6% or more, 99.7% or more, 99.8% or more, 99.9% or more, or 100% of the occurrences of the one or more sense codons in the parent prokaryotic genome are replaced with synonymous sense codons. In some embodiments 90% or more, 95% or more, 98% or more, 99% or more, 99.5% or more, 99.6% or more, 99.7% or more, 99.8% or more, 99.9% or more, or 100% of the occurrences of TCG and/or TCA in the parent prokaryotic genome are replaced with AGC and/or AGT, most preferably 90% or more, 95% or more, 98% or more, 99% or more, 99.5% or more, 99.6% or more, 99.7% or more, 99.8% or more, 99.9% or more, or 100% of the occurrences of TCG in the parent prokaryotic genome are replaced with AGC and/or 90%, 95%, 90% or more, 95% or more, 98% or more, 99% or more, 99.5% or more, 99.6% or more, 99.7% or more, 99.8% or more, 99.9% or more, or 100% of the occurrences of TCA in the parent prokaryotic genome are replaced with AGT.

In some embodiments the synthetic prokaryotic genome comprises 10 or fewer, 5 or fewer, or no occurrences of the amber stop codon (TAG), preferably wherein 90% or more, 95% or more, 98% or more, 99% or more, or all of the occurrences of TAG in the parent prokaryotic genome are replaced with TAA.

In some embodiments 99.9% or more, or 100% of the occurrences of two or more sense codons, preferably two sense codons, in the parent prokaryotic genome are replaced with synonymous sense codons, and all of the occurrences of TAG in the parent prokaryotic genome are replaced with TAA.

One or more pairs of genes which share an overlapping region comprising the one or more sense codons in the parent prokaryotic genome may be refactored, preferably wherein the one or more pairs of genes are those in which replacement of one or more of the sense codons with synonymous sense codons would change the encoded protein sequence of both or either of the pair of genes.

In some embodiments for pairs of genes in opposite orientations, a synthetic insert is inserted between the genes, wherein the synthetic insert comprises the overlapping region; and/or for pairs of genes in the same orientation, a synthetic insert is inserted between the genes, wherein the synthetic insert comprises: (i) a stop codon; (ii) about 20-200 bp from upstream of the overlapping region; and (iii) the overlapping region.

In a further aspect the present invention provides a polynucleotide comprising twenty or more, thirty or more, forty or more, fifty or more, 100 or more essential genes with no occurrences of one or more sense codons. In some embodiments the one or more sense codons consist of one sense codon or two sense codons, preferably two sense codons.

In some embodiments the one or more sense codons are selected from TCG, TCA, TCT, TCC, AGT, AGC, GCG, GCA, GCT, GCC, CTG, CTA, CTT, CTC, TTG, and TTA, preferably the one or more sense codons are selected from TCG, TCA, AGT, AGC, GCG, GCA, CTG, CTA, TTG, and TTA, more preferably the one or more sense codons are selected from TCG, TCA, AGT, AGC, TTG, TTA, GCG and GCA, most preferably the one or more sense codons are TCG and/or TCA.

The occurrences of the one or more sense codons in the genes may be replaced with synonymous sense codons, preferably TCG codons are replaced with AGC and/or TCA codons are replaced with AGT.

The essential genes may comprise essential genes selected from one or more of the list consisting of: ribF, IspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, yafF, hemB, secD, secF, ribD, ribE, thiL, dxs, ispA, dnaX, adk, hemH, lpxH, cysS, folD, entD, mrdB, mrdA, nadD, holA, ripB, leuS, Int, glnS, fldA, cydA, infA, cydC, ftsK, lolA, serS, rpsA, msbA, lpxK, kdsB, mukF, mukE, mukB, asnS, fabA, mviN, me, fabD, fabG, acpP, tmk, holB, lolC, lolD, lolE, purB, minE, minD, pth, prsA, ispE, lolB, hemA, prfA, prmC, kdsA, topA, ribA, fabI, tyrS, ribC, ydiL, pheT, pheS, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, mc, lepB, rpoE, pssA, yfiO, rplS, trmD, rpsP, ffh, grpE, csrA, ispF, ispD, ftsB, eno, pyrG, chpR, lgt, fbaA, pgk, yqgD, metK, yqgF, plsC, ygiT, parE, ribB, cca, ygjD, tdcF, yraL, yhbV, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, secY, rplO, rpmD, rpsE, rplR, rplF, rpsH, rpsN, rplE, rplX, rplN, rpsQ, rpmC, rplP, rpsC, rplV, rpsS, rplB, rplW, rplD, rplC, rpsJ, fusA, rpsG, rpsL, trpS, yrfF, asd, rpoH, ftsX, ftsE, ftsY, yhhQ, bcsB, glyQ, gpsA, rfak, kdtA, coaD, rpmB, dfp, dut, gmk, spoT, gyrB, dnaN, dnaA, rpmH, mnpA, yidC, tnaB, glmS, glmU, wzyE, hemD, hemC, yigP, ubiB, ubiD, hemG, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, and dnaC.

In a further aspect the present invention provides a prokaryotic host cell comprising a synthetic prokaryotic genome according to the present invention or a polynucleotide according to the present invention.

The prokaryotic host cell may be viable. The prokaryotic host cell may be a bacterial cell, preferably an *Escherichia coli*, *Salmonella enterica*, or *Shigella dysenteriae* cell. Preferably the host cell is suitable for use in production of polypeptides comprising one or more non-proteinogenic amino acids, preferably two or more non-proteinogenic amino acids, most preferably three or more non-proteinogenic amino acids.

In a further aspect the present invention provides use of a prokaryotic host cell according to the present invention for producing polypeptides comprising one or more non-proteinogenic amino acids, preferably two or more non-proteinogenic amino acids, most preferably three or more non-proteinogenic amino acids.

In a further aspect the present invention provides a method for producing a synthetic genome comprising:
(a) providing a parent genome;
(b) carrying out one or more rounds of recombination-mediated genetic engineering on the parent genome, to produce two or more different partially synthetic genomes; and
(c) carrying out one or more rounds of directed conjugation with the two or more different partially synthetic genomes to produce a synthetic genome;

wherein the partially synthetic genomes each comprise a synthetic region that has 50 or fewer, 20 or fewer, 10 or fewer, 5 or fewer, or 0 occurrences of each of one or more sense codons; or wherein the partially synthetic genomes each comprise a synthetic region that has less than 10%, 5%, 2%, 1%, 0.5%, 0.1% of the occurrences of each of one or more sense codons, relative to the corresponding region in the parent genome.

The synthetic regions may collectively cover 90% or greater, 95% or greater, 99% or greater or 100% of the parent genome. In some embodiments the synthetic regions are 10-1000 kb, 50-1000 kb, 100-1000 kb, or 100-500 kb in size.

The method may further comprise testing the viability of the partially synthetic genomes after each round of recombination-mediated genetic engineering and/or after each round of directed conjugation.

The two or more different partially synthetic genomes may comprise at least one partially synthetic donor genome and at least one partially synthetic recipient genome. In some embodiments the at least one partially synthetic donor genome comprises a synthetic region and a first selectable marker flanked by two homology regions immediately downstream of an origin of transfer; and the at least one partially synthetic recipient genomes comprise a second selectable marker flanked by two corresponding homology regions, optionally wherein the first selectable marker comprises a positive selectable marker, and/or the second selectable marker comprises a negative selectable marker. In some embodiments the synthetic region present in the at least one partially synthetic recipient genomes is outside the region flanked by the homology regions. In some embodiments the method further comprises one or more rounds of selection for the selectable markers.

The one or more rounds of recombination-mediated genetic engineering may comprise one or more rounds of replicon excision for enhanced genome engineering through programmed recombination (REXER).

The synthetic genome may be a synthetic prokaryotic genome according to the present invention.

In a further aspect the present invention provides a synthetic prokaryotic genome produced by the method of the present invention.

DESCRIPTION OF DRAWINGS

FIG. 1A, The defined recoding scheme for synonymous codon compression. Synonymous serine codons and three stop codons used in the genome of WT *E. coli* are shown. Systematically implementing a defined recoding scheme for synonymous codon compression recodes target codons to defined synonyms, and replaces the amber stop codon TAG with the ochre stop codon TAA. This creates an organism with a recoded genome that uses a reduced number of serine and termination codons.

FIG. 1B, Refactoring of 3', 3' overlaps enables their independent recoding. The overlap between two open reading frames (ORF-1 and ORF-2) is duplicated, creating a synthetic insert. This enables independent recoding of ORFs.

FIG. 1C, Refactoring 5', 3' overlaps. The overlap plus 20 bp upstream is duplicated to generate a synthetic insert.

When the overlap is longer than 1 bp at the end of the upstream ORF, an in-frame TAA is introduced in the beginning of the synthetic insert; this in-frame stop codon ensures termination of translation from the original RBS. Thus, all full-length translation of the downstream ORF is initiated from the reconstructed RBS in the synthetic insert.

Figure 1A:
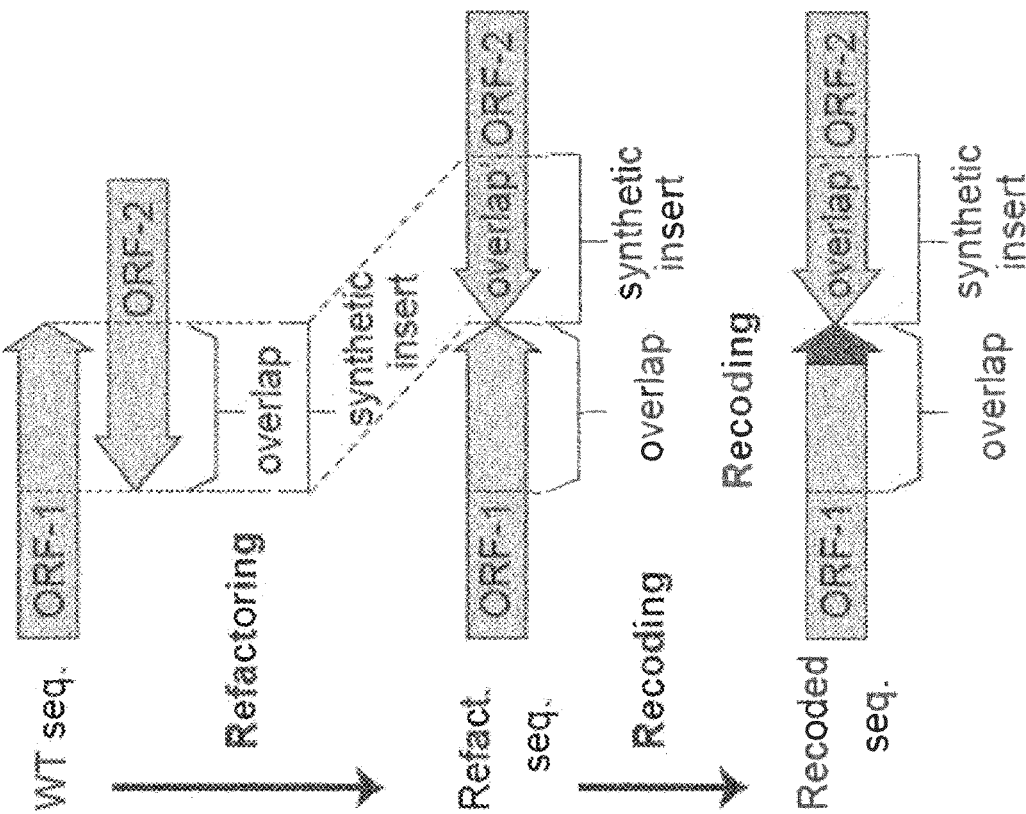
FIGS. 1A-1D—Design of the synthetic genome implementing a defined recoding scheme for synonymous codon compression.
Figure 1B:
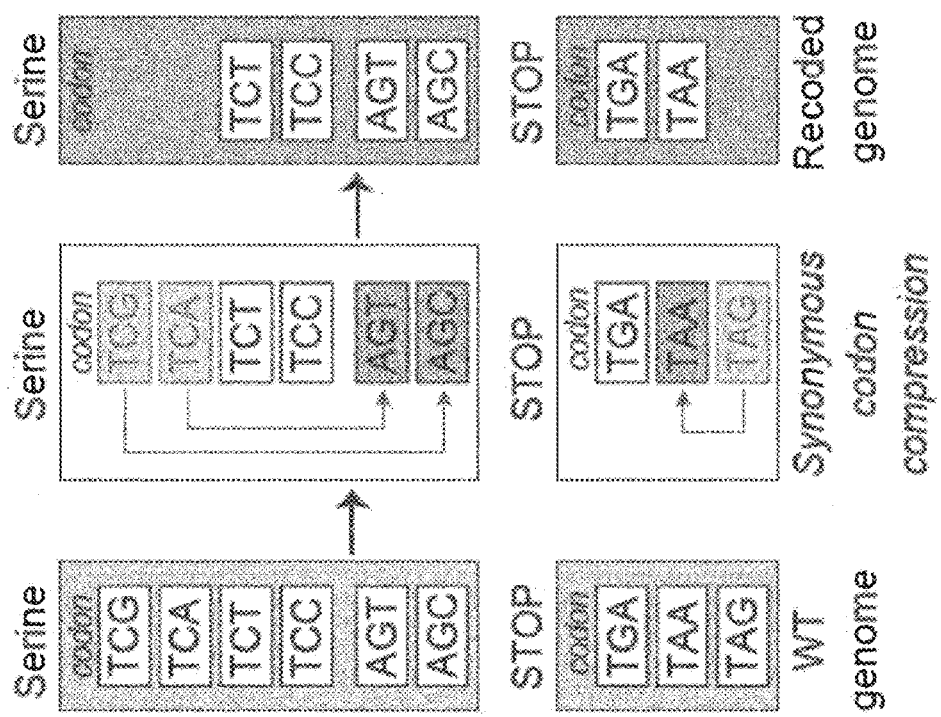
Figure 1C:
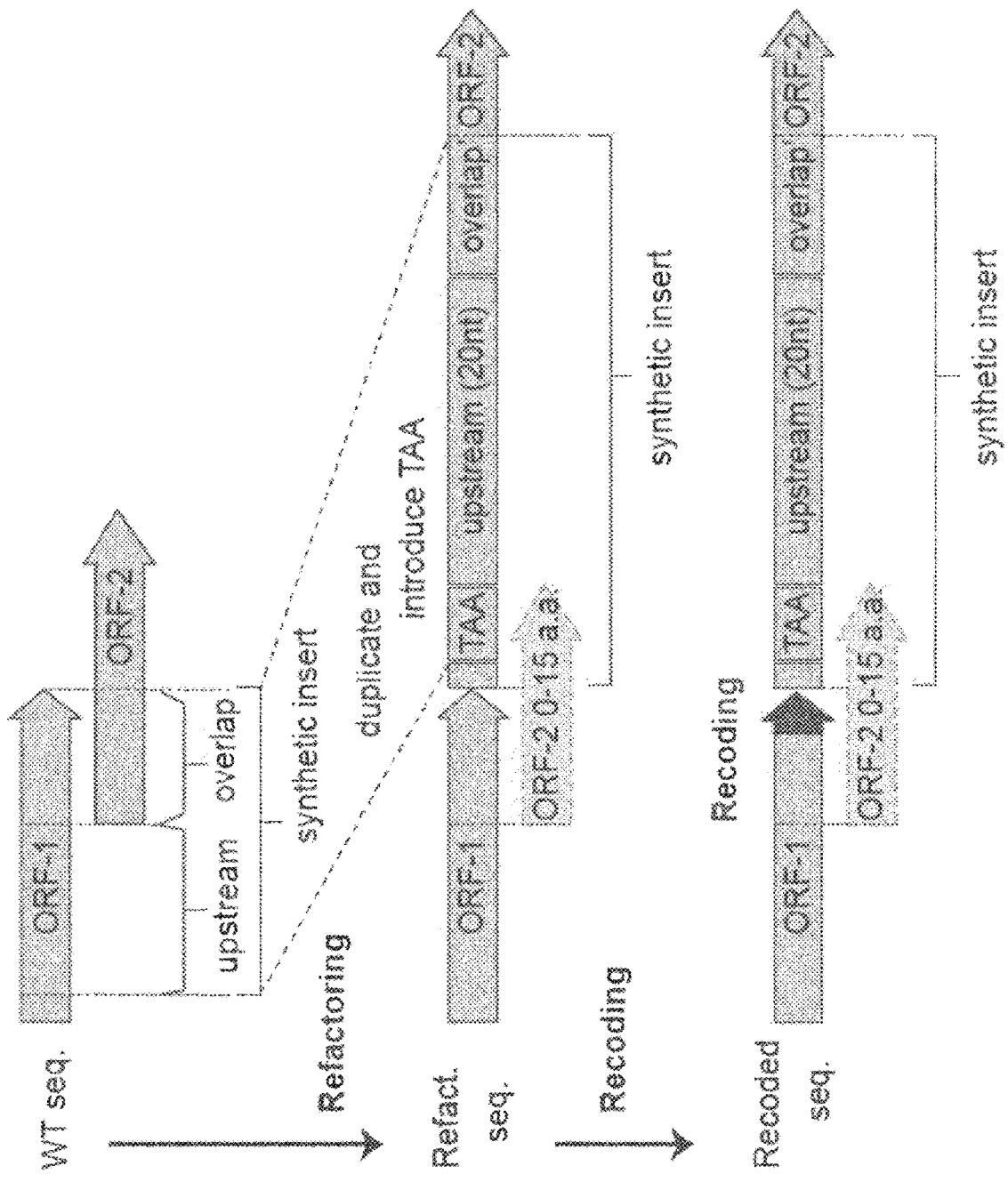
Figure 1D:
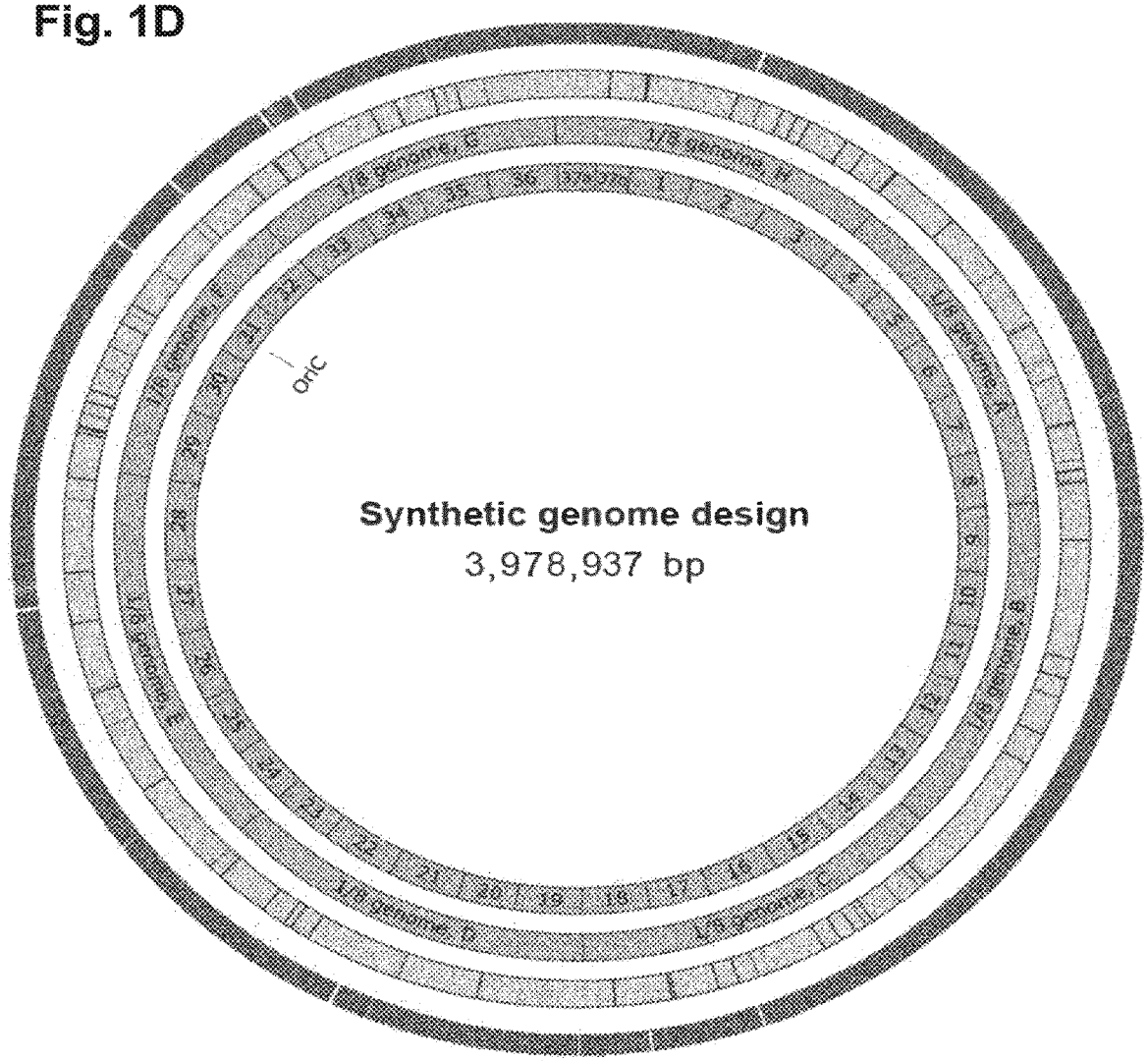

FIG. 1D, Map of the synthetic genome design with all TCG, TCA and TAG codons removed. Outer ring: 18,218 positions of all TCG→AGC, TCA→AGT and TAG→TAA recoding. Grey ring: 12 positions of designed silent mutations in overlaps, 21 refactoring of 3', 3' overlaps (b) and 58 refactoring of 5' 5' overlaps (c). The two inner rings illustrate the genome sections. Outer ring: the eight genome sections (A-H) of the synthetic genome design. Inner ring: 37 fragments of approximately 100 kb each. Fragment 37 is shown as 37a and 37b to reflect the final assembly. oriC: Origin of replication.

Figure 2A:
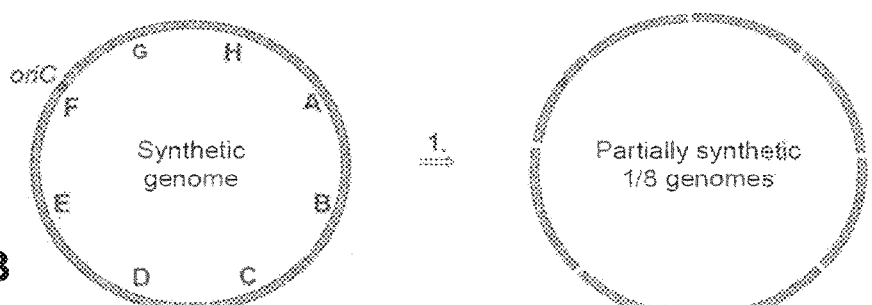
Figure 2B:
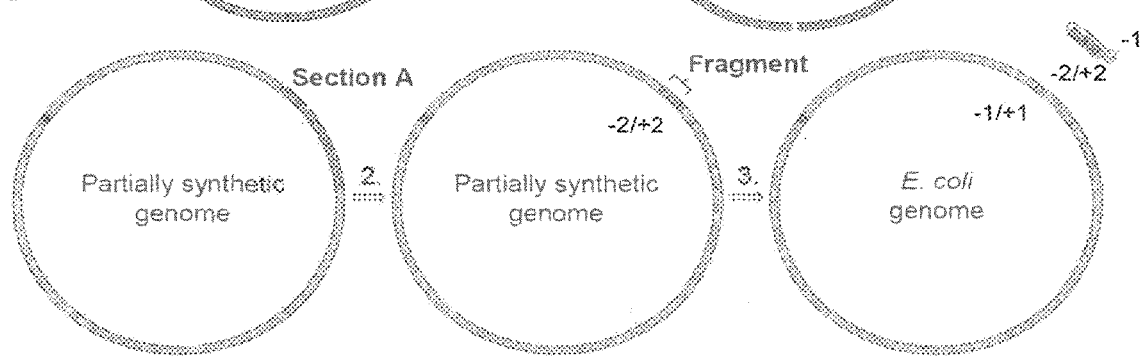
Figure 2C:
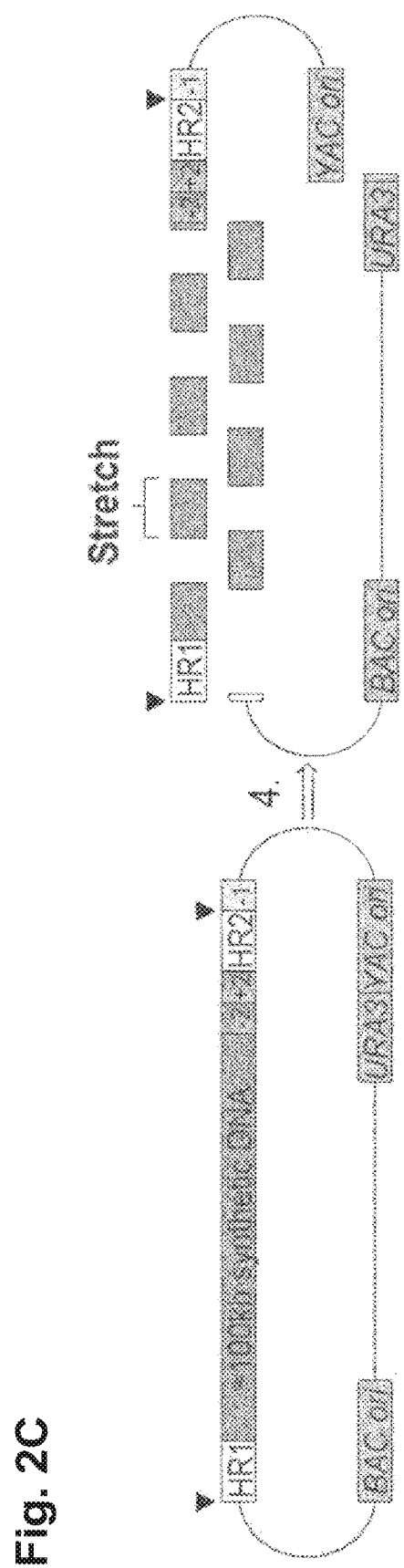

FIGS. 2A-2C—Retrosynthesis of the synthetic genome.

Figure 10:
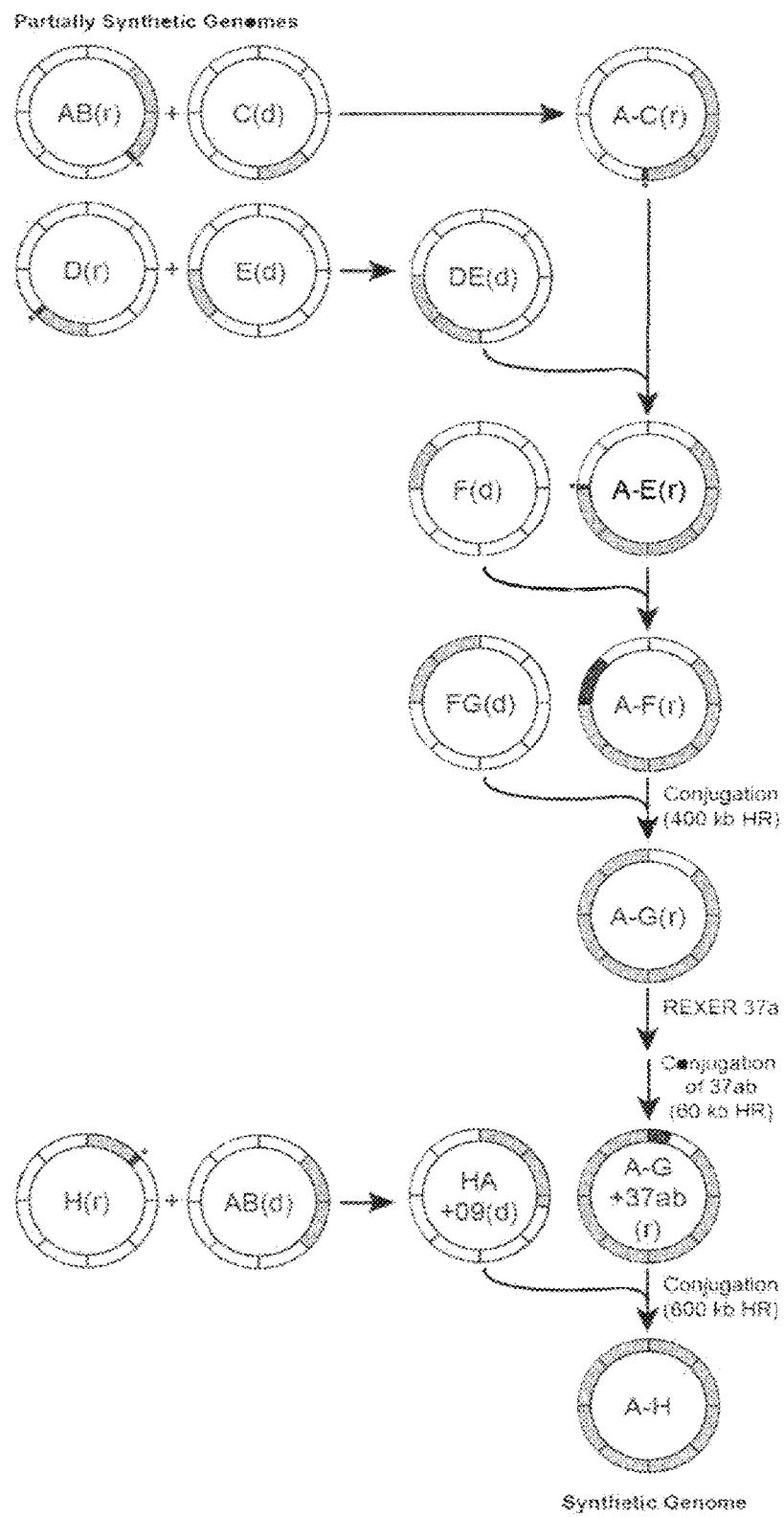
Figure 11A:
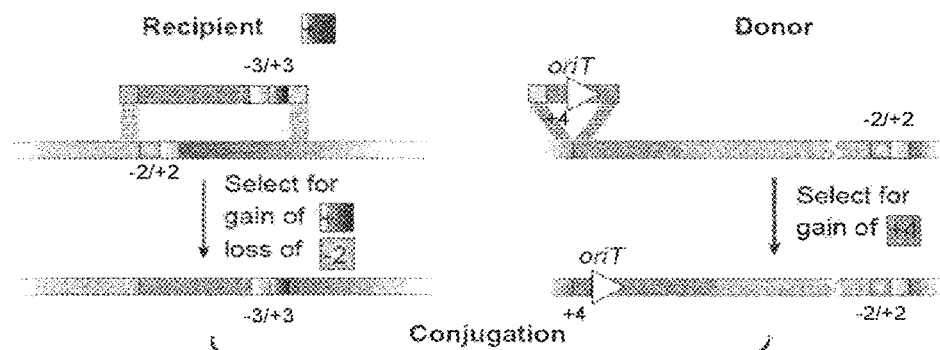
Figure 11B:
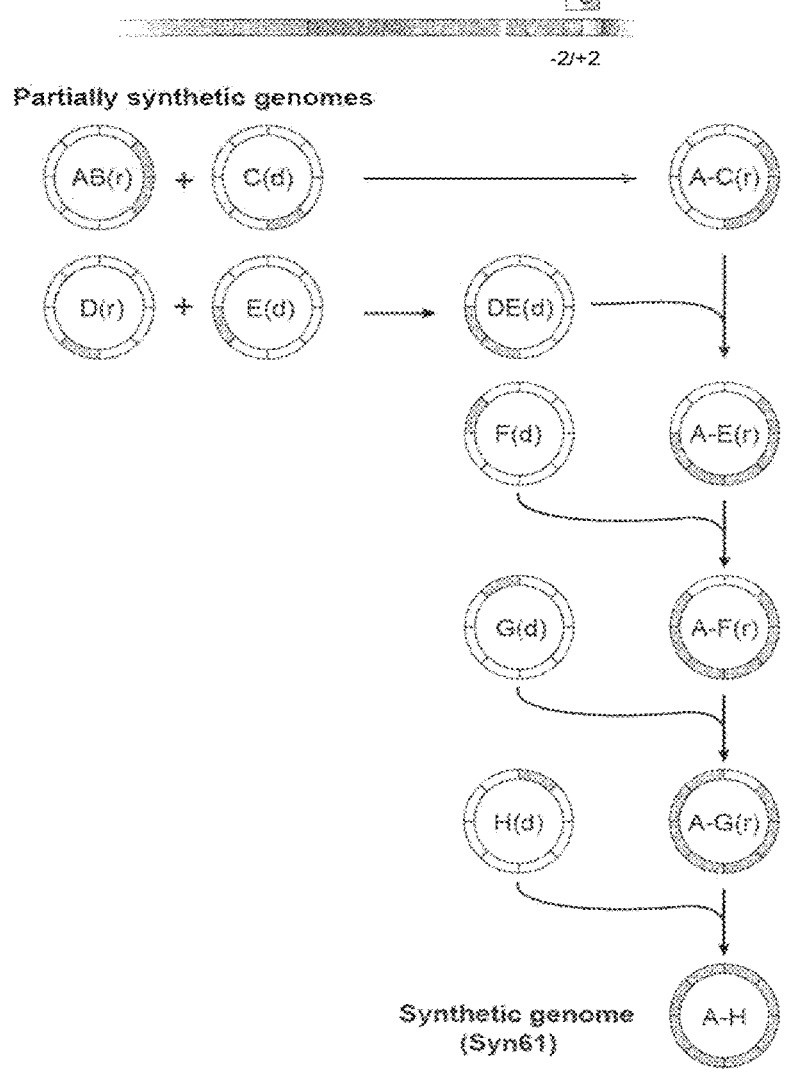

FIG. 2A, Disconnecting the genome into eight sections. The synthetic genome was disconnected into sections A-H, with each section corresponding to approximately 0.5 Mb (step 1). The position of the replication origin oriC (orange square) is indicated. Sections were assembled into a completely recoded genome (in the forward sense, opposite direction of retrosynthesis arrow) by directed conjugation (FIGS. 10 11A, and 11B).

FIG. 2B, Disconnecting genome sections into 100 kb fragments. Sections are further disconnected into four to five fragments of around 100 kb each. Section A is depicted, and other sections were treated similarly. Nearly all sections were constructed entirely through consecutive REXER steps (FIG. 3), by GENESIS (FIG. 4). Each step replaced around 100 kb of wild-type genomic sequence with 100 kb of synthetic fragment (step 2 and 3). Double selection markers composed of negative selection marker−1 (rpsL), and positive selection marker+1 (Kan$^R$), and a negative selection marker−2 (SacB), and positive selection marker +2 (Cm$^R$), were used in alternating rounds of REXER to realize GENESIS.

FIG. 2C, Disconnecting each 100 kb synthetic fragment into 10 kb synthetic stretches. Each 100 kb synthetic fragment is further disconnected into 9 to 14 short synthetic stretches of around 10 kb in length (step 4). The BACs carrying 100 kb synthetic fragments were assembled by homologous recombination in yeast. Each BAC contains Cas9 cleavage sites (black triangles) enabling excision of the synthetic DNA in vivo, homology regions (HR1 and HR2) for targeting recombination, the appropriate double selection cassette (+2, −2 indicated) for selecting during REXER and GENESIS, a negative selection marker (−1 indicated) to enable loss of the backbone following REXER, a BAC YAC origin and URA3 marker for maintenance in E. coli and S. cerevisiae.

Figure 3:
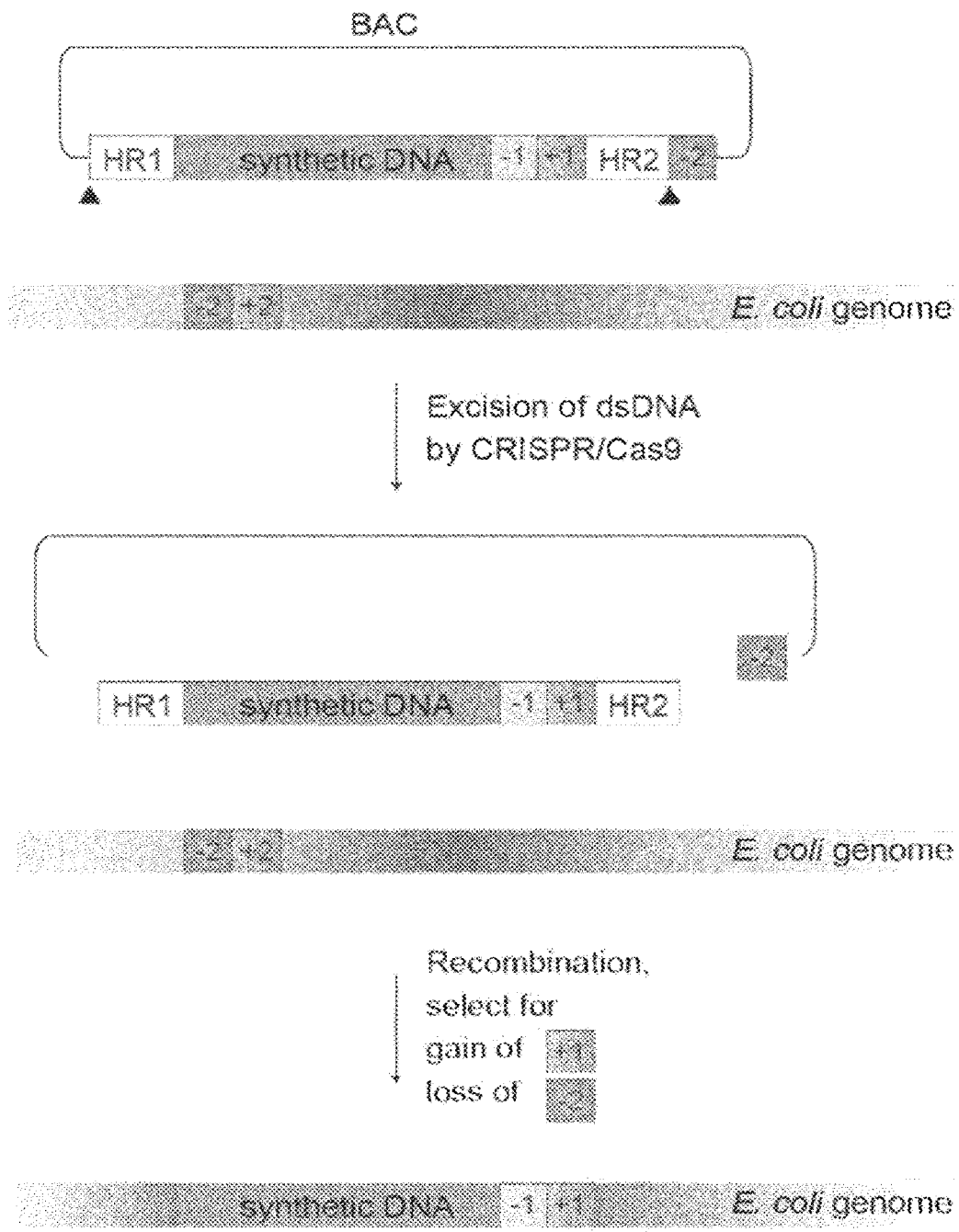
Figure 4:
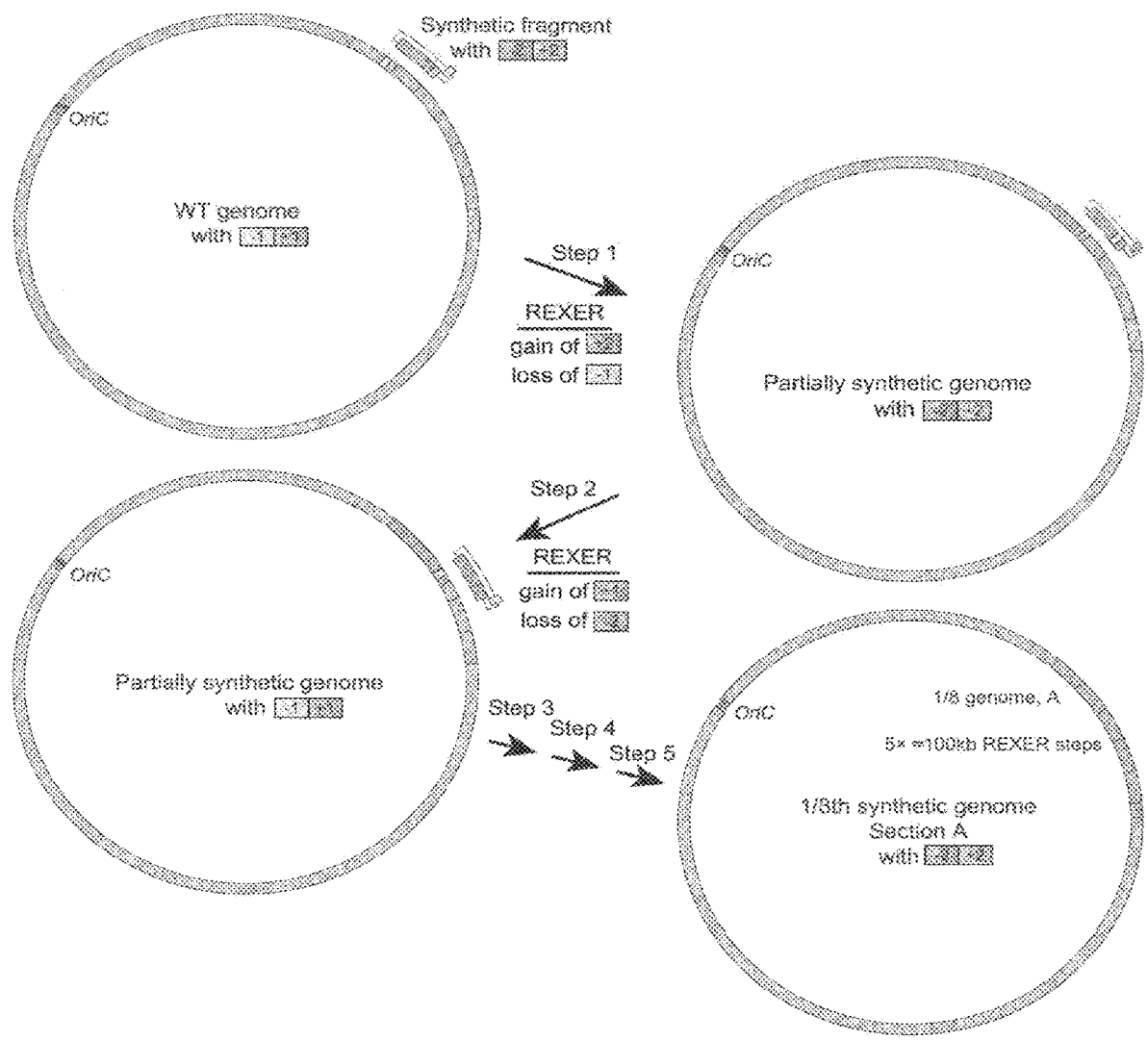

FIG. 3—Using 100 kb fragments of synthetic DNA to replace the corresponding regions in the genome through REXER.

REXER (replicon excision for enhanced genome engineering through programmed recombination) utilizes CRISPR/Cas9 and lambda-red mediated recombination to replace genomic DNA with synthetic DNA provided from an episome (BAC). This enables large regions of the genome (>100 kb) to be replaced by synthetic DNA (Wang, K., et al., 2016. Nature, 539(7627), 59-64; WO 2018/020248). The black triangles denote the location of CRISPR protospacers, which are cleaved by Cas9 to liberate the synthetic DNA (pink) cassette from the BAC flanked by homology regions (HRs). Homology regions 1 and 2 (HR1, HR2) program the location of recombination into the E. coli genome. Selection cassette−1/+1 ensures the integration of the synthetic DNA, while selection cassette−2/+2 on the genome ensures the removal of the corresponding wt DNA. In the example shown in the figure, +1 is Kan$^R$, −1 is rpsL, +2 is Cm$^R$, −2 is sacB.

FIG. 4—GENESIS enables the stepwise replacement of genomic DNA by synthetic DNA to generate recoded sections.

Iterative cycles of REXER (see FIG. 3), with alternating choices of positive and negative selection cassettes, enables genome stepwise interchange synthesis (GENESIS) (Wang, K., et al., 2016. Nature, 539(7627), 59-64). This enables large sections of the synthetic genome to be assembled through the iterative addition of fragments that replace the corresponding genomic sequence, in a clockwise manner. The first REXER of a 100 kb synthetic fragment of DNA leaves a −1/+1 selection cassette on the genome which acts as a landing site for the downstream integration of a second fragment of synthetic DNA harbouring a −2/+2 selection cassette. In the example shown, +1 is Kan$^R$, −1 is rpsL, +2 is Cm$^R$, −2 is sacB, but the same logic can be used with different permutations of markers on the genome and the BAC.

FIGS. 5A-D—Recoding ftsI-murE and map in fragment 1.

Figure 5A:
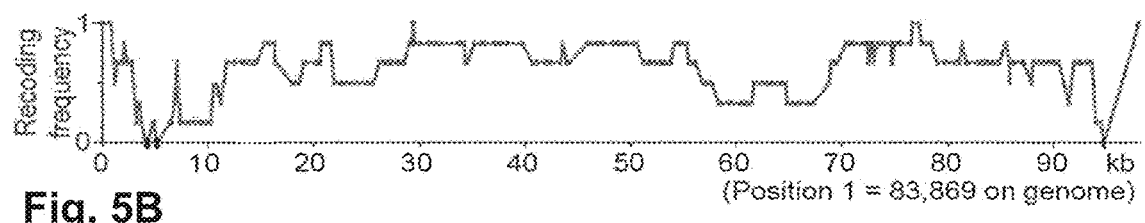

FIG. 5A, Recoding landscape of fragment 1. We sequenced six clones post-REXER. Each dot represents the frequency of recoding within the sequenced clones (y axis) for a target codon at the indicated position in the genome (x axis). Black dots indicate positions where we did not observe recoding. Four codons and a refactoring of ftsI-murE and one codon in map were rejected.

Figure 5B:
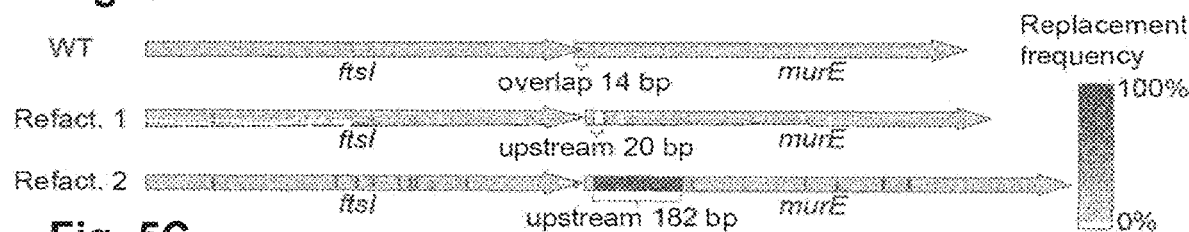

FIG. 5B, Refactoring the 14 bp ftsI-murE overlap. The codons and overlaps are grey scaled by their post-REXER replacement frequency in the clones sequenced. Using our initial refactoring scheme (1), in which the overlap plus 20 bp of upstream sequence was duplicated; we did not observe replacement of the overlap by synthetic DNA (in the six clones sequenced post-REXER). Refactoring scheme 2, which duplicates the overlap plus 182 bp of upstream sequence, resulted in complete recoding of this region in 12 of 16 post-REXER clones sequenced.

Figure 5C:
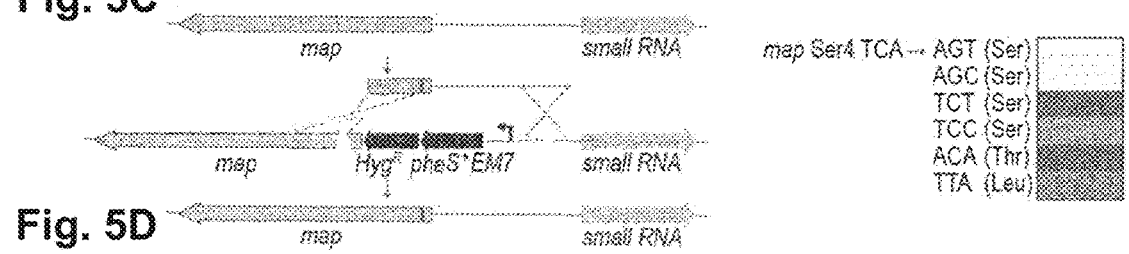

FIG. 5C, Testing alternative codons at Ser4 in map. A double-selection marker, pheS*-Hyg$^R$ on a constitutive EM7 promoter, was introduced upstream of map followed by a RBS. We replaced the cassette using linear double stranded DNA that introduces alternative codons at position four (as indicated), via lambda red recombination and negative selection for loss of pheS*. DNA with AGC and AGT did not integrate (0/16 clones); we recovered one clone for AGC, but sequencing revealed it contained a mutant AAC (Asn) codon. TCT (6/8), TCC (6/16), ACA (6/8), and TTA (4/8) were allowed.

Figure 5D:
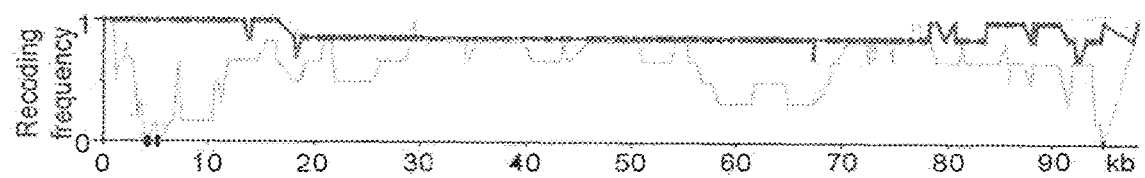

FIG. 5D, Recoding landscape over the genomic region shown in (a) following REXER with a BAC containing Refactoring scheme 2 for the ftsI-murE overlap and TCT at position 4 in map. 2/7 post-REXER clones were completely refactored and recoded, and each target codon was replaced in at least 5/7 clones. The data from (a) is shown for comparison.

FIGS. 6A-D—Recoding rne and yceQ in fragment 9.

FIG. 6A, Recoding landscape of fragment 9. Our designed, synthetic sequence of fragment 9 was integrated into the genome by REXER and 19 clones were completely sequenced by NGS. The recoding landscape graph shows the frequency at which each target codon was recoded across the 19 clones. While most codon replacements were accepted, recoding of a 26 kb region was consistently rejected; codon positions with a recoding frequency of zero in all the sequenced clones are indicated by black dots. To pinpoint the problematic sequence, 10 kb stretches of the genome (G2-7) were deleted in the presence of the episomal copy of synthetic fragment 9. The synthetic sequence was sufficient to support deletion of all stretches except G4 (dark grey box), suggesting that the underlying problem is within this stretch. 0/19 clones were completely recoded.

FIG. 6B, Recoding landscape of stretch G4. Following REXER across the 10 kb stretch 'G4' and sequencing of ten clones the recoding landscape shown was generated. This revealed a clear recoding minima at yceQ, a 'gene' that encodes a predicted protein, for which there is no evidence of transcription, protein synthesis or homologs (Pundir, S., et al., 2017. Methods Mol Biol, 1558, 41-55). All target codons in yceQ were recoded at least once in individual clones, but never simultaneously; thus, the minimum of the recoding landscape does not go to zero, and 0/10 clones were completely recoded. This is consistent with epistasis between the targeted positions. In the map below the recoding landscape, sequences annotated as essential and target codons are shown. The sequence position (x axis) is with reference to panel a.

Figure 6C:
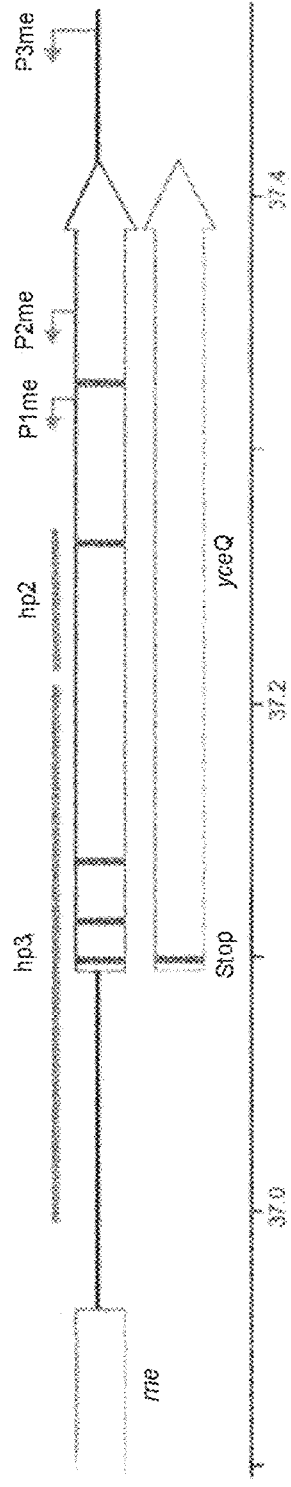

FIG. 6C, Altered design of region surrounding rne in fragment 9. Top, original design of yceQ recoding and rne (encoding RNAse E) regulatory sequences. Target codons are shown. Prne1,2,3, are the promoters for the essential gene rne; these are found in and around the hypothetical gene yceQ. The −10 sequence of the major promoter P1rne is mutated by our initial design. Sequence containing hairpin 1 (hp1) and hairpin 2 (hp2) that bind to RNAse E to mediate transcript degradation are shown; this sequence encompasses the remaining target codons and is also mutated by our initial design. Bottom, the second codon in yceQ was replaced with a stop codon and the remaining target codons retained their original sequence. The sequence position (x axis) is with reference to panel a.

Figure 6D:
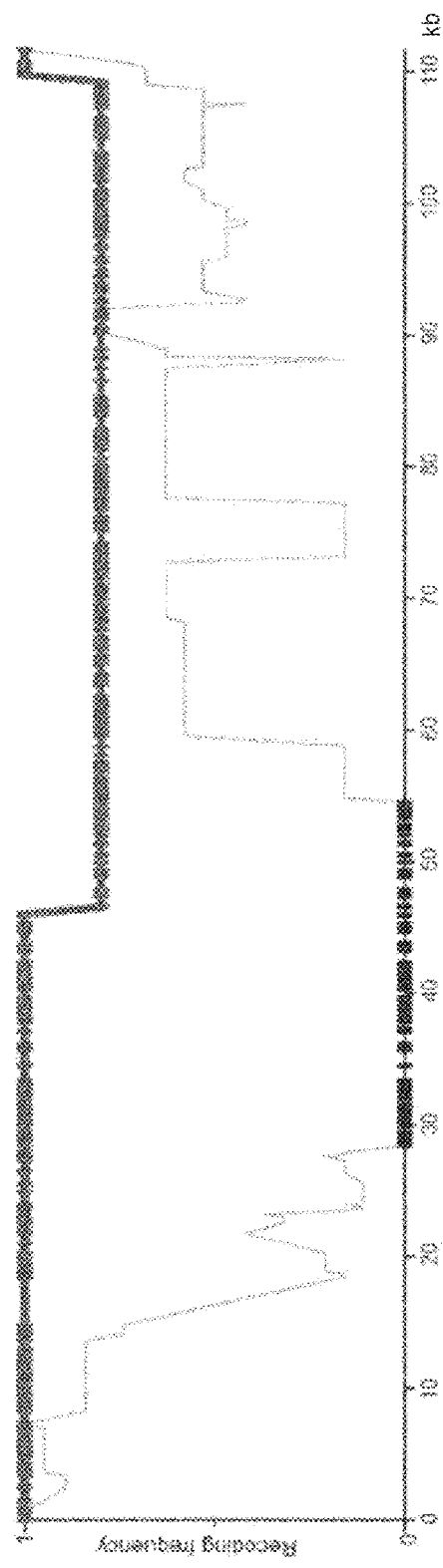

FIG. 6D, This modified fragment 9, from c, was integrated on the genome, resulting in complete recoding in 4/5 clones sequenced. The axes of the graph are the same as in FIG. 6A. The recoding landscape for the modified fragment 9, derived from sequencing 5 clones, is shown in purple. The data from panel a is reproduced for comparison.

FIGS. 7A-7D—Recoding yaaY in fragment 37a.

Figure 7A:
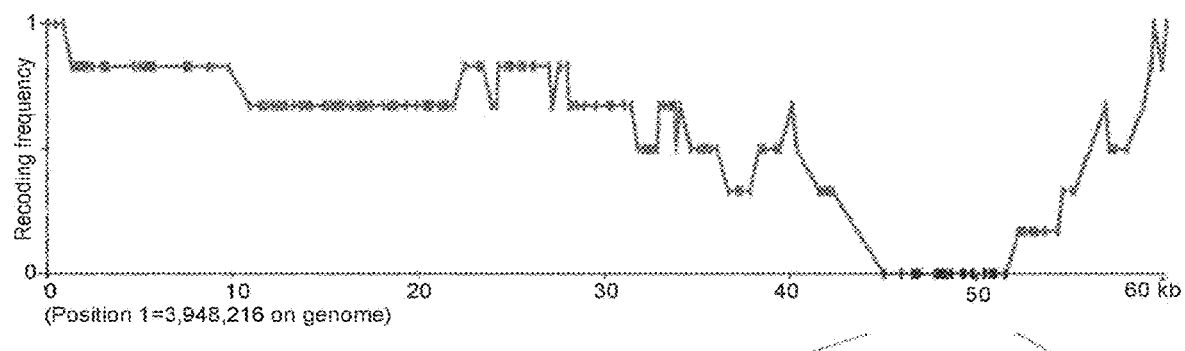
Figure 7A:
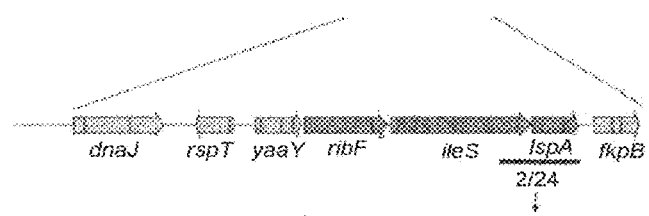

FIG. 7A, Recoding landscape of fragment 37a. Our designed, synthetic sequence of fragment 37a was integrated into the genome by REXER and 6 clones were completely sequenced by NGS. While most codon replacements were accepted, recoding of a 6.5 kb region was consistently rejected. Target codon positions that were never recoded in the six clones sequenced are indicated by black dots.

Figure 7B:
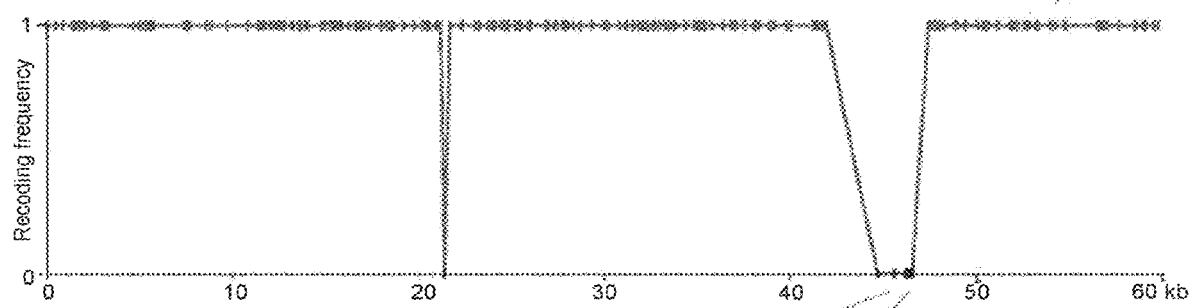
Figure 7B:
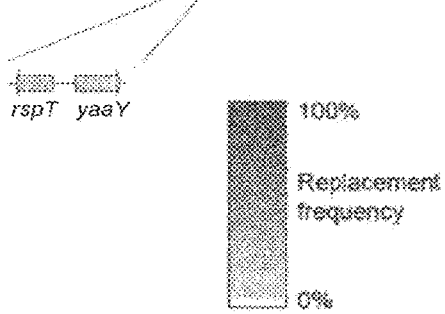

FIG. 7B, Identification of the problematic target codon. Within the identified 6.5 kb problematic region we first focused on codons in essential genes (dark grey arrows) over non-essential genes (light grey arrows). Sanger sequencing (black bar) of 24 clones showed that 2 clones were recoded in all 6 target codons within a sub-section of the essential genes. Further Sanger sequencing of the remaining target codons in essential genes in these two clones revealed that 1 clone was recoded at all 17 target codons. This clone was completely sequenced by NGS and used to generate a recoding landscape, in which each target codon is either recoded or not recoded. This allowed us, in combination with the recoding landscape in (a), to identify a problematic region 1.8 kb upstream of ribF. Here we focused on the 4 target codons in the genes rpsT and yaaY as the nearest codons to the essential ribF gene. Sanger sequencing of 33 clones across this sequence revealed only 1 codon that was never recoded, the codon for Ser70 in the hypothetical gene yaaY (sequencing results are shown as grey scaled on the gene map of rspT and yaaY). We therefore investigated alternative codon replacements in yaaY.

Figure 7C:
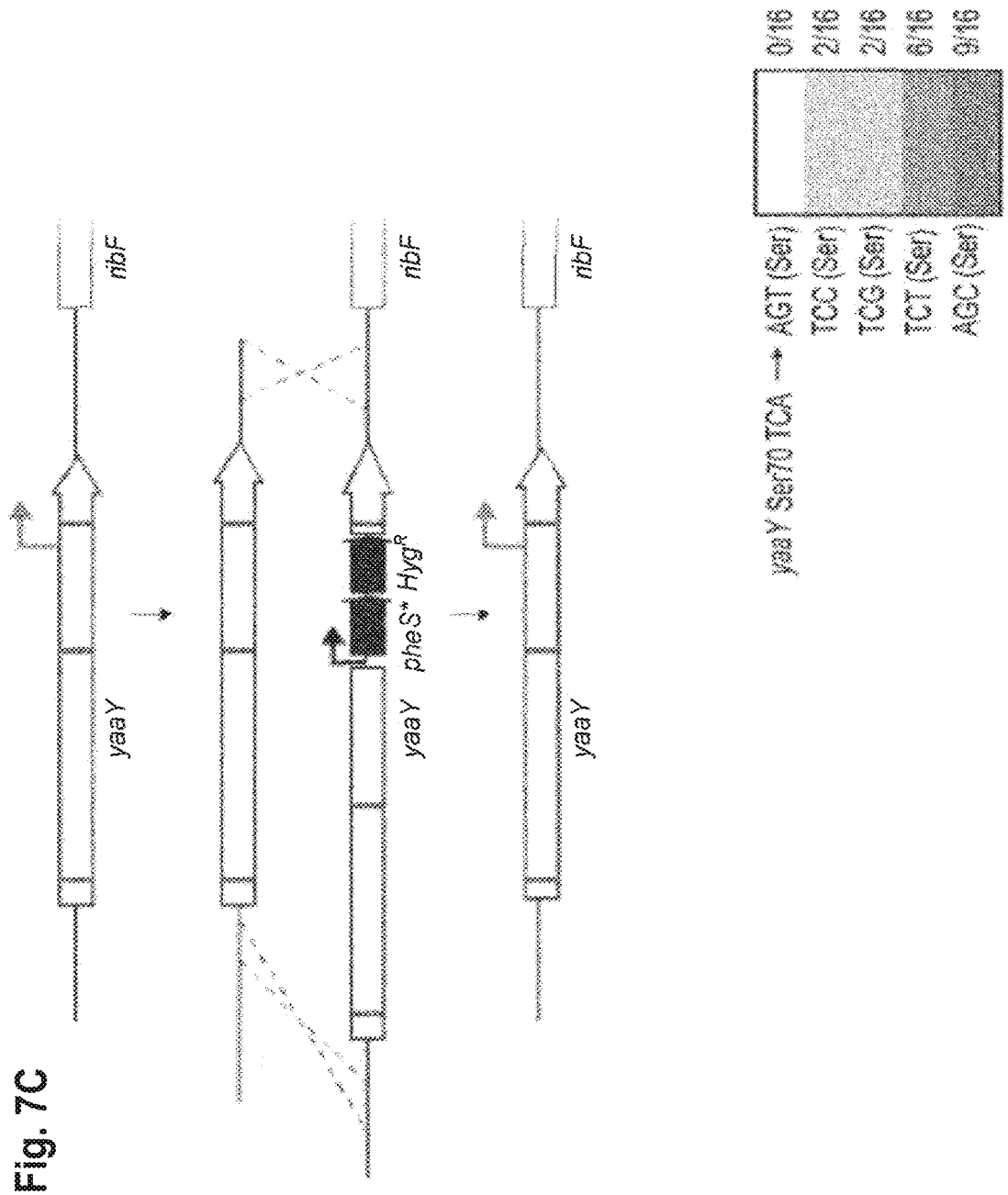

FIG. 7C, Alternative codon replacement in the hypothetical gene yaaY. At position Ser70 in this gene, replacement of TCA with AGT was not successful. To investigate alternative codon replacement schemes, a double-selection marker, pheS*-Hyg$^R$ on a constitutive EM7 promoter followed by a RBS was introduced into yaaY 12 bp upstream of the codon for Ser70. The negative selection marker was then used to select for clones that had replaced the cassette using linear double stranded DNA that introduces alternative codons at position seventy, via lambda red recombination. While linear double stranded DNA with AGT did not integrate (0/16 clones) integration of dsDNA with TCC (2/16), TCG (2/16), TCT (6/16) and AGC (9/16) proved viable.

Figure 7D:
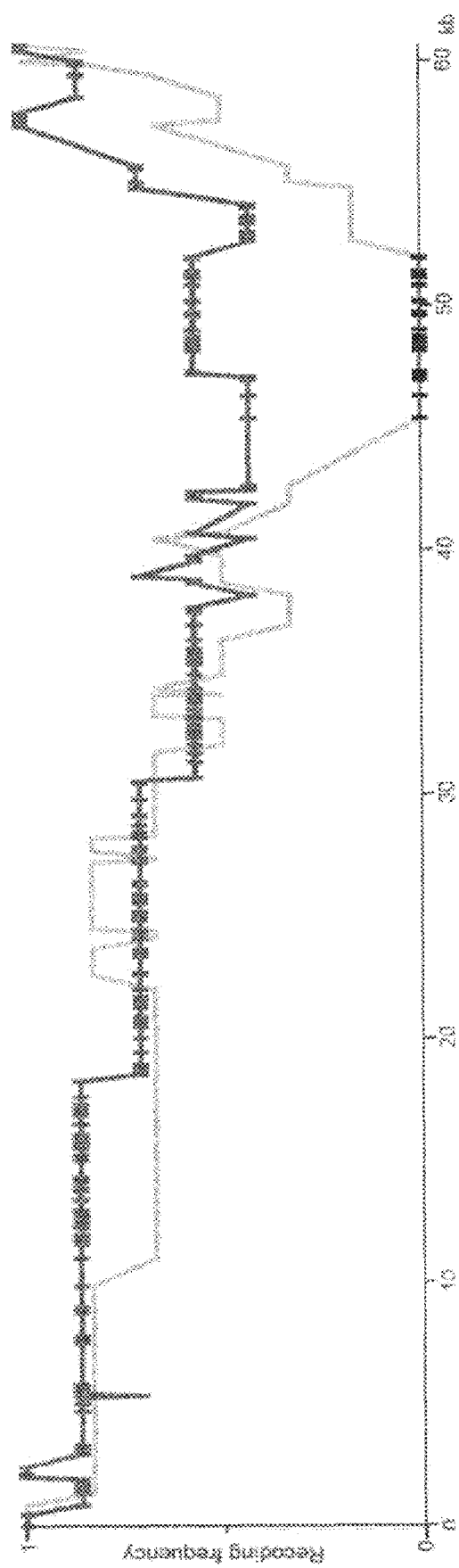

FIG. 7D, Recoding landscape of REXER with a BAC containing a corrected version of fragment 37a, bearing AGC at position Ser70 in the hypothetical gene yaaY. When integrated by REXER, we identified 1/7 completely recoded clones. AGC at position Ser70 in yaaY was introduced in 4/7 clones.

Figures 8A, 8B:
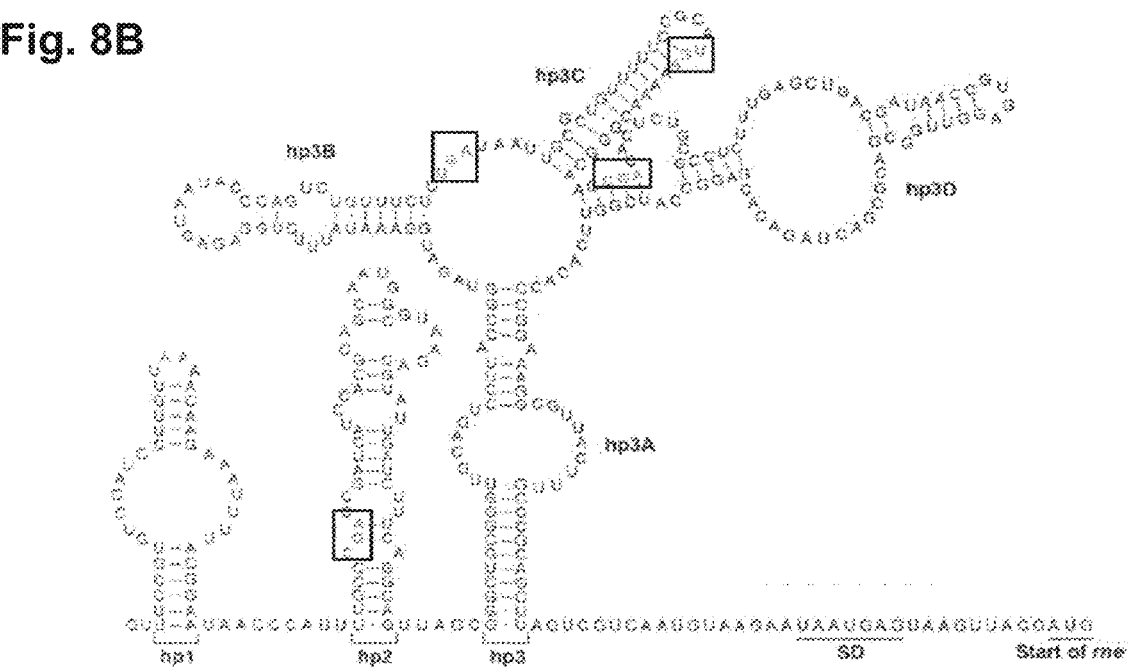

FIGS. 8A and 8B—Substitutions in the hypothetical gene yceQ overlap with regulatory elements in rne that encodes the essential protein RNAse E.

FIG. 8A, In our original design, a programmed substitution of a TCA to AGT in the hypothetical gene yceQ leads to mutation of the −10 promoter element of P1rne, (boxed). The transcriptional start site (tss) of this promoter, for rne transcription, is indicated by an arrow; this is the major promoter for rne transcription.

FIG. 8B, Target codon substitutions overlap with and may potentially disrupt the key regulatory hairpins hp2 and hp3 in the long 5' UTR of the rne transcript. hp2 and hp3 mediate the regulatory feedback loop in which RNAse E is recruited to the mRNA to promote degradation of its own transcript. Shown is a schematic of the wild-type secondary structure of the rne 5' UTR (Diwa, A., et al., 2000 Genes Dev 14, 1249-1260). The target codons for synonymous replacement are highlighted.

Figure 9A:
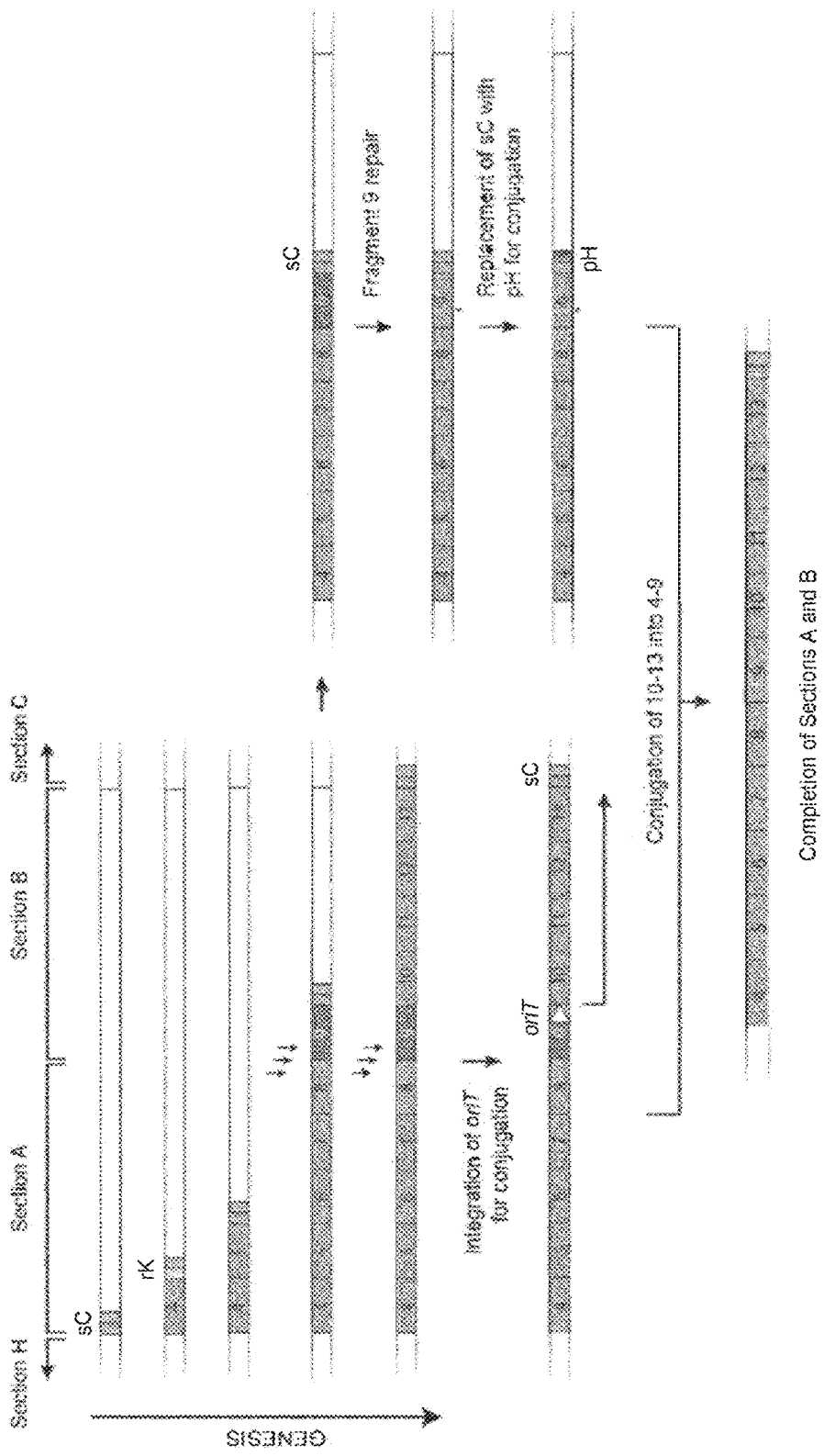
Figure 9B:
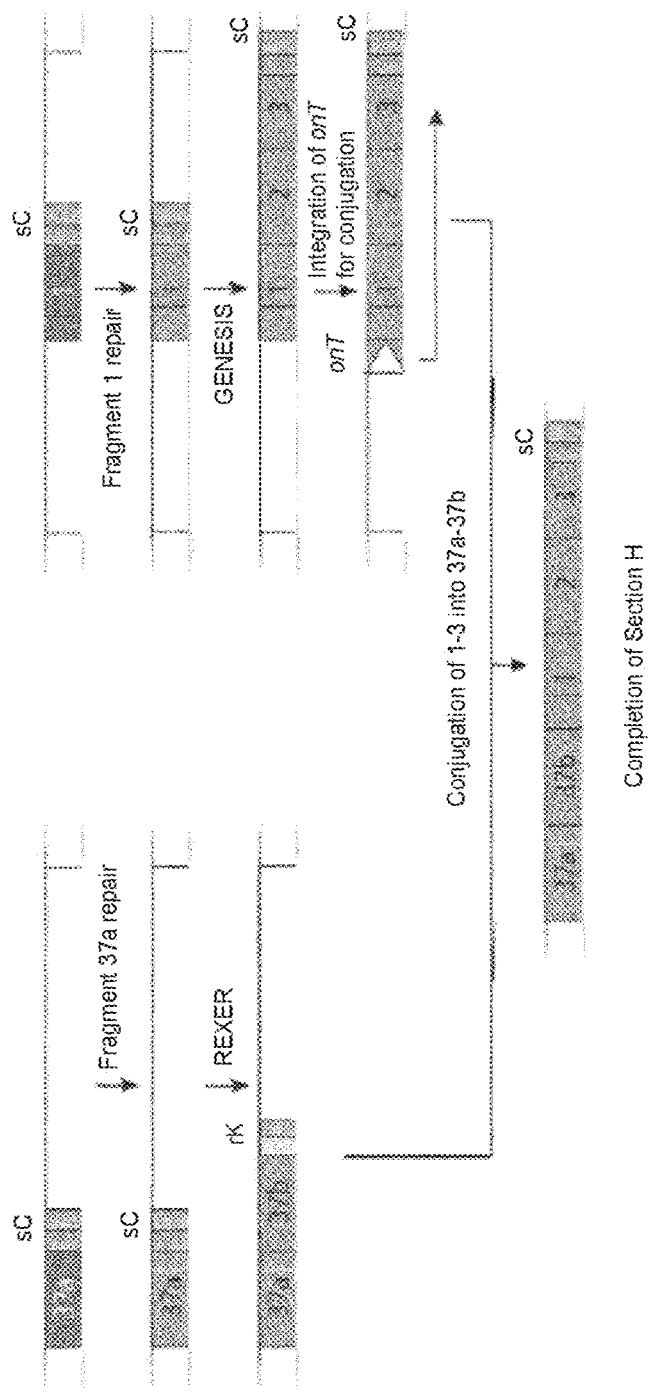

FIGS. 9A and 9B—Completing Sections A-B and H.

FIG. 9A, GENESIS was initiated with fragment 4 and proceeded smoothly until fragment 9, in which we were unable to recode yceQ. Identifying and fixing the problems with our initial design of fragment 9 was carried out as described in FIGS. 6A-6B, by means of introducing a stop codon at the start of the predicted yceQ ORF. Following a swap of the sacB-Cm$^R$ (sC) double selection cassette at the end of fragment 9 for a pheS*-Hyg$^R$ (pH) double selection cassette this strain was ready to act as the recipient for conjugation to assemble a strain in which fragments 4-13 (sections A+B) are fully recoded. In parallel, we continued to recode the strain containing the recoded fragments 4 to incomplete fragment 9 by GENESIS; this generated a second strain for assembly in which fragments 4-8 and 10-13 were completely recoded, and fragment 9 was partially recoded. We then integrated oriT 3 kb upstream of the start of fragment 10 in the second strain to generate a donor for conjugation to assemble a strain in which fragments 4-13 (sections A+B) are fully recoded. Conjugation of the donor and recipient strains resulted in a strain in which sections A and B are fully recoded.

FIG. 9B, Individual REXER of fragments 37a and 1 led to incomplete recoding. We carried out troubleshooting of both independently (FIGS. 5A-5D and 7A-7D). The repairs are indicated. Each strain then served as a starting point for two independent sets of GENESIS—one generated 37a-37b (on the left) and ended with an rpsL-Kan$^R$ (rK) cassette and one generated 1-3 (on the right) and ending in a sacB-Cm$^R$ cassette. We integrated an oriT 3 kb upstream of the start of fragment 1, and this strain served as a donor for the directed conjugation of 1-3 into 37a-37b. The correct product was selected for by the gain of Cm$^R$ and the loss of rpsL. This resulted in the completion of section H in a single strain.

FIG. 10—Assembly of an organism with a fully synthetic genome via conjugation of recoded genome sections.

Synthetic genomic sections from multiple, individual partially-recoded genomes were assembled into a single, fully-recoded genome via conjugation (Ma, N. J., et al., 2014. Nat Protoc 9, 2285-2300). The donor (d) and recipient (r) strains harbour unique recoded genomic sections; recoded overlapping homology regions (3 kb to 400 kb) were utilized to seamlessly recombine the strains. Small homology regions ranging from 3-5 kb are denoted with an asterisk (*). Conjugations for which we used greater than 5 kb homology (HR) are indicated with text. For assembly, the recoded genomic content from the donor was conjugated in a clockwise manner to replace the corresponding wt genomic section in the recipient. The origin of strain AB and H is described in detail in FIGS. 9A and 9B, while all other individual synthetic genomes were generated by GENESIS (FIG. 4). Conjugation followed by recombination proceeded until the final, fully-recoded, A-H strain was assembled and sequence verified by NGS sequencing.

FIGS. 11A and 11B—Assembly of recoded genome sections into a fully-recoded organism.

FIG. 11A, Schematic assembly of partially synthetic donor and recipient genomes into a more synthetic genome, through conjugation. In the recipient cell, the recoded genome section is extended with recoded DNA, commonly 3-4 kb, by a lambda red mediated recombination and positive and negative selection; this step takes advantage of the genomic markers at the end of the recoded sequence that are introduced by GENESIS, and provides a homology region with the end of the recoded fragment in the donor strain. The donor strain is prepared by integration of an origin of transfer (oriT) at the end of the recoded DNA. The indicated positive and negative selections ensure the survival of recipient strains, and select for recipients that have successfully integrated the synthetic DNA from the donor. An F' plasmid containing a mutation in the onT sequence that makes it non-transferrable was used to facilitate conjugation of the donor genome to the recipient. +2, Cm$^R$; -2, SacB; +3, Hyg$^R$; -3, pheS*; +4 Gentamycin$^R$; +5, Tetracycline$^R$.

FIG. 11B, Synthetic genomic sections from multiple, individual partially-recoded genomes were assembled into a single, fully-recoded genome via the indicated sequence of conjugations. The donor (d) and recipient (r) strains harbor unique recoded genomic sections. The recoded genomic content from the donor was conjugated in a clockwise manner to replace the corresponding WT genomic section in the recipient. Conjugation proceeded until the final, fully-recoded A-H strain was assembled. FIG. 10 shows the process in more detail, including all homology regions.

Figure 12A:
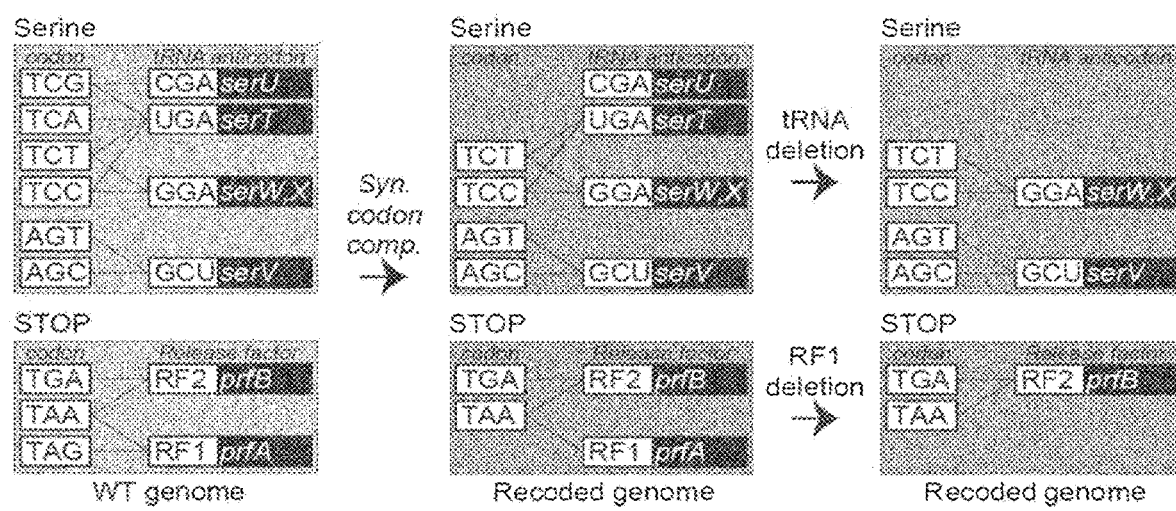
Figure 12B:
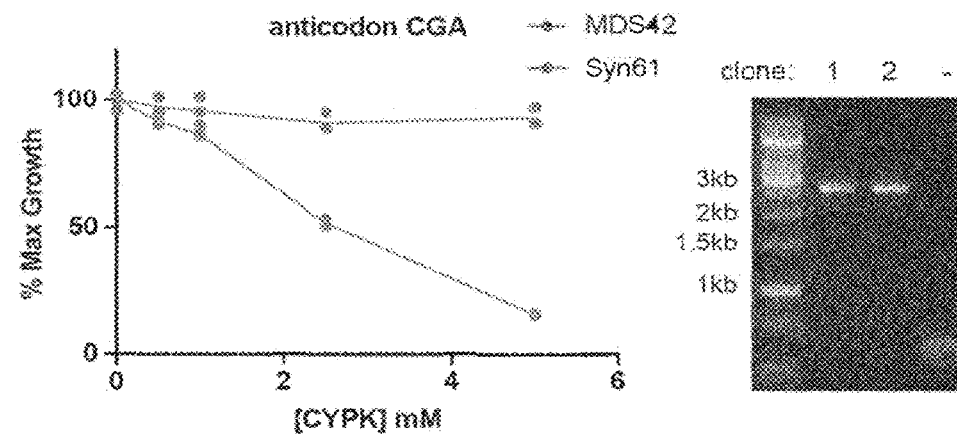
Figure 12C:
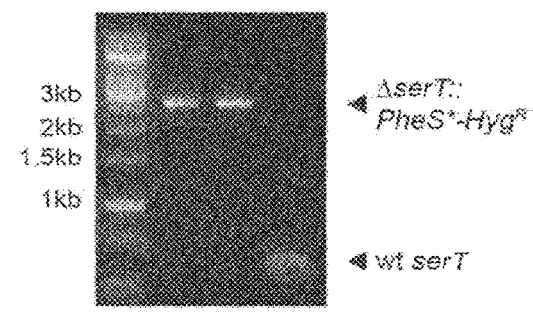

FIGS. 12A-12C—Functional consequences of synonymous codon compression in Syn61.

FIG. 12A, Synonymous codon compression and deletion of prfA, serU and serT. The grey box shows the serine codons and stop codons, together with the tRNAs and release factors that decode them in WT E. coli (WT genome). tRNA anticodons and release factors are connected to the codons they read by black lines. The tRNA and release factor genes are shown in the black boxes. serT is the sole tRNA that decodes TCA codons in WT E. coli, and is absolutely essential. Synonymous codon compression (Syn. Codon. Comp.) leads to a recoded genome in which i) tRNAs with CGA anticodons should have no cognate codons and ii) serT should be dispensable. All factors that read the target codons should be dispensable in Syn61.

FIG. 12B, Co-translational incorporation of the non canonical amino acid (ncAA) Nε-(((2-methylcycloprop-2-en-1-yl) methoxy) carbonyl)-L-lysine (CYPK), using the orthogonal MmPylRS/tRNA$^{Pyl}_{CGA}$ pair, was toxic in MDS42 but not Syn61. When provided with CYPK, this pair will incorporate the ncAA in response to TCG codons in a dose dependent manner. In MDS42 this incorporation leads to mis-synthesis of the proteome and toxicity. However, in Syn61, which does not contain TCG codons, this is non-toxic. The lines follow the mean of three biological replicates (each shown as a dot) at each [CYPK] (0 mM, 0.5 mM, 1 mM, 2.5 mM and 5 mM). "% Max Growth" was determined by the final $OD_{600}$ with the indicated concentration of CYPK divided by the final $OD_{600}$ in the absence of CYPK. Final $OD_{600}$s were determined after 600 min.

FIG. 12C, Synonymous codon compression enables deletion of serT in Syn61. PCR flanking the serT locus before (−) and after (clones 1 and 2) replacement with a PheS*-Hyg$^R$ cassette. Also see FIGS. 14A-14F. Full gels in FIGS. 16A-16C.

FIGS. 13A-13D—Characterization of an organism with a fully synthetic genome.

Figure 13A:
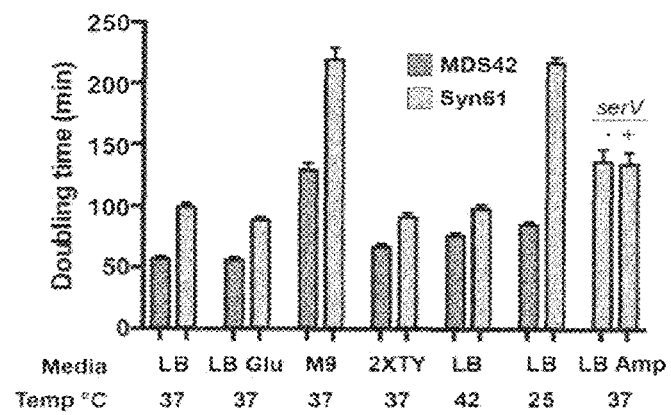

FIG. 13A, Doubling times for Syn61 and MDS42. Our fully synthetic, recoded E. coli Syn61 has a doubling time 1.6 times higher than that of the parent strain MDS42 (Posfai, G. et al., 2006. Science 312, 1044-1046) when grown in standard media conditions (90.1 min vs. 57.6 min in LB+2% glucose). The ratio of growth rates between Syn61 and MDS42 in LB (decreased carbon catabolite repression) at 37° C. is 1.7, in M9 minimal media is 1.7, in richer media (2XTY) is 1.4, in LB at 25° C. is 2.5, and in LB at 42° C. is 1.3. Listed are the doubling times for MDS42 and Syn61, respectively, in different media conditions: LB at 37° C., 58.3 min, and 100.6 min; LB+2% Glucose, 57.6 min, and 90.1 min; M9 minimal media, 130.5 min, and 221.1 min; 2XTY, 68.2 min, 92.6 min; LB at 25° C., 86.3 min, and 218.4 min; LB at 42° C., 77.4 min, and 99.7 min. Syn61 harboring a plasmid without (−) or with (+) serV exhibited a growth rate ratio of 0.99 (138.3 min vs. 136.2 min). Doubling times represent the average of ten independently grown biological replicates of each strain±standard deviation from the mean (see Methods).

Figure 13B:
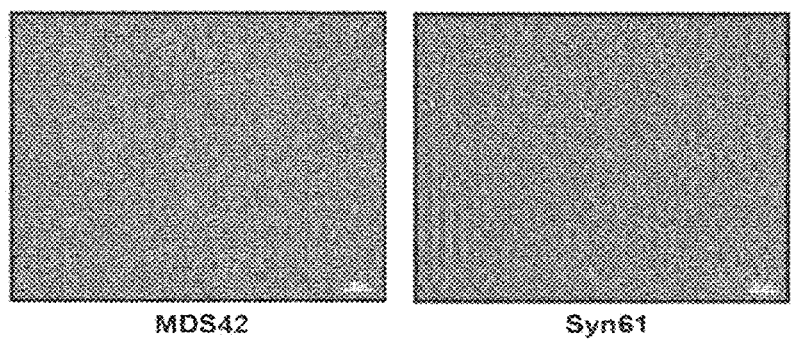

FIG. 13B, Representative microscopy images of E. coli strain MDS42 and Syn61. Samples were imaged on an upright Zeiss Axiophot phase contrast microscope using a 63×1.25NA Plan Neofluar phase objective (see Methods).

Figure 13C:
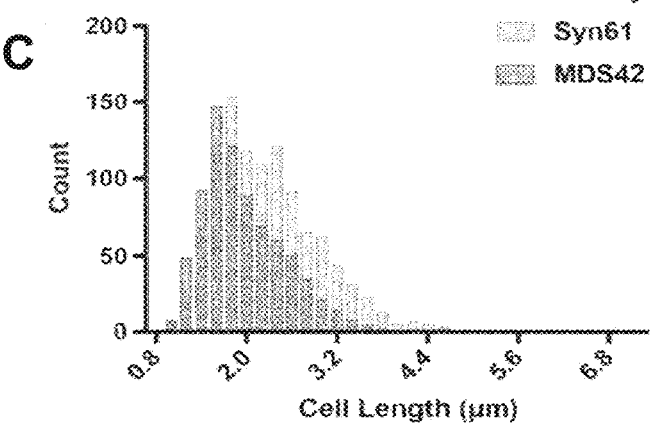

FIG. 13C, Histogram of cell lengths quantified from microscopy images of strains MDS42 and Syn61. The mean cell length for MDS42 was 1.97±0.57 μm and for Syn61 was 2.3±0.74 μm. Images of n=500 cells were taken during exponential growth phase for both strains. Cell length measurements were made with Nikon NIS Elements software (see Methods).

Figure 13D:
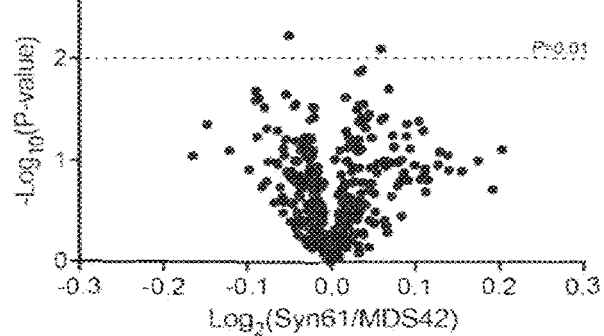

FIG. 13D, Label-free quantification of the MDS42 and Syn61 proteomes. Each strain was grown in three biological replicates. Each biological replicate was analysed by tandem mass spectrometry in technical duplicate. Technical duplicates of biological replicates were merged. A total of 1,084 proteins were quantified across the samples. P-values for abundance differences were calculated by two-sample T-test for the proteins quantified in at least two biological replicates. The data showed that the abundance of three proteins was significantly (P=0.01) different between the strains: Aminopeptidase N (P04825) and peptidase T (P29745) were overrepresented in Syn61, while 30S ribosomal protein S20 (P0A7U7) was underrepresented. No protein differed in abundance, as judged by LFQ values, by more than 1.14 fold between strains.

FIGS. 14A-14F—Consequences of synonymous codon compression in Syn61.

Figure 14A:
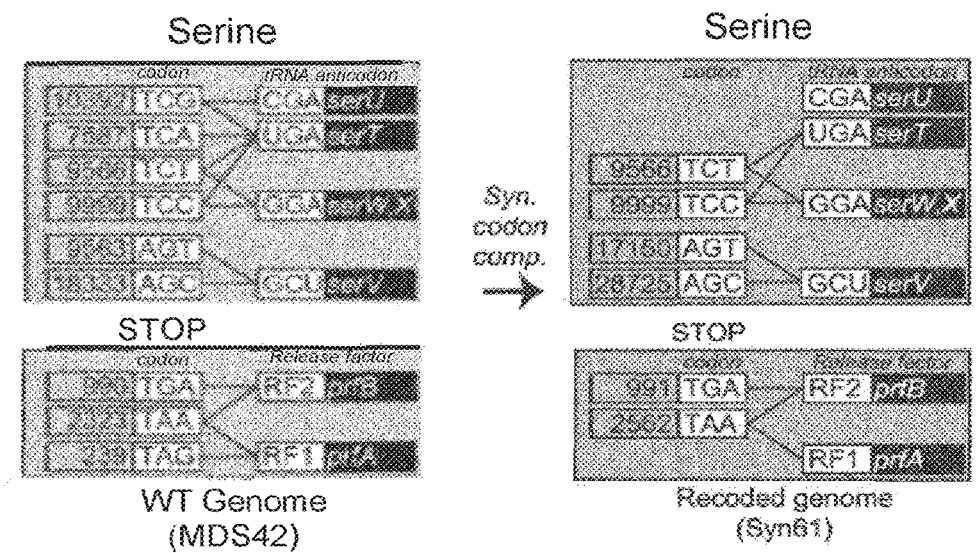

FIG. 14A, Synonymous codon compression and deletion of prfA, serU and serT in E. coli. The grey box shows the E. coli serine codons and stop codons, together with the tRNAs and release factors that decode them in WT E. coli (WT genome). tRNA anticodons and release factors are connected to the codons they read by black lines. The tRNA and release factor genes are shown in the black boxes. Synonymous codon compression (Syn. Codon. Comp.) leads to Syn61 cells with a recoded genome in which TCG and TCA codons are removed. The abundance of each codon is listed in its box.

Figure 14B:
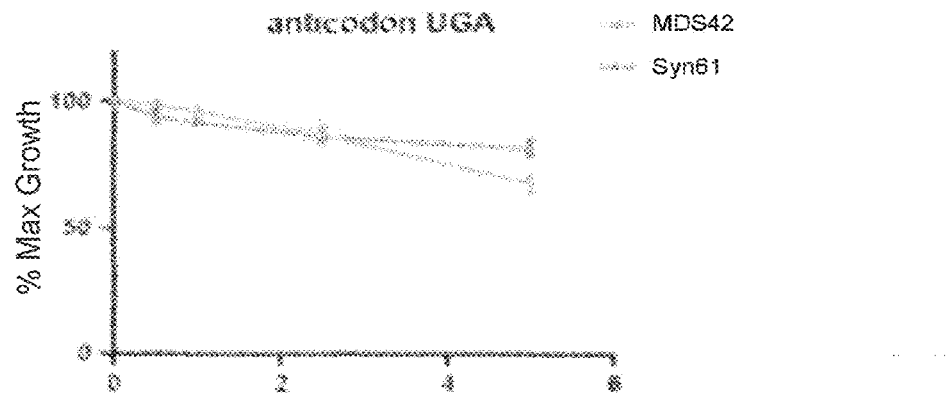

FIG. 14B, As in FIG. 12B, but with the indicated MmPylRS/tRNA$^{Pyl}$ anticodon, UGA. There are less cognate codons to this tRNA in Syn61 than in MDS42, therefore CYPK addition might be expected to be less toxic in Syn61, as observed.

Figure 14C:
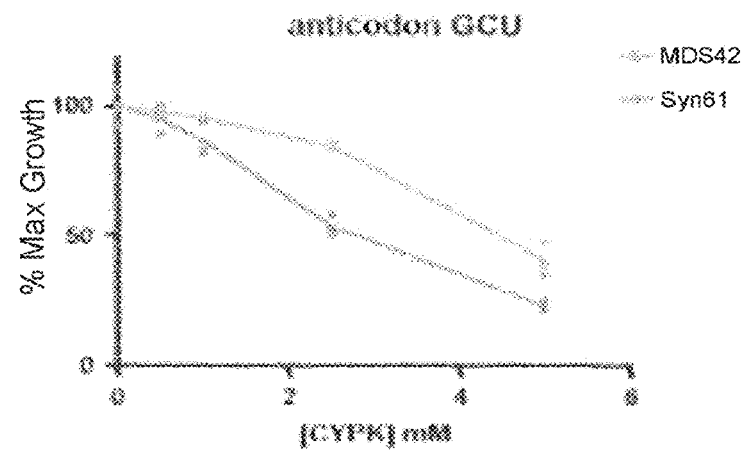

FIG. 14C, As in FIG. 12B, but with the indicated MmPylRS/tRNA$^{Pyl}$ anticodon, GCU. There are more cognate codons to this tRNA in Syn61 than in MDS42, therefore CYPK addition might be expected to be more toxic in Syn61, as observed.

Figure 14D:
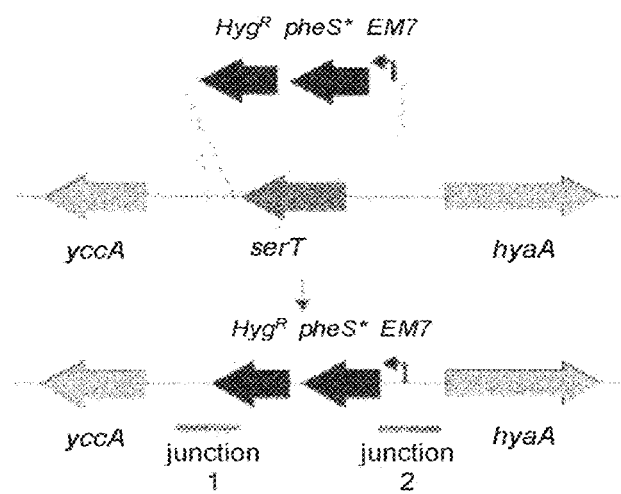

FIG. 14D, serT (dark grey) is deleted by insertion of a PheS*-Hyg$^R$ cassette (black) via lambda-red mediated recombination. Recombination yields new junctions 1 and 2, as indicated. For each recombination, both junctions were sequence-verified by Sanger sequencing. Above the Sanger chromatograms, the arrows indicate the precise location of the junction, the sequence corresponding to the selection cassette and the bar corresponds to the genomic sequence flanking the selection cassette. The primers used to generate selection cassettes with suitable homologies to serU, serT and prfA for recombination are provided in FIG. 23.

Figure 14E:
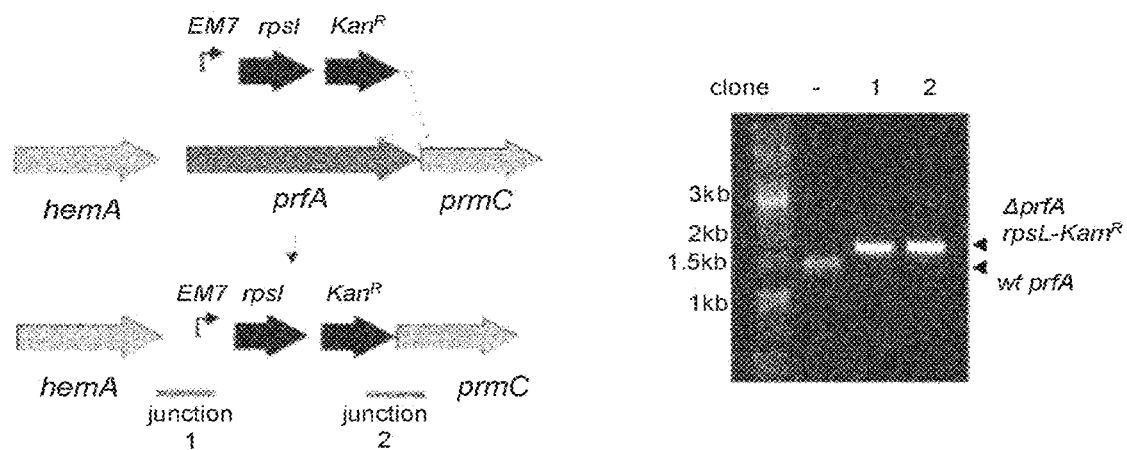

FIG. 14E, prfA (dark grey) is deleted by insertion of an rpsL-Kan$^R$ (in black) via lambda-red mediated homologous recombination. The agarose gels are annotated as described in FIG. 12C and the rest of the data is annotated as described in the description of FIG. 14D. Full gel available in FIG. 16A.

Figure 14F:
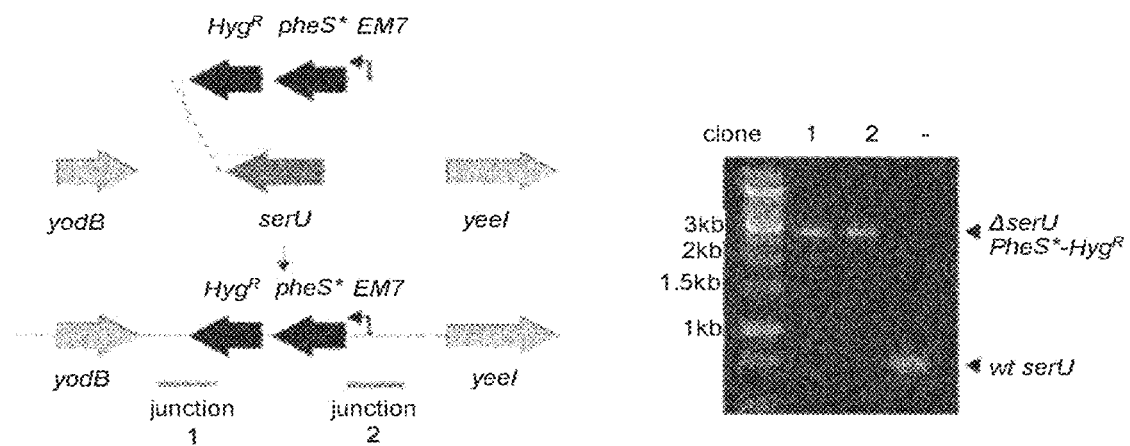
Figure 14F:
Figure 14F:
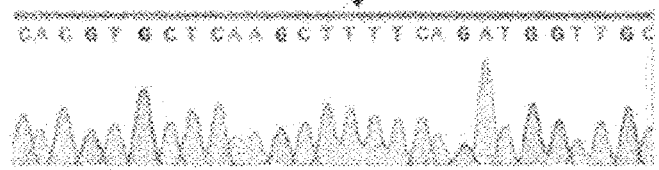

FIG. 14F, serU (dark grey) is deleted by insertion of a PheS*-Hyg$^R$ cassette (in black) via lambda-red mediated recombination. The agarose gels are annotated as described in FIG. 12C and the rest of the data is annotated as described in the description of FIG. 14D. Full gel available in FIG. 16B.

Figure 15A:
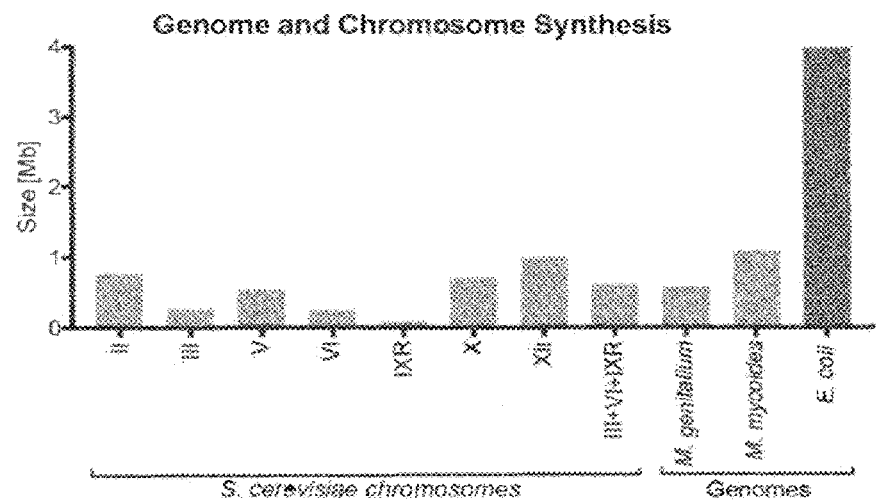
Figure 15B:
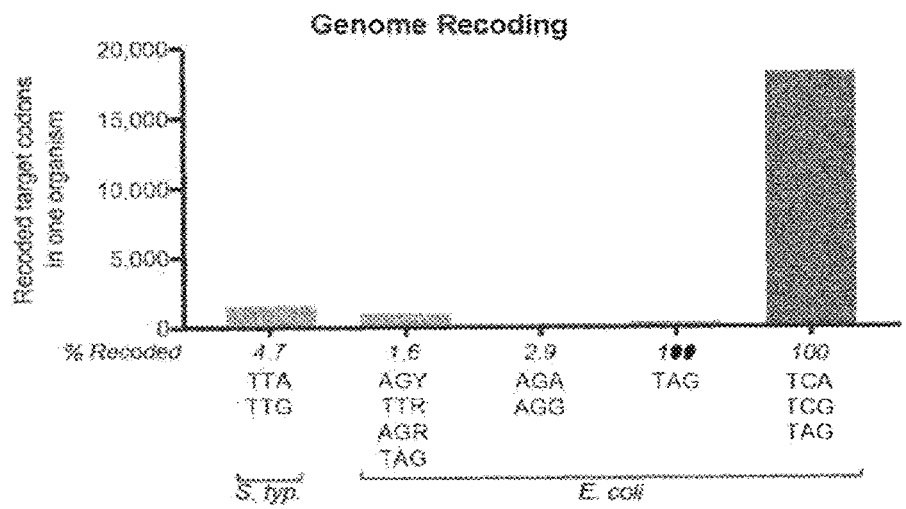
Figure 15C:
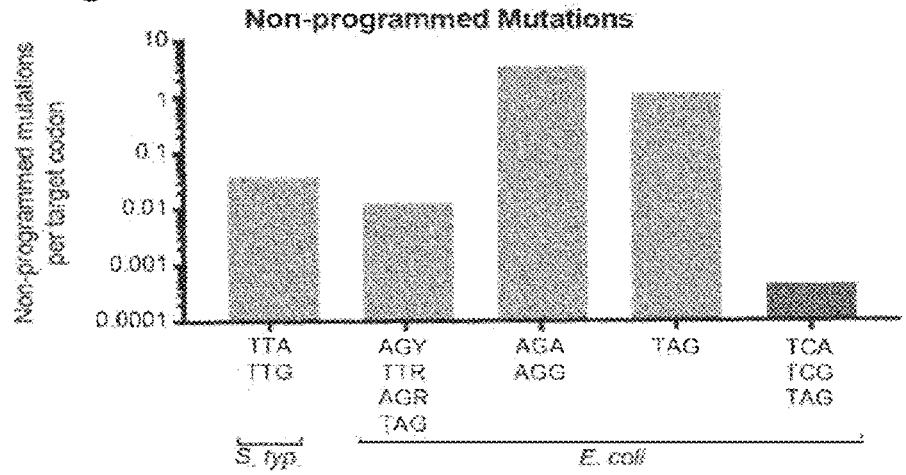

FIGS. 15A-C—The scale of genome synthesis and scale and fidelity of recoding.

FIG. 15A, Genome and chromosome synthesis. The size (Mb) of synthetic genomes that have been produced for M. genitalium and M. mycoides (Gibson, D. G. et al., 2008. Science 319, 1215-1220; and Gibson, D. G. et al., 2010. Science 329, 52-56) and several S. cerevisiae chromosomes (Shen, Y. et al., 2017. Science 355, aaf4791; Annaluru, N. et al., 2014. Science 344, 55-58; Xie, Z. X. et al., 2017. Science 355, aaf4704; Mitchell, L. A. et al., 2017. Science 355, aaf4831; Dymond, J. S. et al., 2011. Nature 477, 471-476; Wu, Y. et al., 2017. Science 355, aaf4706; Zhang, W. et al., 2017. Science 355, aaf3981; and Richardson, S. M. et al., 2017. Science 355, 1040-1044) are shown in light grey. The size of the synthetic E. coli genome presented here is shown in dark grey.

FIG. 15B, Genome recoding efforts. Attempts to recode target codons TTA and TTG in S. typhimurium (Lau, Y. H. et al., 2017. Nucleic Acids Res 45, 6971-6980); AGC, AGT, TTG, TTA, AGA, AGG, and TAG in E. coli (Ostrov, N. et al., 2016. Science 353, 819-822); AGA and AGG in E. coli (Napolitano, M. G. et al., 2016. Proc Natl Acad Sci USA 113, E5588-5597), as well as recoding of all TAG in E. coli (Lajoie, M. J. et al., 2013. Science 342, 357-360) are shown in light grey. Compared to removal of all TCA, TCG, and TAG in E. coli presented here (dark grey). The total number of codons recoded in a single strain are shown on the graph, and the maximum percentage of target codons recoded in a single strain in each effort is indicated.

FIG. 15C, Number of reported non-programmed mutations and indels as a function of the number of target codons recoded for the experiments shown in b.

Figure 16A:
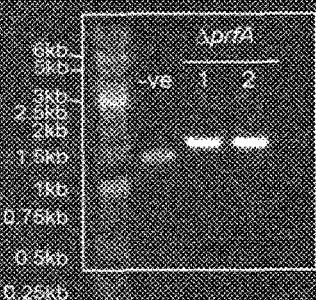
Figure 16B:
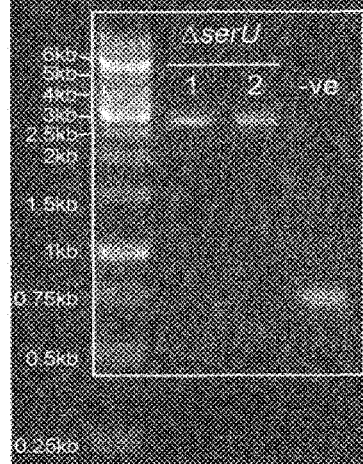
Figure 16C:
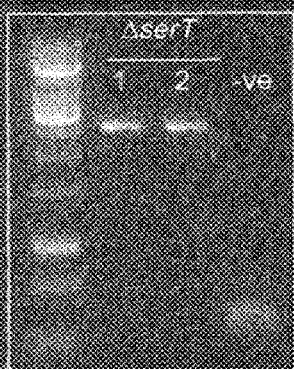

FIGS. 16A-16C—Full gels for FIG. 12

FIG. 16A, A full gel is shown corresponding to the gel in FIG. 14E. The molecular size standards are annotated and the area shown in the relevant Figure is indicated by a white outline.

FIG. 16B, A full gel is shown corresponding to the gel in FIG. 14F. The molecular size standards are annotated and the area shown in the relevant Figure is indicated by a white outline.

FIG. 16C, A full gel is shown corresponding to the gel in FIG. 12C. The molecular size standards are annotated and the area shown in the relevant Figure is indicated by a white outline.

Figure 17:

FIG. 17—Codon and anticodon interactions in the E. coli genome 28 sense codons are highlighted in grey, along with the amber stop codon. The genome wide removal of these sense codons, but not other sense codons, would enable all their cognate tRNA to be deleted without removing the ability to decode one or more sense codons remaining in the genome. This is necessary but not sufficient for the reassignment of sense codons to unnatural monomers. Serine, leucine and alanine codon boxes are highlighted because the endogenous aminoacyl-tRNA synthetases for these amino acids do not recognize the anticodons of their cognate tRNAs. This may facilitate the assignment of codons within these boxes to new amino acids through the introduction of tRNAs bearing cognate anticodons that do not direct mis-aminocylation by endogenous synthetases. The number of total codon counts for all 64 triplet codons in the MDS42 genome (GenBank accession no. AP012306), all known codon-anticodon interactions through both Watson-Crick base-paring and wobbling, base modification on tRNA anticodons, tRNA genes, and measured in vivo tRNA relative abundance are reported. This analysis identifies 10 codons from the serine, leucine, and alanine groups (serine codon TCG, TCA, AGT, AGC; leucine codon CTG, CTA, TTG, TTA; and alanine codon GCG, GCA) satisfy both the codon-anticodon interaction and aminoacyl-tRNA synthetases recognition criteria for codon reassignment.

Figure 18:
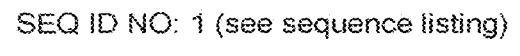

FIG. 18—Designed synthetic E. coli genome (SEQ ID NO: 1)

A version of the E. coli MDS42 genome in which the serine codons TCG and TCA and the stop codon TAG in open reading frames (ORFs) are systematically replaced by their synonyms AGC, AGT, and TAA, respectively. Using the defined rules for synonymous codon compression and refactoring a genome is designed in which all 18,218 target codons are recoded to their target synonyms.

Figure 19:
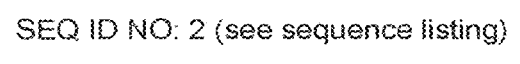

FIG. 19—Final synthetic *E. coli* genome (Syn61) (SEQ ID NO: 2)

Sequence of *E. coli* Syn61, in which all $1.8 \times 10^4$ target codons in the genome are recoded. The synthesis of our recoded genome introduced only eight non-programmed mutations (Table 6), four of these mutations arose during the preparation of the 100 kb BACs, and four during the recoding process.

FIGS. 20A-20N—BACs for assembling synthetic genome

FIG. 20A, BAC-sacB-CmR-rpsL. The nucleotide sequence for an annotated BAC vector harbouring a sacB-CmR selection cassette flanked upstream by a 5' homology region (HR) and CRISPR/Cas9 protospacer sequence (spacer 1). The sacB-CmR cassette is flanked downstream by a 3' homology region, a CRISPR/Cas9 protospacer sequence (spacer 2), and an rpsL selection marker.

FIG. 20B,—BAC-rpsL-KanR-sacB. The nucleotide sequence for an annotated BAC vector harbouring an rpsL-KanR selection cassette flanked upstream by a 5' homology region (HR) and CRISPR/Cas9 protospacer sequence (spacer 1). The rpsL-KanR cassette is flanked downstream by a 3' homology region, a CRISPR/Cas9 protospacer sequence (spacer 2), and a sacB selection marker.

FIG. 20C, BAC-rpsL-KanR-pheS*-HygR. The nucleotide sequence for an annotated BAC vector harbouring an rpsL-KanR selection cassette flanked upstream by a 5' homology region (HR) and CRISPR/Cas9 protospacer sequence (spacer 1). The rpsL-KanR cassette is flanked downstream by a 3' homology region, a CRISPR/Cas9 protospacer sequence (spacer 2), and a pheS*-HygR selection marker.

FIGS. 20D-20N, Table of BAC Construction. Oligonucleotides and selection markers used to construct BACs with synthetic DNA for REXER and homology regions between synthetic DNA fragments. The second tab lists the plasmid backbone and protospacer sequences used for REXER.

FIGS. 21A and 21B—Exemplary spacer plasmid maps

FIG. 21A, Spacer plasmid map. Exemplary map of pKW1_MB1amp_Spacers_REXER2 containing the CRISPR insert with spacer sequences used as linear or circular spacers for REXER.

FIG. 21B, Second generation spacer plasmid map. Exemplary map of pKW3_MB1amp_Spacers_REXER2 containing the CRISPR insert with spacer sequences used as circular 2nd generation spacers for REXER.

FIGS. 22A-22E—Constructs for conjugation

FIG. 22A, Gentamycin resistance OriT cassette.

FIGS. 22B-22D, Primers for conjugation constructs. Oligonucleotide primers used for conjugation.

FIG. 22E, pJF146. F' plasmid that does not self-transfer.

FIG. 23—Primers for deletion experiments

Oligonucleotide primers used for deletion of the tRNAs serT and serU and release factor prfA in Syn61.

DETAILED DESCRIPTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Synthetic Genomes
Genomes

As used herein, a "genome" is the genetic material of an organism, including both genes and non-coding DNA. As used herein, a "synthetic genome" is a synthetically-built genome. Typically a synthetic genome will be produced by genetic modification of a pre-existing (i.e. "parent") genome. Thus, a synthetic genome may be derived from a parent genome, i.e. identical to a parent genome, except comprising one or more genetic modifications. The skilled person will be able to readily identify the parent genome on which a synthetic genome is based and the genetic modifications carried out. As used herein, a "parent genome" may be any naturally-occurring, commercially-available, deposited, catalogued or otherwise well-known genome, or derivative thereof.

The synthetic genome of the present invention is a synthetic prokaryotic genome. A prokaryote is a unicellular organism that lacks a membrane-bound nucleus, mitochondria, or any other membrane-bound organelle. Prokaryotes are divided into two domains, Archaea and Bacteria. The genome of prokaryotic organisms generally is a circular, double-stranded piece of DNA, multiple copies of which may exist at any time.

Preferably, the synthetic genome of the present invention is a synthetic bacterial genome. Preferably the synthetic bacterial genome is suitable for heterologous protein production, in particular the production of polypeptides comprising one or more non-proteinogenic amino acids (for instance those described by Ferrer-Miralles, N. and Villaverde, A., 2013. Microbial Cell Factories, 12:113). Suitable bacterial genomes include: escherichia (e.g. *Escherichia coli*), caulobactera (e.g. *Caulobacter crescentus*), phototrophic bacteria (e.g. *Rodhobacter sphaeroides*), cold adapted bacteria (e.g. *Pseudoalteromonas haloplanktis, Shewanella* sp. strain Ac10), pseudomonads (e.g. *Pseudomonas fluorescens, Pseudomonas putida, Pseudomonas aeruginosa*), halophilic bacteria (e.g. *Halomonas elongate, Chromohalobacter salexigens*), streptomycetes (e.g. *Streptomyces lividans, Streptomyces griseus*), nocardia (e.g. *Nocardia lactamdurans*), mycobacteria (e.g. *Mycobacterium smegmatis*), coryneform bacteria (e.g. *Corynebacterium glutamicum, Corynebacterium ammoniagenes, Brevibacterium lactofermentum*), bacilli (e.g. *Bacillus subtilis, Bacillus brevis, Bacillus megaterium, Bacillus licheniformis, Bacillus amyloliquefaciens*), and lactic acid bacteria (e.g. *Lactococcus lactis, Lactobacillus plantarum, Lactobacillus casei, Lactobacillus reuteri, Lactobacillus gasseri*) genomes. In some embodiments the synthetic genome is a synthetic gram-negative bacterial genome.

Bacterial genomes can range in size anywhere from about 130 kb to over 14 Mb. Thus, in some embodiments the synthetic prokaryotic genome of the present invention is 100 kb to 20 Mb, or 130 kb to 15 Mb, or 200 kb to 15 Mb, or 300 kb to 15 Mb, or 500 kb to 15 Mb, or 1 Mb to 15 Mb, or 1 Mb to 10 Mb, or 1 Mb to 8 Mb, or 1 Mb to 6 Mb, or 2 Mb to 6 Mb, or 2 Mb to 5 Mb, or 3 Mb to 5 Mb, or about 4 Mb in size. The synthetic prokaryotic genome may comprise 100 or more, 200 or more, 300 or more, 400 or more, 500 or more, 600 or more, 700 or more, 800 or more, 900 or more, 1000 or more, 1500 or more, or 2000 or more genes, preferably 1000 or more genes. The synthetic prokaryotic genome may comprise 100 or more, 200 or more, 300 or more, 400 or more, 500 or more, 600 or more, 700 or more, 800 or more, 900 or more, 1000 or more, 1500 or more, or 2000 or more genes for which there is evidence of translation and/or of the predicted protein product, preferably 1000 or more genes. Preferably the synthetic prokaryotic genome comprises 100 or more, 200 or more, 300 or more, 400 or more, 500 or more essential genes, preferably 300 or more essential genes.

Preferably, the synthetic genome of the present invention is a synthetic *Escherichia coli, Salmonella enterica*, or *Shigella dysenteriae* genome. These are phylogenetically related species as disclosed by Lukjancenko, O., et al., 2010. Microbial ecology, 60(4), pp. 708-720; and Karberg, K. A., et al., 2011. PNAS, 108(50), pp. 20154-20159.

More preferably, the synthetic genome of the present invention is a synthetic *E. coli* genome. The parent genome may be any suitable *E. coli* genome including MDS42, K-12, MG1655, BL21, BL21(DE3), AD494, Origami, HMS174, BLR(DE3), HMS174(DE3), Tuner(DE3), Origami2(DE3), Rosetta2(DE3), Lemo21(DE3), NiCo21 (DE3), T7 Express, SHuffle Express, C41(DE3), C43(DE3), and m15 pREP4 or derivatives thereof (Rosano, G. L. and Ceccarelli, E. A., 2014. Frontiers in microbiology, 5, p. 172). Most preferably, the parent genome is MDS42, MG1655, or BL21 or a derivative thereof. MG1655 is considered as the wild type strain of *E. coli*. The GenBank ID of genomic sequence of this strain is U00096. BL21 is widely available commercially. For example, it can be purchased from New England BioLabs with catalog number C2530H.

In some embodiments the synthetic genome is a reduced synthetic genome or a minimal synthetic genome. A "reduced genome" is one in which the size of the parent genome has been reduced by removing non-essential genes and/or non-coding regions. A "minimal genome" is a genome which has been reduced to its minimal size whilst remaining viable e.g. by deletion of all non-essential regions of the genome.

The synthetic genome of the present invention may be a viable genome. As used herein, a "viable genome" refers to a genome that contains nucleic acid sequences sufficient to cause and/or sustain viability of a cell, e.g., those encoding molecules required for replication, transcription, translation, energy production, transport, production of membranes and cytoplasmic components, and cell division.

Preferably one or more tRNA or release factors may be deleted from the synthetic genome and the synthetic genome may remain viable. For example, a tRNA which decodes only the one or more sense codons that have been replaced (or deleted) may be dispensable. Similarly, a tRNA which decodes the one or more sense codons that have been replaced (or deleted) may be dispensable if the remaining sense codons that it decodes may also be decoded by an alternative tRNA. For example, serT, encoding tRNA$^{Ser}_{UGA}$, is the only tRNA that decodes TCA codons in *E. coli*, and is therefore normally essential. However, if the synthetic genome does not contain TCA codons then serT may be dispensable.

Sense Codons

The current invention provides a synthetic prokaryotic genome comprising 5 or fewer occurrences of one or more sense codons; and/or a synthetic prokaryotic genome derived from a parent genome, wherein the synthetic prokaryotic genome comprises less than 10%, 5%, 2%, 1%, 0.5%, 0.1% of the occurrences of one or more sense codons, relative to the parent genome; and/or a synthetic prokaryotic genome comprising 100 or more, 200 or more, or 1000 or more genes with no occurrences of one or more sense codons.

The one or more sense codons may consist of one, two, three, four, five, six, seven, or eight sense codons. Preferably, the one or more sense codons consist of one sense codon or two sense codons, most preferably two sense codons.

The synthetic prokaryotic genome may comprise 5 or fewer (e.g. 5, 4, 3, 2, 1), or no occurrences of one or more (e.g. 1, 2, 3, 4, 5, 6, 7, or 8) sense codons. In some embodiments the synthetic prokaryotic genome comprises 5 or fewer (e.g. 5, 4, 3, 2, 1, 0) of each of the one or more (e.g. 1, 2, 3, 4, 5, 6, 7, or 8) sense codons. In other embodiments the synthetic prokaryotic genome comprises 5 or fewer (e.g. 5, 4, 3, 2, 1, 0) of the one or more (e.g. 1, 2, 3, 4, 5, 6, or 8) sense codons combined (i.e. in total). In preferred embodiments the synthetic prokaryotic genome comprises no occurrences of one sense codon. In other preferred embodiments the synthetic prokaryotic genome comprises no occurrences of two sense codons.

The synthetic prokaryotic genome may be derived from a parent genome and comprise 5 or fewer (e.g. 5, 4, 3, 2, 1), or no occurrences of one or more (e.g. 1, 2, 3, 4, 5, 6, 7, or 8) native sense codons. In some embodiments the synthetic prokaryotic genome comprises 5 or fewer (e.g. 5, 4, 3, 2, 1, 0) of each of the one or more (e.g. 1, 2, 3, 4, 5, 6, 7, or 8) native sense codons. In other embodiments the synthetic prokaryotic genome comprises 5 or fewer (e.g. 5, 4, 3, 2, 1, 0) of the one or more (e.g. 1, 2, 3, 4, 5, 6, 7, or 8) native sense codons combined (i.e. in total). In preferred embodiments the synthetic prokaryotic genome is derived from a parent genome and comprises no occurrences of one native sense codon. In other preferred embodiments the synthetic prokaryotic genome is derived from a parent genome and comprises no occurrences of two native sense codons.

In some embodiments the synthetic prokaryotic genome comprises 100 or more, 200 or more, 300 or more, 400 or more, 500 or more, 600 or more, 700 or more, 800 or more, 900 or more, 1000 or more, 1500 or more, or 2000 or more genes, preferably 1000 or more genes. In some embodiments the genes are those for which there is evidence of translation and/or of the predicted protein product. For example, the synthetic prokaryotic genome may comprise 100 or more, 200 or more, 300 or more, 400 or more, 500 or more 600 or more, 700 or more, 800 or more, 900 or more, 1000 or more, 1500 or more, or 2000 or more genes, preferably 1000 or more genes for which there is evidence of translation and/or of the predicted protein product. Preferably the synthetic prokaryotic genome comprises 100 or more, 200 or more, 300 or more, 400 or more, 500 or more essential genes, preferably 300 or more essential genes. Preferably the (essential) genes have no occurrences of the one or more sense codons.

The synthetic prokaryotic genome may comprise less than 10%, 5%, 2%, 1%, 0.5%, 0.1% of the occurrences of one or more (e.g. 1, 2, 3, 4, 5, 6, 7, or 8) sense codons, relative to the parent genome. In some embodiments the synthetic prokaryotic genome comprises less than 10%, 5%, 2%, 1%, 0.5%, 0.1% of the occurrences of each of the one or more (e.g. 1, 2, 3, 4, 5, 6, 7, or 8) sense codons, relative to the parent genome. In other embodiments the synthetic prokaryotic genome comprises less than 10%, 5%, 2%, 1%, 0.5%, 0.1% of the occurrences of the one or more (e.g. 1, 2, 3, 4, 5, 6, 7, or 8) sense codons combined, relative to the parent genome. In preferred embodiments the synthetic prokaryotic genome comprises less than 10%, 5%, 2%, 1%, 0.5%, 0.1% of one sense codon, relative to the parent genome. In other preferred embodiments the synthetic prokaryotic genome comprises less than 10%, 5%, 2%, 1%, 0.5%, 0.1% of two sense codons, relative to the parent genome.

The synthetic prokaryotic genome may comprise 100 or more, 200 or more, or 1000 or more genes with no occurrences of one or more (e.g. 1, 2, 3, 4, 5, 6, 7, or 8) sense codons. Preferably, all or substantially all the genes in the synthetic prokaryotic genome have no occurrences of the one or more (e.g. 1, 2, 3, 4, 5, 6, 7, or 8) sense codons. In preferred embodiments, all or substantially all the genes in the synthetic prokaryotic genome have no occurrences of one sense codon. In other preferred embodiments, all or substantially all the genes in the synthetic prokaryotic genome have no occurrences of two sense codons. By substantially all is meant all but 10 or fewer (e.g. 10, 9, 8, 7, 6, 5, 4, 3, 2, 1, or 0) genes comprise occurrences of the one or more sense codons.

The synthetic prokaryotic genome may comprise 100 or more, 200 or more, or 1000 or more genes with no occurrences of one or more (e.g. 1, 2, 3, 4, 5, 6, 7, or 8) native sense codons. Preferably, all or substantially all the genes in the synthetic prokaryotic genome have no occurrences of the one or more (e.g. 1, 2, 3, 4, 5, 6, 7, or 8) native sense codons. In preferred embodiments, all or substantially all the genes in the synthetic prokaryotic genome have no occurrences of one native sense codon. In other preferred embodiments, all or substantially all the genes in the synthetic prokaryotic genome have no occurrences of two native sense codons. By substantially all is meant all but 10 or fewer (e.g. 10, 9, 8, 7, 6, 5, 4, 3, 2, 1, or 0) genes comprise occurrences of the one or more native sense codons.

Preferably the genes encode proteins (e.g. the genes are those for which there is evidence of translation and/or of the predicted protein product) and/or the genes are essential genes. Thus, in more preferred embodiments the synthetic prokaryotic genome comprises 100 or more, 200 or more, or 1000 or more protein-encoding and/or 100 or more, 200 or more, or 300 or more essential genes with no occurrences of one or two sense codons. In other more preferred embodiments all or substantially all the protein-encoding and/or essential genes in the synthetic prokaryotic genome comprise no occurrences of one or two sense codons.

In preferred embodiments no proteins are translated from any of the remaining occurrences of the one or more sense codons and/or genes comprising the remaining occurrences of the one or more sense codons are putative or non-coding genes. In some embodiments the translation of the genes comprising the remaining occurrences of the one or more sense codons is reduced and/or prevented (e.g. the genes may comprise stop codons in the 5' sequence).

Any remaining occurrences of the sense codons may be necessary to ensure that the synthetic prokaryotic genome is viable. For example, one or more, preferably all, of the remaining occurrences of the one or more sense codons in the synthetic prokaryotic genome may be present in the regulatory elements of essential genes; and/or one or more, preferably all, of the remaining occurrences of the one or more sense codons may be in genes in which there is no evidence for translation or the predicted protein product (i.e. putative or non-coding genes).

As used herein, a "sense codon" is a nucleotide triplet that codes for an amino acid. Thus, sense codons may be identified in a genome by gene prediction, i.e. by identifying regions of the genome that code for proteins (i.e. genes) and the corresponding open reading frames (ORFs). Typically, genomes naturally comprise 61 sense codons: GCT, GCC, GCA, GCG, CGT, CGC, CGA, CGG, AGA, AGG, AAT, AAC, GAT, GAC, TGT, TGC, CAA, CAG, GAA, GAG, GGT, GGC, GGA, GGG, CAT, CAC, ATT, ATC, ATA, TTA, TTG, CTT, CTC, CTA, CTG, AAA, AAG, ATG, TTT, TTC, CCT, CCC, CCA, CCG, TCT, TCC, TCA, TCG, AGT, AGC, ACT, ACC, ACA, ACG, TGG, TAT, TAC, GTT, GTC, GTA, and GTG (read from 5' to 3' on the coding strand of DNA). The standard genetic code encodes the 20 canonical amino acids using the 61 triplet codons. 18 of the 20 amino acids are encoded by more than one synonymous codon (see FIG. 17). The one or more sense codons may be one or more native sense codons, i.e. sense codons which are present in the parent genome.

The 61 sense codons in DNA are transcribed into corresponding mRNA and subsequently decoded by one or more tRNAs. tRNAs carry an amino acid to a ribosome as directed by the sense codons in the mRNA. The tRNAs can recognise one or more sense codons via a complementary anticodon. A sequence of sense codons is subsequently translated into a polypeptide (i.e. a sequence of amino acids). Codon and anticodon interactions in the *E. coli* genome are shown in FIG. 17.

Preferably, the genome wide removal of the one or more sense codons, but not other sense codons, enables all the cognate tRNA corresponding to said one or more sense codons to be deleted without removing the ability to decode the one or more sense codons remaining in the genome. Thus, the one or more sense codons may be selected from: TCG, TCA, AGT, AGC, GCG, GCA, GTG, GTA, CTG, CTA, TTG, TTA, ACG, ACA, CCG, CCA, CGG, CGA, CGT, CGC, AGG, AGA, GGG, GGA, GGT, GGC, ATT, and ATC.

Aminoacyl-tRNA synthetases for serine, leucine and alanine do not recognize the anticodons of their cognate tRNAs. This may facilitate the assignment of codons within these boxes to new amino acids through the introduction of tRNAs bearing cognate anticodons that do not direct misaminoacylation by endogenous synthetases. Thus, the one or more sense codons may be selected from: TCG, TCA, TCT, TCC, AGT, AGC, GCG, GCA, GCT, GCC, CTG, CTA, CTT, CTC, TTG, and TTA.

Preferably, the one or more sense codons fulfill both these criteria, thus the one or more sense codons may be selected from: TCG, TCA, AGT, AGC, GCG, GCA, CTG, CTA, TTG, and TTA. More preferably, the one of more sense codons are selected from TCG, TCA, AGT, AGC, TTG, TTA, GCG and GCA. Most preferably, the one of more sense codons are TCG and/or TCA.

Preferably, one or more sense codons are removed such that the genome is compatible with codon reassignment to non-proteinogenic amino acids. Thus, the one or more sense codons may comprise one or more of TCA, CTA, or TTA. Alternatively, two or more sense codons are removed, wherein the two or more sense codons comprise one or more of the sense codon pairs, selected from the group consisting of: GCG and GCA; GCT and GCC; TCG and TCA; AGT and AGC; TCT and TCC; CTG and CTA; TTG and TTA; and CTT and CTC. Preferably, two or more sense codons are removed, wherein the two or more sense codons comprise one or more of the sense codon pairs, selected from the group consisting of: GCG and GCA; TCG and TCA; AGT and AGC; CTG and CTA; and TTG and TTA. More preferably, the two or more sense codons comprise TCG and TCA.

To achieve removal of sense codons they may be replaced with synonymous sense codons. This is preferable to ensure that the encoded protein sequence is not changed. For instance, the present invention provides a synthetic prokaryotic genome wherein 90% or more, 95% or more, 98% or more, 99% or more, 99.5% or more, 99.6% or more, 99.7% or more, 99.8% or more, 99.9% or more, or 100% of the occurrences of one or more sense codons in the parent genome are replaced with synonymous sense codons. The person skilled in the art is able to deduce suitable synonymous sense codon replacements. For example, in *E. coli*, typically TCG, TCA, TCT, TCC, AGT and AGC all encode serine; typically GCG, GCA, GCT and GCC all encode alanine; typically CTG, CTA, CTT, CTC, TTG and TTA all encode leucine.

In some embodiments, the replacement is a defined replacement, i.e. one sense codon is replaced with a single synonymous sense codon. Preferably, 90% or more, 95% or more, 98% or more, 99% or more, 99.5% or more, 99.6% or more, 99.7% or more, 99.8% or more, 99.9% or more, or 100% of the occurrences of one or more sense codons in the parent genome are replaced with a defined (i.e. single) synonymous sense codon.

For example, the defined replacement may be: GCG replaced with either GCT or GCC; GCA replaced with either GCT or GCC; TCG replaced with any one of TCT, TCC, AGT, or AGC; TCA replaced with any one of TCT, TCC, AGT, or AGC; AGT replaced with any one of TCG, TCA, TCT, or TCC; AGC replaced with any one of TCG, TCA, TCT, or TCC; CTG replaced with any one of CTT, CTC, TTG or TTA; CTA replaced with any one of CTT, CTC, TTG or TTA; TTG replaced with any one of CTG, CTA, CTT or CTC; or TTA replaced with any one of CTG, CTA, CTT or CTC. Preferably the one or more defined sense codon replacements are selected from one or more of: GCG to either GCT or GCC; GCA to either GCT or GCC; TCG to either AGT or AGC; TCA to either AGT or AGC; AGT to either TCA or TCT; AGC to either TCG or TCC or TCA; TTG to CTT; and TTA to CTC. More preferably, TCG and/or TCA are replaced with AGC and/or AGT. Most preferably, TCG is replaced with AGC and/or TCA is replaced with AGT.

Preferably, the defined replacement is such that the genome is compatible with codon reassignment to non-proteinogenic amino acids. For example: (i) GCG may be replaced with either GCT or GCC, and GCA may be replaced with either GCT or GCC; (ii) TCG may be replaced with any of TCT, TCC, AGT, or AGC, and TCA may be replaced with any of TCT, TCC, AGT, or AGC; (iii) AGT may be replaced with any of TCG, TCA, TCT, or TCC, and AGC may be replaced with any of TCG, TCA, TCT, or TCC; (iv) CTG may be replaced with any of CTT, CTC, TTG or TTA, and CTA may be replaced with any of CTT, CTC, TTG or TTA; or (v) TTG may be replaced with any of CTG, CTA, CTT or CTC, and TTA may be replaced with any of CTG, CTA, CTT or CTC.

Preferably, the defined replacement scheme is one or more of those listed in the table below:

| Codon 1 | | Codon 2 | |
| --- | --- | --- | --- |
| From | To | From | To |
| GCG | GCT | GCA | GCT |
| GCG | GCT | GCA | GCC |
| GCG | GCC | GCA | GCT |
| GCG | GCC | GCA | GCC |
| TCG | TCT | TCA | TCT |
| TCG | TCT | TCA | TCC |
| TCG | TCT | TCA | AGT |
| TCG | TCT | TCA | AGC |
| TCG | TCC | TCA | TCT |
| TCG | TCC | TCA | TCC |
| TCG | TCC | TCA | AGT |
| TCG | TCC | TCA | AGC |
| TCG | AGT | TCA | TCT |
| TCG | AGT | TCA | TCC |
| TCG | AGT | TCA | AGT |
| TCG | AGT | TCA | AGC |
| TCG | AGC | TCA | TCT |
| TCG | AGC | TCA | TCC |
| TCG | AGC | TCA | AGT |
| TCG | AGC | TCA | AGC |
| AGT | TCG | AGC | TCG |
| AGT | TCG | AGC | TCA |
| AGT | TCG | AGC | TCT |
| AGT | TCG | AGC | TCC |
| AGT | TCA | AGC | TCG |
| AGT | TCA | AGC | TCA |
| AGT | TCA | AGC | TCT |
| AGT | TCA | AGC | TCC |
| AGT | TCT | AGC | TCG |
| AGT | TCT | AGC | TCA |
| AGT | TCT | AGC | TCT |
| AGT | TCT | AGC | TCC |
| AGT | TCC | AGC | TCG |
| AGT | TCC | AGC | TCA |
| AGT | TCC | AGC | TCT |
| AGT | TCC | AGC | TCC |
| CTG | CTT | CTA | CTT |
| CTG | CTT | CTA | CTC |
| CTG | CTT | CTA | TTG |
| CTG | CTT | CTA | TTA |
| CTG | CTC | CTA | CTT |
| CTG | CTC | CTA | CTC |
| CTG | CTC | CTA | TTG |
| CTG | CTC | CTA | TTA |
| CTG | TTG | CTA | CTT |
| CTG | TTG | CTA | CTC |
| CTG | TTG | CTA | TTG |
| CTG | TTG | CTA | TTA |
| CTG | TTA | CTA | CTT |
| CTG | TTA | CTA | CTC |
| CTG | TTA | CTA | TTG |
| CTG | TTA | CTA | TTA |
| TTG | CTG | TTA | CTG |
| TTG | CTG | TTA | CTA |
| TTG | CTG | TTA | CTT |
| TTG | CTG | TTA | CTC |
| TTG | CTA | TTA | CTG |
| TTG | CTA | TTA | CTA |
| TTG | CTA | TTA | CTT |
| TTG | CTA | TTA | CTC |
| TTG | CTT | TTA | CTG |
| TTG | CTT | TTA | CTA |
| TTG | CTT | TTA | CTT |
| TTG | CTT | TTA | CTC |
| TTG | CTC | TTA | CTG |
| TTG | CTC | TTA | CTA |
| TTG | CTC | TTA | CTT |
| TTG | CTC | TTA | CTC |
| GCT | GCG | GCC | GCG |
| GCT | GCG | GCC | GCA |
| GCT | GCA | GCC | GCG |
| GCT | GCA | GCC | GCA |
| TCA | TCG | | |
| TCA | TCT | | |
| TCA | TCC | | |
| TCA | AGT | | |
| TCA | AGC | | |
| TCT | TCG | TCC | TCG |
| TCT | TCG | TCC | TCA |
| TCT | TCG | TCC | AGT |
| TCT | TCG | TCC | AGC |
| TCT | TCA | TCC | TCG |
| TCT | TCA | TCC | TCA |
| TCT | TCA | TCC | AGT |
| TCT | TCA | TCC | AGC |
| TCT | AGT | TCC | TCG |
| TCT | AGT | TCC | TCA |

-continued

| Codon 1 | | Codon 2 | |
|---|---|---|---|
| From | To | From | To |
| TCT | AGT | TCC | AGT |
| TCT | AGT | TCC | AGC |
| TCT | AGC | TCC | TCG |
| TCT | AGC | TCC | TCA |
| TCT | AGC | TCC | AGT |
| TCT | AGC | TCC | AGC |
| CTA | CTG | | |
| CTA | CTT | | |
| CTA | CTC | | |
| CTA | TTG | | |
| CTA | TTA | | |
| TTA | CTG | | |
| TTA | CTA | | |
| TTA | CTT | | |
| TTA | CTC | | |
| TTA | TTG | | |
| CTT | CTG | CTC | CTG |
| CTT | CTG | CTC | CTA |
| CTT | CTG | CTC | TTG |
| CTT | CTG | CTC | TTA |
| CTT | CTA | CTC | CTG |
| CTT | CTA | CTC | CTA |
| CTT | CTA | CTC | TTG |
| CTT | CTA | CTC | TTA |
| CTT | TTG | CTC | CTG |
| CTT | TTG | CTC | CTA |
| CTT | TTG | CTC | TTG |
| CTT | TTG | CTC | TTA |
| CTT | TTA | CTC | CTG |
| CTT | TTA | CTC | CTA |
| CTT | TTA | CTC | TTG |
| CTT | TTA | CTC | TTA |

Preferably, none of these codon replacements affect ribosomal binding sites (AGGAGG), which are highly conserved regulatory sequences in *E. coli*. The selected codon replacements may be tested on a small test region (e.g. a 20 kb region of the genome rich in both essential target genes and target codons) to assess viability. If the codon replacements are not viable on the small test region they may be disregarded.

When replacement of one or more sense codons in the parent genome with defined replacement synonymous sense codons does not result in a viable genome, alternative replacement synonymous sense codons may be used. For instance, 99.9% of the occurrences of one or more sense codons in the parent genome may be replaced with a defined (i.e. single) synonymous sense codon, and the remaining 0.1% with alternative synonymous sense codons. For example, 99.9% of the occurrences of TCG may be replaced with AGC and 0.1% replaced with TCT, TCC, AGT or AGC; and/or 99.9% of the occurrences of TCA may be replaced with AGT and 0.1% replaced with TCT, TCC, AGT or AGC.

As used herein, a "stop codon" is a nucleotide triplet that codes for termination of translation into proteins. Typically, genomes naturally comprise 3 stop codons: TAA ("ochre"), TGA ("opal" or "umber") and TAG ("amber").

In some embodiments the synthetic prokaryotic genome further comprises 10 or fewer, 5 or fewer, or no occurrences of one or two stop codons, preferably 10 or fewer, 5 or fewer, or no occurrences of the amber stop codon (TAG). Preferably wherein 90% or more, 95% or more, 98% or more, 99% or more, or all of the occurrences of TAG in the parent prokaryotic genome are replaced with TAA (the ochre stop codon). In preferred embodiments the synthetic prokaryotic genome comprises no occurrences of the amber stop codon (TAG), optionally wherein all of the occurrences of TAG in the parent prokaryotic genome are replaced with TAA (the ochre stop codon).

Accordingly, in preferred embodiments the synthetic prokaryotic genome of the present invention comprises no occurrences of one or more, or two or more sense codons and no occurrences of one stop codon, preferably the amber stop codon (TAG). In more preferred embodiments the synthetic prokaryotic genome of the present invention comprises no occurrences of two sense codons, preferably TCG and TCA, and no occurrences of the amber stop codon (TAG), optionally wherein TCG, TCA and TAG in the parent prokaryotic genome are replaced with synonymous codons, for example 99.9% or more of the occurrences of TCG in the parent prokaryotic genome are replaced with AGC, 99.9% or more of the occurrences of TCA in the parent prokaryotic genome are replaced with AGT and all of the occurrences of TAG in the parent prokaryotic genome are replaced with TAA.

In some embodiments the synthetic prokaryotic genome comprises a polynucleotide sequence which is at least 80%, 85%, 90%, 95%, 98%, 99%, 99.5%, 99.8%, or 99.9% identical to SEQ ID NO: 1 or SEQ ID NO:2.

The invention provides a synthetic prokaryotic genome which is at least 98%, 98.5%, 99%, 99.5%, 99.6%, 99.7%, 99.8%, 99.9%, 99.95% or 100% identical to SEQ ID NO:1 or SEQ ID NO: 2

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible (reflecting higher relatedness between the two compared sequences) will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid-Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Suitably, the sequence identity may be determined across the entirety of the sequence. Suitably, the sequence identity may be determined across the entirety of the candidate sequence being compared to a sequence recited herein.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix (the default matrix for the BLAST suite of programs). GCG Wisconsin programs generally use either the public default values or a custom symbol comparison table if supplied (see user manual for further details). Preferably, the public default values for the GCG package, or in the case of other software the default matrix, such as BLOSUM62, are used.

Once the software has produced an optimal alignment, it is possible to calculate % sequence identity. The software typically does this as part of the sequence comparison and generates a numerical result.

Refactoring

Genomes contain numerous overlapping open reading frames (ORFs), which can be classified as 3', 3' (between ORFs in opposite orientations) or 5', 3' (between ORFs in the same orientation). The one or more sense codons (i.e. those to be replaced) may be found within both classes of overlap in the parent genome.

If the replacement of the one or more sense codons of each ORF within an overlap can be achieved without changing the encoded protein sequence of either ORF (i.e. by introducing synonymous codon(s)) then it may not be necessary to edit (e.g. refactor) the parent genome. However, when the encoded protein sequence is changed by the replacement of the one or more sense codons, (i.e. one or more synonymous sense codons are not introduced into one or both of the ORFs), then it may be necessary to edit (e.g. refactor) the parent genome.

Thus, in some embodiments one or more pairs of genes which share an overlapping region comprising the one or more sense codons in the parent genome are refactored. "Refactored" means that the genes are reorganised to prevent changes to the encoded protein sequences.

Preferably, the pairs of genes are those in which sense codon replacements (e.g. defined synonymous codon replacements) would change the encoded protein sequence of both or either of the pair of genes. Most preferably, all pairs of genes which share an overlapping region comprising the one or more sense codons in the parent genome are refactored, wherein the pairs of genes are those in which sense codon replacements (e.g. defined synonymous codon replacements) would change the encoded protein sequence of both or either of the pair of genes.

For 3',3' overlaps (i.e. pairs of genes in opposite orientations) a synthetic insert may be inserted between the genes. For 3',3' overlaps the synthetic insert may comprise the overlapping region.

For 5', 3' overlaps (i.e. pairs of genes in the same orientation, comprising an upstream gene and a downstream gene) a synthetic insert may be inserted between the genes. For 5',3' overlaps the synthetic insert may comprise: (i) a stop codon; (ii) about 20-200 bp, or 20-100 bp, or 20-50 bp, from upstream of the overlapping region; and (iii) the overlapping region. Preferably, the synthetic insert comprises: (i) a stop codon; (ii) about 20 bp from upstream of the overlapping region; and (iii) the overlapping region. This preserves the sequence of the RBS for the downstream ORF and the distance between this RBS and its start codon.

In preferred embodiments the stop codon is in frame with the original start site for the downstream gene. Preferably the stop codon is TAA.

Aside from the specific mutations described above, i.e. those aimed at reducing the amount of one or more sense codons (e.g. replacements of one or more sense codons and/or refactoring) and those aimed at reducing the amount of amber stop codons, the synthetic prokaryotic genome may comprise 1000 or fewer, 100 or fewer, 50 or fewer, 20 or fewer, 10 or fewer additional (i.e. non-programmed) mutations relative to the parent genome. Preferably the synthetic prokaryotic genome comprises $2 \times 10^{-4}$ or fewer additional or non-programmed mutations per target codon (i.e. per occurrence of the one or more sense codons in the parent genome).

Polynucleotides

The invention provides polynucleotides comprising one or more genes with no occurrences of one or more sense codons. The polynucleotides may comprise two or more, three or more, four or more, five or more, ten or more, twenty or more, thirty or more, forty or more, fifty or more, 100 or more, 200 or more, 500 or more, 600 or more, 700 or more, 800 or more, 900 or more, 1000 or more, 1500 or more, or 2000 or more genes with no occurrences of one or more sense codons. Preferably, the polynucleotides comprise 100 or more genes with no occurrences of one or more sense codons. More preferably, the polynucleotides comprise 1000 or more genes with no occurrences of one or more sense codons.

The one or more sense codons may consist of one, two, three, four, five, six, seven, or eight sense codons. Preferably, the one or more sense codons consist of one sense codon or two sense codons, most preferably two sense codons. Thus, in preferred embodiments the polynucleotides comprise 100 or more genes with no occurrences of one or two sense codons. In other preferred embodiments the polynucleotides comprise 1000 or more genes with no occurrences of one or two sense codons.

The one or more sense codons may be selected from: TCG, TCA, AGT, AGC, GCG, GCA, GTG, GTA, CTG, CTA, TTG, TTA, ACG, ACA, CCG, CCA, CGG, CGA, CGT, CGC, AGG, AGA, GGG, GGA, GGT, GGC, ATT, and ATC. Alternatively, the one or more sense codons may be selected from: TCG, TCA, TCT, TCC, AGT, AGC, GCG, GCA, GCT, GCC, CTG, CTA, CTT, CTC, TTG, and TTA. Preferably, the one or more sense codons are selected from: TCG, TCA, AGT, AGC, GCG, GCA, CTG, CTA, TTG, and TTA. More preferably, the one or more sense codons are selected from TCG, TCA, TTG, TTA, GCG and GCA. Most preferably, the one of more sense codons are TCG and/or TCA.

The one or more sense codons in the genes may be replaced with synonymous sense codons. Preferably, the replacement is a defined replacement, i.e. one sense codon is replaced with a single synonymous sense codon.

For example GCG may be replaced with GCT or GCC; GCA may be replaced with GCT or GCC; TCG may be replaced with TCT, TCC, AGT, or AGC; TCA may be replaced with TCT, TCC, AGT, or AGC; AGT may be replaced with TCG, TCA, TCT, or TCC; AGC may be replaced with TCG, TCA, TCT, or TCC; CTG may be replaced with CTT, CTC, TTG or TTA; CTA may be replaced with CTT, CTC, TTG or TTA; TTG may be replaced with CTG, CTA, CTT or CTC; or TTA may be replaced with CTG, CTA, CTT or CTC. Preferably the one or more defined sense codon replacements are selected from: GCG to GCT or GCC; GCA to GCT or GCC; TCG to AGT or AGC; TCA to AGT or AGC; AGT to TCA or TCT; AGC to TCG or TCC or TCA; TTG to CTT; and TTA to CTC. More preferably, TCG and/or TCA are replaced with AGC and/or AGT. Most preferably, TCG are replaced with AGC and/or TCA are replaced with AGT.

In some embodiments the genes are those for which there is evidence of translation and/or of the predicted protein product.

In preferred embodiments the genes are essential genes. The essential genes may be selected from one ore more of the list consisting of: ribF, IspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, yafF, hemB, secD, secF, ribD, ribE, thiL, dxs, ispA, dnaX, adk, hemH, lpxH, cysS, folD, entD, mrdB, mrdA, nadD, holA, rlpB, leuS, lnt, glnS, fldA, cydA, infA, cydC, ftsK, lolA, serS, rpsA, msbA, lpxK, kdsB, mukF, mukE, mukB, asnS, fabA, mviN, rne, fabD, fabG, acpP, tmk, holB, lolC, lolD, lolE, purB, minE, minD, pth, prsA, ispE, lolB, hemA, prfA, prmC, kdsA, topA, ribA, fabI, tyrS, ribC, ydiL, pheT, pheS, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, lepB, rpoE, pssA, yfiO, rplS, trmD, rpsP, ffh, grpE, csrA, ispF, ispD, ftsB, eno, pyrG, chpR, lgt, fbaA, pgk, yqgD, metK, yqgF, plsC, ygiT, parE, ribB, cca, ygjD, tdcF, yraL, yhbV, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, secY, rplO, rpmD, rpsE, rplR, rplF, rpsH, rpsN, rplE, rplX, rplN, rpsQ, rpmC, rplP, rpsC, rplV, rpsS, rplB, rplW, rplD, rplC, rpsJ, fusA, rpsG, rpsL, trpS, yrfF, asd, rpoH, ftsX, ftsE, ftsY, yhhQ, bcsB, glyQ, gpsA, rfak, kdtA, coaD, rpmB, dfp, dut, gmk, spoT, gyrB, dnaN, dnaA, rpmH, rnpA, yidC, tnaB, glmS, glmU, wzyE, hemD, hemC, yigP, ubiB, ubiD, hemG, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, and dnaC.

Preferably, the essential genes may be selected from one ore more of the list consisting of: ribF, IspA, ispH, dapB, folA, imp, yabQ, lpxC, secM, secA, can, folK, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, yafF, hemB, secD, secF, ribD, ribE, thiL, dxs, ispA, dnaX, adk, hemH, lpxH, cysS, folD, entD, mrdB, mrdA, nadD, holA, ripB, leuS, lnt, ginS, fldA, cydA, infA, cydC, ftsK, lolA, serS, rpsA, msbA, lpxK, kdsB, mukF, mukE, mukB, asnS, fabA, mviN, rne, fabD, fabG, acpP, tmk, holB, lolC, lolD, lolE, purB, minE, minD, pth, prsA, ispE, lolB, hemA, prfA, prmC, kdsA, topA, ribA, fabI, tyrS, ribC, ydiL, pheT, pheS, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, lepB, rpoE, pssA, yfiO, rplS, trmD, rpsP, ffh, grpE, csrA, ispF, ispD, ftsB, eno, pyrG, chpR, lgt, fbaA, pgk, yqgD, metK, yqgF, plsC, ygiT, parE, ribB, cca, ygjD, tdcF, yraL, yhbV, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, secY, rplO, rpmD, rpsE, rplR, rplF, rpsH, rpsN, rplE, rplX, rplN, rpsQ, rpmC, rplP, rpsC, rplV, rpsS, rplB, rplW, rplD, rplC, rpsJ, fusA, rpsG, rpsL, trpS, yrfF, asd, rpoH, ftsX, ftsE, ftsY, yhhQ, bcsB, glyQ, gpsA, rfaK, kdtA, coaD, rpmB, dfp, dut, gmk, spoT, gyrB, dnaN, dnaA, rpmH, mpA, yidC, tnaB, glmS, glmU, wzyE, hemD, hemC, yigP, ubiB, ubiD, hemG, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, and dnaC.

Accordingly, the invention provides polynucleotides comprising one or more essential genes with no TCG codons and/or TCA codons, wherein the one or more essential genes is selected from the list consisting of: ribF, IspA, ispH, dapB, folA, imp, yabQ, lpxC, secM, secA, can, folK, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, yafF, hemB, secD, secF, ribD, ribE, thiL, dxs, ispA, dnaX, adk, hemH, lpxH, cysS, folD, entD, mrdB, mrdA, nadD, holA, ripB, leuS, lnt, glnS, fldA, cydA, infA, cydC, ftsK, lolA, serS, rpsA, msbA, lpxK, kdsB, mukF, mukE, mukB, asnS, fabA, mviN, me, fabD, fabG, acpP, tmk, holB, lolC, lolD, lolE, purB, minE, minD, pth, prsA, ispE, lolB, hemA, prfA, prmC, kdsA, topA, ribA, fabI, tyrS, ribC, ydiL, pheT, pheS, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, lepB, rpoE, pssA, yfiO, rplS, trmD, rpsP, ffh, grpE, csrA, ispF, ispD, ftsB, eno, pyrG, chpR, lgt, fbaA, pgk, yqgD, metK, yqgF, plsC, ygiT, parE, ribB, cca, ygjD, tdcF, yraL, yhbV, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, secY, rplO, rpmD, rpsE, rplR, rplF, rpsH, rpsN, rplE, rplX, rplN, rpsQ, rpmC, rplP, rpsC, rplV, rpsS, rplB, rplW, rplD, rplC, rpsJ, fusA, rpsG, rpsL, trpS, yrfF, asd, rpoH, ftsX, ftsE, ftsY, yhhQ, bcsB, glyQ, gpsA, rfaK, kdtA, coaD, rpmB, dfp, dut, gmk, spoT, gyrB, dnaN, dnaA, rpmH, mpA, yidC, tnaB, glmS, glmU, wzyE, hemD, hemC, yigP, ubiB, ubiD, hemG, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, and dnaC. Preferably, the polynucleotides comprise two or more, three or more, four or more, five or more, ten or more, twenty or more, thirty or more, forty or more, fifty or more, 100 or more, or 200 or more essential genes with no TCG codons and/or TCA codons.

In some embodiments the polynucleotide comprises a polynucleotide sequence which is at least 80%, 85%, 90%, 95%, 98%, 99%, 99.5%, 99.8%, or 99.9%, or 100% identical to SEQ ID NO: 1 or SEQ ID NO:2 or to any fragment of SEQ ID NO:1 or SEQ ID NO:2, preferably wherein the fragment is at least 10 kb, 20 kb, 50 kb, 100 kb, or 500 kb in length.

Preferably the polynucleotide is viable. I.e. the polynucleotide may incorporated into a genome such that the genome is a viable genome. Preferably, the polynucleotide may replace a corresponding region of the parent genome and retain viability of said genome. As used herein, a "viable genome" refers to a genome that contains nucleic acid sequences sufficient to cause and/or sustain viability of a cell, e.g., those encoding molecules required for replication, transcription, translation, energy production, transport, production of membranes and cytoplasmic components, and cell division. Thus, the present invention also provides a viable synthetic prokaryotic genome (e.g. a viable synthetic *E. coli* genome) comprising the polynucleotide of the present invention.

The invention provides a polynucleotide which is at least 98%, 98.5%, 99%, 99.5%, 99.6%, 99.7%, 99.8%, 99.9%, 99.95% or 100% identical to SEQ ID NO:1 or SEQ ID NO:2 or to any fragment of SEQ ID NO: 1 or SEQ ID NO:2, preferably wherein the fragment is at least 10 kb, 20 kb, 50 kb, 100 kb, or 500 kb in length.

Host Cells and Uses Thereof

Host Cells

The invention also provides a host cell comprising the synthetic prokaryotic genome or the polynucleotide of the invention. The host cell may be an isolated host cell.

The host cell of the present invention is a prokaryotic cell. More preferably, the host cell is a bacterial cell. Preferably the bacterial host cell is suitable for heterologous protein production, in particular the production of polypeptides comprising one or more non-proteinogenic amino acids (for instance those described by Ferrer-Miralles, N. and Villaverde, A., 2013. Microbial Cell Factories, 12:113). Suitable bacterial host cells include: escherichia (e.g. *Escherichia coli*), caulobacteria (e.g. *Caulobacter crescentus*), phototrophic bacteria (e.g. *Rodhobacter sphaeroides*), cold adapted bacteria (e.g. *Pseudoalteromonas haloplanktis, Shewanella* sp. strain Ac10), pseudomonads (e.g. *Pseudomonas fluorescens, Pseudomonas putida, Pseudomonas aeruginosa*), halophilic bacteria (e.g. *Halomonas elongate, Chromohalobacter salexigens*), streptomycetes (e.g. *Streptomyces lividans, Streptomyces griseus*), nocardia (e.g. *Nocardia lactamdurans*), mycobacteria (e.g. *Mycobacterium smegmatis*), coryneform bacteria glutamicum, (e.g. *Corynebacterium Corynebacterium ammoniagenes, Brevibacterium lactofermentum*), bacilli (e.g. *Bacillus subtilis, Bacillus brevis, Bacillus megaterium, Bacillus licheniformis, Bacillus amyloliquefaciens*), and lactic acid bacteria (e.g. *Lactococcus lactis, Lactobacillus plantarum, Lactobacillus casei, Lactobacillus reuteri, Lactobacillus gasseri*). In some embodiments the bacterial host cell is gram-negative bacterium.

Preferably, the host cell is an *Escherichia coli, Salmonella enterica*, or *Shigella dysenteriae*. More preferably, the host cell is an *E. coli*. Suitable *E. coli* host cells include MDS42, K-12, MG1655, BL21, BL21(DE3), AD494, Origami, HMS174, BLR(DE3), HMS174(DE3), Tuner(DE3), Origami2(DE3), Rosetta2(DE3), Lemo21(DE3), NiCo21 (DE3), T7 Express, SHuffle Express, C41(DE3), C43(DE3), and m15 pREP4 or derivatives thereof (Rosano, G. L. and Ceccarelli, E. A., 2014. Frontiers in microbiology, 5, p. 172). Most preferably, the host cell is MDS42, MG1655, or BL21 or a derivative thereof. MG1655 is considered as the wild type strain of *E. coli*. The GenBank ID of genomic sequence of this strain is U00096. BL21 is widely available commercially. For example, it can be purchased from New England BioLabs with catalog number C2530H.

The host cell may preferably be the same as that from which the synthetic prokaryotic genome or polynucleotide is from (or derived from). For example, if the synthetic prokaryotic genome is a synthetic *E. coli* genome then the host cell is preferably an *E. coli*. When the parent genome of a cell has been modified to produce the synthetic prokaryotic genome of the present invention, the host cell is preferably the same cell, i.e. preferably the host cell comprising the synthetic prokaryotic genome is the same as the host cell of the parent genome (the parent host cell).

The host cell may be viable, i.e. able to grow and replicate.

When the genome of a cell has been modified to produce the synthetic prokaryotic genome of the present invention, the synthetic prokaryotic genome is preferably one which, when present in the parent host cell, does not substantially decrease the growth rate. Thus, preferably the host cell comprising the synthetic prokaryotic genome does not have a substantially decreased growth rate relative to the host cell comprising the parent genome. In some embodiments the host cell comprising the synthetic prokaryotic genome has a doubling time less than 4 times, 3 times, 2 times, or about 1.6 times, slower than the host cell comprising the host cell comprising the parent genome. The doubling time can be determined by any method known to those of skill in the art. In some embodiments the doubling time is determined at 37° C., 25° C. or 42° C., in LB media.

When the genome of a cell has been modified to produce the synthetic prokaryotic genome of the present invention, the synthetic prokaryotic genome is preferably one which, when present in the parent host cell, does not cause any substantial phenotypical changes. Thus, preferably the host cell comprising the synthetic prokaryotic genome does not have any substantial phenotypical changes relative to the host cell comprising the parent genome. In some embodiments the host cell comprising the synthetic prokaryotic genome has a mean cell length less than 100%, 50%, or about 20% greater than the host cell comprising the parent genome. For example, the cell length may be about 1.5 to 3 microns. The cell length can be determined by any method known to those of skill in the art. In some embodiments the host cell comprising the synthetic prokaryotic genome has a proteome that is not substantially different from the proteome of the host cell comprising the parent genome. The proteome can be determined by any method known to those of skill in the art.

Reassignment to Alternative Canonical Amino Acids

In some embodiments the one or more sense codons (i.e. those removed from the parent genome) are reassigned to encode alternative canonical amino acids. For example, if TCG and TCA have been removed, one or both may be reassigned to encode a canonical amino acid other than serine (e.g. alanine).

For instance, the synthetic prokaryotic genome of the present invention substantially or completely lacks one or more sense codons. Therefore, one or more tRNA or release factors may be deleted from the synthetic genome. For instance, a tRNA which decodes the one or more sense codons that have been replaced (or deleted) may be deleted from the synthetic prokaryotic genome. A tRNA which decodes one or more sense codons that have been replaced (or deleted) may be deleted and the synthetic prokaryotic genome will remain viable if the tRNA decodes only the one or more sense codons that have been replaced (or deleted); or alternatively if the tRNA decodes one or more sense codons that have been replaced (or deleted) and one or more sense codons that have not been replaced (or deleted), if the tRNA is dispensable for the one or more sense codons that have not been replaced (or deleted) (i.e. the one or remaining sense codons which the tRNA decodes are decoded by one or more alternative tRNAs). For example, if the synthetic prokaryotic genome lacks TCA sense codons, serT, encoding tRNA$^{Ser}_{UGA}$, may be deleted and/or if the synthetic prokaryotic genome lacks TCG sense codons, serU, encoding tRNA$^{Ser}_{CGA}$, may be deleted. The deletion of one or more tRNAs may be used, for instance, in combination with a reassigned, endogenous tRNA or an orthogonal aminoacyl-tRNA synthetase/tRNA pair to reassign the one or more sense codons to an alternative amino acid.

For example, if TCG and TCA have been removed from the synthetic prokaryotic genome, serT, encoding tRNA$^{Ser}_{UGA}$, and serU, encoding tRNA$^{Ser}_{CGA}$, may be deleted from the synthetic prokaryotic genome, and either the tRNA$_{CGA}$ can be reassigned (e.g. to tRNA$^{Ala}_{CGA}$) an orthogonal aminoacyl-tRNA synthetase/tRNA$_{CGA}$ pair may be introduced to the host cell (e.g. by a heterologous nucleic acid or by incorporation into the synthetic prokaryotic genome) to reassign TCG to an alternative canonical amino acid. Thus, in some embodiments, the host cell of the present invention further comprises one or more reassigned tRNAs and/or one or more heterologous nucleotides (e.g. plasmids) encoding one orthogonal aminoacyl-tRNA synthetase (aaRS)-tRNA pair. In some embodiments the host cell of the present invention further comprises a plasmid encoding an orthogonal aminoacyl-tRNA synthetase (aaRS)-tRNA pair. Alternatively, the orthogonal aminoacyl-tRNA synthetase (aaRS)-tRNA pair may be introduced into the host cell by incorporation into the synthetic prokaryotic genome. Thus, in some embodiments the synthetic prokaryotic genome encodes an orthogonal aminoacyl-tRNA synthetase (aaRS)-tRNA pair, preferably wherein the gene encoding the native tRNA has been deleted from the parent prokaryotic genome. In preferred embodiments the host cell of the present invention further comprises one or more reassigned tRNAs. Methods for reassigning tRNAs will be well known to those of skill in the art.

The reassignment to encode alternative canonical amino acids may increase biosafety. Thus, in some embodiments the host cell of the present invention has increased biosafety. Accordingly, the present invention provides host cells with improved biosafety.

For example, the reassignment to encode alternative canonical amino acids may render the host cell comprising the synthetic prokaryotic genome resistant to bacteriophage infection. One or more bacteriophage genes will typically comprise the one or more sense codons, thus when the one or more bacteriophage genes are translated an alternative canonical amino acid may be incorporated into the corresponding bacteriophage proteins. The incorporation of an alternative canonical amino acid may destabilise, disrupt or reduce the activity of said proteins, thus reducing the infectivity of the bacteriophage and rendering the host cell resistant to bacteriophage infection.

Thus, in some embodiments the host cell of the present invention is resistant to phage infection. For example, when the genome of a cell has been modified to produce the synthetic prokaryotic genome of the present invention, the synthetic prokaryotic genome may be one which, when present in the parent host cell, increases resistance to phage infection. Thus, in some embodiments the host cell comprising the synthetic prokaryotic genome has increased phage resistance relative to the host cell comprising the parent genome.

Accordingly, the present invention provides phage-resistant host cells and host cells with increased phage resistance.

The reassignment to encode alternative canonical amino acids may also allow genetic material, e.g. antibiotic resistance genes, to be designed such that they are functional in the recoded strain, but not in wild type strains. For example, the genetic material may be incorporated into the host cell of the present invention (e.g. by a heterologous nucleic acid or by incorporation into the synthetic prokaryotic genome) such that the host cell will grow in certain conditions (e.g. in the presence of an antibiotic), but other host cells (e.g. the parent host cell) will not. Thus, in some embodiments the host cell of the present invention may render a composition comprising the host cell more resistant to contamination by other host cells (e.g. other prokaryotes).

Reassignment to Non-Proteinogenic Amino Acids

In some embodiments the one or more sense codons (i.e. those removed from the parent genome) are reassigned to encode non-canonical amino acids (non-proteinogenic amino acids).

Thus, the present invention provides for use of a host cell according to the present invention for producing polypeptides comprising one or more non-proteinogenic amino acids, preferably two or more non-proteinogenic amino acids, most preferably three or more non-proteinogenic amino acids.

The present invention also provides polypeptides obtained or obtainable by using a host cell according to the present invention. In some embodiments, the polypeptides comprise one or more non-proteinogenic amino acids, preferably two or more non-proteinogenic amino acids, most preferably three or more non-proteinogenic amino acids. Thus, the present invention also provides polypeptides comprising two or more non-proteinogenic amino acids and polypeptides comprising three or more non-proteinogenic amino acids.

As used herein, "non-proteinogenic amino acids" (also known as "non-coded amino acids" or "noncanonical amino acids") are amino acids that are not naturally encoded or found in the genetic code. Despite the use of only 22 amino acids by the translational machinery to assemble proteins (the proteinogenic amino acids-20 in the standard genetic code and an additional 2 that can be incorporated by special translation mechanisms), over 140 amino acids are known to occur naturally in proteins and thousands more may occur in nature or be synthesized in the laboratory. Thus, non-proteinogenic amino acids may comprise any amino acid excluding L-alanine, L-cysteine, L-aspartic acid, L-glutamic acid, L-phenylalanine, glycine, L-histidine, L-isoleucine, L-lysine, L-leucine, L-methionine, L-asparagine, L-proline, L-glutamine, L-arginine, L-serine, L-threonine, L-valine, L-tryptophan and L-tyrosine, and optionally L-pyrrolysine and L-selenocysteine.

In some embodiments, the non-proteinogenic amino acids are unnatural amino acids (UAAs).

The non-proteinogenic amino acid or UAA is not particularly limited. Suitable non-proteinogenic amino acid and UAAs will be well known to those of skill in the art, for example those disclosed in Neumann, H., 2012. FEBS letters, 586(15), pp. 2057-2064; and Liu, C. C. and Schultz, P. G., 2010. Annual review of biochemistry, 79, pp. 413-444. In some embodiments the non-proteinogenic amino acid and/or UAAs are selected from one or more of: p-Acetylphenylalanine, m-Acetylphenylalanine, O-allyltyrosine, Phenylselenocysteine, p-Propargyloxyphenylalanine, p-Azidophenylalanine, p-Boronophenylalanine, O-methyltyrosine, p-Aminophenylalanine, p-Cyanophenylalanine, m-Cyanophenylalanine, p-Fluorophenylalanine, p-Iodophenylalanine, p-Bromophenylalanine, p-Nitrophenylalanine, L-DOPA, 3-Aminotyrosine, 3-Iodotyrosine, p-Isopropylphenylalanine, 3-(2-Naphthyl) alanine, Biphenylalanine, Homoglutamine, D-tyrosine, p-Hydroxyphenyllactic acid, 2-Aminocaprylic acid, Bipyridylalanine, HQ-alanine, p-Benzoylphenylalanine, o-Nitrobenzylcysteine, o-Nitrobenzylserine, 4,5-Dimethoxy-2-nitrobenzylserine, o-Nitrobenzyllysine, o-Nitrobenzyltyrosine, 2-Nitrophenylalanine, Dansylalanine, p-Carboxymethylphenylalanine, 3-Nitrotyrosine, Sulfotyrosine, Acetyllysine, Methylhistidine, 2-Aminononanoic acid, 2-Aminodecanoic acid, Pyrrolysine, Cbz-lysine, Boc-lysine and Allyloxycarbonyllysine.

Prokaryotes, e.g. *E. coli*, are not typically able to incorporate most eukaryotic post-translational modifications, such as ubiquitination, glycosylation and phosphorylation, nor are they typically capable of other eukaryotic maturation processes, and proteolytic protein maturation. In addition, correct disulphide bond formation and lipopolysaccharide contaminations can be troublesome (see Ovaa, H., 2014. Frontiers in chemistry, 2, p. 15). However, therapeutic proteins, such as antibodies, enzymes and cytokines commonly carry post-translational modifications and disulphide bonds, and often require proteolytic maturation to attain their correctly folded state. Thus, the majority of therapeutic proteins are produced in eukaryotic and mammalian cell systems. However, expression in prokaryotic host cells e.g. *E. coli* is in general cheaper, more susceptible to genetic modifications, and versatile with regard to mutant library development, and suitable for industrial scale fermentation (Ovaa, H., 2014. Frontiers in chemistry, 2, p. 15).

Thus, in some embodiments the polypeptides are therapeutic polypeptides, preferably wherein mammalian protein modifications have been introduced via one or more non-proteinogenic amino acids. For example, amber codon suppression has previously been used to incorporate one or more non-proteinogenic amino acids (i.e. mammalian protein modifications) into therapeutic polypeptides. The present invention allows two or more non-proteinogenic amino acids to be incorporated. Thus, the present invention provides a therapeutic polypeptide comprising two or more non-proteinogenic amino acids.

The synthetic prokaryotic genome of the present invention substantially or completely lacks one or more sense codons, therefore one or more tRNA or release factors may be deleted from the synthetic genome. For example, a tRNA which decodes only the one or more sense codons that have been replaced (or deleted) may be deleted from the synthetic prokaryotic genome. For example, if the synthetic prokaryotic genome lacks TCA sense codons, serT, encoding tRNA$^{Ser}_{UGA}$, may be deleted and/or if the synthetic prokaryotic genome lacks TCG sense codons, serU, encoding tRNA$^{Ser}_{CGA}$, may be deleted. The synthetic prokaryotic genome may then be used (in conjunction with an orthogonal aminoacyl-tRNA synthetase-tRNA pair) to direct the incorporation of non-proteinogenic amino acids into proteins.

Genetic code expansion uses an orthogonal aminoacyl-tRNA synthetase (aaRS)-tRNA pair to direct the incorporation of non-proteinogenic amino acids into proteins, in response to an unassigned codon (e.g. the amber stop codon, UAG) introduced at the desired site in a gene of interest. The orthogonal synthetase does not recognize endogenous tRNAs, and specifically aminoacylates an orthogonal cognate tRNA (which is not an efficient substrate for endogenous synthetases) with the non-proteinogenic amino acids provided to (or synthesized by) the cell (Chin, J. W., 2017. Nature, 550(7674), 53-60). The person skilled in the art would be able to identify and/or generate suitable orthogonal aminoacyl-tRNA synthetase (aaRS)-tRNA pairs (e.g. Elliott, T. S. et al., 2014. Nat Biotechnol 32, 465-472; Elliott, T. S., et al., 2016. Cell Chem Biol 23, 805-815; and Krogager, T. P. et al., 2018. Nat Biotechnol 36, 156-159). Thus, in some embodiments, the host cell of the present invention further comprises one or more heterologous nucleotides (e.g. plasmids) encoding one orthogonal aminoacyl-tRNA synthetase (aaRS)-tRNA pair. In preferred embodiments the host cell of the present invention further comprises a plasmid encoding an orthogonal aminoacyl-tRNA synthetase (aaRS)-tRNA pair. Alternatively, the orthogonal aminoacyl-tRNA synthetase (aaRS)-tRNA pair may be introduced into the host cell by incorporation into the synthetic prokaryotic genome. Thus, in some embodiments the synthetic prokaryotic genome encodes an orthogonal aminoacyl-tRNA synthetase (aaRS)-tRNA pair, preferably wherein the gene encoding the native tRNA has been deleted from the parent prokaryotic genome.

Thus, in some embodiments the host cell of the present invention further comprises one or more heterologous nucleotides (e.g. plasmids) which comprise one or more genes comprising said sense codons. In preferred embodiments the host cell further comprises a plasmid comprising a gene comprising said sense codons. The one or more sense codons may be present in a desired site in the gene, preferably wherein the desired site allows incorporation of one or more non-proteinogenic amino acids (i.e. mammalian protein modifications) into polypeptides, preferably therapeutic polypeptides.

In other embodiments said sense codons may be present in one or more genes in the synthetic prokaryotic genome (for example, the heterologous nucleotide may be incorporated into the synthetic prokaryotic genome). The one or more sense codons may be present in a desired site in the gene, preferably wherein the desired site allows incorporation of one or more non-proteinogenic amino acids (i.e. mammalian protein modifications) into polypeptides, preferably therapeutic polypeptides.

For example, if TCG and TCA have been removed from the synthetic prokaryotic genome, serT, encoding tRNA$^{Ser}_{UGA}$, and serU, encoding tRNA$^{Ser}_{CGA}$, may be deleted from the synthetic prokaryotic genome, and an orthogonal aminoacyl-tRNA synthetase/tRNA$_{CGA}$ pair may be used in combination with (heterologous) genes comprising the TCG codon, to encode polypeptides comprising one or more non-proteinogenic amino acid. Thus, the host cell of the present invention may, for instance, further comprise: (i) a plasmid encoding an orthogonal aminoacyl-tRNA synthetase/tRNA$_{CGA}$ pair; and (ii) a plasmid comprising a gene comprising one or more TCG codons. Similarly, if AGT and AGC are removed, serV, encoding tRNA$^{Ser}_{GCU}$ may be deleted from the synthetic prokaryotic genome, and an orthogonal aminoacyl-tRNA synthetase/tRNA$_{ACU}$ pair and/or an orthogonal aminoacyl-tRNA synthetase/tRNA$_{GCU}$ pair may be used. Similarly, if CTG and CTA are removed, leuP, Q, T, V encoding tRNA$^{Leu}_{CAG}$, and leuW, encoding tRNA$^{Leu}_{UAG}$, may be deleted from the synthetic prokaryotic genome, and an orthogonal aminoacyl-tRNA synthetase/tRNA$_{CAG}$ pair may be used. Similarly, if TTG and TTA are removed, leuX, encoding tRNA$^{Leu}_{CAA}$, and leuZ, encoding tRNA$^{Leu}_{UAA}$, may be deleted from the synthetic prokaryotic genome, and an orthogonal aminoacyl-tRNA synthetase/tRNA$_{CAA}$ pair and/or an orthogonal aminoacyl-tRNA synthetase/tRNA$_{UAA}$ pair may be used may be used. Similarly, if GCG and GCA are removed, alaT, U, V, encoding tRNA$^{Ala}_{UGC}$ may be deleted from the synthetic prokaryotic genome, and an orthogonal aminoacyl-tRNA synthetase/tRNA$_{CGC}$ pair may be used.

In some embodiments the synthetic prokaryotic genome lacks genes encoding release factors (e.g. RF1) and/or the host cell lacks release factors (e.g. RF1) to increase the efficiency of incorporation of non-proteinogenic amino acids.

Method for Producing a Synthetic Genome

In one aspect, the invention provides a method for producing a synthetic genome comprising:
(a) providing a parent genome;
(b) carrying out one or more rounds of recombination-mediated genetic engineering on the parent genome, to produce two or more different partially synthetic genomes; and
(c) carrying out one or more rounds of directed conjugation with the two or more different partially synthetic genomes to produce a synthetic genome.

Recombination-Mediated Genetic Engineering

Preferably one or more rounds of recombination-mediated genetic engineering are used to edit 10-1000 kb, 50-1000 kb, 100-1000 kb, or 100-500 kb of the parent genome to provide two or more different partially synthetic genomes. Thus, in preferred embodiments each round of recombination-mediated genetic engineering inserts or replaces 10 kb or more, 50 kb or more, 100 kb or more, or about 100 kb of DNA in the parent genome.

As used herein, the term "recombination-mediated genetic engineering" (also known as "recombineering") is a method for genetic engineering (i.e. editing genomes) based on homologous recombination systems. Typically recombineering is based on homologous recombination in *Escherichia coli* mediated by bacteriophage proteins, either RecE/RecT from Rac prophage or Redαβδ from bacteriophage lambda. Any suitable method of recombination-mediated genetic engineering may be used. Methods for recombination-mediated genetic engineering will be well known to those of skill in the art.

In "classical recombination" (exemplified by lambda red mediated recombination in *E. coli*), short regions of synthetic DNA may be inserted into the genome or used to replace genomic DNA in a two-step process: i) transformation of cells with linear double stranded DNA (dsDNA) carrying a stretch of synthetic DNA, coupled with a positive selection marker, and flanked by a homology region (HR) to the target region of the genome on each end, and ii) recombination mediated by the homologous regions, followed by selection for genomic integration by virtue of the positive selection marker. This approach can be used to insert or replace 2-3 kb of genomic DNA. Thus, if classical recombination is used, many rounds of recombination-mediated genetic engineering would be required to edit 100-500 kb of the parent genome.

Thus, in preferred embodiments the one or more rounds of recombination-mediated genetic engineering comprise one or more rounds of replicon excision for enhanced genome engineering through programmed recombination (REXER).

REXER is described in WO 2018/020248 (herein incorporated by reference). Each round of REXER may be used to insert or replace about 50 kb to 250 kb, or about 100 kb of DNA in the parent genome.

Thus, the one or more rounds of recombination-mediated genetic engineering may comprise:
i) providing a host cell (e.g. *E. coli*), wherein the host cell comprises an episomal replicon (e.g. a plasmid or a bacterial artificial chromosome) and a target nucleic acid (e.g. the genome), wherein the episomal replicon comprises a donor nucleic acid sequence (i.e. a synthetic region), wherein the donor nucleic acid sequence comprises in order: 5'-homologous recombination sequence 1-sequence of interest-homologous recombination sequence 2-3', wherein the sequence of interest comprises a positive selectable marker, and wherein the target nucleic acid comprises in order: 5'-homologous recombination sequence 1-negative selectable marker-homologous recombination sequence 2-3';
ii) providing helper protein(s) capable of supporting nucleic acid recombination in said host cell (e.g. lambda Red proteins);
iii) providing helper protein(s) and/or RNAs capable of supporting nucleic acid excision in said host cell (e.g. CRISPR/Cas9 proteins/RNAs);
iv) inducing excision of said donor nucleic acid sequence;
v) incubating to allow recombination between the excised donor nucleic acid and said target nucleic acid; and
vi) selecting for recombinants having incorporated said donor nucleic acid into said target nucleic acid.

Suitably selecting for recombinants having incorporated said donor nucleic acid into said target nucleic acid comprises selection for gain of the positive selectable marker of the donor nucleic acid and loss of the negative selectable marker of the target nucleic acid. Suitably selection for gain of the positive selectable marker of the donor nucleic acid and loss of the negative selectable marker of the target nucleic acid is carried out simultaneously. Suitably said sequence of interest comprises both a positive selectable marker and a negative selectable marker. Suitably the negative selectable marker is selected from the group consisting of sacB (sucrose sensitivity), rpsL (S12 ribosomal protein-streptomycin sensitivity), or phe$^{ST251A\_A294G}$ (4-chlorophenylalanine sensitivity). Suitably the positive selectable marker is selected from the group consisting of Cm$^R$ (chloramphenicol resistance), Kan$^R$ (kanamycin resistance), Hyg$^R$ (hygromycin resistance), Gentamycin$^R$ (gentamycin resistance), or tetracycline$^R$ (tetracycline resistance). Suitably the step of selecting for recombinants comprises sequential selection for said positive and negative markers, or sequential selection for said negative and positive markers. Suitably the step of selecting for recombinants comprises simultaneous selection for said positive and negative markers.

Suitably said method as described above further comprises the step of inducing at least one double stranded break in the target nucleic acid sequence, wherein said double stranded break is between said homologous recombination sequence 1 and said homologous recombination sequence 2. Suitably at least two double stranded breaks are induced in the target nucleic acid sequence, wherein each said double stranded break is between said homologous recombination sequence 1 and said homologous recombination sequence 2.

Suitably said excised donor nucleic acid begins with said homologous recombination sequence 1 and ends with said homologous recombination sequence 2.

Suitably said episomal replicon comprises a negative selectable marker independent of the donor nucleic acid sequence. Suitably said method comprises the further step of selecting for loss of the episomal replicon by selecting for loss of said negative selectable marker independent of the donor nucleic acid sequence. Suitably said episomal replicon comprises in order: excision cut site 1-donor nucleic acid sequence-excision cut site 2. Suitably said target nucleic acid possesses its own origin of replication capable of functioning within said host cell. Suitably said episomal replicon is a plasmid nucleic acid. Suitably said episomal replicon is a bacterial artificial chromosome (BAC). Suitably said target nucleic acid is the host cell genome.

The episomal replicon (e.g. BAC) may be assembled by homologous recombination, for example in *S. cerevisiae*, as described in Kouprina, N., et al., 2004. Methods Mol Biol 255, 69-89. The assembly may combine: 7-14 stretches of synthetic DNA, each 6-13 kb in length; a selection construct (comprising a negative selection marker and/or a positive selection marker); and a BAC shuttle vector backbone. The stretches of synthetic DNA may collectively correspond to the donor nucleic acid sequence (i.e. the synthetic region) in the episomal replicon, wherein each stretch comprises 80-200 bp of overlapping DNA sequence with each other, and wherein the overlap regions are free of any recoding targets. The stretches may be supplied in pSC101 or pST vectors flanked by suitable restriction sites (e.g. BsaI, AvrII, SpeI, or XbaI). Thus, during assembly the synthetic DNA stretches may be excised by digestion with the corresponding restriction enzymes. Assembly of the episomal replicon may be verified by sequencing.

Suitably the two homology regions may be 30-100 bp, or 40-50 bp, or about 50 bp in length.

CRISPR/Cas9 machinery may be used to for excision. In some embodiments the CRISPR/Cas9 machinery comprises Cas9, tracrRNA and two spacer RNAs, wherein the spacer RNAs target the two homology regions for excision. In preferred embodiments, the spacer RNAs are linear double stranded spacers. In other embodiments, the CRISPR/Cas9 machinery comprises Cas9 and two sgRNAs, wherein the sgRNAs target the two homology regions for excision.

Lambda red recombination machinery may be used for recombination. The lambda red recombination machinery may comprise lambda alpha/beta/gamma.

The method may comprise performing one or more rounds of REXER, i.e. the steps as described above with a first donor nucleic acid sequence, choosing further donor sequence(s) contiguous with said first donor nucleic acid sequence, and repeating said steps with said further donor nucleic acid sequence(s) until the partially synthetic genome has been assembled. This is known as genome stepwise interchange synthesis (GENESIS), described in Wang, K. et al., 2016. Nature 539, 59-64 and is shown schematically in FIG. 4.

In preferred embodiments the donor sequence(s) correspond to regions of the synthetic genome according to the present invention and/or to polynucleotides according to the present invention.

Thus, the donor sequence(s) (i.e. synthetic region) may comprise 20 or fewer occurrences of one or more sense codons; and/or the donor sequence(s) may comprise 10 or more, 20 or more, or 100 or more genes with no occurrences of one or more sense codons.

The donor sequence(s) (i.e. synthetic region) may be identical to sequences (i.e. non-synthetic regions) of the parent genome except that they have 50 or fewer, 20 or fewer, 10 or fewer, 5 or fewer, or 0 occurrences of each of one or more sense codons; and/or comprise less than 10%, 5%, 2%, 1%, 0.5%, 0.1% of the occurrences of each of one or more sense codons, relative to the corresponding region in the parent genome; and/or comprise 10 or more, 20 or more, or 100 or more genes with no occurrences of one or more sense codons.

The donor sequence(s) (i.e. synthetic region) may also be refactored relative to the sequences (i.e. non-synthetic regions) of the parent genome. For 3',3' overlaps (i.e. pairs of genes in opposite orientations) a synthetic insert may be inserted between the genes. For 3',3' overlaps the synthetic insert may comprise the overlapping region. For 5', 3' overlaps (i.e. pairs of genes in the same orientation) a synthetic insert may be inserted between the genes. For 5', 3' overlaps the synthetic insert may comprise: (i) a stop codon; (ii) about 20-200 bp, or 20-100 bp, or 20-50 bp, from upstream of the overlapping region; and (iii) the overlapping region. Preferably, the synthetic insert comprises: (i) a stop codon; (ii) about 20 bp from upstream of the overlapping region; and (iii) the overlapping region. In preferred embodiments the stop codon is in frame with the original start site for the downstream gene. Preferably the stop codon is TAA.

Preferably the donor sequence(s) (i.e. synthetic region) are collectively 50-10000 kb, 100-5000 kb, 100-2000 kb, 100-1000 kb, or 100-500 kb in size. Preferably each donor sequence is 50-300 kb, 100-200 kb, or about 100 kb in size.

Accordingly, the donor sequences may each be about 100 kb in size and identical to corresponding sequences of the parent genome, except they comprise no occurrences of one or more sense codons and all pairs of genes which share an overlapping region comprising the one or more sense codons in the parent genome are refactored, wherein the pairs of genes are those in which sense codon replacements would change the encoded protein sequence of both or either of the pair of genes.

In preferred embodiments the viability of the genome is tested after each round of recombination-mediated genetic engineering. In some embodiments the sequence of the genome is verified after each round of recombination-mediated genetic engineering.

Partially Synthetic Genomes

The present invention provides two or more different partially synthetic genomes.

As used herein a "partially synthetic genome" is a genome in which one or more contiguous regions of the parent genome have been edited (i.e. the partially synthetic genomes comprise one or more synthetic regions), wherein one or more contiguous (synthetic) regions do not cover the whole of the parent genome. Preferably, the partially synthetic genomes of the present invention have one contiguous (synthetic) region. In contrast, a "synthetic genome" may comprise genome edits which cover substantially all of the parent genome.

The partially synthetic genomes of the present invention may be prokaryotic genomes. Preferably, the partially synthetic genomes of the present invention are bacterial genomes. More preferably, the partially synthetic genomes of the present invention are *Escherichia coli, Salmonella enterica*, or *Shigella dysenteriae* genomes. Most preferably, the partially synthetic genomes of the present invention are *E. coli* genomes. In some embodiments the partially synthetic genomes are reduced or minimal partially synthetics genomes. In preferred embodiments, the partially synthetic genomes are viable genomes.

In some embodiments the partially synthetic genomes of the present invention are 100 kb to 20 Mb, or 130 kb to 15 Mb, or 200 kb to 15 Mb, or 300 kb to 15 Mb, or 500 kb to 15 Mb, or 1 Mb to 15 Mb, or 1 Mb to 10 Mb, or 1 Mb to 8 Mb, or 1 Mb to 6 Mb, or 2 Mb to 6 Mb, or 2 Mb to 5 Mb, or 3 Mb to 5 Mb, or about 4 Mb in size.

The partially synthetic genomes may comprise a synthetic region that has 50 or fewer, 20 or fewer, 10 or fewer, 5 or fewer, or 0 occurrences of each of one or more sense codons; or the partially synthetic genomes may comprise a synthetic region that has less than 10%, 5%, 2%, 1%, 0.5%, 0.1% of the occurrences of each of one or more sense codons, relative to the corresponding region in the parent genome.

Preferably, the synthetic regions are 50-10000 kb, 100-5000 kb, or 100-500 kb in size.

Thus, the partially synthetic genomes may comprise one or more contiguous regions of 100-5000 kb that have 10 or fewer, 5 or fewer, or no occurrences of each of one or more sense codons; and/or the partially synthetic genomes may comprise one or more contiguous regions of 100-5000 kb that have less than 10%, 5%, 2%, 1%, 0.5%, 0.1% of the occurrences of each of one or more sense codons, relative to the corresponding region in the parent genome; and/or the partially synthetic genomes may comprise one or more contiguous regions of 100-5000 kb that have 10 or more, 20 or more, or 100 or more genes with no occurrences of one or more sense codons.

The remainder of the partially synthetic genome (i.e. the non-synthetic region(s)) may have un-altered sense codons. Thus, the partially synthetic genomes may comprise one or more non-synthetic region(s) that have 100% or 99% of the occurrences of each sense codons, relative to the corresponding region in the parent genome; and/or the partially synthetic genomes may comprise one or more non-synthetic region(s) that have 100 or more genes with occurrences of each sense codon. The non-synthetic regions may be 500 kb to 20 Mb, or 500 kb to 10 Mb, or 500 kb to 5 Mb, or about 3.5 Mb in size.

For example, the partially synthetic genomes may comprise one contiguous region (i.e. a synthetic region) of 100-5000 kb that has 10 or more, 20 or more, or 100 or more genes with no occurrences of one or more sense codons and one contiguous region of 500 kb-10000 kb (i.e. a non-synthetic region) that has 100 or more genes with occurrences of each sense codon.

The two or more different partially synthetic genomes may be derived from the same parent genome, i.e. comprise substantially the same sequences, e.g. the two or more different partially synthetic genomes may share 90%, 95%, 99%, or 99.5% sequence identity.

The two or more different partially synthetic genomes may comprise one or more synthetic regions, such that the synthetic regions collectively cover 90% or greater, 95% or greater, 99% or greater or 100% of the parent genome. Preferably, the two or more different partially synthetic genomes each comprise one or more synthetic regions, wherein the synthetic regions do not substantially overlap, (e.g. the overlap between synthetic regions is 10 kb or less, preferably about 3-4 kb). Thus, the two or more different partially synthetic genomes may each comprise one unique or substantially unique synthetic region.

Thus, in preferred embodiments the two or more different partially synthetic genomes each comprise one contiguous synthetic region of 100-5000 kb that has 10 or more, 20 or more, or 100 or more genes with no occurrences of one or more sense codons and one non-synthetic contiguous region of 500 kb-10000 kb that has 100 or more genes with occurrences of each sense codon; wherein the synthetic regions collectively cover substantially all of the parent genome and wherein the synthetic regions do not substantially overlap.

The two or more different partially synthetic genomes may be suitable for directed conjugation. Thus, in preferred embodiments the two or more different partially synthetic genomes comprise at least one partially synthetic donor genome and at least one partially synthetic recipient genome. The method of the invention may comprise a further step of one or more rounds of recombination-mediated genetic engineering, preferably lambda red mediated genetic engineering (prior to directed conjugation) to provide at least one partially synthetic donor genome and at least one partially synthetic recipient genome. The method may further comprise one or more rounds of selection for the at least one partially synthetic donor genome and at least one partially synthetic recipient genome.

The at least one partially synthetic donor genome may comprise a synthetic region and a first selectable marker flanked by two homology regions immediately downstream of an origin of transfer; and the at least one partially synthetic recipient genome may comprise a second selectable marker flanked by two corresponding homology regions, optionally wherein the first selectable marker comprises a positive selectable marker, and/or the second selectable marker comprises a negative selectable marker.

Suitably the negative selectable marker is selected from the group consisting of sacB (sucrose sensitivity), rpsL (S12 ribosomal protein-streptomycin sensitivity), or phe$^{S T2514\_A294G}$ (4-chlorophenylalanine sensitivity). Suitably the positive selectable marker is selected from the group consisting of $Cm^R$ (chloramphenicol resistance), $Kan^R$ (kanamycin resistance), $Hyg^R$ (hygromycin resistance), Gentamycin$^R$ (gentamycin resistance), or tetracycline$^R$ (tetracycline resistance). The selectable markers may be different to those in the one or more steps of recombination-mediated genetic engineering.

Preferably the synthetic region present in the at least one partially synthetic recipient genomes is outside the region flanked by the homology regions, i.e. the synthetic regions do not substantially overlap. Preferably the homology regions are 3 kb to 500 kb in length, most preferably about 3-5 kb.

Directed Conjugation

One or more rounds of directed conjugation may be carried out on the two or more different partially synthetic genomes of the present invention to produce a synthetic genome.

Each round of directed conjugation may be used to provide partially synthetic genomes with larger contiguous synthetic regions. For example, after the one or more rounds of recombination-mediated genetic engineering there may be 8 partially synthetic genomes, each with a contiguous synthetic region of about 500 kb. After a first round of directed conjugation, two of the partially synthetic genomes may be combined to provide 6 partially synthetic genomes, each with a contiguous synthetic region of about 500 kb and 1 partially synthetic genome with contiguous synthetic region of about 1 Mb. A second round may provide either 5 partially synthetic genomes, each with a contiguous synthetic region of about 500 kb and 1 partially synthetic genome with contiguous synthetic region of about 1.5 Mb; or 4 partially synthetic genomes, each with a contiguous synthetic region of about 500 kb and 2 partially synthetic genome each with a contiguous synthetic region of about 1 Mb. After several rounds of directed conjugation a completely synthetic genome (i.e. one with a contiguous synthetic region of about 4 Mb) may be provided. An example is shown schematically in FIGS. 10 and 11B.

Any suitable method of directed conjugation may be used. Methods of directed conjugation will be well known to those of skill in the art, for instance as described by Ma, N.J., Moonan, D. W. and Isaacs, F. J., 2014. Nature Protocols, 9(10), p. 2285. The route to the synthetic genome is not limited.

Thus, the one or more rounds of directed conjugation may comprise:
i) providing a first host cell comprising a partially synthetic recipient genome, and a second host cell comprising a partially synthetic donor genome and a conjugative plasmid;
ii) a step of conjugation of the partially synthetic recipient genome and partially synthetic donor genome; and
iii) selecting for recombinants having incorporated the synthetic region of the donor genome into the partially synthetic recipient genome.

The partially synthetic donor genome may comprise a synthetic region and a first selectable marker flanked by two homology regions immediately downstream of an origin of transfer; and the partially synthetic recipient genomes may comprise a second selectable marker flanked by two corresponding homology regions, optionally wherein the first selectable marker comprises a positive selectable marker, and/or the second selectable marker comprises a negative selectable marker. Thus, step (iii) may comprise selection for said selectable markers, i.e. selection for gain of the first selectable marker and loss of the second selectable marker.

Suitably the negative selectable marker is selected from the group consisting of sacB (sucrose sensitivity), rpsL (S12 ribosomal protein-streptomycin sensitivity), or phe$^{ST251A\_A294G}$ (4-chlorophenylalanine sensitivity). Suitably the positive selectable marker is selected from the group consisting of Cm$^R$ (chloramphenicol resistance), Kan$^R$ (kanamycin resistance), Hyg$^R$ (hygromycin resistance), Gentamycin$^R$ (gentamycin resistance), or tetracycline$^R$ (tetracycline resistance). The selectable markers may be different to those in the one or more steps of recombination-mediated genetic engineering.

Preferably the homology regions are 3 kb to 500 kb in length, most preferably about 3-5 kb. Preferably, the homology regions are 50 kb to 500 kb when the step of directed conjugation is the final step of directed conjugation.

Step (ii) may comprise incubating the first host cell and the second host cell. For example, first host cell and the second host cell may be mixed, transferred onto a suitable medium (e.g. agar plates) and incubated at about 37° C. for about 1-3 hours.

The conjugative plasmid may be an F plasmid, preferably wherein the conjugative plasmid does not comprise an origin of transfer. (e.g FIG. 22C).

In preferred embodiments the viability of the genome is tested after each round of directed conjugation. Advantageously, this verifies that the genome edits (e.g. sense codon replacements) result in a viable genome, and allows for non-permitted edits to be corrected. In some embodiments the sequence of the genome is verified after each round of directed conjugation.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press.

EXAMPLES

Example 1—Design of a Genome with Synonymous Codon Compression

We first designed a version of the *E. coli* MDS42 genome (Uniprot accession number AP012306.1) in which the serine codons TCG and TCA and the stop codon TAG in open reading frames (ORFs) are systematically replaced by their synonyms AGC, AGT, and TAA, respectively (FIG. 1A, FIG. 18, SEQ ID NO: 1). We have previously shown that this defined recoding scheme for synonymous codon compression is allowed on a 20 kb region of the *E. coli* genome rich in essential genes (Wang, K. et al., 2016. Nature 539, 59-64). However, this region only accounts for 0.46% of the target codons in the genome.

*E. coli* contains numerous overlapping open reading frames (ORFs), and we classify the overlaps as 3', 3' (between ORFs in opposite orientations) or 5', 3' (between ORFs in the same orientation). Targeted codons are found within both classes of overlap. If the recoding of each ORF within a 3', 3' overlap could be achieved without changing the encoded protein sequence of either ORF—i.e.: by introducing synonymous codon(s)—then the overlap structure was maintained and the sequences were directly recoded. However, when this was not possible we duplicated the overlapping region, and individually recoded each ORFs (FIG. 1B, Table 1).

For 5', 3' overlaps we separated the ORFs by duplicating both the region of overlap between the ORFs and the 20 bp sequence upstream of the overlap. This refactoring allows us to recode each ORF independently (FIG. 1C, Table 1). Our strategy preserves the sequence of the RBS for the downstream ORF and the distance between this RBS and its start codon.

Using the defined rules for synonymous codon compression and refactoring we designed a genome in which all 18,218 target codons are recoded to their target synonyms (FIG. 1D).

TABLE 1

Overlaps and refactoring
Listed are the 92 cases of overlaps accounted for by refactoring in the MDS42 designed
genome (FIG. 18, SEQ ID NO: 1). Provided is additional information about genomic location,
surrounding genes, overlap length, codons changed, and the refactoring strategy implemented.

| Overlap No. | Overlap type | Up-stream gene | Down-stream gene | Start | End | Start | End | Overlap length | Codons changed | Strategy | Refactoring length |
|---|---|---|---|---|---|---|---|---|---|---|---|
| 1 | Head-to-tail | kefF | kefC | 42,594 | 42,625 | 42,594 | 42,601 | 8 | 1 | Duplication + in-frame TAA STOP codon + 20 nt insertion | 32 |
| 2 | Head-to-tail | ftsI | murE | 88,023 | 88,060 | 87,991 | 88,004 | 14 | 1 | Duplication + in-frame TAA STOP codon + 20 nt insertion | 38 |
| 3 | Head-to-tail | murF | mraY | 90,897 | 90,928 | 90,827 | 90,833 | 7 | 1 | Duplication + in-frame TAA STOP codon + 20 nt insertion | 32 |
| 4 | Head-to-tail | yaeQ | yaeJ | 203,847 | 203,875 | 203,694 | 203,697 | 4 | 1 | Duplication + in-frame TAA STOP codon + 20 nt insertion | 29 |
| 5 | Tail-to-tail | yafJ | yafK | 234,139 | 234,168 | 233,927 | 233,956 | 30 | 1 | Duplication | 30 |
| 6 | Head-to-tail | yahE | yahF | 263,179 | 263,213 | 262,967 | 262,977 | 11 | 1 | Duplication + in-frame TAA STOP codon + 20 nt insertion | 35 |
| 7 | Head-to-tail | codB | codA | 282,607 | 282,641 | 282,360 | 282,370 | 11 | 1 | Duplication + in-frame TAA STOP codon + 20 nt insertion | 35 |
| 8 | Head-to-tail | mhpD | mhpF | 299,392 | 299,420 | 299,110 | 299,113 | 4 | 1 | Duplication + in-frame TAA STOP codon + 20 nt insertion | 29 |
| 9 | Head-to-tail | yajL | panE | 351,696 | 351,757 | 351,347 | 351,384 | 38 | 2 | Duplication + in-frame TAA STOP codon + 20 nt insertion | 62 |
| 10 | Head-to-tail | mdlA | mdlB | 378,752 | 378,783 | 378,379 | 378,386 | 8 | 1 | Duplication + in-frame TAA STOP codon + 20 nt insertion | 32 |
| 11 | Head-to-tail | hemH | aes | 407,162 | 407,162 | 406,757 | 406,760 | 4 | 1 | Slietn mutation CGC to CGT (Arg) | |
| 12 | Head-to-tail | ybbL | ybbM | 424,731 | 424,768 | 424,326 | 424,339 | 14 | 1 | Duplication + in-frame TAA STOP codon + 20 nt insertion | 38 |
| 13 | Head-to-tail | ybbO | tesA | 427,336 | 427,370 | 426,882 | 426,892 | 11 | 1 | Duplication + in-frame TAA STOP codon + 20 nt insertion | 35 |
| 14 | Head-to-tail | citG | citX | 521,504 | 521,553 | 521,000 | 521,025 | 26 | 2 | Duplication + in-frame TAA STOP codon + 20 nt insertion | 50 |
| 15 | Head-to-tail | nei | abrB | 609,986 | 609,987 | 609,456 | 609,459 | 4 | 2 | Silent mutations CAC to CAT (His), GCC to GCT (Ala) | |
| 16 | Tail-to-tail | ybhQ | ybhR | 688,302 | 688,340 | 687,735 | 687,773 | 39 | 1 | Duplication | 39 |
| 17 | Head-to-tail | ybhG | ybiH | 693,272 | 693,292 | 692,705 | 692,705 | 1 | 1 | Duplication + in-frame TAA STOP codon + 20 nt insertion | 21 |
| 18 | Head-to-tail | ylil | yliJ | 743,178 | 743,178 | 742,587 | 742,590 | 4 | 1 | Silent mutation AGC to AGT (Ser) | |
| 19 | Head-to-tail | ybjR | ybjS | 769,064 | 769,064 | 768,473 | 768,476 | 4 | 1 | Silent mutation CGC to CGT (Arg) | |
| 20 | Head-to-tail | ycaR | kdsB | 834,173 | 834,201 | 833,585 | 833,588 | 4 | 1 | Duplication + in-frame TAA STOP codon + 20 nt insertion | 29 |
| 21 | Tail-to-tail | ycbJ | ycbC | 835,996 | 836,019 | 835,355 | 835,378 | 24 | 2 | Duplication | 24 |
| 22 | Head-to-tail | ycbW | ycbX | 869,865 | 869,865 | 869,224 | 869,227 | 4 | 1 | Silent mutation GTC to GTT (Val) | |
| 23 | Tail-to-tail | yccR | yccS | 885,142 | 885,179 | 884,463 | 884,500 | 38 | 1 | Duplication | 38 |
| 24 | Head-to-tail | hyaC | hyaD | 899,182 | 899,210 | 898,503 | 898,506 | 4 | 1 | Duplication + in-frame TAA STOP codon + 20 nt insertion | 29 |
| 25 | Head-to-tail | hyaE | hyaF | 900,190 | 900,218 | 899,482 | 899,485 | 4 | 1 | Duplication + in-frame TAA STOP codon + 20 nt insertion | 29 |
| 26 | Tail-to-tail | torT | torR | 912,244 | 912,271 | 911,479 | 911,506 | 28 | 1 | Duplication | 28 |
| 27 | Head-to-tail | torA | torD | 916,781 | 916,809 | 916,016 | 916,019 | 4 | 1 | Duplication + in-frame TAA STOP codon + 20 nt insertion | 29 |
| 28 | Head-to-tail | ycfM | ycfN | 995,426 | 995,469 | 994,632 | 994,651 | 20 | 1 | Duplication + in-frame TAA STOP codon + 20 nt insertion | 44 |
| 29 | Head-to-tail | sapC | sapB | 1,159,586 | 1,159,623 | 1,158,734 | 1,158,747 | 14 | 1 | Duplication + in-frame TAA STOP codon + 20 nt insertion | 38 |
| 30 | Head-to-tail | ycjV | ymjB | 1,186,895 | 1,186,915 | 1,186,018 | 1,186,018 | 1 | 1 | Duplication + in-frame TAA STOP codon + 20 nt insertion | 21 |
| 31 | Tail-to-tail | rimL | ydcK | 1,212,937 | 1,212,945 | 1,212,031 | 1,212,039 | 9 | 1 | Duplication | 9 |
| 32 | Head-to-tail | ddpD | ddpC | 1,266,751 | 1,266,779 | 1,265,841 | 1,265,844 | 4 | 1 | Duplication + in-frame TAA STOP codon + 20 nt insertion | 29 |
| 33 | Head-to-tail | ego | IsrC | 1,310,781 | 1,310,812 | 1,309,846 | 1,309,852 | 7 | 1 | Duplication + in-frame TAA STOP codon + 20 nt insertion | 32 |
| 34 | Tail-to-tail | ydjQ | ydjR | 1,506,953 | 1,506,993 | 1,505,945 | 1,505,985 | 41 | 1 | Duplication | 41 |
| 35 | Head-to-tail | astA | astC | 1,513,357 | 1,513,385 | 1,512,345 | 1,512,348 | 4 | 1 | Duplication + in-frame TAA STOP codon + 20 nt insertion | 29 |
| 36 | Tail-to-tail | nudG | ynjH | 1,524,518 | 1,524,552 | 1,523,446 | 1,523,480 | 35 | 1 | Duplication | 35 |
| 37 | Tail-to-tail | yeaL | yeaM | 1,556,017 | 1,556,060 | 1,554,901 | 1,554,944 | 44 | 3 | Duplication | 44 |
| 38 | Head-to-tail | yebS | yebT | 1,598,772 | 1,598,827 | 1,597,656 | 1,597,687 | 32 | 2 | Duplication + in-frame TAA STOP codon + 20 nt insertion | 56 |
| 39 | Head-to-tail | exoX | ptrB | 1,608,100 | 1,608,100 | 1,606,925 | 1,606,928 | 4 | 1 | Silent mutation GAC to GAT (Asp) | |
| 40 | Head-to-tail | znuC | znuB | 1,624,732 | 1,624,760 | 1,623,560 | 1,623,563 | 4 | 1 | Duplication + in-frame TAA STOP codon + 20 nt insertion | 29 |
| 41 | Head-to-tail | otsA | otsB | 1,646,196 | 1,646,245 | 1,644,969 | 1,644,994 | 26 | 1 | Duplication + in-frame TAA STOP codon + 20 nt insertion | 50 |
| 42 | Tail-to-tail | yedA | vsr | 1,668,526 | 1,668,537 | 1,667,263 | 1,667,274 | 12 | 1 | Duplication | 12 |
| 43 | Head-to-tail | vsr | dcm | 1,668,997 | 1,669,040 | 1,667,714 | 1,667,733 | 20 | 1 | Duplication + in-frame TAA STOP codon + 20 nt insertion | 44 |

TABLE 1-continued

Overlaps and refactoring
Listed are the 92 cases of overlaps accounted for by refactoring in the MDS42 designed
genome (FIG. 18, SEQ ID NO: 1). Provided is additional information about genomic location,
surrounding genes, overlap length, codons changed, and the refactoring strategy implemented.

| Overlap No. | Overlap type | Upstream gene | Downstream gene | Start | End | Start | End | Overlap length | Codons changed | Strategy | Refactoring length |
|---|---|---|---|---|---|---|---|---|---|---|---|
| 44 | Tail-to-tail | yegV | yegW | 1,757,516 | 1,757,542 | 1,756,182 | 1,756,208 | 27 | 2 | Duplication | 27 |
| 45 | Head-to-tail | yehP | yehQ | 1,784,581 | 1,784,609 | 1,783,247 | 1,783,250 | 4 | 1 | Duplication + in-frame TAA STOP codon + 20 nt insertion | 29 |
| 46 | Head-to-tail | yeiT | yeiA | 1,810,775 | 1,810,806 | 1,809,412 | 1,809,418 | 7 | 1 | Duplication + in-frame TAA STOP codon + 20 nt insertion | 32 |
| 47 | Head-to-tail | ccmF | ccME | 1,866,667 | 1,866,695 | 1,865,268 | 1,865,271 | 4 | 1 | Duplication + in-frame TAA STOP codon + 20 nt insertion | 29 |
| 48 | Head-to-tail | napB | napH | 1,870,510 | 1,870,538 | 1,869,082 | 1,869,085 | 4 | 1 | Duplication + in-frame TAA STOP codon + 20 nt insertion | 29 |
| 49 | Head-to-tail | napH | napG | 1,871,399 | 1,871,436 | 1,869,932 | 1,869,945 | 14 | 1 | Duplication + in-frame TAA STOP codon + 20 nt insertion | 38 |
| 50 | Head-to-tail | yfbG | yfbH | 1,941,876 | 1,941,904 | 1,940,385 | 1,940,388 | 4 | 1 | Duplication + in-frame TAA STOP codon + 20 nt insertion | 29 |
| 51 | Head-to-tail | eutA | eutH | 2,114,032 | 2,114,060 | 2,112,508 | 2,112,511 | 4 | 1 | Duplication + in-frame TAA STOP codon + 20 nt insertion | 29 |
| 52 | Tail-to-tail | csiE | hcaT | 2,213,892 | 2,213,900 | 2,212,334 | 2,212,342 | 9 | 2 | Duplication | 9 |
| 53 | Head-to-tail | yfiM | kgtP | 2,271,633 | 2,271,633 | 2,270,075 | 2,270,078 | 4 | 1 | Silent mutation CAC to CAT (His) | |
| 54 | Head-to-tail | srlA | srlE | 2,338,485 | 2,338,513 | 2,336,927 | 2,336,930 | 4 | 1 | Duplication + in-frame TAA STOP codon + 20 nt insertion | 29 |
| 55 | Head-to-tail | hypB | hypC | 2,363,986 | 2,364,020 | 2,362,399 | 2,362,408 | 10 | 1 | Duplication + in-frame TAA STOP codon + 20 nt insertion | 35 |
| 56 | Head-to-tail | ygbJ | ygbK | 2,374,492 | 2,374,520 | 2,372,870 | 2,372,873 | 4 | 1 | Duplication + in-frame TAA STOP codon + 20 nt insertion | 29 |
| 57 | Head-to-tail | ygcN | ygcO | 2,406,105 | 2,406,139 | 2,404,454 | 2,404,463 | 10 | 1 | Duplication + in-frame TAA STOP codon + 20 nt insertion | 35 |
| 58 | Head-to-tail | ppdC | ygdB | 2,474,986 | 2,475,026 | 2,473,284 | 2,473,299 | 16 | 1 | Duplication + in-frame TAA STOP codon + 20 nt insertion | 41 |
| 59 | Tail-to-tail | lysR | ygeA | 2,492,219 | 2,492,232 | 2,490,478 | 2,490,491 | 14 | 2 | Duplication | 14 |
| 60 | Head-to-tail | hybB | hybA | 2,626,155 | 2,626,189 | 2,624,403 | 2,624,413 | 11 | 1 | Duplication + in-frame TAA STOP codon + 20 nt insertion | 35 |
| 61 | Head-to-tail | yraM | yraN | 2,770,503 | 2,770,570 | 2,768,727 | 2,768,769 | 43 | 1 | Duplication + in-frame TAA STOP codon + 20 nt insertion | 68 |
| 62 | Tail-to-tail | yhbO | yhbP | 2,774,670 | 2,774,690 | 2,772,805 | 2,772,825 | 21 | 1 | Duplication | 21 |
| 63 | Head-to-tail | mreD | mreC | 2,868,593 | 2,868,613 | 2,866,727 | 2,866,727 | 1 | 1 | Duplication + 20 nt insertion | 21 |
| 64 | Head-to-tail | yheT | yheU | 2,938,030 | 2,938,061 | 2,936,144 | 2,936,150 | 7 | 1 | Duplication + in-frame TAA STOP codon + 20 nt insertion | 32 |
| 65 | Tail-to-tail | yhhA | ugpQ | 3,037,319 | 3,037,332 | 3,035,387 | 3,035,400 | 14 | 1 | Duplication | 14 |
| 66 | Head-to-tail | nikD | nikE | 3,067,725 | 3,067,753 | 3,065,793 | 3,065,796 | 4 | 1 | Duplication + in-frame TAA STOP codon + 20 nt insertion | 29 |
| 67 | Head-to-tail | bcsC | bcsZ | 3,130,042 | 3,130,085 | 3,128,062 | 3,128,080 | 19 | 1 | Duplication + in-frame TAA STOP codon + 20 nt insertion | 44 |
| 68 | Head-to-tail | bcsA | yhjQ | 3,136,149 | 3,136,177 | 3,134,140 | 3,134,143 | 4 | 1 | Duplication + in-frame TAA STOP codon + 20 nt insertion | 29 |
| 69 | Head-to-tail | bcsE | bcsF | 3,138,967 | 3,138,995 | 3,136,933 | 3,136,936 | 4 | 1 | Duplication + in-frame TAA STOP codon + 20 nt insertion | 29 |
| 70 | Tail-to-tail | yiaC | bisC | 3,155,063 | 3,155,094 | 3,152,968 | 3,152,999 | 32 | 1 | Duplication | 32 |
| 71 | Head-to-tail | xylG | xylH | 3,173,279 | 3,173,325 | 3,171,184 | 3,171,206 | 23 | 1 | Duplication + in-frame TAA STOP codon + 20 nt insertion | 47 |
| 72 | Head-to-tail | sgbU | sgbE | 3,189,692 | 3,189,723 | 3,187,550 | 3,187,556 | 7 | 1 | Duplication + in-frame TAA STOP codon + 20 nt insertion | 32 |
| 73 | Tail-to-tail | yibQ | yibD | 3,320,449 | 3,320,462 | 3,218,261 | 3,218,274 | 14 | 1 | Duplication | 14 |
| 74 | Head-to-tail | yicG | ligB | 3,250,889 | 3,250,889 | 3,248,701 | 3,248,704 | 4 | 1 | Silent mutation CAC to CAT (His) | |
| 75 | Head-to-tail | yidG | yidH | 3,287,372 | 3,287,406 | 3,285,173 | 3,285,183 | 11 | 1 | Duplication + in-frame TAA STOP codon + 20 nt insertion | 35 |
| 76 | Head-to-tail | cbrA | dgoT | 3,301,877 | 3,301,877 | 3,299,651 | 3,299,654 | 4 | 1 | Silent mutation GGC to GGT (Gly) | |
| 77 | Head-to-tail | rnpA | yidD | 3,316,252 | 3,316,313 | 3,314,029 | 3,314,065 | 37 | 2 | Duplication + in-frame TAA STOP codon + 20 nt insertion | 62 |
| 78 | Tail-to-tail | rbsR | hsrA | 3,370,718 | 3,370,752 | 3,368,398 | 3,368,432 | 35 | 4 | Duplication | 35 |
| 79 | Head-to-tail | yigM | metR | 3,443,509 | 3,443,621 | 3,441,076 | 3,441,188 | 113 | 4 | Duplication | 113 |
| 80 | Head-to-tail | tatD | rfaH | 3,455,982 | 3,455,982 | 3,453,546 | 3,453,549 | 4 | 1 | Silent mutation CTC to CTT (Leu) | |
| 81 | Head-to-tail | cpxA | cpxR | 3,536,622 | 3,536,650 | 3,534,185 | 3,534,188 | 4 | 1 | Duplication + in-frame TAA STOP codon + 20 nt insertion | 29 |
| 82 | Head-to-tail | pflD | pflC | 3,577,933 | 3,577,991 | 3,575,471 | 3,575,505 | 35 | 1 | Duplication + in-frame TAA STOP codon + 20 nt insertion | 59 |
| 83 | Tail-to-tail | frwD | yijO | 3,579,214 | 3,579,227 | 3,576,679 | 3,576,692 | 14 | 1 | Duplication | 14 |
| 84 | Head-to-tail | murB | birA | 3,604,830 | 3,604,858 | 3,602,295 | 3,602,298 | 4 | 1 | Duplication + in-frame TAA STOP codon + 20 nt insertion | 29 |
| 85 | Head-to-tail | zraR | purD | 3,636,422 | 3,636,422 | 3,633,855 | 3,633,858 | 4 | 1 | Silent mutation AAC to AAT (Asn) | |
| 86 | Head-to-tail | actP | yjcH | 3,716,680 | 3,716,708 | 3,714,112 | 3,714,115 | 4 | 1 | Duplication + in-frame TAA STOP codon + 20 nt insertion | 29 |

TABLE 1-continued

Overlaps and refactoring
Listed are the 92 cases of overlaps accounted for by refactoring in the MDS42 designed genome (FIG. 18, SEQ ID NO: 1). Provided is additional information about genomic location, surrounding genes, overlap length, codons changed, and the refactoring strategy implemented.

| Overlap No. | Overlap type | Upstream gene | Downstream gene | Start | End | Start | End | Overlap length | Codons changed | Strategy | Refactoring length |
|---|---|---|---|---|---|---|---|---|---|---|---|
| 87 | Head-to-tail | phnM | phnL | 3,748,914 | 3,748,942 | 3,746,317 | 3,746,320 | 4 | 1 | Duplication + in-frame TAA STOP codon + 20 nt insertion | 29 |
| 88 | Head-to-tail | dipZ | cutA | 3,796,767 | 3,796,816 | 3,794,120 | 3,794,144 | 25 | 1 | Duplication + in-frame TAA STOP codon + 20 nt insertion | 50 |
| 89 | Head-to-tail | sugE | blc | 3,808,963 | 3,808,963 | 3,806,291 | 3,806,294 | 4 | 1 | Silent mutation CAC to CAT (His) | |
| 90 | Head-to-tail | yjeF | yjeE | 3,827,359 | 3,827,411 | 3,824,687 | 3,824,715 | 29 | 1 | Duplication + in-frame TAA STOP codon + 20 nt insertion | 53 |
| 91 | Tail-to-tail | ytfA | ytfB | 3,859,923 | 3,859,939 | 3,857,181 | 3,857,197 | 17 | 1 | Duplication | 17 |

Example 2—Synthesis of Recoded Sections

We performed a retrosynthesis, analogous to that commonly used for designing synthetic routes to small molecules, on the designed genome (FIGS. 2A-2C). We disconnected the genome into 8 sections, A-H, of approximately 0.5 Mb (FIG. 1D, FIG. 2A, FIG. 18, SEQ ID NO: 1) and then disconnected each section into 4-5 fragments (FIG. 2B). This yielded 37 fragments (FIG. 1D, Table 2) of 91 kb to 136 kb. We placed the boundaries between fragments, and between sections, in intergenic regions between non-essential genes. The fragments were further disconnected into 9-14 stretches of approximately 10 kb (FIG. 2C, Table 2).

We assembled BACs for REXER (FIG. 2C, FIGS. 20A-20N) containing each fragment via homologous recombination in S. cerevisiae (Wang, K. et al., 2016. Nature 539, 59-64; and Kouprina, N., et al., 2004. Methods Mol Biol 255, 69-89). For 36 of the fragments, BAC assembly proceeded smoothly (Table 3). Fragment 37 was challenging to assemble and we therefore split it into two 50 kb fragments (37a and 37b), which were straightforward to assemble (Table 3).

We initiated genome replacement in seven distinct strains, via REXER. The start point for REXER in each strain corresponds to the beginning of sections A, C, D, E, F, G or H (FIG. 1D, 2B, FIG. 3); section B was subsequently built on section A, as described below. We marked the start point of genome replacement in each strain by the introduction of a cassette bearing a positive and negative selection marker. We introduced Cas9 (Jiang, W., et al., 2013. Nat Biotechnol 31, 233-239), the lambda red recombination machinery (Datsenko, K. A. & Wanner, B. L., 2000. Proc Natl Acad Sci USA 97, 6640-6645), and the BAC containing the first recoded fragment for each section into the relevant strain, and initiated replacement of genomic DNA by the addition of DNA encoding the relevant Cas9 spacers (Jiang, W., et al., 2013. Nat Biotechnol 31, 233-239) to the cells. Cas9 mediated excision of the recoded DNA from the BAC and lambda red mediated recombination of this DNA into the genome led to replacement of a section of genomic DNA with recoded DNA, removal of the positive and negative selection markers from the genome, and introduction of new, orthogonal, positive and negative selection markers. Clones that had recombined over the target region were selected on the basis of having lost the negative selection marker from the genome and gained the positive selection marker from the BAC.

In each strain, the positive and negative selection markers that are introduced in the first REXER provide a template for the next round of REXER, enabling genome stepwise interchange synthesis (GENESIS) (FIG. 2B, FIG. 4). We used plasmid encoded spacers for early rounds of REXER (Table 4, FIGS. 20D-20N, 21A, and 21B). However, we subsequently found that REXER could be initiated by the electroporation of linear double stranded spacers generated by PCR (Table 4, FIG. 21A). Since these spacers do not propagate through cell division this enabled the cells from one step of REXER to be used more rapidly for the next step of REXER. This advance accelerated GENESIS. For sections A, C, D, E, F, and G we proceeded with GENESIS in a clockwise direction for 4-5 steps of REXER, until we had replaced approximately 0.5 Mb of genomic DNA with synthetic DNA. Because section A was initiated first, and was completed ahead of the other sections, we proceeded with GENESIS through section B upon reaching the end of section A.

Following each REXER we sequenced the resulting genomes to identify cells that were fully recoded over the targeted region of the genome (Table 4). In parallel, we carried out a large number of single step REXERs (Table 4) to rapidly identify 100 kb regions of the genome that may be challenging to recode, before we arrived at them through GENESIS. For 35 of the 38 steps, including all of sections A, C, D, E, F and G, we were able to completely recode the targeted genomic sequence by GENESIS. We only observed incomplete replacement of the corresponding genomic region by synthetic DNA for fragment 9, in section B, and for fragments 37a and 1, in section H, (Table 4).

TABLE 2

Table MDS42 10 kb stretches
The genomic locations are listed for all of the 10 kb stretches which comprise the designed synthetic MDS42 genome.

| Stretch | 5' start . . . 3'end | Length (bp) |
|---|---|---|
| 100k01-01 | 83,869 . . . 95,593 | 11725 |
| 100k01-02 | 95,399 . . . 101,629 | 6231 |
| 100k01-03 | 101,435 . . . 112,646 | 11212 |
| 100k01-04 | 112,448 . . . 122,780 | 10333 |
| 100k01-05 | 122,621 . . . 132,166 | 9546 |
| 100k01-06 | 131,945 . . . 144,626 | 12682 |
| 100k01-07 | 144,430 . . . 156,454 | 12025 |
| 100k01-08 | 156,309 . . . 162,400 | 6092 |
| 100k01-09 | 162,193 . . . 173,408 | 11216 |
| 100k01-10 | 173,127 . . . 181,748 | 8622 |
| 100k02-01 | 181,678 . . . 191,139 | 9462 |
| 100k02-02 | 191,016 . . . 201,015 | 10000 |
| 100k02-03 | 200,896 . . . 212,598 | 11703 |

TABLE 2-continued

Table MDS42 10 kb stretches
The genomic locations are listed for all of the 10 kb stretches which comprise the designed synthetic MDS42 genome.

| Stretch | 5' start . . . 3'end | Length (bp) |
|---|---|---|
| 100k02-04 | 212,483 . . . 220,477 | 7995 |
| 100k02-05 | 220,357 . . . 229,377 | 9021 |
| 100k02-06 | 229,255 . . . 237,503 | 8249 |
| 100k02-07 | 237,380 . . . 248,528 | 11149 |
| 100k02-08 | 248,409 . . . 259,180 | 10772 |
| 100k02-09 | 259,061 . . . 269,318 | 10258 |
| 100k02-10 | 269,196 . . . 279,245 | 10050 |
| 100k02-11 | 279,122 . . . 289,733 | 10612 |
| 100k02-12 | 289,609 . . . 303,206 | 13598 |
| 100k03-01 | 303,144 . . . 313,764 | 10621 |
| 100k03-02 | 313,641 . . . 325,092 | 11452 |
| 100k03-03 | 324,973 . . . 334,137 | 9165 |
| 100k03-04 | 334,018 . . . 343,618 | 9601 |
| 100k03-05 | 343,499 . . . 353,344 | 9846 |
| 100k03-06 | 353,225 . . . 362,491 | 9267 |
| 100k03-07 | 362,373 . . . 371,912 | 9540 |
| 100k03-08 | 371,794 . . . 380,649 | 8856 |
| 100k03-09 | 380,534 . . . 393,822 | 13289 |
| 100k03-10 | 393,703 . . . 405,214 | 11512 |
| 100k03-11 | 405,100 . . . 415,406 | 10307 |
| 100k03-12 | 415,290 . . . 425,574 | 10285 |
| 100k03-13 | 425,457 . . . 437,443 | 11987 |
| 100k04-01 | 437,351 . . . 447,358 | 10008 |
| 100k04-02 | 447,239 . . . 457,565 | 10327 |
| 100k04-03 | 457,446 . . . 466,960 | 9515 |
| 100k04-04 | 466,841 . . . 476,935 | 10095 |
| 100k04-05 | 476,816 . . . 486,528 | 9713 |
| 100k04-06 | 486,409 . . . 496,230 | 9822 |
| 100k04-07 | 496,111 . . . 506,009 | 9899 |
| 100k04-08 | 505,890 . . . 515,348 | 9459 |
| 100k04-09 | 515,231 . . . 525,913 | 10683 |
| 100k04-10 | 525,799 . . . 532,888 | 7090 |
| 100k05-01 | 532,792 . . . 543,100 | 10309 |
| 100k05-02 | 542,981 . . . 555,707 | 12727 |
| 100k05-03 | 555,591 . . . 566,274 | 10684 |
| 100k05-04 | 566,155 . . . 576,486 | 10332 |
| 100k05-05 | 576,367 . . . 588,061 | 11695 |
| 100k05-06 | 587,942 . . . 598,541 | 10600 |
| 100k05-07 | 598,422 . . . 609,162 | 10741 |
| 100k05-08 | 609,043 . . . 617,744 | 8702 |
| 100k05-09 | 617,625 . . . 628,315 | 10691 |
| 100k05-10 | 628,200 . . . 637,895 | 9696 |
| 100k06-01 | 637,794 . . . 648,173 | 10380 |
| 100k06-02 | 648,059 . . . 658,187 | 10129 |
| 100k06-03 | 658,075 . . . 666,632 | 8558 |
| 100k06-04 | 666,513 . . . 676,267 | 9755 |
| 100k06-05 | 676,148 . . . 683,859 | 7712 |
| 100k06-06 | 683,740 . . . 694,050 | 10311 |
| 100k06-07 | 693,931 . . . 705,086 | 11156 |
| 100k06-08 | 704,967 . . . 716,428 | 11462 |
| 100k06-09 | 716,309 . . . 727,640 | 11332 |
| 100k06-10 | 727,521 . . . 736,154 | 8634 |
| 100k06-11 | 736,035 . . . 741,978 | 5944 |
| 100k07-01 | 741,877 . . . 751,411 | 9535 |
| 100k07-02 | 751,295 . . . 763,017 | 11723 |
| 100k07-03 | 762,898 . . . 772,642 | 9745 |
| 100k07-04 | 772,523 . . . 782,523 | 10001 |
| 100k07-05 | 782,406 . . . 794,373 | 11968 |
| 100k07-06 | 794,255 . . . 804,092 | 9838 |
| 100k07-07 | 803,973 . . . 813,644 | 9672 |
| 100k07-08 | 813,527 . . . 823,429 | 9903 |
| 100k07-09 | 823,322 . . . 834,999 | 11678 |
| 100k07-10 | 834,886 . . . 846,335 | 11450 |
| 100k08-01 | 846,246 . . . 856,634 | 10389 |
| 100k08-02 | 856,515 . . . 868,063 | 11549 |
| 100k08-03 | 867,948 . . . 878,862 | 10915 |
| 100k08-04 | 878,744 . . . 889,954 | 11211 |
| 100k08-05 | 889,835 . . . 901,127 | 11293 |
| 100k08-06 | 901,008 . . . 912,978 | 11971 |
| 100k08-07 | 912,859 . . . 922,812 | 9954 |
| 100k08-08 | 922,693 . . . 933,969 | 11277 |
| 100k08-09 | 933,850 . . . 939,693 | 5844 |
| 100k09-01 | 939,575 . . . 949,128 | 9554 |
| 100k09-02 | 949,010 . . . 959,384 | 10375 |
| 100k09-03 | 959,266 . . . 969,156 | 9891 |
| 100k09-04 | 969,037 . . . 978,088 | 9052 |
| 100k09-05 | 977,982 . . . 985,362 | 7381 |
| 100k09-06 | 985,252 . . . 993,763 | 8512 |
| 100k09-07 | 993,644 . . . 1,002,701 | 9058 |
| 100k09-08 | 1,002,582 . . . 1,012,585 | 10004 |
| 100k09-09 | 1,012,466 . . . 1,022,792 | 10327 |
| 100k09-10 | 1,022,673 . . . 1,032,409 | 9737 |
| 100k09-11 | 1,032,290 . . . 1,041,958 | 9669 |
| 100k09-12 | 1,041,839 . . . 1,051,279 | 9441 |
| 100k10-01 | 1,051,179 . . . 1,059,299 | 8121 |
| 100k10-02 | 1,059,181 . . . 1,068,249 | 9069 |
| 100k10-03 | 1,068,138 . . . 1,078,645 | 10508 |
| 100k10-04 | 1,078,526 . . . 1,085,635 | 7110 |
| 100k10-05 | 1,085,516 . . . 1,096,452 | 10937 |
| 100k10-06 | 1,096,333 . . . 1,105,535 | 9203 |
| 100k10-07 | 1,105,418 . . . 1,116,898 | 11481 |
| 100k10-08 | 1,116,780 . . . 1,128,058 | 11279 |
| 100k10-09 | 1,127,939 . . . 1,138,744 | 10806 |
| 100k10-10 | 1,138,625 . . . 1,146,843 | 8219 |
| 100k11-01 | 1,146,759 . . . 1,156,879 | 10121 |
| 100k11-02 | 1,156,760 . . . 1,167,593 | 10834 |
| 100k11-03 | 1,167,474 . . . 1,179,239 | 11766 |
| 100k11-04 | 1,179,121 . . . 1,188,001 | 8881 |
| 100k11-05 | 1,187,883 . . . 1,195,638 | 7756 |
| 100k11-06 | 1,195,519 . . . 1,204,931 | 9413 |
| 100k11-07 | 1,204,812 . . . 1,215,685 | 10874 |
| 100k11-08 | 1,215,566 . . . 1,224,906 | 9341 |
| 100k11-09 | 1,224,787 . . . 1,234,403 | 9617 |
| 100k11-10 | 1,234,284 . . . 1,241,004 | 6721 |
| 100k12-01 | 1,240,898 . . . 1,250,323 | 9426 |
| 100k12-02 | 1,250,204 . . . 1,259,727 | 9524 |
| 100k12-03 | 1,259,614 . . . 1,270,832 | 11219 |
| 100k12-04 | 1,270,713 . . . 1,279,720 | 9008 |
| 100k12-05 | 1,279,601 . . . 1,290,366 | 10766 |
| 100k12-06 | 1,290,252 . . . 1,300,202 | 9951 |
| 100k12-07 | 1,300,085 . . . 1,308,976 | 8892 |
| 100k12-08 | 1,308,863 . . . 1,318,474 | 9612 |
| 100k12-09 | 1,318,355 . . . 1,326,702 | 8348 |
| 100k12-10 | 1,326,583 . . . 1,337,691 | 11109 |
| 100k12-11 | 1,337,572 . . . 1,347,802 | 10231 |
| 100k13-01 | 1,347,689 . . . 1,357,497 | 9809 |
| 100k13-02 | 1,357,378 . . . 1,369,231 | 11854 |
| 100k13-03 | 1,369,112 . . . 1,378,621 | 9510 |
| 100k13-04 | 1,378,502 . . . 1,387,714 | 9213 |
| 100k13-05 | 1,387,595 . . . 1,396,821 | 9227 |
| 100k13-06 | 1,396,702 . . . 1,407,244 | 10543 |
| 100k13-07 | 1,407,125 . . . 1,417,810 | 10686 |
| 100k13-08 | 1,417,698 . . . 1,428,675 | 10978 |
| 100k13-09 | 1,428,564 . . . 1,439,655 | 11092 |
| 100k13-10 | 1,439,544 . . . 1,451,233 | 11690 |
| 100k13-11 | 1,451,116 . . . 1,455,004 | 3889 |
| 100k14-01 | 1,454,886 . . . 1,463,884 | 8999 |
| 100k14-02 | 1,463,770 . . . 1,472,031 | 8262 |
| 100k14-03 | 1,471,918 . . . 1,482,535 | 10618 |
| 100k14-04 | 1,482,417 . . . 1,491,781 | 9365 |
| 100k14-05 | 1,491,664 . . . 1,501,050 | 9387 |
| 100k14-06 | 1,500,931 . . . 1,508,216 | 7286 |
| 100k14-07 | 1,508,097 . . . 1,515,854 | 7758 |
| 100k14-08 | 1,515,737 . . . 1,526,355 | 10619 |
| 100k14-09 | 1,526,250 . . . 1,535,249 | 9000 |
| 100k14-10 | 1,535,130 . . . 1,543,987 | 8858 |
| 100k14-11 | 1,543,868 . . . 1,552,890 | 9023 |
| 100k14-12 | 1,552,774 . . . 1,564,280 | 11507 |
| 100k15-01 | 1,564,174 . . . 1,574,973 | 10800 |
| 100k15-02 | 1,574,856 . . . 1,586,003 | 11148 |
| 100k15-03 | 1,585,891 . . . 1,596,793 | 10903 |
| 100k15-04 | 1,596,677 . . . 1,604,287 | 7611 |
| 100k15-05 | 1,604,170 . . . 1,613,369 | 9200 |
| 100k15-06 | 1,613,258 . . . 1,621,511 | 8254 |
| 100k15-07 | 1,621,392 . . . 1,631,869 | 10478 |
| 100k15-08 | 1,631,750 . . . 1,643,142 | 11393 |

TABLE 2-continued

Table MDS42 10 kb stretches
The genomic locations are listed for all of the 10 kb stretches which comprise the designed synthetic MDS42 genome.

| Stretch | 5' start . . . 3'end | Length (bp) |
|---|---|---|
| 100k15-09 | 1,643,023 . . . 1,652,391 | 9369 |
| 100k15-10 | 1,652,280 . . . 1,662,654 | 10375 |
| 100k15-11 | 1,662,547 . . . 1,667,544 | 4998 |
| 100k16-01 | 1,667,429 . . . 1,679,240 | 11812 |
| 100k16-02 | 1,679,126 . . . 1,690,153 | 11028 |
| 100k16-03 | 1,690,044 . . . 1,700,055 | 10012 |
| 100k16-04 | 1,699,936 . . . 1,708,018 | 8083 |
| 100k16-05 | 1,707,899 . . . 1,721,060 | 13162 |
| 100k16-06 | 1,720,941 . . . 1,734,097 | 13157 |
| 100k16-07 | 1,733,974 . . . 1,740,645 | 6672 |
| 100k16-08 | 1,740,525 . . . 1,752,444 | 11920 |
| 100k16-09 | 1,752,326 . . . 1,762,779 | 10454 |
| 100k16-10 | 1,762,660 . . . 1,771,814 | 9155 |
| 100k16-11 | 1,771,695 . . . 1,779,795 | 8101 |
| 100k17-01 | 1,779,708 . . . 1,790,152 | 10445 |
| 100k17-02 | 1,790,035 . . . 1,799,410 | 9376 |
| 100k17-03 | 1,799,291 . . . 1,809,349 | 10059 |
| 100k17-04 | 1,809,230 . . . 1,820,280 | 11051 |
| 100k17-05 | 1,820,169 . . . 1,830,728 | 10560 |
| 100k17-06 | 1,830,609 . . . 1,841,564 | 10956 |
| 100k17-07 | 1,841,445 . . . 1,847,824 | 6380 |
| 100k17-08 | 1,847,705 . . . 1,856,025 | 8321 |
| 100k17-09 | 1,855,909 . . . 1,868,109 | 12201 |
| 100k17-10 | 1,867,998 . . . 1,875,399 | 7402 |
| 100k18-01 | 1,875,300 . . . 1,884,607 | 9308 |
| 100k18-02 | 1,884,488 . . . 1,895,099 | 10612 |
| 100k18-03 | 1,894,990 . . . 1,902,141 | 7152 |
| 100k18-04 | 1,902,022 . . . 1,912,147 | 10126 |
| 100k18-05 | 1,912,028 . . . 1,924,232 | 12205 |
| 100k18-06 | 1,924,113 . . . 1,935,491 | 11379 |
| 100k18-07 | 1,935,372 . . . 1,948,704 | 13333 |
| 100k18-08 | 1,948,593 . . . 1,958,709 | 10117 |
| 100k18-09 | 1,958,599 . . . 1,968,337 | 9739 |
| 100k18-10 | 1,968,218 . . . 1,980,692 | 12475 |
| 100k19-01 | 1,980,585 . . . 1,991,063 | 10479 |
| 100k19-02 | 1,990,945 . . . 2,000,511 | 9567 |
| 100k19-03 | 2,000,394 . . . 2,009,738 | 9345 |
| 100k19-04 | 2,009,619 . . . 2,021,044 | 11426 |
| 100k19-05 | 2,020,925 . . . 2,032,356 | 11432 |
| 100k19-06 | 2,032,247 . . . 2,042,778 | 10532 |
| 100k19-07 | 2,042,664 . . . 2,051,421 | 8758 |
| 100k19-08 | 2,051,315 . . . 2,060,546 | 9232 |
| 100k19-09 | 2,060,429 . . . 2,070,495 | 10067 |
| 100k19-10 | 2,070,376 . . . 2,080,816 | 10441 |
| 100k19-11 | 2,080,701 . . . 2,086,225 | 5525 |
| 100k20-01 | 2,086,123 . . . 2,098,560 | 12438 |
| 100k20-02 | 2,098,441 . . . 2,109,119 | 10679 |
| 100k20-03 | 2,109,000 . . . 2,119,224 | 10225 |
| 100k20-04 | 2,119,107 . . . 2,128,815 | 9709 |
| 100k20-05 | 2,128,696 . . . 2,140,138 | 11443 |
| 100k20-06 | 2,140,019 . . . 2,148,124 | 8106 |
| 100k20-07 | 2,148,005 . . . 2,159,046 | 11042 |
| 100k20-08 | 2,158,927 . . . 2,168,048 | 9122 |
| 100k20-09 | 2,167,929 . . . 2,176,912 | 8984 |
| 100k21-01 | 2,176,796 . . . 2,187,752 | 10957 |
| 100k21-02 | 2,187,633 . . . 2,199,463 | 11831 |
| 100k21-03 | 2,199,344 . . . 2,209,310 | 9967 |
| 100k21-04 | 2,209,193 . . . 2,220,948 | 11756 |
| 100k21-05 | 2,220,829 . . . 2,231,253 | 10425 |
| 100k21-06 | 2,231,134 . . . 2,242,692 | 11559 |
| 100k21-07 | 2,242,573 . . . 2,251,251 | 8679 |
| 100k21-08 | 2,251,132 . . . 2,261,427 | 10296 |
| 100k21-09 | 2,261,308 . . . 2,271,269 | 9962 |
| 100k21-10 | 2,271,152 . . . 2,281,408 | 10257 |
| 100k21-11 | 2,281,307 . . . 2,288,918 | 7612 |
| 100k22-01 | 2,288,816 . . . 2,298,876 | 10061 |
| 100k22-02 | 2,298,760 . . . 2,308,882 | 10123 |
| 100k22-03 | 2,308,763 . . . 2,319,092 | 10330 |
| 100k22-04 | 2,318,973 . . . 2,329,598 | 10626 |
| 100k22-05 | 2,329,483 . . . 2,340,583 | 11101 |
| 100k22-06 | 2,340,464 . . . 2,351,317 | 10854 |
| 100k22-07 | 2,351,225 . . . 2,362,005 | 10781 |
| 100k22-08 | 2,361,906 . . . 2,372,531 | 10626 |
| 100k22-09 | 2,372,430 . . . 2,383,456 | 11027 |
| 100k22-10 | 2,383,337 . . . 2,394,208 | 10872 |
| 100k22-11 | 2,394,089 . . . 2,404,790 | 10702 |
| 100k23-01 | 2,404,684 . . . 2,415,521 | 10838 |
| 100k23-02 | 2,415,402 . . . 2,425,882 | 10481 |
| 100k23-03 | 2,425,783 . . . 2,436,334 | 10552 |
| 100k23-04 | 2,436,215 . . . 2,445,909 | 9695 |
| 100k23-05 | 2,445,795 . . . 2,455,395 | 9601 |
| 100k23-06 | 2,455,304 . . . 2,465,797 | 10494 |
| 100k23-07 | 2,465,678 . . . 2,476,456 | 10779 |
| 100k23-08 | 2,476,337 . . . 2,484,906 | 8570 |
| 100k23-09 | 2,484,787 . . . 2,494,483 | 9697 |
| 100k23-10 | 2,494,384 . . . 2,504,089 | 9706 |
| 100k24-01 | 2,504,021 . . . 2,514,161 | 10141 |
| 100k24-02 | 2,514,042 . . . 2,522,657 | 8616 |
| 100k24-03 | 2,522,558 . . . 2,532,585 | 10028 |
| 100k24-04 | 2,532,466 . . . 2,542,012 | 9547 |
| 100k24-05 | 2,541,893 . . . 2,551,511 | 9619 |
| 100k24-06 | 2,551,392 . . . 2,560,716 | 9325 |
| 100k24-07 | 2,560,597 . . . 2,571,096 | 10500 |
| 100k24-08 | 2,570,983 . . . 2,582,088 | 11106 |
| 100k24-09 | 2,581,969 . . . 2,591,097 | 9129 |
| 100k24-10 | 2,590,993 . . . 2,600,564 | 9572 |
| 100k25-01 | 2,600,470 . . . 2,610,521 | 10052 |
| 100k25-02 | 2,610,402 . . . 2,620,532 | 10131 |
| 100k25-03 | 2,620,433 . . . 2,630,974 | 10542 |
| 100k25-04 | 2,630,855 . . . 2,640,909 | 10055 |
| 100k25-05 | 2,640,790 . . . 2,651,714 | 10925 |
| 100k25-06 | 2,651,615 . . . 2,663,606 | 11992 |
| 100k25-07 | 2,663,487 . . . 2,676,074 | 12588 |
| 100k25-08 | 2,675,955 . . . 2,684,604 | 8650 |
| 100k25-09 | 2,684,486 . . . 2,694,189 | 9704 |
| 100k25-10 | 2,694,070 . . . 2,702,813 | 8744 |
| 100k26-01 | 2,702,720 . . . 2,713,409 | 10690 |
| 100k26-02 | 2,713,290 . . . 2,723,932 | 10643 |
| 100k26-03 | 2,723,813 . . . 2,734,707 | 10895 |
| 100k26-04 | 2,734,609 . . . 2,744,645 | 10037 |
| 100k26-05 | 2,744,565 . . . 2,755,298 | 10734 |
| 100k26-06 | 2,755,179 . . . 2,763,894 | 8716 |
| 100k26-07 | 2,763,778 . . . 2,774,027 | 10250 |
| 100k26-08 | 2,773,908 . . . 2,784,122 | 10215 |
| 100k26-09 | 2,784,005 . . . 2,793,207 | 9203 |
| 100k26-10 | 2,793,088 . . . 2,802,862 | 9775 |
| 100k26-11 | 2,802,743 . . . 2,812,001 | 9259 |
| 100k26-12 | 2,811,882 . . . 2,821,709 | 9828 |
| 100k27-01 | 2,821,611 . . . 2,829,258 | 7648 |
| 100k27-02 | 2,829,139 . . . 2,840,747 | 11609 |
| 100k27-03 | 2,840,629 . . . 2,850,303 | 9675 |
| 100k27-04 | 2,850,184 . . . 2,861,747 | 11564 |
| 100k27-05 | 2,861,628 . . . 2,874,224 | 12597 |
| 100k27-06 | 2,874,125 . . . 2,883,204 | 9080 |
| 100k27-07 | 2,883,085 . . . 2,892,886 | 9802 |
| 100k27-08 | 2,892,767 . . . 2,903,307 | 10541 |
| 100k27-09 | 2,903,192 . . . 2,912,470 | 9279 |
| 100k27-10 | 2,912,359 . . . 2,925,141 | 12783 |
| 100k27-11 | 2,925,022 . . . 2,934,913 | 9892 |
| 100k27-12 | 2,934,794 . . . 2,947,632 | 12839 |
| 100k28-01 | 2,947,528 . . . 2,958,629 | 11102 |
| 100k28-02 | 2,958,510 . . . 2,969,760 | 11251 |
| 100k28-03 | 2,969,641 . . . 2,979,981 | 10341 |
| 100k28-04 | 2,979,863 . . . 2,991,128 | 11266 |
| 100k28-05 | 2,991,016 . . . 3,001,647 | 10632 |
| 100k28-06 | 3,001,530 . . . 3,011,921 | 10392 |
| 100k28-07 | 3,011,802 . . . 3,017,818 | 6017 |
| 100k28-08 | 3,017,699 . . . 3,029,508 | 11810 |
| 100k28-09 | 3,029,389 . . . 3,040,739 | 11351 |
| 100k28-10 | 3,040,621 . . . 3,049,609 | 8989 |
| 100k28-11 | 3,049,490 . . . 3,061,680 | 12191 |
| 100k28-12 | 3,061,561 . . . 3,073,892 | 12332 |
| 100k28-13 | 3,073,773 . . . 3,083,864 | 10092 |
| 100k29-01 | 3,083,760 . . . 3,093,964 | 10205 |
| 100k29-02 | 3,093,855 . . . 3,104,401 | 10547 |
| 100k29-03 | 3,104,282 . . . 3,115,243 | 10962 |

TABLE 2-continued

Table MDS42 10 kb stretches
The genomic locations are listed for all of the 10 kb stretches which comprise the designed synthetic MDS42 genome.

| Stretch | 5' start . . . 3'end | Length (bp) |
|---|---|---|
| 100k29-04 | 3,115,124 . . . 3,126,447 | 11324 |
| 100k29-05 | 3,126,328 . . . 3,137,036 | 10709 |
| 100k29-06 | 3,136,946 . . . 3,146,763 | 9818 |
| 100k29-07 | 3,146,648 . . . 3,157,292 | 10645 |
| 100k29-08 | 3,157,193 . . . 3,166,872 | 9680 |
| 100k29-09 | 3,166,754 . . . 3,176,818 | 10065 |
| 100k29-10 | 3,176,729 . . . 3,190,320 | 13592 |
| 100k29-11 | 3,190,200 . . . 3,197,411 | 7212 |
| 100k29-12 | 3,197,292 . . . 3,205,624 | 8333 |
| 100k30-01 | 3,205,520 . . . 3,215,838 | 10319 |
| 100k30-02 | 3,215,720 . . . 3,223,955 | 8236 |
| 100k30-03 | 3,223,836 . . . 3,232,308 | 8473 |
| 100k30-04 | 3,232,188 . . . 3,242,559 | 10372 |
| 100k30-05 | 3,242,448 . . . 3,252,486 | 10039 |
| 100k30-06 | 3,252,362 . . . 3,261,740 | 9379 |
| 100k30-07 | 3,261,617 . . . 3,271,913 | 10297 |
| 100k30-08 | 3,271,802 . . . 3,282,128 | 10327 |
| 100k30-09 | 3,282,026 . . . 3,292,438 | 10413 |
| 100k30-10 | 3,292,317 . . . 3,301,878 | 9562 |
| 100k30-11 | 3,301,760 . . . 3,308,902 | 7143 |
| 100k30-12 | 3,308,784 . . . 3,319,704 | 10921 |
| 100k31-01 | 3,319,643 . . . 3,330,096 | 10454 |
| 100k31-02 | 3,329,973 . . . 3,339,866 | 9894 |
| 100k31-03 | 3,339,748 . . . 3,347,473 | 7726 |
| 100k31-04 | 3,347,354 . . . 3,353,926 | 6573 |
| 100k31-05 | 3,353,798 . . . 3,358,503 | 4706 |
| 100k31-06 | 3,358,382 . . . 3,364,683 | 6302 |
| 100k31-07 | 3,364,562 . . . 3,372,812 | 8251 |
| 100k31-08 | 3,372,694 . . . 3,381,488 | 8795 |
| 100k31-09 | 3,381,367 . . . 3,391,350 | 9984 |
| 100k31-10 | 3,391,231 . . . 3,397,632 | 6402 |
| 100k31-11 | 3,397,509 . . . 3,405,953 | 8445 |
| 100k31-12 | 3,405,834 . . . 3,412,263 | 6430 |
| 100k32-01 | 3,412,160 . . . 3,425,218 | 13059 |
| 100k32-02 | 3,425,094 . . . 3,436,233 | 11140 |
| 100k32-03 | 3,436,117 . . . 3,447,693 | 11577 |
| 100k32-04 | 3,447,587 . . . 3,458,871 | 11285 |
| 100k32-05 | 3,458,754 . . . 3,473,651 | 14898 |
| 100k32-06 | 3,473,525 . . . 3,485,082 | 11558 |
| 100k32-07 | 3,484,960 . . . 3,495,175 | 10216 |
| 100k32-08 | 3,495,050 . . . 3,505,175 | 10126 |
| 100k32-09 | 3,505,056 . . . 3,511,192 | 6137 |
| 100k32-10 | 3,511,087 . . . 3,521,547 | 10461 |
| 100k33-01 | 3,521,422 . . . 3,532,175 | 10754 |
| 100k33-02 | 3,532,076 . . . 3,542,259 | 10184 |
| 100k33-03 | 3,542,143 . . . 3,552,029 | 9887 |
| 100k33-04 | 3,551,907 . . . 3,560,073 | 8167 |
| 100k33-05 | 3,559,950 . . . 3,569,315 | 9366 |
| 100k33-06 | 3,569,198 . . . 3,580,065 | 10868 |
| 100k33-07 | 3,579,946 . . . 3,589,870 | 9925 |
| 100k33-08 | 3,589,750 . . . 3,598,037 | 8288 |
| 100k33-09 | 3,597,917 . . . 3,608,905 | 10989 |
| 100k33-10 | 3,608,783 . . . 3,621,964 | 13182 |
| 100k33-11 | 3,621,843 . . . 3,631,892 | 10050 |
| 100k34-01 | 3,631,790 . . . 3,639,310 | 7521 |
| 100k34-02 | 3,639,199 . . . 3,648,860 | 9662 |
| 100k34-03 | 3,648,743 . . . 3,659,291 | 10549 |
| 100k34-04 | 3,659,171 . . . 3,667,138 | 7968 |
| 100k34-05 | 3,667,024 . . . 3,676,694 | 9671 |
| 100k34-06 | 3,676,571 . . . 3,684,078 | 7508 |
| 100k34-07 | 3,683,940 . . . 3,692,892 | 8953 |
| 100k34-08 | 3,692,772 . . . 3,702,686 | 9915 |
| 100k34-09 | 3,702,582 . . . 3,711,607 | 9026 |
| 100k34-10 | 3,711,488 . . . 3,719,178 | 7691 |
| 100k34-11 | 3,719,064 . . . 3,726,219 | 7156 |
| 100k35-01 | 3,726,119 . . . 3,735,813 | 9695 |
| 100k35-02 | 3,735,698 . . . 3,745,893 | 10196 |
| 100k35-03 | 3,745,767 . . . 3,756,900 | 11134 |
| 100k35-04 | 3,756,781 . . . 3,767,315 | 10535 |
| 100k35-05 | 3,767,195 . . . 3,776,515 | 9321 |
| 100k35-06 | 3,776,395 . . . 3,786,445 | 10051 |
| 100k35-07 | 3,786,327 . . . 3,797,101 | 10775 |
| 100k35-08 | 3,796,976 . . . 3,806,009 | 9034 |
| 100k35-09 | 3,805,910 . . . 3,815,399 | 9490 |
| 100k35-10 | 3,815,281 . . . 3,823,285 | 8005 |
| 100k35-11 | 3,823,166 . . . 3,832,032 | 8867 |
| 100k35-12 | 3,831,909 . . . 3,837,828 | 5920 |
| 100k36-01 | 3,837,736 . . . 3,847,670 | 9935 |
| 100k36-02 | 3,847,551 . . . 3,856,620 | 9070 |
| 100k36-03 | 3,856,499 . . . 3,865,869 | 9371 |
| 100k36-04 | 3,865,746 . . . 3,874,026 | 8281 |
| 100k36-05 | 3,873,919 . . . 3,880,887 | 6969 |
| 100k36-06 | 3,880,768 . . . 3,891,155 | 10388 |
| 100k36-07 | 3,891,032 . . . 3,899,094 | 8063 |
| 100k36-08 | 3,898,973 . . . 3,909,104 | 10132 |
| 100k36-09 | 3,908,980 . . . 3,916,124 | 7145 |
| 100k36-10 | 3,916,005 . . . 3,926,250 | 10246 |
| 100k36-11 | 3,926,131 . . . 3,933,174 | 7044 |
| 100k36-12 | 3,933,053 . . . 3,942,133 | 9081 |
| 100k36-13 | 3,942,027 . . . 3,948,320 | 6294 |
| 100k37-01 | 3,948,216 . . . 3,958,890 | 10675 |
| 100k37-02 | 3,958,767 . . . 3,967,811 | 9045 |
| 100k37-03 | 3,967,690 . . . 3,977,596 | 9907 |
| 100k37-04 | 3,977,471 . . . 9193 | 10660 |
| 100k37-05 | 9077 . . . 15,244 | 6168 |
| 100k37-06 | 15,125 . . . 22,052 | 6928 |
| 100k37-07 | 21,933 . . . 29,499 | 7567 |
| 100k37-08 | 29,374 . . . 36,759 | 7386 |
| 100k37-09 | 36,643 . . . 45,184 | 8542 |
| 100k37-10 | 45,085 . . . 53,037 | 7953 |
| 100k37-11 | 52,911 . . . 61,413 | 8503 |
| 100k37-12 | 61,285 . . . 70,337 | 9053 |
| 100k37-13 | 70,221 . . . 78,586 | 8366 |
| 100k37-14 | 78,465 . . . 83,922 | 5458 |

TABLE 3

Table of BAC Assemblies
Success rate of BAC assembly in yeast, followed by transformation into *E. coli* and verification by NGS.

| | | Yeast | | | *E. coli* |
|---|---|---|---|---|---|
| Section | Fragment | # of 10kb stretches | # of junctions genotyped | Genotyped clones (correct/total) | Sequence verified BACs (correct/total) |
| H | 1 | 10 | 8 | 4/4 | 4/4 |
|   | 2 | 12 | 7 | 17/23 | 5/11 |
|   | 3 | 13 | 0 | 1/1 | 1/1 |
| A | 4 | 10 | 11 | 7/30 | 2/3 |
|   | 5 | 10 | 5 | 23/24 | 2/4 |
|   | 6 | 11 | 7 | 6/15 | 1/4 |
|   | 7 | 10 | 2 | 16/24 | 1/4 |
|   | 8 | 9 | 6 | 13/15 | 1/6 |
| B | 9 | 12 | | | 5/8 |
|   | 10 | 10 | 5 | 9/22 | 1/4 |
|   | 11 | 10 | 6 | 8/8 | 1/4 |
|   | 12 | 11 | 12 | 3/4 | 1/3 |
|   | 13 | 11 | 6 | 11/22 | 6/11 |
| C | 14 | 12 | 7 | 12/12 | 4/4 |
|   | 15 | 11 | 7 | 11/12 | 4/4 |
|   | 16 | 11 | | | 4/4 |
|   | 17 | 10 | 6 | 9/15 | 3/4 |
|   | 18 | 10 | 11 | 7/8 | 1/7 |
| D | 19 | 11 | 12 | 4/24 | 1/3 |
|   | 20 | 9 | | | 1/3 |
|   | 21 | 11 | 12 | 3/16 | 3/3 |
|   | 22 | 11 | 10 | 3/24 | 2/3 |
|   | 23 | 10 | 11 | 4/11 | 2/4 |

TABLE 3-continued

Table of BAC Assemblies
Success rate of BAC assembly in yeast, followed by
transformation into *E. coli* and verification by NGS.

| Section | Fragment | # of 10kb stretches | # of junctions genotyped | Genotyped clones (correct/total) | Sequence verified BACs (correct/total) |
|---|---|---|---|---|---|
| E | 24 | 10 | 11 | 11/11 | 3/4 |
|   | 25 | 10 | 10 | 5/24 | 1/3 |
|   | 26 | 12 | 11 | 6/7 | 4/4 |
|   | 27 | 12 | 5 | 8/24 | 3/5 |
|   | 28 | 13 | 9 | 4/24 | 1/4 |
| F | 29 | 12 | 13 | 8/24 | 1/8 |
|   | 30 | 12 | 9 | 6/22 | 1/1 |
|   | 31 | 12 | 12 | 7/8 | 6/8 |
|   | 32 | 9 | 9 | 8/24 | 1/4 |
| G | 33 | 12 | 13 | 6/32 | 2/4 |
|   | 34 | 11 | 12 | 8/24 | 3/5 |
|   | 35 | 12 | 7 | 5/24 | 2/3 |
|   | 36 | 13 | 14 | 4/48 | 1/1 |
| H | 37 | 14 | 1 | 0/56 |  |
|   | 37a | 7 | 7 | 10/16 | 3/3 |
|   | 37b | 7 | 7 | 1/16 | 1/1 |

TABLE 4

Table of REXER experiments
Individual or sequential integration of synthetic fragments into the genome by REXER. The
table indicates the success rate of each integration, and details which spacers and markers
that were employed.

Individual REXER

| Sect. | Frag. | recorded/ total | Spacers Lin | Spacers Circ | Spacers 2nd gen | Markers 3' to synthetic DNA | Markers on BAC | Comments |
|---|---|---|---|---|---|---|---|---|
| H | 1 | 0/6, (2/7)** |  | x |  | sacB-CmR | rpsL | **After altering refactoring of ftsI-murE |
|   | 2 | 1/5 | x |  |  | rpsL-KanR | pheS*-HygR | and recoding of map. |
|   | 3 | 1/1 | x |  |  | sacB-CmR | rpsL |  |
| A | 4 | 1/6 |  | x |  | rpsL-KanR | sacB |  |
|   | 5 | 3/6 |  | x |  | sacB-CmR | rpsL |  |
|   | 6 |  |  |  |  | rpsL-KanR | pheS*-HygR |  |
|   | 7 | 3/6 | x |  |  | sacB-CmR | rpsL |  |
|   | 8 |  |  |  |  | rpsL-KanR | pheS*-HygR |  |
| B | 9 |  |  |  |  | sacB-CmR | rpsL |  |
|   | 10 |  |  |  |  | rpsL-KanR | pheS*-HygR |  |
|   | 11 | 1/2 | x |  |  | sacB-CmR | rpsL |  |
|   | 12 | 2/4 | x |  |  | rpsL-KanR | pheS*-HygR |  |
|   | 13 | 2/4 | x |  |  | sacB-CmR | rpsL |  |
| C | 14 | 5/8 | x |  |  | rpsL-KanR | sacB |  |
|   | 15 |  |  |  |  | sacB-CmR | rpsL |  |
|   | 16 |  |  |  |  | rpsL-KanR | pheS*-HygR |  |
|   | 17 |  |  |  |  | sacB-CmR | rpsL |  |
|   | 18 | 1/2 | x |  |  | rpsL-KanR | sacB |  |
| D | 19 | 7/9 | x |  |  | sacB-CmR | rpsL |  |
|   | 20 |  |  |  |  | rpsL-KanR | sacB |  |
|   | 21 | 3/5 | x |  |  | sacB-CmR | rpsL |  |
|   | 22 | 6/6 | x |  |  | rpsL-KanR | pheS*-HygR |  |
|   | 23 | 6/6 | x |  |  | sacB-CmR | rpsL |  |
| E | 24 | 2/7 | x |  |  | rpsL-KanR | pheS*-HygR |  |
|   | 25 | 1/3 | x |  |  | sacB-CmR | rpsL |  |
|   | 26 | 2/3 | x |  |  | rpsL-KanR | pheS*-HygR |  |
|   | 27 | 1/8 | x |  |  | sacB-CmR | rpsL | Point mutation in non-essential gene |
|   | 28 | 2/7 | x |  |  | rpsL-KanR | pheS*-HygR | Point mutation in non-essential gene, introducing STOP codon |
| F | 29 | 6/6 | x |  |  | sacB-CmR | rpsL |  |
|   | 30 |  |  |  |  | rpsL-KanR | pheS*-HygR |  |
|   | 31 | 2/5 | x |  |  | sacB-CmR | rpsL |  |
|   | 32 |  |  |  |  | rpsL-KanR | pheS*-HygR |  |
| G | 33 | 4/8 | x |  |  | sacB-CmR | rpsL |  |
|   | 34 | 3/5 | x |  |  | rpsL-KanR | pheS*-HygR |  |
|   | 35 |  |  |  |  | sacB-CmR | rpsL |  |
|   | 36 |  |  |  |  | rpsL-KanR | pheS*-HygR |  |
| H | 37a | 0/6, (1/7)# |  | x |  | sacB-CmR | rpsL | #After recoding of yaaY |
|   |  |  |  |  |  | rpsL-KanR | pheS*-AprR | Point mutation in non-essential gene |
|   | 37b | 3/6 | x |  |  |  |  |  |

TABLE 4-continued

Table of REXER experiments
Individual or sequential integration of synthetic fragments into the genome by REXER. The table indicates the success rate of each integration, and details which spacers and markers that were employed.

Sequential REXER

| Sect. | Frag. | recorded/ total | Spacers Lin | Spacers Circ | 2nd gen | 2nd gen REXER4 | Markers 3' to synthetic DNA | Markers on BAC | Comments |
|---|---|---|---|---|---|---|---|---|---|
| H | 1 | | | | | | sacB-CmR | rpsL | |
|   | 2 | 2/7 | | | x | | rpsL-KanR | pheS*-HygR | |
|   | 3 | 3/5 | | | x | | sacB-CmR | rpsL | |
| A | 4 | | | | | | rpsL-KanR | sacB | |
|   | 5 | 3/6 | x | | | | sacB-CmR | rpsL | |
|   | 6 | 4/6 | x | | | | rpsL-KanR | pheS*-HygR | |
|   | 7 | 5/8 | x | | | | sacB-CmR | rpsL | |
|   | 8 | 3/6 | x | | | | rpsL-KanR | pheS*-HygR | |
| B | 9 | 0/29, (4/5)# | x | | | | sacB-CmR | rpsL | #After altering recoding of yceQ. |
|   | 10 | 1/8 | x | | | | rpsL-KanR | pheS*-HygR | |
|   | 11 | 2/6 | x | | | | sacB-CmR | rpsL | |
|   | 12 | 1/6 | — | — | — | — | rpsL-KanR | pheS*-HygR | Conjugated into 4-11 from individual 100k12 strain |
|   | 13 | 7/8 | x | | | | sacB-CmR | rpsL | |
| C | 14 | | | | | | rpsL-KanR | sacB | |
|   | 15 | 3/5 | x | | | | sacB-CmR | rpsL | |
|   | 16 | 4/9 | x | | | | rpsL-KanR | pheS*-HygR | |
|   | 17 | 4/8 | x | | | | sacB-CmR | rpsL | |
|   | 18 | 5/10 | x | | | | rpsL-KanR | sacB | |
| D | 19 | | | | | | sacB-CmR | rpsL | |
|   | 20 | 3/4 | | | | x | rpsL-KanR | sacB | 3rd gen REXER4 |
|   | 21 | 1/7 | x | | | | sacB-CmR | rpsL | Required Streptomycin at 4000 ug/mL |
|   | 22 | 6/6 | x | | | | rpsL-KanR | pheS*-HygR | |
|   | 23 | 4/6 | x | | | | sacB-CmR | rpsL | |
| E | 24 | | | | | | rpsL-KanR | pheS*-HygR | |
|   | 25 | 2/6 | x | | | | sacB-CmR | rpsL | |
|   | 26 | 4/6 | x | | | | rpsL-KanR | pheS*-HygR | |
|   | 27 | 3/6 | x | | | | sacB-CmR | rpsL | |
|   | 28 | 3/8 | | x | | | rpsL-KanR | pheS*-HygR | |
| F | 29 | | | | | | sacB-CmR | rpsL | |
|   | 30 | 2/3 | x | | | | rpsL-KanR | pheS*-HygR | |
|   | 31 | 2/10 | x | | | | sacB-CmR | rpsL | |
|   | 32 | 4/4 | x | | | | rpsL-KanR | pheS*-HygR | |
| G | 33 | | | | | | sacB-CmR | rpsL | |
|   | 34 | 1/8 | x | | | | rpsL-KanR | pheS*-HygR | |
|   | 35 | 6/6 | x | | | | sacB-CmR | rpsL | |
|   | 36 | 3/7 | x | | | | rpsL-KanR | pheS*-HygR | |
| H | 37a | | | | | | sacB-CmR | rpsL | |
|   | 37b | 3/5 | x | | | | rpsL-KanR | pheS*-AprR | |

Sequential REXER

Example 3—Identifying and Repairing Design Flaws

Sequencing several clones following REXER allows us to score the frequency with which each target codon is recoded and thereby compile a recoding landscape for the genomic region. From the recoding landscape with fragment 1 we directly identified the fourth codon (Ser4, TCA) in map, an essential gene encoding methionine amino peptidase, as recalcitrant to recoding by our defined scheme (FIG. 5A). We also identified a second region, which encompasses a 14 bp overlap of the essential genes ftsI and murE, and several serine codons in ftsI and murE, which was not replaced by our recoded and refactored sequence. Since we have previously recoded this region with the same recoding scheme, when duplicating the overlap plus 182 bp rather than the 20 bp used here (Wang, K. et al., 2016. Nature 539, 59-64) (FIG. 1C), we conclude that the defect in the synthetic DNA for this region is in its refactoring rather than in its recoding. REXER with a new fragment 1 BAC, which contained both the extended refactoring (FIG. 5B) and a TCA to TCT mutation at Ser4 in map (FIG. 5C, Table 5) enabled complete recoding of the targeted 100 kb region of the genome (FIG. 5D).

From the post-REXER recoding landscape for fragment 9 we identified a 26 kb genomic region that was never recoded (FIGS. 6A-6D). Efforts to delete 10 kb regions of the genome within and around this region, in the presence of a BAC containing recoded fragment 9, narrowed down the region that was challenging to recode to 10 kb of the genome. REXER across the 10 kb genomic-region revealed a minimum within the resulting recoding landscape at yceQ. This identified the five target codons within yceQ as problematic to recode. Similarly, the recoding landscape following REXER with fragment 37a, followed by further sequencing allowed us to identify a single codon at the 3' end of yaaY, which was never recoded (FIGS. 7A-7D).

yceQ and yaaY both encode 'predicted proteins', multiple insertions in yceQ are viable, and there is no evidence of mRNA production and/or protein synthesis from these predicted genes (Pundir, S., et al., 2017. Methods Mol Biol 1558, 41-55). Notably, the codons that are recalcitrant to recoding within yceQ and yaaY all lie within the 5' untranslated regions (UTRs) of essential genes. We suggest that the sequence changes introduced by recoding yceQ and yaaY negatively affect the regulation of the adjacent essential genes. Indeed, the target codons in yceQ map to RNA secondary structures and promoter elements within the 5'UTR of rne (encoding the essential ribonuclease RNase E) (FIGS. 8A and 8B) and these sequences are essential for controlling RNAse E homeostasis (Schuck, A., et al. 2009. Mol Microbiol 72, 470-478).

We fixed fragment 9 by introducing a stop codon into the 5' sequence of yceQ; this minimizes any potential translation but retains the native sequence for regulating rne transcription (FIGS. 6A-6D, Table 5). REXER with this new BAC, led to complete recoding of the corresponding 100 kb genomic-region (FIGS. 6A-6B, Table 5). REXER with a new BAC, containing fragment 37a with a TCA to AGC substitution at the problematic codon in yaaY, led to complete recoding of the corresponding region of the genome (FIGS. 7A-7D, Table 5).

Having pinpointed and fixed all the initially problematic sequences we completed the assembly of a strain in which sections A and B are fully recoded (FIGS. 9A and 9B), and the assembly of a strain in which section H is entirely recoded (Table 5, FIGS. 9A and 9B). This completed the assembly of all the sections in seven distinct strains.

TABLE 5

Table of oligonucleotides used for site directed mutagenesis approaches to identify alternative viable recoding solutions.
Alternative recoding mutagenesis-oligos

| Frag. | Target gene | Purpose | Oligo F (5'→3') | Oligo R (5'→3') | Template |
|---|---|---|---|---|---|
| 1 | ftsI-murE | Integrate pheS*-HygR | aaatgaatttgtgattaatcaaggcgaggggacaggtggcagaagctaaAAGCTTGAGCACGTGTTGACAATAATCATCGG (SEQ ID NO: 327) | gcgtctggcaccacggagcagaaggtgcgcaaattacgatctgccacTTATTCCTTTGCCCTCGGACGAGTGCTGG (SEQ ID NO: 328) | pheS*-HygR |
| 1 | ftsI-murE | Ser4 AGT | Aaaaagtcggccggacggtc (SEQ ID NO: 329) | gcaataatggcagccaccacccttg (SEQ ID NO: 330) | Synthetic DNA Ser r.s.3 (Wang et al., Nature 2016) |
| 1 | map | Integrate pheS*-HygR | gcgacgcgcattttttcgatatctctggggtcttgatTGAgatagccatGATTGTCCTCCTTATTCCTTTGCCCTCGGACGAGTGCTGG (SEQ ID NO: 331) | ggcacttacatatatattgtcggtatcaccgacgctgatggacagaattaAAGCTTGAGCACGTGTTGACAATAATCATCGG (SEQ ID NO: 332) | pheS*-HygR |
| 1 | map | Ser4 AGT | cacttcggcagccagtcggccagcgacgcgcattttttcgatatcttctggggtcttgatACTgatagccattaattctgtccatcagcgtcggtgataccgac (SEQ ID NO: 333) | taacgggtctggtgaccgaagtgaac (SEQ ID NO: 334) | MDS42 wt |
| 1 | map | Ser4 AGC | cacttcggcagccagtcggccagcgacgcgcattttttcgatatcttctggggtcttgatGCTgatagccattaattctgtccatcagcgtcggtgataccgac (SEQ ID NO: 335) | taacgggtctggtgaccgaagtgaac (SEQ ID NO: 336) | MDS42 wt |
| 1 | map | Ser4 TCT | cacttcggcagccagtcggccagcgacgcgcattttttcgatatcttctggggtcttgatAGagatagccattaattctgtccatcagcgtcggtgataccgac (SEQ ID NO: 337) | taacgggtctggtgaccgaagtgaac (SEQ ID NO: 338) | MDS42 wt |
| 1 | map | Ser4 TCC | cacttcggcagccagtcggccagcgacgcgcattttttcgatatcttctggggtcttgatGGAgatagccattaattctgtccatcagcgtcggtgataccgac (SEQ ID NO: 339) | taacgggtctggtgaccgaagtgaac (SEQ ID NO: 340) | MDS42 wt |
| 1 | map | Ser4 ACA | cacttcggcagccagtcggccagcgacgcgcattttttcgatatcttctggggtcttgatTGTgatagccattaattctgtccatcagcgtcggtgataccgac (SEQ ID NO: 341) | taacgggtctggtgaccgaagtgaac (SEQ ID NO: 342) | MDS42 wt |
| 1 | map | Ser4 TTA | cacttcggcagccagtcggccagcgacgcgcattttttcgatatcttctggggtcttgatTAAgatagccattaattctgtccatcagcgtcggtgataccgac (SEQ ID NO: 343) | taacgggtctggtgaccgaagtgaac (SEQ ID NO: 344) | MDS42 wt |
| 9 | yceQ | Integrate pheS*-HygR | gtcgcgtcgccaacctcacgttatcgtcagctcaagagagcgcagagtgAAGCTTGAGCACGTGTTGACAATAATCATCGG (SEQ ID NO: 345) | tgataaatggtaaagtcatcttgctataacaaggcttgcagtggaataaTTATTCCTTTGCCCTCGGACGAGTGCTGG (SEQ ID NO: 346) | pheS*-HygR |
| 9 | yceQ | Ser2 TGA, Ser7 + 15 + 57 + 78 WT | ctcgtgtctagtcgcgtcgccaacctcacggttatcgtcagctgcaaagagcgcagagtgTGAgttgcccgTTTTTCActgccggaaaacacagcgcaattaTCAaaga (SEQ ID NO: 347) | caccagcaagaagtgaaaaactgtgagtaagc (SEQ ID NO: 348) | MDS42 wt |

TABLE 5-continued

Table of oligonucleotides used for site directed mutagenesis approaches to identify alternative viable recoding solutions.

Alternative recoding mutagenesis-oligos

| Frag. | Target gene | Purpose | Oligo F (5'→3') | Oligo R (5' 3') | Template |
|---|---|---|---|---|---|
| 37a | yaaY | Integrate pheS*-HygR | tgattagcgtactcaatgccggttaaccttgaccgctgtacaagtataAAGCTTGAGCACGTGTTGACAATTAATCATCGG (SEQ ID NO: 349) | agattatgtatgccgcgtatcagcttcatgtctggctcaaaacagTGAaaatcgtccgagTATTCCTTTGCCCTCGGACGAGTGCTGG (SEQ ID NO: 350) | pheS*-HygR |
| 37a | yaaY | Ser70 AGC | aaaggtgaagacaaagccgctatcgaag (SEQ ID NO: 351) | ggctgagattatgtatgccgcgtatcagcttcatgtctggctcaaaacagGCTaaatcgtccgagtataccttgtacagcggtcaaggttaac (SEQ ID NO: 352) | Partially recoded clone |
| 37a | yaaY | Ser70 AGT | aaaggtgaagacaaagccgctatcgaag (SEQ ID NO: 353) | ggctgagattatgtatgccgcgtatcagcttcatgtctggctcaaaacagACTaaatcgtccgagtataccttgtacagcggtcaaggttaac (SEQ ID NO: 354) | Partially recoded clone |
| 37a | yaaY | Ser70 TCC | aaaggtgaagacaaagccgctatcgaag (SEQ ID NO: 355) | ggctgagattatgtatgccgcgtatcagcttcatgtctggctcaaaacagGGAaatcgtccgagtataccttgtacagcggtcaaggttaac (SEQ ID NO: 356) | Partially recoded clone |
| 37a | yaaY | Ser70 TCG | aaaggtgaagacaaagccgctatcgaag (SEQ ID NO: 357) | ggctgagattatgtatgccgcgtatcagcttcatgtctggctcaaaacagCGAaatcgtccgagtataccttgtacagcggtcaaggttaac (SEQ ID NO: 358) | Partially recoded clone |
| 37a | yaaY | Ser70 TCT | aaaggtgaagacaaagccgctatcgaag (SEQ ID NO: 359) | ggctgagattatgtatgccgcgtatcagcttcatgtctggctcaaaacagAGAaatcgtccgagtataccttgtacagcggtcaaggttaac (SEQ ID NO: 360) | Partially recoded clone |

Example 4—Assembly of a Recoded Genome

We developed a conjugation-based strategy (Isaacs, F. J. et al., 2011. Science 333, 348-353; Ma, N. J., et al., 2014. Nat Protoc 9, 2285-2300; and Lederberg, J. & Tatum, E. L., 1946. Nature 158, 558) to assemble the recoded sections into a single genome. Our strategy assembles the recoded genome in a clockwise manner by conjugating recoded 'donor' sections, containing the origin of transfer (oriT), into their adjacent recoded 'recipient' sections, that have been extended to provide homology to the donor (FIG. 10, FIG. 11a, FIG. 22A-22D). This generates a new genome that contains the recoded sections of both the donor and the recipient. The cells containing this new genome can then be used as a recipient for the next recoded donor, and iteration of the process enables the recoded genome to be assembled through the addition of recoded sections to an increasingly recoded recipient (FIG. 10, FIG. 11A, and FIG. 11B). Donor cells contained a version of the F' plasmid that facilitates transfer of the donor genome to the recipient cells but, unlike standard F' plasmids, is not competent to transfer itself to recipient cells (FIG. 22E); as a result this F' plasmid does not have to be lost from the recipient cells after every conjugation. This accelerated our workflow.

We initiated conjugation by mixing donor and recipient cells, and varied the time and conditions of conjugation to control the extent of genome transfer from the donor to the recipient. Following conjugation between the donor and the recipient cells, we selected for recipient cells, and then for those recipients that had gained the positive marker at the end of the recoded sequence from the donor, and lost the negative marker at the end of the extension in the recipient (FIG. 11A).

We performed a convergent synthesis of a genome recoded through sections A-E (FIG. 10, FIG. 11B). We then used the A-E strain as a recipient for F, generating a recoded strain, A-F. A-F was then used as a recipient for F-G, generating A-G; this conjugation used a much longer shared recoded sequence (0.4 Mb) between the donor and recipient strains to increase conjugation efficiency.

To create a completely recoded genome we first created a recipient strain by introducing 37a and 37b into A-G to create A-G-37ab (providing a 115 kb homology region with the final donor). We created the final donor strain by conjugation between strain H and strain AB, which yielded strain H-A-09, in which H, A and fragment 9 from section B are recoded (FIG. 10, FIG. 11B). The additional sequence from A and B was added to H to ensure that we did not erase the recoding in A in the final conjugation. The final conjugation between the H-A-09 donor strain and A-G-37ab recipient strain led to the synthesis of E. coli, which we name E. coli Syn61, in which all $1.8 \times 10^4$ target codons in the genome are recoded (FIG. 19, SEQ ID NO: 2). The synthesis of our recoded genome introduced only eight non-programmed mutations (Table 6); four of these mutations arose during the preparation of the 100 kb BACs, and four during the recoding process.

TABLE 6

Differences between initial design and Syn61 sequence
Table of design optimizations and non-programmed mutations. At 7 target codons we could not implement our defined recoding scheme. For the final genome we found viable alternative codons that were in accordance with our recoding scheme and a refactoring solution for a problematic recoding area in fragment 1. Additionally, we assembled 8 single nucleotide mutations in the final genome, which arose either in preparation of the 100 kb BACs or during recoding.

| Section | Fragment | Position* | Original design | Final genome | Consequence | Origin |
|---|---|---|---|---|---|---|
| \multicolumn{7}{c}{Design optimisations} | | | | | | |
| H | 37a | 16,213 | AGT | AGC | Viable recoding of S70 in yaaY | |
| H | 1 | 88,037 | 1 nt + TAA + 20 nt | 4 nt + TGA + 182 nt | Viable separation of ftsI and murE | |
| H | 1 | 178,509 | AGT | TCT | Viable recoding of S4 in map | |
| B | 9 | 976,671 | AGC | TGA | Disruption of pseudogene yceQ to preserve viable expression of me | |
| | | 976,686 | AGT | TCA | | |
| | | 976,710 | AGT | TCA | | |
| | | 976,836 | AGC | TCG | | |
| | | 976,899 | AGT | TCA | | |
| \multicolumn{7}{c}{Non-programmed mutations} | | | | | | |
| H | 37b | 53,145 | G | A | Intergenic region | In DNA synthesis or BAC assembly |
| C | 15 | 1,579,495 | C | T | D434D in sdaA (non-essential gene) | In DNA synthesis or BAC assembly |
| D | 21 | 2,288,863 | T | — | Deletion in yfiL (non-essential gene) | During recoding |
| E | 27 | 2,885,875 | A | G | T369A in acrF (non-essential gene) | In transfer from DH10b to MDS42 |
| E | 28 | 3,031,081 | C | A | S119I in gntK (non-essential gene) | In DNA synthesis or BAC assembly |
| F | 30 | 3,252,858 | T | C | S10S in gmK (essential gene) | During recoding |
| F | 30 | 3,252,920 | A | G | Y31C in gmK (essential gene) | During recoding |
| F | 30 | 3,319,703 | A | G | Intergenic region | During recoding |

*Position in designed genome (Supplementary data 2).

Example 5—Consequences of Synonymous Codon Compression in Syn61

Syn61 doubled only 1.6 times slower than MDS42 in LB plus glucose at 37° C., and this ratio increased at 25° C., and decreased at 42° C. (FIG. 13A). Syn61 contains 65% more AGT and AGC codons than MDS42, but providing additional copies of serV, the tRNA that decodes these codons (FIG. 12A), did not increase growth (FIG. 13A); this suggests serV is not limiting. Imaging Syn61 cells suggests they are slightly longer than MDS42 (FIGS. 13B and 13C). The proteome of Syn61 was comparable to that of MDS42 (FIG. 13D). Co-translational incorporation of a non-canonical amino acid, using an orthogonal aminoacyl-tRNA synthetase/tRNA$_{CGA}$ pair, targeted to TCG codons was extremely toxic in MDS42, but completely non-toxic in Syn61; providing phenotypic validation for the removal of TCG codons in Syn61 (FIG. 12B). This approach also provided additional insights (FIGS. 14A-14C). serT, encoding tRNA$^{Ser}_{UGA}$, is the only tRNA that decodes TCA codons in *E. coli*, and is therefore essential. Since Syn61 does not contain TCA codons serT should be dispensable in our strain. Indeed we demonstrated that we could easily remove serT (FIG. 12C, FIG. 14D, FIG. 23), as well as serU and prfA, in Syn61 (FIGS. 14E, 14F, and 23). These data provide functional confirmation that we have removed the target codons from the genome, show that the tRNAs and release factor that decode the target codons can be removed in Syn61, and demonstrate unique properties of Syn61 that arise from recoding.

Example 6—Discussion

We have created *E. coli* in which we have replaced the entire 4 Mb genome with synthetic DNA; the scale of genomic replacement in our experiments is approximately 4 times larger than previously reported for genome replacement in *mycoplasma* or chromosome replacement in a single strain of *S. cerevisiae* (FIG. 15A).

We have demonstrated the genome-wide removal of all known, $1.8 \times 10^4$, target codons (two sense codons, TCG and TCA, the amber codon, TAG) in a single strain of *E. coli*. Our work removes 60 times more codons than experiments removing the amber stop codons by site-directed mutagenesis (FIG. 15B). Moreover, it demonstrates complete, and genome-wide, recoding of all targeted sense codons (FIG. 15B). Thus, we have created a synthetic organism that uses 61 codons instead of the normal 64. The new organism uses a reduced number of sense codons to encode the 20 canonical amino acids.

Our synthetic genome contains only $2 \times 10^{-4}$ non-programmed mutations per target codon (FIG. 15C). This compares favorably to 1.05 non-programmed mutations per target codon reported for replacing the amber codons by site-directed mutagenesis methods (Lajoie, M. J. et al., 2013. Science 342, 357-360) (FIG. 15C).

Our final synthetic genome was recoded using defined refactoring and recoding schemes; using a recoding rule we previously determined on just 83 (0.43%) of the target codons in the genome (Wang, K. et al. 2016. Nature 539, 59-64). The recoding rule worked at 99.9% of the $1.8 \times 10^4$ target codons in the genome, while the refactoring rules worked at 99% of overlaps.

Corrections to our initial recoding scheme were necessary at just seven of the $1.8 \times 10^4$ target codons in the whole genome. While one of these codons was in an essential gene the other six were within the 5' UTRs of essential genes. Thus, all but one of the changes to our defined recoding scheme correct for unintended alterations to the 5' UTRs of essential genes, rather than for direct effects of altered synonyms on translation.

The strategies we have developed for disconnecting a designed genome into sections, fragments, and stretches, and realizing the design through the convergent, seamless and robust integration of REXER, GENESIS and directed conjugation, provides a blueprint for future genome syntheses. In future work we will further characterize the consequences of synonymous codon compression in *E. coli* Syn61, and test additional recoding schemes in *E. coli* and other organisms. In addition we will test sense codon reassignment for non-canonical biopolymer synthesis.

Example 7—Methods

Recoded Genome Design

We based our synthetic genome design on the sequence of the *E. coli* MDS42 genome (accession number AP012306.1, released 7 Oct. 2016), which has 3547 annotated CDS. We manually curated the starting genome annotation to remove three CDS and add another twelve. The three predicted CDS removed were htgA, ybbV, and yzfA; there is no evidence that these sequences encode proteins (Pundir, S., et al., 2017. Methods Mol Biol 1558, 41-55), and these sequences completely or largely overlap with better characterised genes, which would make it difficult to recode them without disrupting their overlapping genes or creating large repetitive regions. Conversely, the pseudogenes ydeU, ygaY, pbl, yghX, yghY, agaW, yhiK, yhjQ, rph, ysdC, glvG, and cybC were promoted to CDS. To enable negative selection with rpsL, we mutated the genomic copy of rpsL to rpsL$^{K43R}$. Finally, deep sequencing of our in-house MDS42 revealed a 51 bp insertion between mrcB and hemL which had not been reported in AP012306.1. We manually introduced and annotated this insertion in our starting genome sequence.

We produced a custom Python script that i) identifies and recodes all target codons, and ii) identifies and resolves overlapping gene sequences that contain target codons. From our curated MDS42 starting sequence, we used the script to generate a new synthetic genome in which all TCG, TCA and TAG codons were replaced with AGC, AGT and TAA respectively. The script reported 91 CDS with overlaps containing target codons. In 33 instances, genes were overlapping tail-to-tail (3', 3') (Table 1); 12 of these could be recoded by introducing a silent mutation in the overlapping gene, while the remaining 21 were duplicated to separate the genes (FIG. 1B). 58 instances of genes overlapping head-to-tail (5', 3') were resolved by duplicating the overlap plus 20 bp of upstream sequence to allow endogenous expression of the downstream gene (FIG. 1C). For overlaps longer than 1 bp, an in-frame TAA was introduced to terminate expression from the original RBS for the downstream gene. prfB (release-factor RF-2) was not annotated as a CDS in our starting MDS42 genome due to its regulatory internal stop codon, and we therefore recoded all the target codons in the gene manually, thereby maintaining the internal stop codon. The resulting genome design contained 3556 CDS with 1,156,625 codons of which 18,218 were recoded (FIG. 18, SEQ ID NO: 1).

Retrosynthesis of Recoded Stretches

We divided the designed genome into 37 fragments of between 91 and 136 kb. We chose the boundary sequences that delimit these fragments so that: i) they consist of a 5'-NGG-3' PAM to allow REXER4 to be used for integration if necessary, ii) the PAM does not sit within 50 bp of a target codon, iii) the PAM is in-between non-essential genes and iv) the PAM does not disturb any annotated features such as promoters. We called the regions ~50-100 bp upstream and downstream of these boundaries 'landing sites', and these are annotated as Lxx, where xx is the number of the upstream fragment, e.g. L01 is the landing site between fragment 1 and 2. In our design, a landing site sequence is contained in the 3' end of a fragment and the 5' end of the next—as a result all 37 fragments contain overlapping homologies of 54-155 bp with their neighbouring fragment.

Each fragment was further broken down to 7-14 stretches of 4-15 kb. We designed the stretches so that they contain overlaps of 80-200 bp with each other, and the overlap regions were defined at intergenic regions free of any recoding targets. A total of 409 stretches were synthesised (GENEWIZ, USA) and supplied in pSC101 or pST vectors flanked by BsaI, AvrII, SpeI, or XbaI restriction sites. The synthetic stretches naturally did not contain at least one of these restriction sites.

Construction of Selection Cassettes and Plasmids for REXER/GENESIS

The cloning procedures described in this section were performed in E. coli DH10b, which is resistant to streptomycin by virtue of an rpsLK43R mutation. The plasmid pKW20_CDFtet_pAraRedCas9_tracrRNA used throughout this study encodes Cas9 and the lambda-red recombination components alpha/beta/gamma under the control of an arabinose-inducible promoter, as well as a tracrRNA under its native promoter, as previously described (Wang, K. et al., 2016. Nature 539, 59-64).

The protospacers for REXER are encoded in the plasmid pKW1_MB1$_{Amp}$_Spacer (FIG. 21A), which contains a pMB1 origin of replication, an ampicillin resistance marker and the protospacer array under the control of its endogenous promoter as previously described (Wang, K. et al., 2016. Nature 539, 59-64). From this plasmid we constructed the derivative pKW3_MB1$_{Amp}$_Trac$^K$_Spacer (Table 5), which additionally contains a tracrRNA upstream of the protospacer array. For this we introduced a PCR product containing tracrRNA with its modified endogenous promoter into the BamHI site of pKW1_MB1$_{Amp}$_Spacer via Gibson assembly using the NEBuilder HiFi Master Mix. From this plasmid a derivative that additionally encodes Cas9 was constructed, also by Gibson assembly, and named pKW5_MB1$_{Amp}$_Trac$^K$_Cas9_Spacer.

For each REXER step, a derivative of one of these three plasmids was constructed to harbour a protospacer/direct repeat array containing 2 (REXER2) or 4 (REXER4) protospacers, corresponding to the target sequences for cutting the BAC and genome. The different protospacer arrays were constructed from overlapping oligos through multiple rounds of PCR—the products were inserted by Gibson assembly between restriction sites AccI and EcoRI in the backbone of pKW1_MB1$_{Amp}$_Spacer, pKW3_MB1$_{Amp}$_Trac$^K$_Spacer or pKW5_MB1$_{Amp}$_Trac$^K$_Cas9_Spacer. The protospacer arrays resulting from each assembly were verified to be mutation-free by Sanger sequencing.

The positive-negative selection cassettes used in in REXER and GENESIS are −1/+1 (rpsL-Kan$^R$), −2/+2 (sacB-Cm$^R$) and −3/+3 (phe$^{ST251A\_A294G}$-Hyg$^R$). −1/+1 and −2/+2 are as previously described (Wang, K. et al., 2016. Nature 539, 59-64). In −3/+3, phe$^{ST251A\_A294G}$ is dominant lethal in the presence of 4-chlorophenylalanine, and Hyg$^R$ confers resistance to hygromycin. Both proteins are expressed polycistronically under control of the EM7 promoter. The −3/+3 cassette was synthesised de novo. The −3/+3 cassette is also referred to as pheS*/Hyg$^R$.

Construction of E. coli Strains Containing Double Selection Cassettes at Genomic Landing Sites.

According to our design, each region of the genome that is targeted for replacement by a synthetic fragment is flanked by an upstream landing site and a downstream landing site; these genomic landing site sequences are the same as the landing site sequences described above. Initiation of REXER/GENESIS requires the insertion of a double selection cassette in the upstream genomic landing site. We inserted double selection cassettes at the landing sites through lambda-red mediated recombination. Briefly, either the sacB-Cm$^R$ or the rpsL-Kan$^R$ cassettes were PCR amplified with primers containing homology regions to the genomic landing sites of interest. For recombination experiments, we prepared electrocompetent cells as described previously (Wang, K. et al., 2016. Nature 539, 59-64) and electroporated 3 µg of the purified PCR product into 100 ML of MDS42$^{rpsLK43R}$ cells harbouring the pKW20_CDFtet_pAraRedCas9_tracrRNA plasmid expressing the lambda-red alpha/beta/gamma genes. The recombination machinery was induced, under control of the arabinose promoter (pAra), with L-arabinose added at 0.5% for 1 hour starting at OD$_{600}$=0.2. Pre-induced cells were electroporated and then recovered for 1 hour at 37° C. in 4 mL of super optimal broth (SOB) medium. Cells were then diluted into 100 ml of LB medium with 10 µg/mL tetracycline and grown for 4 hours at 37° C., 200 rpm. The cells were subsequently spun down, resuspended in 4 mL of H$_2$O, serially diluted, plated and incubated overnight at 37° C. on LB agar plates containing 10 µg/mL tetracycline, 18 µg/mL chloramphenicol (for sacB-Cm$^R$) or 50 µg/mL kanamycin (for rpsL-Kan$^R$).

BAC Assembly and Delivery

We constructed Bacterial Artificial Chromosomes (BACs) shuttle vectors that contained 97-136 kb of synthetic DNA. On the 5' side, the synthetic DNA was flanked by a region of homology to the genome (HR1), and a Cas9 cut site. On the 3' side the synthetic DNA was flanked by a double selection cassette, a region of homology to the genome (HR2), and a second Cas9 cut site. The BAC also contained a negative selection marker, a BAC origin, a URA marker and YAC origin (CEN6 centromere fused to an autonomously replicating sequence (CEN/ARS)) (FIGS. 2C and 20A-20C).

BACs were assembled by homologous recombination in S. cerevisiae. Each assembly combined i) 7-14 stretches of synthetic DNA, each 6-13 kb in length, with ii) a selection construct (see below) and iii) a BAC shuttle vector backbone (FIGS. 20A-20C, Wang, K. et al., 2016. Nature 539, 59-64).

Synthetic DNA stretches were excised by digestion with BsaI, AvrII, SpeI, or XbaI restriction sites from their source vectors provided by GENEWIZ. In the case of AvrII, SpeI, and XbaI, restriction digests were followed by Mung Bean nuclease treatment to remove sticky ends.

Selection constructs contained a region of homology to the 3' most stretch of the fragment, a double selection cassette (sacB-Cm$^R$ or rpsL-Kan$^R$) a region of homology (HR2) to the targeted genomic locus, a negative selection marker (rpsL, sacB or pheS*-Hyg$^R$) and YAC. For specific double selection cassettes, negative selection markers, and homology region sequences see FIG. 20D-20N. We assembled episomal versions of the selection constructs in a pSC101 backbone from 3 PCR fragments with NEBuilder HiFi DNA Assembly Master Mix.

The episomal versions were designed so that restriction digestion with BsaI yielded a DNA fragment for BAC assembly.

The BAC backbone containing a BAC origin and a URA3 marker was amplified by PCR using a previously described BAC (Wang, K. et al., 2016. Nature 539, 59-64) as a template, and the PCR product used for BAC assembly. The primers used for these PCR assemblies are listed in FIG. 20D-20N.

To assemble the stretches, selection construct, and BAC backbone, 30-50 fmol of each piece of DNA was transformed into S. cerevisiae spheroplasts; these were prepared as previously described (Kouprina, N., et al., 2004. Methods Mol Biol 255, 69-89). Following assembly we identified yeast clones potentially harbouring correctly assembled BACs by colony PCR at the junctions of overlapping fragments and vector-insert junctions. Clones that appeared correct by colony PCR were sequence verified by NGS after transformation into E. coli, as described below.

The assembled BACs were extracted from yeast with the Gentra Puregene Yeast/Bact. Kit (Qiagen) following the manufacturer's instructions. MDS42$^{rpsLK43R}$ cells were transformed with the assembled BAC by electroporation. Due to the large size of the BACs we sometimes observed inefficient electroporation into target cells. Consequently, we introduced an oriT-Apramycin cassette provided as a PCR product with 50 bp homology regions by lambda-red-mediated recombination (as described above) into some BACs post assembly (FIGS. 20A-20C). This facilitated transfer of BACs, from E. coli that had been successfully transformed, to other strains by conjugation.

Synthesis of Recoded Sections by REXER and GENESIS

We used various genomic and plasmid selection markers for sequential REXER experiments (GENESIS) (Table 4). We used an rpsL-Kan$^R$ (−1/+1) or sacB-Cm$^R$ (−2/+2) cassette at genomic landing sites for selection. We used rpsL-Kan$^R$-sacB (−1/+1,−2), rpsL-Kan$^R$-pheS*-Hyg$^R$ (−1/+1,−3/+3) or sacB-Cm$^R$-rpsL (−2/+2,−1) cassettes as episomal selection markers.

For each REXER, MDS42$^{rpsLK43R}$ cells containing pKW20_CDFtet_pAraRedCas9_tracrRNA and a double selection cassette at the relevant upstream genomic landing site were transformed with the relevant BAC. We plated cells on LB agar supplemented with 2% glucose, 5 µg/ml tetracycline and antibiotic selecting for the BAC (i.e. 18 µg/ml chloramphenicol or 50 µg/ml kanamycin). We inoculated individual colonies into LB medium with 5 µg/ml tetracycline and the BAC specific antibiotic and grew cells overnight at 37° C., 200 rpm. The overnight culture was diluted in LB medium with 5 µg/ml tetracycline, and the BAC specific antibiotic, to OD600=0.05 and grown at 37° C. with shaking for about 2 h, until OD600=0.2. To induce lambda-red expression we added arabinose powder to the culture to a final concentration of 0.5% and the incubated the culture for one additional hour at 37° C. with shaking. We harvested the cells at OD600≈0.6, and made the cells electro-competent as described previously (Wang, K. et al., 2016. Nature 539, 59-64).

For each REXER experiment a linear dsDNA protospacer array was PCR amplified from pKW1_MB1Amp_Spacers using universal primers (FIG. 21A). Approximately 5-10 µg of the resulting DpnI digested and purified PCR product was transformed into 100 µL electro-competent and induced cells. Cells were recovered in 4 ml SOB medium for 1 h at 37° C. and then diluted to 100 mL LB supplemented with 5 µg/mL tetracycline and antibiotic selecting for the BAC and incubated for another 4 h at 37° C. with shaking. Alternatively, electrocompetent and induced cells were transformed with 5 µg of circular protospacer array (pKW1_MB1Amp_Spacers or pKW3_MB1Amp_Spacers plasmid) and after 1 h recovery in SOB medium at 37° C. transferred into 100 mL LB supplemented with 100 µg/mL ampicillin for another 4 h at 37° C. with shaking (FIGS. 21A and 21B). If REXER2 was not sufficient we performed REXER4 using pKW5_MB1Amp_Spacers plasmid as previously described (Wang, K. et al., 2016. Nature 539, 59-64).

We spun down the culture and resuspended it in 4 ml Milli-Q filtered water and spread in serial dilutions on selection plates of LB agar with 5 µg/ml tetracycline, an agent selecting against the negative selection marker and an antibiotic selecting for the positive marker originating from the BAC. The plates were incubated at 37° C. overnight. Multiple colonies were picked, resuspended in Milli-Q filtered water, and arrayed on several LB agar plates supplemented with 50 µg/ml kanamycin, 18 µg/ml chloramphenicol, 200 µg/ml streptomycin, 7.5% sucrose or 2.5 mM 4-chloro-phenylalanine. Colony PCR was also performed from resuspended colonies using both a primer pair flanking the genomic locus of the landing site and the position of the newly integrated selection cassette from the BAC. REXER-mediated recombination results in an approximately 500 bp band at the upstream genomic locus with a 2.5 kb (rK-landing site) or 3.5 kb (sC-landing site) band for the control MDS42$^{rk}$/MDS42$^{sC}$ strain indicating successful removal of the landing site from the genome. Primer pairs flanking the 3' end of the replaced DNA generate an approximately 2.5 kb (rK selection cassette on pBAC) or 3.5 kb (sC selection cassette on pBAC) band and a 500 bp band for the control MDS42$^{rk}$/MDS42$^{sC}$ strain indicating successful integration of the selection markers.

If a plasmid based circular protospacer array was used in the previous REXER experiment the plasmid had to be lost before the next experiment. Thus, a successful clone from the first REXER experiment was grown in LB supplemented with 2% glucose, 5 µg/mL tetracycline and antibiotic selecting for the positive marker in the genome to a dense culture at 37° C. with shaking. 2 µL of the culture were then streaked out on an LB agar plate with the same supplements and incubated at 37° C. overnight. Several colonies were arrayed in replica on LB agar plate and LB agar plate supplemented with 100 µg/mL ampicillin to screen for the loss of the plasmid.

BAC Editing

When encountering loss-of-function mutations in a selection cassette on BACs in E. coli, the faulty cassette was replaced with a suitable double selection cassette provided (FIG. 20D-20N) as a PCR-product flanked by 50 bp homology regions and integrated by lambda-red-mediated recombination.

Changes in the synthetic, recoded sequence of a BAC, either to correct spontaneous mutations or change recoded codons, were introduced by a two-step replacement approach; For BACs containing the selection cassettes −2/+2 and −1 in the end of the recoded sequence, the −3/+3 cassette was provided as a PCR-product flanked by 50 bp-homology regions targeting the desired locus and integrated by lambda-red-mediated recombination followed by selection for +3. Due to the homology between the recoded DNA and the genome, some of the resulting clones would contain −3/+3 on the BAC and some on the genome. To identify clones with the cassette on the BAC, clones were plated in replica on agar plates selecting (1) for +3, (2) against −3, and (3) for +2 and against −3; Only clones surviving on plate (1) and (2) but not on (3) have the −3/+3 cassette integrated on the BAC. The location of the cassette was verified by purifying the BAC using QIAprep Spin Miniprep Kit followed by genotyping. In a second step, the −3/+3 cassette was replaced by providing a PCR-product of the desired sequence flanked by 50 bp-homology regions and integrated by lambda-red-mediated recombination followed by selection for +2 and against −3. The BAC was genotyped as above and sequence-verified by NGS.

Preparing a Non-Transferable F' Plasmid and Conjugative Transfer of Episomes

We created the version of the F' plasmid used for conjugation of genomic DNA, as well as transfer of BACs between strains, to enable transfer of sequences bearing oriT without transfer of the F' plasmid itself (FIG. 22E). We achieved this by deleting the nick-site in the origin of transfer (oriT) within the F' plasmid itself, a related approach was previously reported (Strand, T. A., et al., 2014. PLOS One 9, e90372). The F' plasmid derivative, pRK24 (addgene #51950), was modified by integrating desired markers as PCR-products flanked by 50 bp-homology regions and integration was performed by lambda-red-mediated recombination using a variant of pKW20 carrying Kan$^R$ instead of Tet$^R$. First, the β-lactamase gene, conferring ampicillin resistance in pRK24, was replaced with the artificial T5-luxABCDE operon (Bryksin, A. V. & Matsumura, I., 2010. PLOS One 5, e13244), which generates bioluminescence that allows visual identification of infected bacterial cells. Next, Tet$^R$ was replaced with T3-aac3 that produces aminoglycoside 3-N-acetyltransferase IV for selection with 50 µg/mL apramycin. Finally, a 24 bp deletion of the nick-site in oriT was made by integrating EM7-bsd that expresses blasticidin-S deaminase, and can be selected for with 50 g/mL blasticidin in low-salt TYE/LB. The resulting F'-plasmid called pJF146 (FIG. 22E), was extracted using QIAprep Spin Miniprep Kit (QIAgen) and transformed by electroporation into donor strains for subsequent conjugation.

Transfer of episomal DNA containing oriT was performed by conjugation (Isaacs, F. J. et al., 2011. Science 333, 348-353; and Ma, N. J., et al. 2014. Nat Protoc 9, 2285-2300). A donor strain was double transformed with pJF146 and an assembled BAC with oriT (see above). A recipient strain was transformed with pKW20. 5 ml of donor and recipient culture were grown to saturation overnight in selective LB media and subsequently washed 3 times with LB media without antibiotics. The resuspended donor and recipient strains were combined in a 4:1 ratio, spotted on TYE agar plates and incubated for 1 h at 37° C. The cells were washed off the plate and spread in serial dilutions on LB agar plates with 2% glucose, 5 g/ml tetracycline selecting for the recipient strain and antibiotic selecting for the BAC. Successful transfer of the BAC was confirmed by colony PCR of the BAC-vector insert junctions.

Assembling a Synthetic Genome from Recoded Sections

Transfer of genomic DNA was combined with subsequent recBCD-mediated recombination to assemble partially synthetic E. coli genomes into a synthetic genome. In preparation of the donor and recipient strains a rpsL-HygR-oriT or Gm$^R$-oriT cassette was supplied as PCR product and integrated into the donor strain genome via lambda-red-mediated recombination (FIGS. 22A-22D). Separately, a pheS*-Hyg$^R$ cassette was integrated approximately 3 kb downstream of the synthetic DNA in the donor strains. This provided a template genomic DNA for PCR amplification of a 3 kb synthetic DNA segment with 3' pheS*-Hyg$^R$ selection cassette. This PCR product was provided to the recipient strains to replace the WT DNA in a lambda-red-mediated recombination. Thereby, the selection marker at the 3' end of the synthetic segment was replaced and a 3 kb homology region to the donor synthetic DNA was generated. This strategy served to systematically generate recipient strains with 3 kb of homology with their respective donors, always with a pheS-Hyg$^R$ at the 3' end. Additionally, the donor strains were transformed with pJF146 and sensitivity to tetracycline was confirmed. In contrast, pKW20 was maintained in the donor strains to confer tetracycline resistance.

For conjugation, donor and recipient strain were grown to saturation overnight in LB medium with 2% glucose, 5 g/ml tetracycline and 50 µg/ml kanamycin or 20 µg/ml chloramphenicol (donor) and 50 µg/ml apramycin and 200 µg/mL hygromycin B (recipient). The overnight cultures were diluted 1:10 in the same selective LB medium and grown to OD$_{600}$=0.5. 50 ml of both donor and recipient culture were washed 3 times with LB medium with 2% glucose and then each resuspended in 400 µl LB medium with 2% glucose. 320 µl of donor was mixed with 80 µl of recipient, spotted on TYE agar plates and incubated at 37° C. The incubation time depended on the length of transferred synthetic DNA and doubling time of the recipient strain and varied from 1 h to 3 h. Cells were washed off the plate and transferred into 100 ml LB medium with 2% glucose and 5 µg/ml tetracycline and incubated at 37° C. for 2 h with shaking. Subsequently 50 µg/ml kanamycin or 20 µg/ml chloramphenicol (selecting for the transferred positive selection marker of the donor) was added, followed by another 2 h incubation at 37° C. The culture was spun down and resuspended in 4 ml Milli-Q filtered water and spread in serial dilutions on selection plates of LB agar with 2% glucose, 5 µg/ml tetracycline, 2.5 mM 4-chloro-phenylalanine and 50 µg/ml kanamycin or 20 µg/ml chloramphenicol. Successful DNA transfer and recombination was determined by colony PCR for the loss of the pheS*-Hyg$^R$ cassette, integration of the donor's selection cassette and absence of the Gm-oriT cassette.

Preparation of Whole-Genome and BAC Libraries for Next-Generation Sequencing

E. coli genomic DNA was purified using the DNEasy™ Blood and Tissue Kit (QIAgen) as per manufacturer's instructions. BACs were extracted from cells with the QIAprep™ Spin Miniprep Kit (QIAgen) as per manufacturer's instructions. We found that this kit was suitable for purification of BACs in excess of 130 kb. We avoided vigorous shaking of the samples throughout purification so as to reduce DNA shearing.

Paired-end Illumina sequencing libraries were prepared using the Illumina Nextera™ XT Kit as per manufacturer's instructions. Sequencing data was obtained in the Illumina MiSeq™, running 2×300 or 2×75 cycles with the MiSeq™ Reagent kit v3.

Sequencing Data Analysis

The standard workflow for sequence analysis in this work is compiled in the iSeq™ package. In short, sequencing reads were aligned to a reference recoded or wild-type genome using bowtie2 with soft-clipping activated (Langmead, B. & Salzberg, S. L., 2012. Nat Methods 9, 357-359). Aligned reads were sorted and indexed with samtools (Li, H. et al., 2009. Bioinformatics 25, 2078-2079). A customised Python script combines functionalities of samtools and igvtools to yield a variant calling summary. This script was used to assess mutations, indels and structural variations, in combination with visual analysis in the Integrative Genomics Viewer (Thorvaldsdottir, H., et al., 2013. Brief Bioinform 14, 178-192).

We produced a custom Python script to generate recoding landscapes across a target genomic region. Briefly, the script takes a BAM alignment file, a reference in fasta and a GeneBank annotation file as inputs. It identifies the target codons for recoding, and compiles the reads that align to these target codons in the alignment file. It then outputs the frequency of recoding at each target codon, and plots these frequencies across the length of the genomic region of interest.

Growth Rate Measurement and Analysis

Bacterial clones were grown overnight at 37° C. in LB with 2% glucose and 100 µg/mL streptomycin. Overnight cultures were diluted 1:50 and monitored for growth while varying temperature (25° C., 37° C., or 42° C.) and media conditions (LB, LB with 2% glucose, M9 minimal media, 2XTY). Measurements of OD$_{600}$ were taken every 5 min for 18 h on a Biomek automated workstation platform with high speed linear shaking.

To determine doubling times, the growth curves were log 2-transformed. At a linear phase of the curve during exponential growth, the first derivative was determined (d(log 2(x))/dt) and ten consecutive time-points with the maximal log 2-derivatives were used to calculate the doubling time for each replicate. A total of 10 independently grown biological replicates were measured for the recoded Syn61 strain and wt MDS42$^{rpsLK43R}$. The mean doubling time and standard deviation from the mean were calculated for all n=10 replicates.

Microscopy and Cell Size Measurement

Cells were grown with shaking in LB supplemented with 100 µg/mL streptomycin to approximately $OD_{600}$=0.2. A thin layer of bacteria was sandwiched between an agarose pad and a coverslip. A standard microscope slide was prepared with a 1% agarose pad (Sigma-Aldrich A4018-5G). A sample of 2 µl to 4 µl of bacterial culture was dropped onto the top of the pad. This was covered by a #1 coverslip supported on either side by a glass spacer matched to the ~1 mm height of the pad. Samples were imaged on an upright Zeiss Axiophot phase contrast microscope using a 63×1.25NA Plan Neofluar phase objective (Zeiss UK, Cambridge, UK). Images were taken using an IDS ueye monochrome camera under control of ueye cockpit software (IDS Imaging Development Systems GmbH, Obersulm, Germany). 10 fields were taken of each sample. Images were loaded in to Nikon NIS Elements software for further quantitation (Nikon Instruments Surrey UK). The General analysis tool was used to apply an intensity threshold to segment the bacteria. A one micron lower size limit was imposed to remove background particulates and dust. Length measurements were subsequently made on the segmented bacteria using the General Analysis quantification tools.

Mass Spectrometry

Three biological replicates were performed for each strain. Proteins from each *Escherichia coli* lysates were solubilized in a buffer containing 6 M urea in 50 mM ammonium bicarbonate, reduced with 10 mM DTT, and alkylated with 55 mM iodoacetamide. After alkylation, proteins were diluted to 1 M urea with 50 mM ammonium bicarbonate, digested with Lys-C (Promega, UK) at a protein to enzyme ratio of 1:50 for 2 hours at 37° C., followed by digestion with Trypsin (Promega, UK) at a protein to enzyme ratio of 1:100 for 12 hours 37° C. The resulting peptide mixtures were acidified by the addition formic acid to a final concentration of 2% v/v. The digests were analysed in duplicate (1 µg initial protein/injection) by nano-scale capillary LC-MS/MS using a Ultimate U3000 HPLC (ThermoScientific Dionex, San Jose, USA) to deliver a flow of approximately 300 nL/min. A C18 Acclaim PepMap100 5 µm, 100 µm×20 mm nanoViper (ThermoScientific Dionex, San Jose, USA), trapped the peptides prior to separation on a C18 Acclaim PepMap 100 3 µm, 75 µm×250 mm nanoViper (ThermoScientific Dionex, San Jose, USA). Peptides were eluted with a 100 minute gradient of acetonitrile (2% to 60%). The analytical column outlet was directly interfaced via a nano-flow electrospray ionisation source, with a hybrid dual pressure linear ion trap mass spectrometer (Orbitrap Velos, ThermoScientific, San Jose, USA). Data dependent analysis was carried out, using a resolution of 30,000 for the full MS spectrum, followed by ten MS/MS spectra in the linear ion trap. MS spectra were collected over a m/z range of 300-2000. MS/MS scans were collected using a threshold energy of 35 for collision induced dissociation. All raw files were processed with MaxQuant 1.5.5.1 using standard settings and searched against an *Escherichia coli* strain K-12 with the *Andromeda* search engine integrated into the MaxQuant software suite. Enzyme search specificity was Trypsin/P for both endoproteinases. Up to two missed cleavages for each peptide were allowed. Carbamidomethylation of cysteines was set as fixed modification with oxidized methionine and protein N-acetylation considered as variable modifications. The search was performed with an initial mass tolerance of 6 ppm for the precursor ion and 0.5 Da for CID MS/MS spectra. The false discovery rate was fixed at 1% at the peptide and protein level. Statistical analysis was carried out using the Perseus (1.5.5.3) module of MaxQuant. Prior to statistical analysis, peptides mapped to known contaminants, reverse hits and protein groups only identified by site were removed. Only protein groups identified with at least two peptides, one of which was unique and two quantitation events were considered for data analysis. For proteins quantified at least once in each strain, the average abundance of each protein across replicates of Syn61 was divided by the abundance in MDS42 replicates, and then log 2-transformed. A P-value for the difference in abundance between strains was calculated by two-sample T-test (Perseus).

Toxicity of CYPK Incorporation Using Orthogonal Aminoacyl-tRNA Synthetases tRNA$_{XXX}$s (Elliott, T. S. Et al., 2014. Nat Biotechnol 32, 465-472; Elliott, T. S., et al., 2016. Cell Chem Biol 23, 805-815; and Krogager, T. P. Et al., 2018. Nat Biotechnol 36, 156-159)

Electrocompetent MDS42 and Syn61 cells were transformed with plasmid pKW1_MmPylS_PylTxxx for expression of PylRS and tRNA$^{Pyl}_{XXX}$, where XXX is the indicated anticodon. Three variants of this plasmid were used, with the anticodon of tRNA$^{Pyl}$ mutated to CGA (pKW1_MmPylS_PylT$_{CGA}$), UGA (pKW1_MmPylS_PylT$_{UGA}$) or GCU (pKW1_MmPylS_PylT$_{GCU}$). Cells were grown over night in LB medium with 75 µg/ml spectinomycin. Overnight cultures were diluted 1:100 into LB supplemented with Nɛ-(((2-methylcycloprop-2-en-1-yl)methoxy) carbonyl)-L-lysine (CYPK) at 0 mM, 0.5 mM, 1 mM, 2.5 mM and 5 mM and growth was measured as described above. "% Max Growth" was determined as the final $OD_{600}$ in the presence of the indicated concentration of CYPK divided by the final $OD_{600}$ in the absence of CYPK. Final $OD_{600}$s were determined after 600 min.

Deletion of prfA, serU and serT by Homologous Recombination

Recoded versions of the pheS*-Hyg$^R$ and rpsL-Kan$^R$ cassettes, according to the recoding scheme described in FIG. 1A, were synthesised de novo, so that expression of the selection proteins would not rely on decoding by serU or serT. For deleting prfA, the recoded rpsL-Kan$^R$ was amplified with oligos containing ~50 bp homology to the prfA flanking genomic sequences. The same was done for serU and serT with recoded selection cassette pheS*-Hyg$^R$. Oligonucleotide sequences are provided in FIG. 23. Syn61 cells harbouring the plasmid pKW20_CDFtet_pAraRedCas9_tracrRNA were made competent as described above, using 2×TY instead of LB. Cells were electroporated with ~8 µg of PCR product, and recovered for 1 hour in 4 mL SOB, then transferred to 100 ml 2×TY supplemented with 5 µg/ml tetracycline. After 4 hours cells were spun down, resuspended in 500 µL H$_2$O and plated in serial dilutions in 2×TY agar plates supplemented with 5 µg/ml tetracycline and 200 µg/ml hygromycin B (for pheS*-Hyg$^R$) or 50 µg/ml kanamycin (for rpsL-Kan$^R$). Deletions were verified in each case by colony PCR with primers flanking the locus of interest.

All publications mentioned in the above specification are herein incorporated by reference. Various modifications and variations of the disclosed methods, cells, compositions and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12385035B2). An electronic copy of the sequence listing will also be available from the USPTO upon request and payment of the fee set forth in 37 CFR 1.19(b)(3).

The invention claimed is:

1. A synthetic *E. coli* genome comprising 5 or fewer occurrences of one or two serine codons,
   wherein the synthetic *E. coli* genome further lacks a functional gene encoding an endogenous cognate tRNA for at least one of the serine codons and wherein each of the serine codons has been recoded such that the endogenous cognate tRNA for the serine codon is dispensable; and
   wherein an *E. coli* comprising the synthetic *E. coli* genome is viable.

2. The synthetic *E. coli* genome according to claim 1, wherein:
   (i) the synthetic *E. coli* genome comprises no occurrences of one or two serine codons;
   (ii) the one or two serine codons are selected from TCG or TCA; and/or
   (iii) the synthetic *E. coli* genome comprises 10 or fewer occurrences, or no occurrences, of the amber stop codon (TAG).

3. A synthetic *E. coli* genome derived from a parent *E. coli* genome, wherein the synthetic *E. coli* genome comprises 10% or less of the occurrences of one or two serine codons, relative to the parent *E. coli* genome,
   wherein the synthetic *E. coli* genome further lacks a functional gene encoding an endogenous cognate tRNA for at least one of the serine codons and wherein each of the serine codons has been recoded such that the endogenous cognate tRNA for the serine codons is dispensable; and
   wherein an *E. coli* comprising the synthetic *E. coli* genome is viable.

4. The synthetic *E. coli* genome according to claim 3, wherein:
   (i) the one or two serine codons are selected from TCG or TCA;
   (iii) 90% or more of the occurrences of the one or two serine codons in the parent *E. coli* genome are replaced with synonymous sense codons;
   (iv) the synthetic *E. coli* genome comprises 10 or fewer occurrences, or no occurrences, of the amber stop codon (TAG);
   (v) 99.9% or more of the occurrences of one or two serine codons in the parent *E. coli* genome are replaced with synonymous sense codons, and wherein all of the occurrences of TAG in the parent *E. coli* genome are replaced with TAA; and/or
   (vi) one or more pairs of genes which share an overlapping region comprising the one or two serine codons in the parent *E. coli* genome are refactored.

5. The synthetic *E. coli* genome according to claim 4, wherein for pairs of genes in opposite orientations, a synthetic insert is inserted between the genes, wherein the synthetic insert comprises the overlapping region; and/or wherein for pairs of genes in the same orientation, a synthetic insert is inserted between the genes, wherein the synthetic insert comprises: (i) a stop codon; (ii) about 20-200 bp from upstream of the overlapping region; and (iii) the overlapping region.

6. An *E. coli* host cell comprising the synthetic *E. coli* genome according to claim 1 or claim 3.

7. A method for production of polypeptides comprising one or more non-proteinogenic amino acids, the method comprising culturing the *E. coli* host cell according to claim 6 under conditions and for a time sufficient for production of polypeptides comprising one or more non-proteinogenic amino acids.

8. The synthetic *E. coli* genome of claim 2 or 4, wherein the synthetic *E. coli* genome lacks a functional serT gene.

9. The synthetic *E. coli* genome of claim 2 or 4, wherein the synthetic *E. coli* genome lacks a functional serU gene.

10. The synthetic *E. coli* genome of claim 2 or 4, wherein the occurrences of the TAG codon have been replaced with TAA.

11. The synthetic *E. coli* genome of claim 10, wherein the synthetic *E. coli* genome lacks a functional prfA gene.

* * * * *